US011127905B2

(12) United States Patent
Xia et al.

(10) Patent No.: US 11,127,905 B2
(45) Date of Patent: Sep. 21, 2021

(54) ORGANIC ELECTROLUMINESCENT MATERIALS AND DEVICES

(71) Applicant: Universal Display Corporation, Ewing, NJ (US)

(72) Inventors: Chuanjun Xia, Lawrenceville, NJ (US); Lichang Zeng, Lawrenceville, NJ (US); Walter Yeager, Yardley, PA (US); Zhiqiang Ji, Hillsborough, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 466 days.

(21) Appl. No.: 15/173,806

(22) Filed: Jun. 6, 2016

(65) Prior Publication Data

US 2017/0033295 A1 Feb. 2, 2017

Related U.S. Application Data

(60) Provisional application No. 62/198,173, filed on Jul. 29, 2015.

(51) Int. Cl.

| | |
|---|---|
| ***H01L 51/00*** | (2006.01) |
| ***C07D 495/04*** | (2006.01) |
| ***C09K 11/06*** | (2006.01) |
| ***C09K 11/02*** | (2006.01) |
| ***H01L 51/50*** | (2006.01) |

(52) U.S. Cl.

CPC ........ *H01L 51/0072* (2013.01); *C07D 495/04* (2013.01); *C09K 11/025* (2013.01); *C09K 11/06* (2013.01); *H01L 51/0071* (2013.01); *H01L 51/0085* (2013.01); *C09K 2211/185* (2013.01); *H01L 51/5016* (2013.01); *H01L 51/5056* (2013.01); *H01L 51/5072* (2013.01); *H01L 51/5096* (2013.01); *H01L 2251/5361* (2013.01)

(58) Field of Classification Search

None

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Kalugin et al. "Synthesis of derivatives of pyrido[3',2':4,5]furo[3,2-c]isoquinoline heterocyclic system" Russian Chemical Bulletin, International Edition, vol. 63, No. 2, p. 426-430, Feb. 2014 (Year: 2014).*

(Continued)

*Primary Examiner* — Magali P Slawski

(74) *Attorney, Agent, or Firm* — Duane Morris LLP

(57) ABSTRACT

Novel compounds that contain azadibenzofuran, azadibenzothiophene, and azadibenzoselenophene with fused rings that can be used as a host material in phosphorescent OLEDs is disclosed.

22 Claims, 2 Drawing Sheets

(56) References Cited

U.S. PATENT DOCUMENTS

| | | | |
|---|---|---|---|
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 9,570,689 | B2 | 2/2017 | Park et al. |
| 10,573,838 | B2 | 2/2020 | Lee et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Pakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2010/0187984 | A1 | 7/2010 | Lin et al. |
| 2010/0295032 | A1* | 11/2010 | Kwong .................. C09K 11/06 257/40 |
| 2011/0260138 | A1 | 10/2011 | Xia et al. |
| 2011/0266526 | A1 | 11/2011 | Ma et al. |
| 2014/0027741 | A1 | 1/2014 | Park et al. |
| 2014/0034915 | A1* | 2/2014 | Lee ..................... H01L 51/0061 257/40 |
| 2015/0060813 | A1 | 3/2015 | Kawakami et al. |
| 2015/0207082 | A1 | 7/2015 | Dyatkin et al. |
| 2016/0141515 | A1* | 5/2016 | Hayama ................. C09K 11/06 257/40 |
| 2017/0141325 | A1* | 5/2017 | Lee ...................... C07D 495/04 |
| 2017/0141331 | A1* | 5/2017 | Kim .................... H01L 51/0052 |
| 2018/0141957 | A1 | 5/2018 | Park et al. |

FOREIGN PATENT DOCUMENTS

| | | |
|---|---|---|
| EP | 2034538 | 3/2009 |
| EP | 2123733 | 11/2009 |
| EP | 3029125 | 6/2016 |
| JP | 200511610 | 1/2005 |
| JP | 2007123392 | 5/2007 |
| JP | 2007254297 | 10/2007 |
| JP | 2008074939 | 4/2008 |
| JP | 2015224250 | 12/2015 |
| KR | 20130109837 | 10/2013 |
| KR | 20140065881 | 5/2014 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2008142976 | 11/2008 |
| WO | 2008143059 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2013154325 | 10/2013 |
| WO | 2014/199637 | 12/2014 |
| WO | 2015/093814 | 6/2015 |
| WO | 2015/199489 | 12/2015 |

(56) References Cited

FOREIGN PATENT DOCUMENTS

| | | |
|---|---|---|
| WO | 2016140497 | 9/2016 |
| WO | 2017010726 | 1/2017 |

OTHER PUBLICATIONS

Görlitzer et al. "Tetracyclische Derivate des Diltiazems aus Auronen und Thioauronen" Pharmazie 58: 177-180 (2003) (Year: 2003).*
*Translation* of Görlitzer et al. "Tetracyclische Derivate des Diltiazems aus Auronen und Thioauronen" Pharmazie 58: 177-180 (2003) (Year: 2019).*
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato)beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).

(56) References Cited

OTHER PUBLICATIONS

Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
K. E. Chippendale, et al., Condensed Thiophen Ring Systems. Part IX.1 Synthesis and Some Reactions of [1] Benzothieno [3,2-c]cinnolines, Journal, Mar. 1972, pp. 2030-2032, J.C.S. Perkin.
Wolfgang Stadlbauer, et al., Synthesis of Benzofuranes by Cyclodehydrogenation of Phenylmalonyl Heterocyclic Compounds, Article, Apr. 1980, pp. 1005-1013, Monatshefte fur Chemie.
Seiji Yamaguchi, et al., The Synthesis of Benzofuroquinolines, X. Some Benzofuro[3,2-c]isoquinoline Derivatives, Article, Sep.-Oct. 1985, pp. 1517-1519, J. Heterocyclic Chem.
Seiji Yamaguchi, et al., The Synthesis of Benzofuroquinolines, V. Some Benzofuro[3,2-c]isoquinoline Derivatives, Article, Mar.-Apr. 1989, pp. 285-287, J. Heterocyclic Chem.
Sudabeh Pakray, et al., The Synthesis of Dimethoxy[1]benzothieno[2-3-c]quinolines, Article, Sep.-Oct. 1986, pp. 1571-1577, J. Heterocyclic Chem.
Jose M. Quintela, et al., Synthesis of Pyrimido[5",4":5',6']Pyrido[2',3':4,5]-Thieno[2,3-c]Pyridazine and Pyridazino [4',3':4,5]-Thieno[3,2-b][1,8]Naphthyridine, New Tetrahete-Rocyclic Ring Systems, 1997 vol. 45, No. 9, pp. 1733-1743, Heterocycles.
Klaus Gorlitzer, et al., Fused Quinolines, IV: 5,11-Dihydrobenzothieno[3,2-b][1]quinolin-11-ones, S,S-Dioxides and Products of Thionation, Mar. 1980, pp. 76-84, Arch. Pharm. (Weinheim).
Edward F. Elslager, et al., Inhibitors of Platelet Aggregation. 3. {[(Dialkylamino)alkyl]thio}heterocyclic Compounds1, Journal, Jul. 1971, pp. 61-65, vol. 15, No. 1, Journal of Medicinal Chemistry.
Luo, Jiann-Kuan et al., "The Synthesis of Difluoro[1]benzothieno[2,3-c]quinolines and Their N-Methyl Quaternary Salts," J. Heterocyclic Chem., vol. 27, 1990, pp. 2047-2052.
Pakray, Sudabeh et al., "The Synthesis of Monomethoxynaphtho[1',2':4,5]thieno[2,3-c]quinolines," J. Heterocyclic Chem., vol. 24, 1987, pp. 231-233.
Pakray, Sudabeh et al., "The Synthesis of Dimethoxy[1]benzothieno[2,3-c]quinolines," J. Heterocyclic Chem., vol. 23, No. 5, 1986, pp. 1571-1577.
Partial European Search Report dated Sep. 7, 2016 for corresponding EP Application No. 16179494.6.
Morreale, Antonio et al., "Arylpiperazines with Serotonin-3 Antagonist Activity: A Comparative Molecular Field Analysis" J. Med. Chem., 1998, vol. 41, pp. 2029-2039.
Anzini, Maurizio et al., "Novel, Potent, and Selective 5-HT3 Receptor Antagonists Based on the Arylpiperazine Skeleton: Synthesis, Structure, Biological Activity, and Comparative Molecular Field Analysis Studies" J. Med. Chem., 1995, vol. 38, pp. 2692-2704.
Gerfaud, Thibaud et al., "Palladium-Catalyzed Annulation of Acyloximes with Arynes (or Alkynes): Synthesis of Phenanthridines and Isoquinolines" Angew. Chem. Int. Ed., 2009, vol. 48, pp. 572-577.
Koltai, E. et al., "A Novel Rearrangement Reaction of 2,5,5-Triaryl-2-Thiazolin-4-Ones During Thiation" Tetrahedron, 1973, vol. 29, pp. 2783-2794.
Notice of Reasons for Rejection dated Dec. 3, 2019 for corresponding JP Application No. 2016-133931.
Notice of Reasons for Rejection dated Jul. 14, 2020 for corresponding Japanese Patent Application No. JP 2016-133931.

* cited by examiner

ORGANIC ELECTROLUMINESCENT MATERIALS AND DEVICES

CROSS-REFERENCE TO RELATED APPLICATIONS

This application claims priority under 35 U.S.C. § 1.119 (e)(1) to U.S. Provisional Application Ser. No. 62/198,173, filed Jul. 29, 2015, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD

The present invention relates to organic compounds for use as hosts or delayed fluorescent emitters in organic light emitting devices such as organic light emitting diodes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted $Ir(ppy)_3$, which has the following structure:

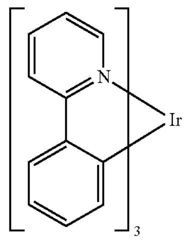

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an embodiment, a compound is provided that has a formula selected from the group consisting of:

Formula I-1

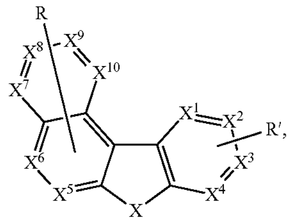

Formula I-2

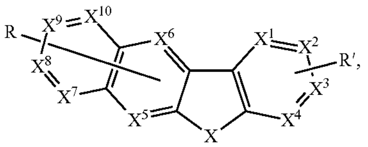

and

Formula I-3

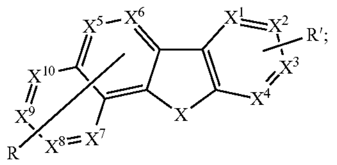

wherein X is selected from the group consisting of O, S, and Se;

wherein $X^1$ to $X^{10}$ are each independently selected from the group consisting of carbon and nitrogen;

wherein at least one of $X^1$ to $X^6$ is nitrogen;

wherein R and R' each independently represent from mono to the possible maximum number of substitutions, or no substitution;

wherein R and R' are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein any adjacent substitutions on the same ring are optionally joined or fused into a ring; and wherein at least one of R and R' is not hydrogen or deuterium;

provided that when adjacent substitutions on $X^5$ and $X^6$ in Formula I-1 and I-3 fuse into a six-member ring, this ring and the ring having $X^7$ to $X^{10}$ can not be pyridine at the same time.

According to another embodiment, a first organic light emitting device is disclosed. The first organic light emitting diode comprises: an anode; a cathode; and an organic layer disposed between the anode and the cathode. The organic layer comprising the novel compound disclosed herein.

The device can be a consumer product, an electronic component module, an organic light-emitting device, and/or a lighting panel.

According to yet another embodiment, a formulation containing the novel compound disclosed herein is provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
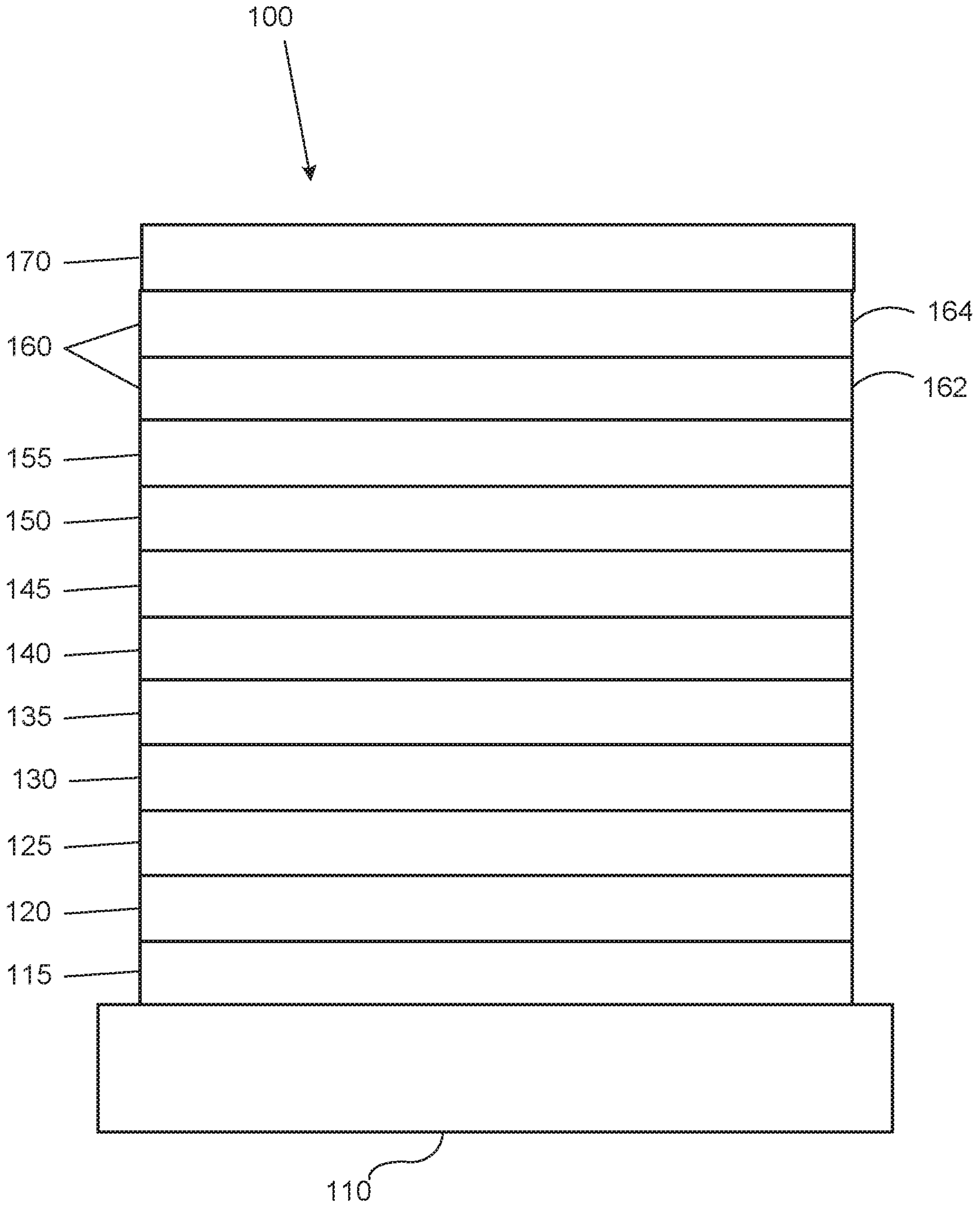
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170.

Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
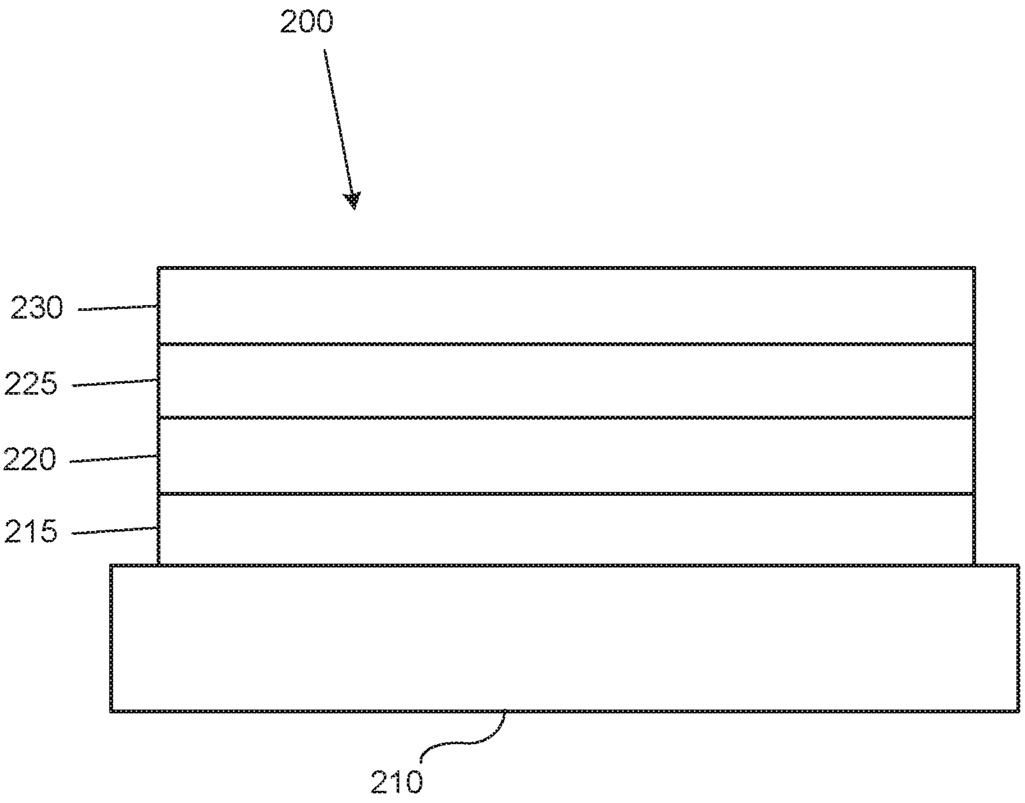
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic ring.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

According to an aspect of the present disclosure, a compound having a formula selected from the group consisting of:

Formula 1-1

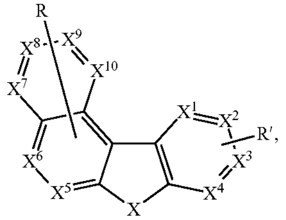

Formula 1-2

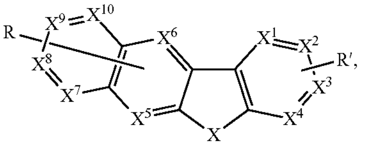

and

Formula 1-3

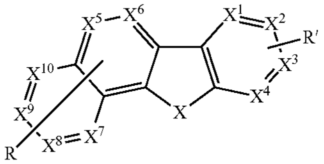

is disclosed wherein X is selected from the group consisting of O, S, and Se;

wherein $X^1$ to $X^{10}$ are each independently selected from the group consisting of carbon and nitrogen;

wherein at least one of $X^1$ to $X^6$ is nitrogen;

wherein R and R' each independently represent from mono to the possible maximum number of substitutions, or no substitution;

wherein R and R' are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein any adjacent substitutions on the same ring are optionally joined or fused into a ring; and wherein at least one of R and R' is not hydrogen or deuterium;

provided that when adjacent substitutions on $X^5$ and $X^6$ in Formula I-1 and I-3 fuse into a six-member ring, this ring and the ring having $X^7$ to $X^{10}$ can not be pyridine at the same time.

In some embodiments of the compound, X is O. In some embodiments, X is S.

In some embodiments of the compound, at least one of $X^5$ and $X^6$ is nitrogen.

In some embodiments of the compound, the adjacent substitutions on $X^5$ and $X^6$ are not joined or fused into a ring.

In some embodiments of the compound, $X^1$ to $X^4$ are all carbon.

In some embodiments of the compound, at least one of $X^1$ to $X^4$ is nitrogen, and at least one of $X^5$ and $X^6$ is nitrogen.

In some embodiments of the compound, at least one of R and R' comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

In some embodiments, the compound has at least five aromatic rings fused together.

In some embodiments, the compound has at least six aromatic rings fused together.

In some embodiments, the compound is selected from the group consisting of:

Formula 2-1

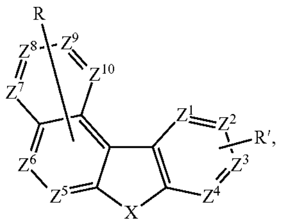

Formula 2-2

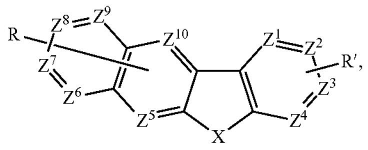

Formula 2-3

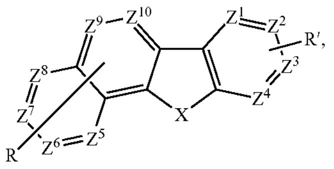

Formula 2-4

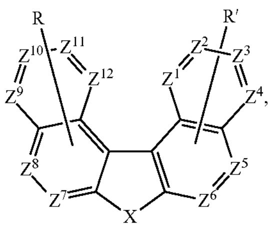

Formula 2-5

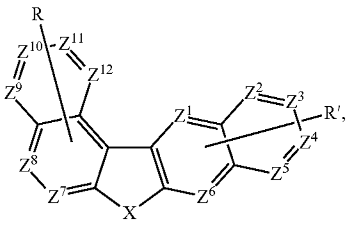

-continued

Formula 2-6

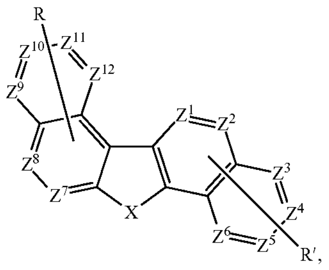

Formula 2-7

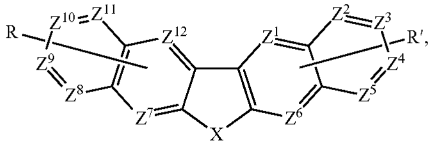

Formula 2-8

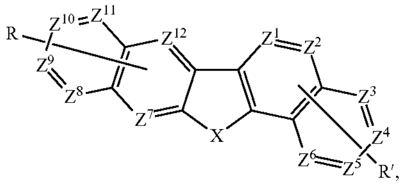

Formula 2-9

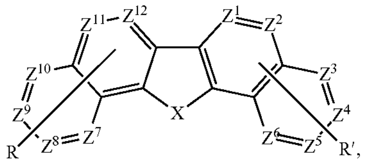

Formula 2-10

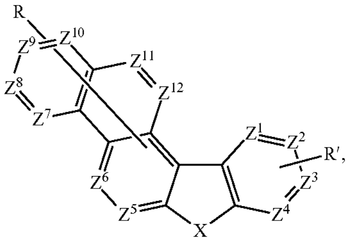

Formula 2-11

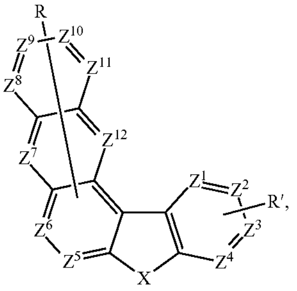

Formula 2-12

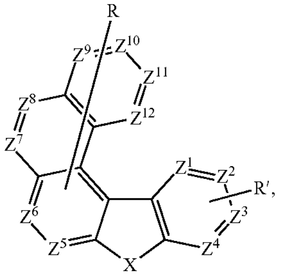

-continued
Formula 2-13
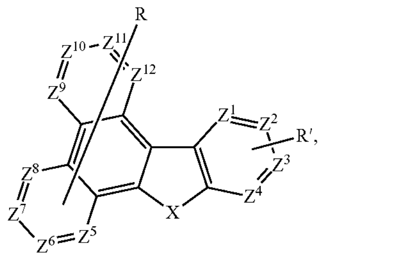
Formula 2-14
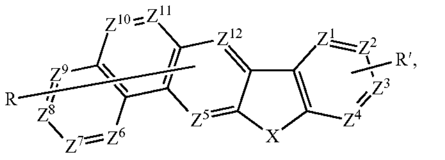
Formula 2-15
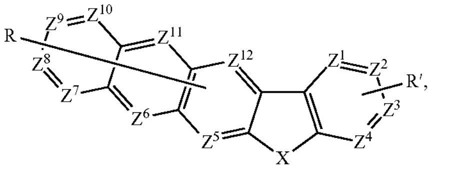
Formula 2-16
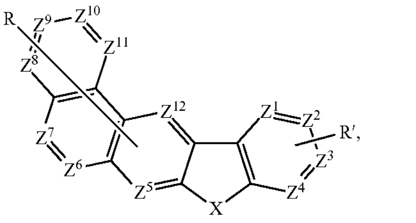
Formula 2-17
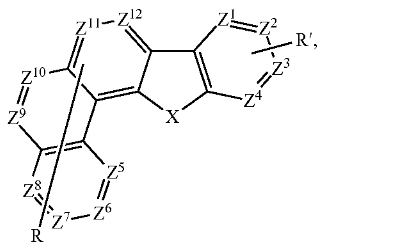
Formula 2-18
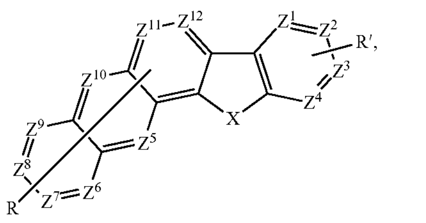
Formula 2-19
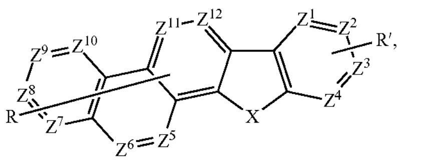
-continued
Formula 2-20
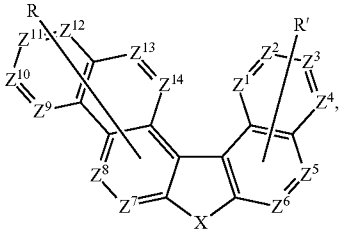
Formula 2-21
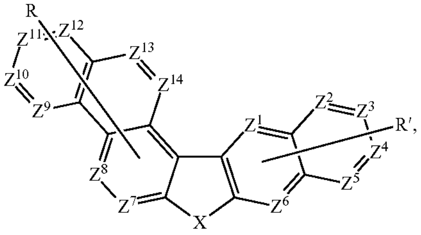
Formula 2-22
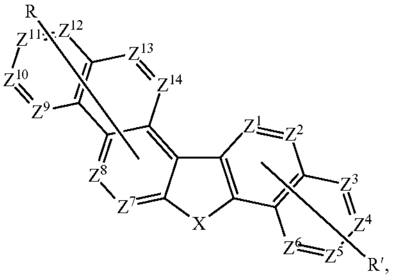
Formula 2-23
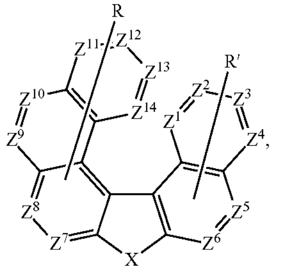
Formula 2-24
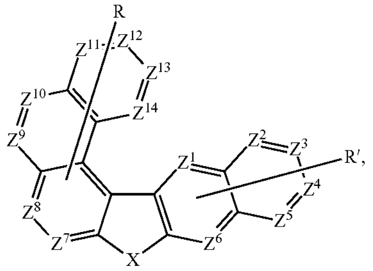
Formula 2-25
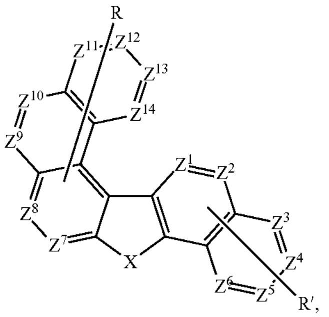

-continued
Formula 2-26
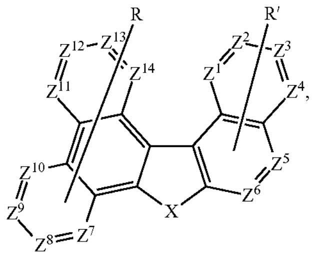
Formula 2-27
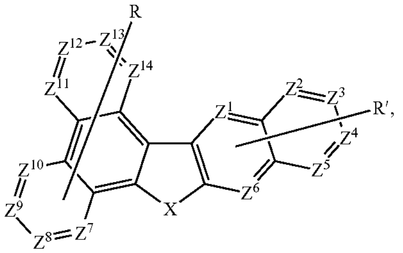
Formula 2-28
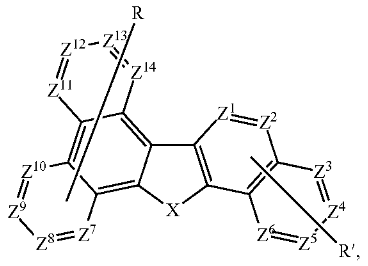
Formula 2-29
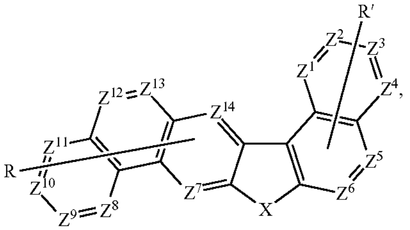
Formula 2-30
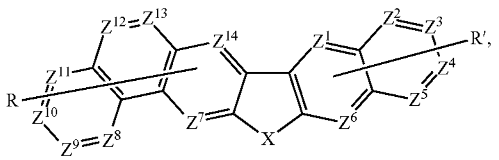
Formula 2-31
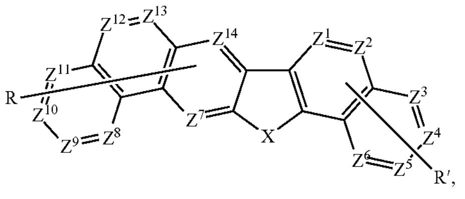
-continued
Formula 2-32
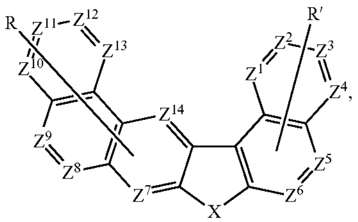
Formula 2-33
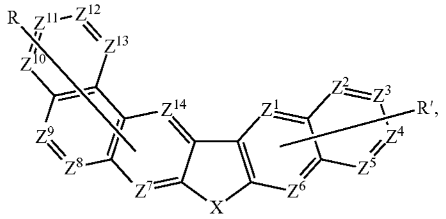
Formula 2-34
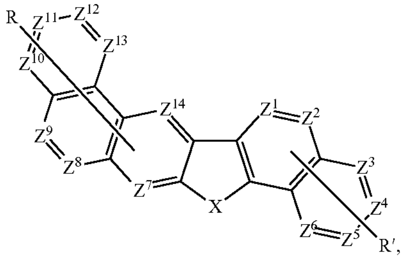
Formula 2-35
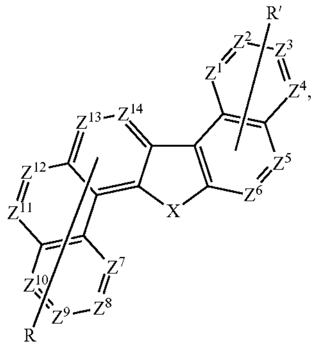
Formula 2-36
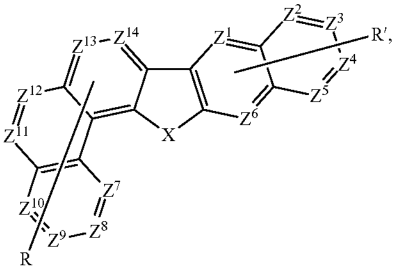
Formula 2-37
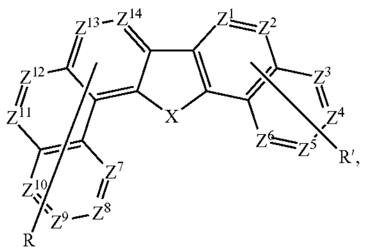

-continued
Formula 2-38
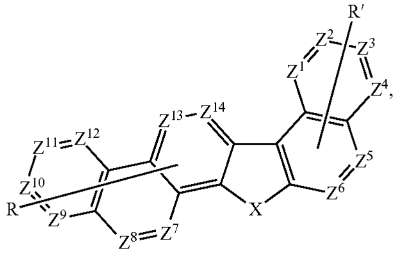
Formula 2-39
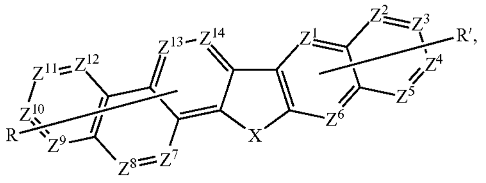
Formula 2-40
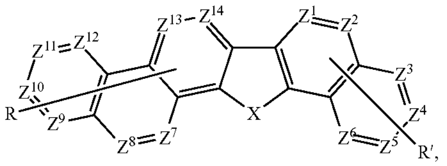
Formula 2-41
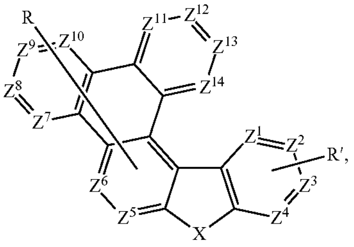
Formula 2-42
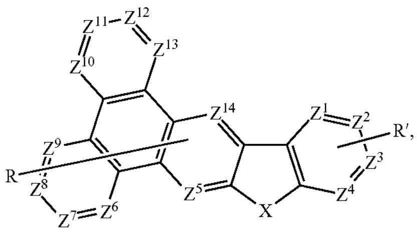
Formula 2-43
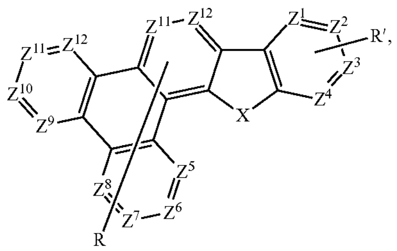
-continued
Formula 2-44
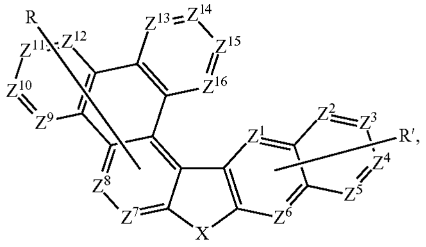
Formula 2-45
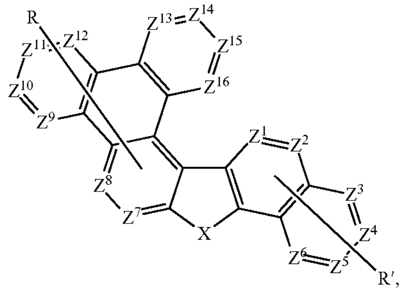
Formula 2-46
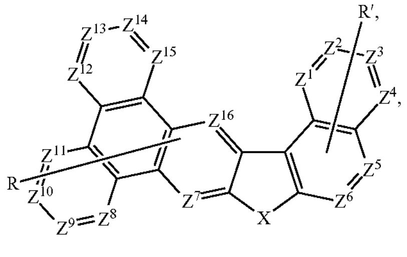
Formula 2-47
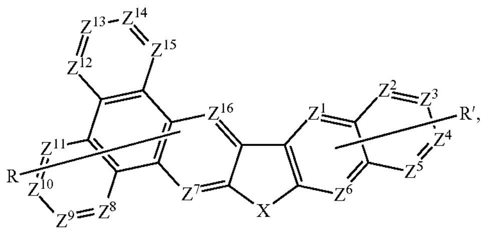
Formula 2-48
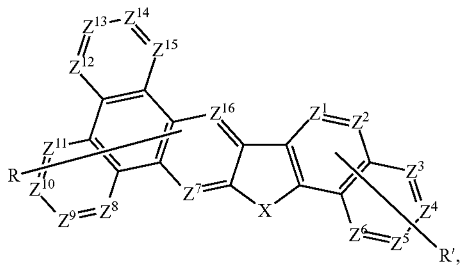

-continued
Formula 2-49
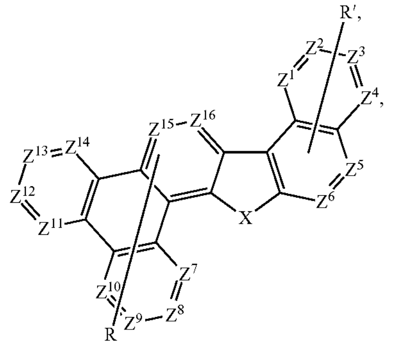
Formula 2-50
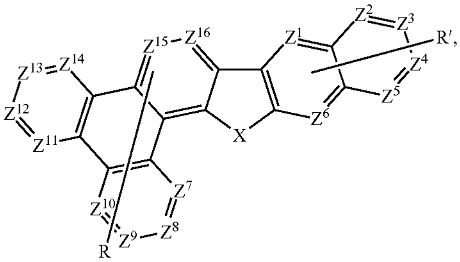
and
Formula 2-51
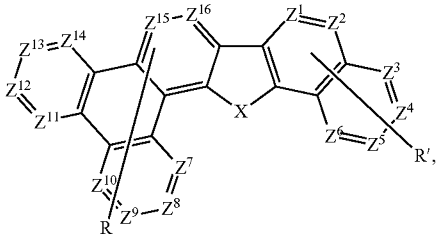
wherein $Z^1$ to $Z^{16}$ are each independently selected from the group consisting of carbon and nitrogen.
In some embodiments, the compound comprises a group selected from the group consisting of:
A[1]
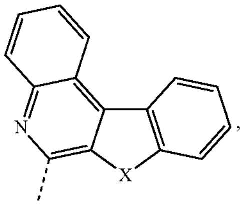
A[2]
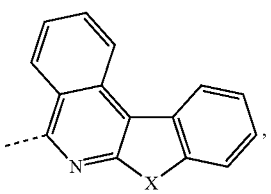
-continued
A[3]
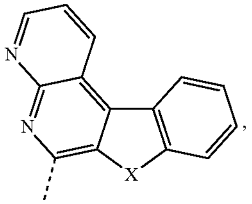
A[4]
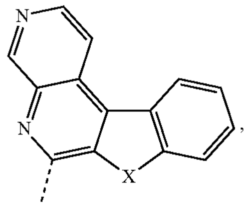
A[5]
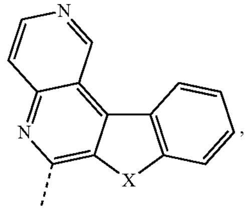
A[6]
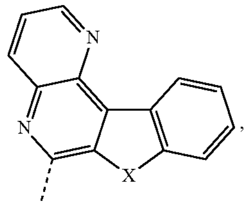
A[7]
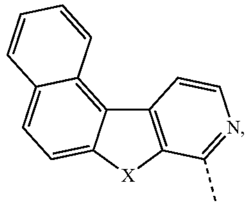
A[8]
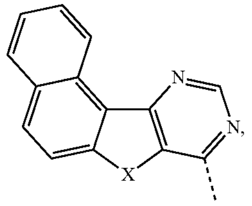
A[9]
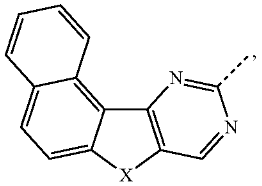

-continued
A10
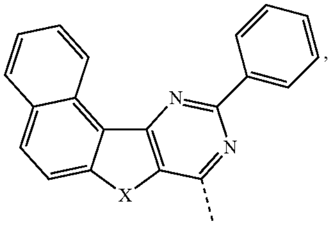
A11
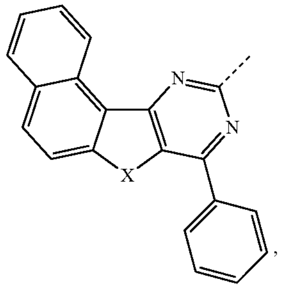
A12
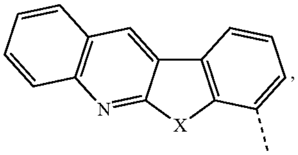
A13
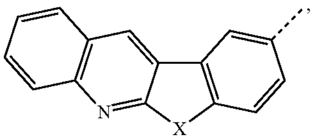
A14
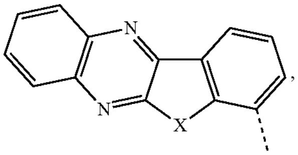
A15
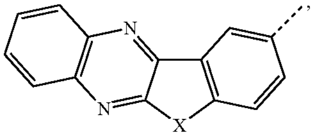
A16
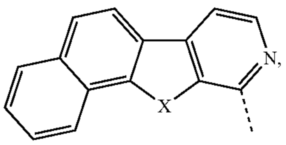
A17
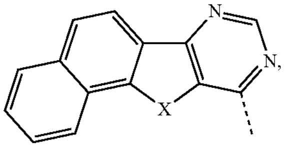
-continued
A18
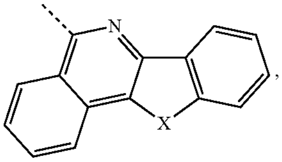
A19
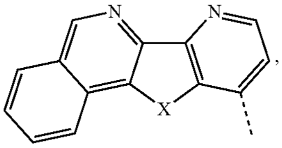
A20
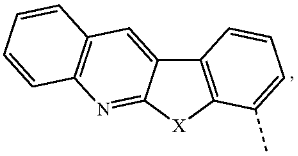
A21
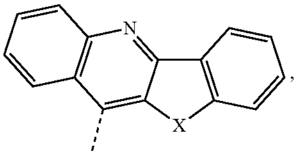
A22
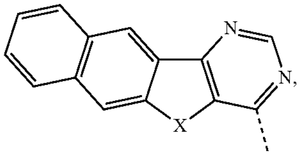
A23
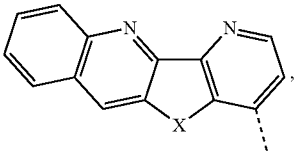
A24
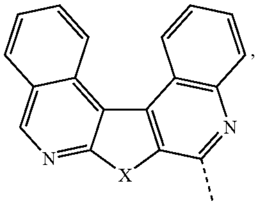
A25
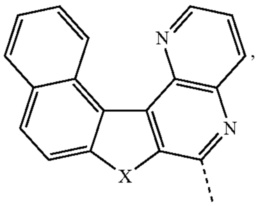

-continued
A26
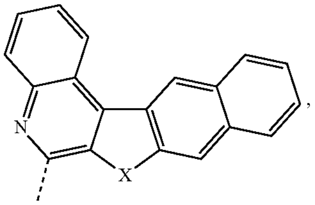,
A27
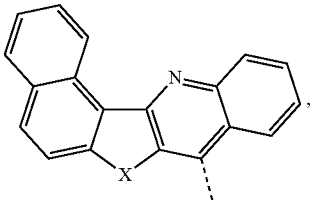,
A28
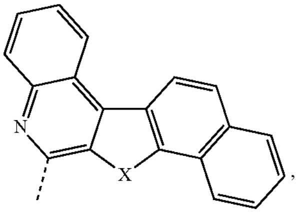,
A29
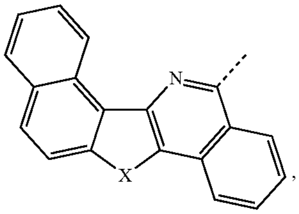,
A30
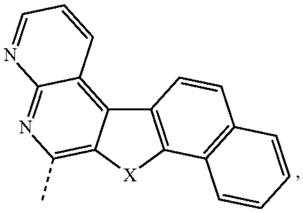,
A31
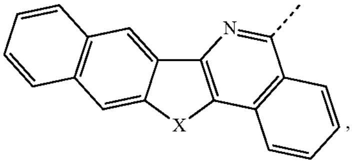,
A32
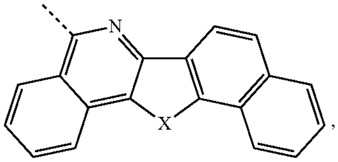,
-continued
A33
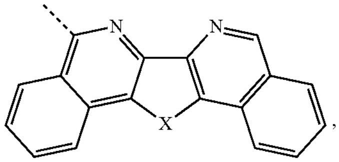,
A34
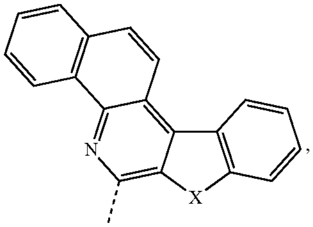,
A35
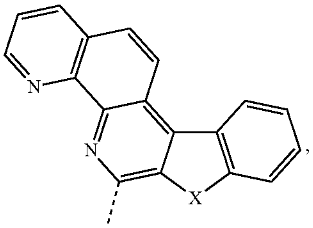,
A36
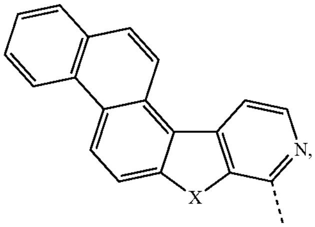
A37
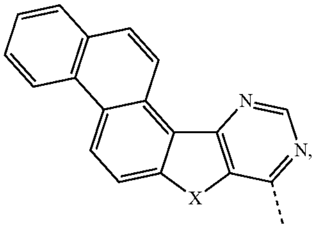
A38
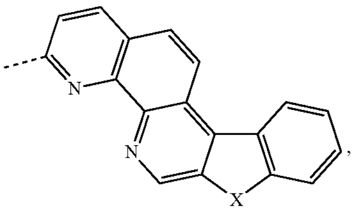,
A39
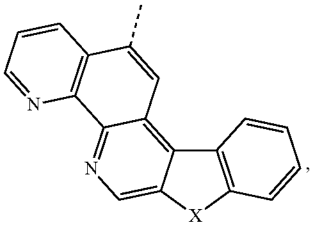, -continued
A[40]
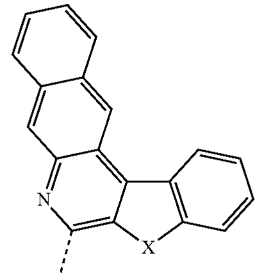
,
A[41]
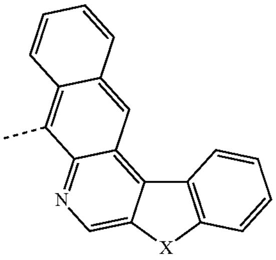
,
A[42]
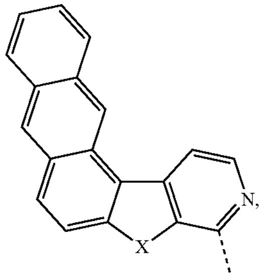
A[43]
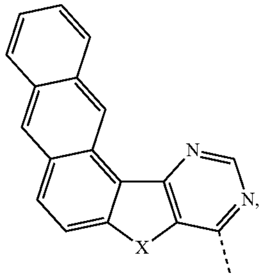
A[44]
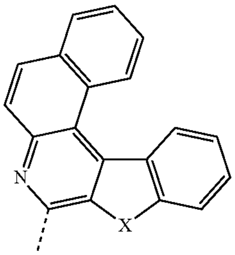
,
-continued
A[45]
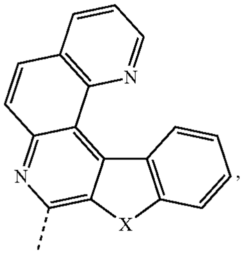
,
A[46]
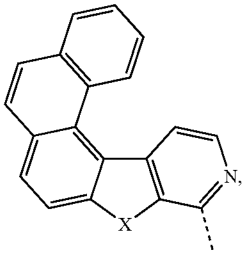
A[47]
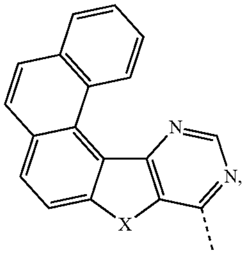
A[48]
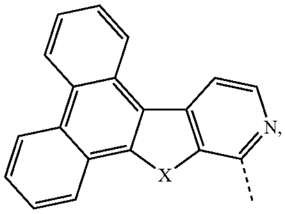
A[49]
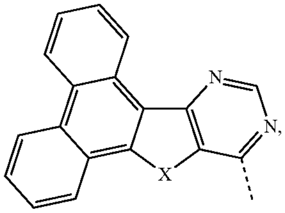
A[50]
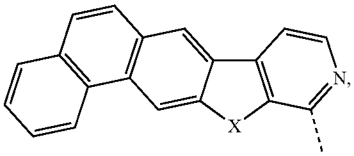
A[51]
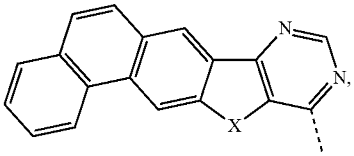

-continued
A[57]
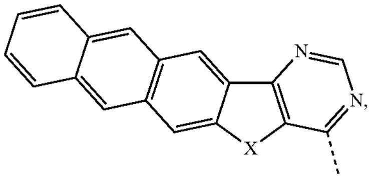
A[58]
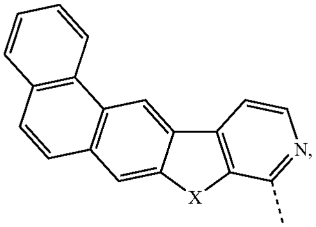
A[59]
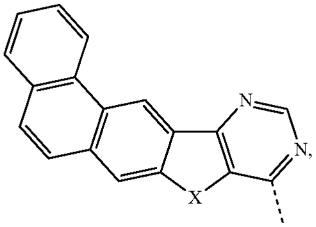
A[60]
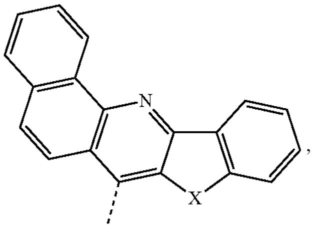
A[61]
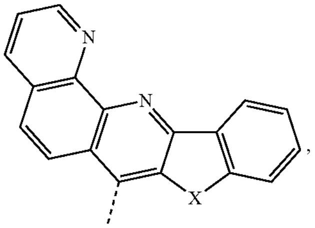
A[62]
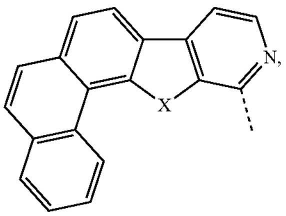
A[63]
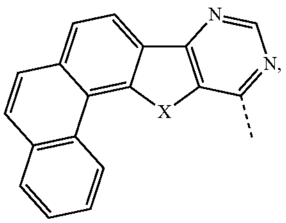
-continued
A[64]
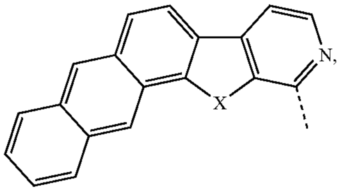
A[65]
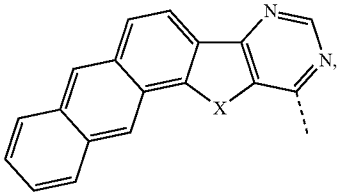
A[66]
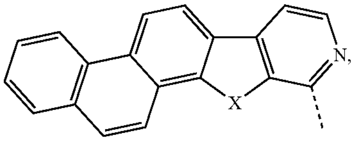
A[67]
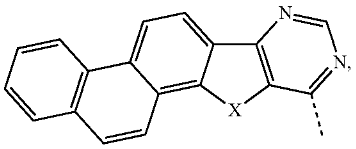
A[68]
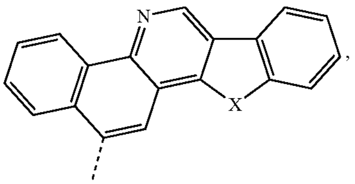
A[69]
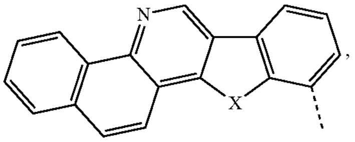
A[70]
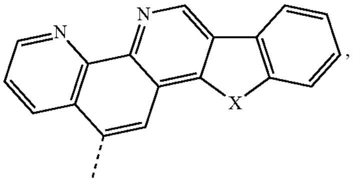
A[71]
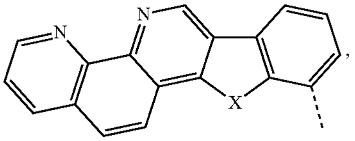
A[72]
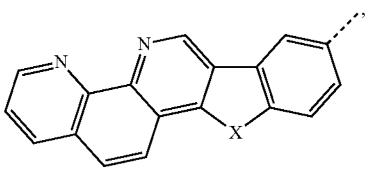

-continued
A[73]
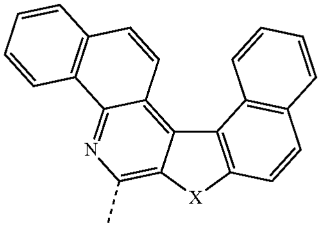,
A[74]
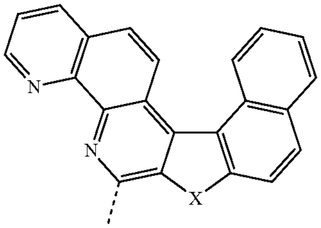,
A[75]
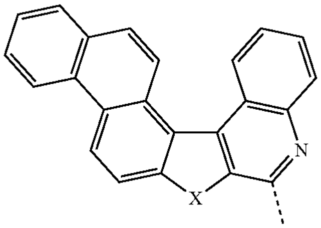,
A[76]
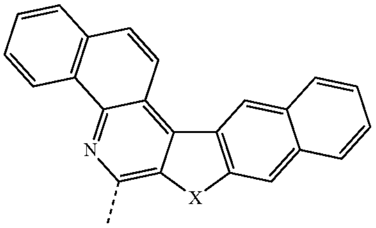,
A[77]
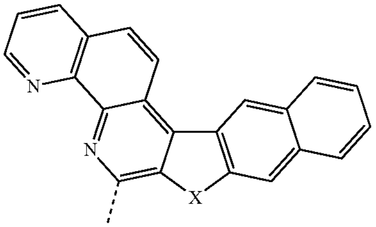,
A[78]
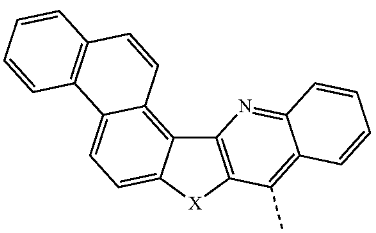,
-continued
A[79]
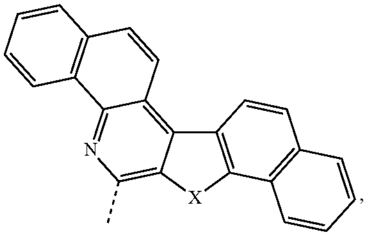,
A[80]
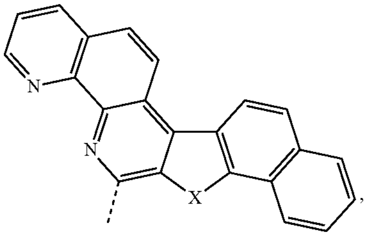,
A[81]
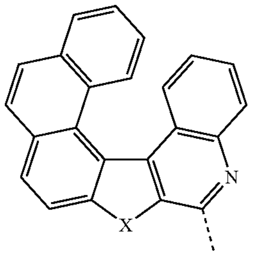,
A[82]
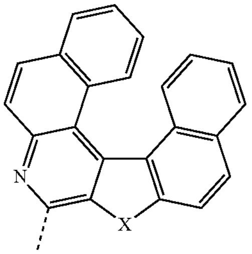,
A[83]
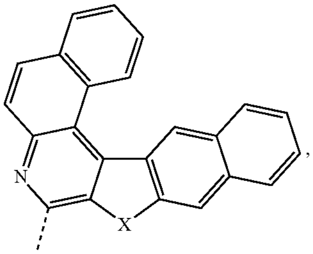,
A[84]
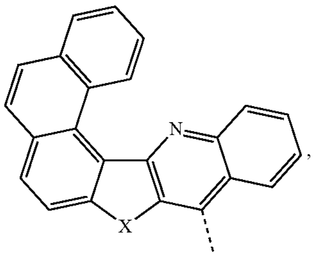, -continued
$A^{85}$
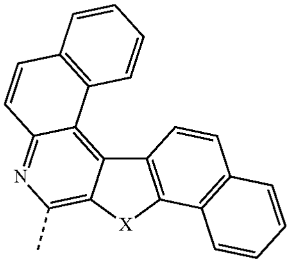
,
$A^{86}$
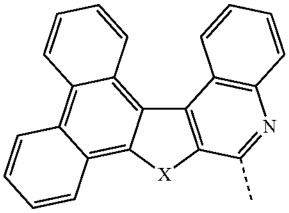
,
$A^{87}$
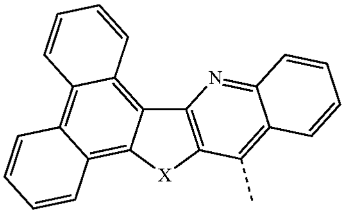
,
$A^{88}$
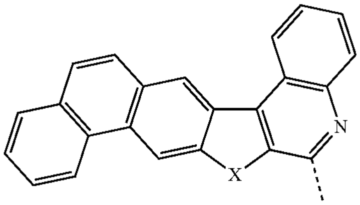
,
$A^{89}$
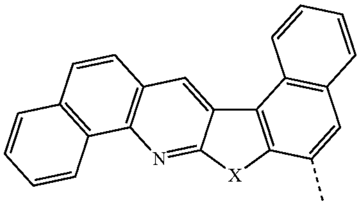
,
$A^{90}$
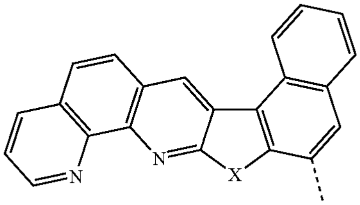
,
$A^{91}$
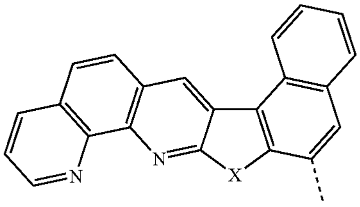
,
-continued
$A^{92}$
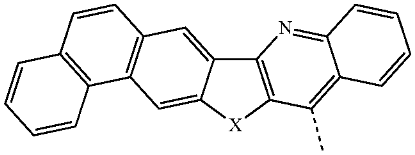
,
$A^{93}$
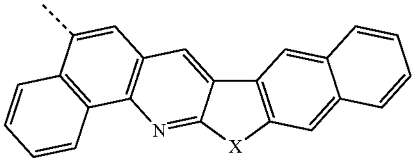
,
$A^{94}$
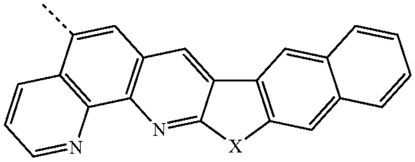
,
$A^{95}$
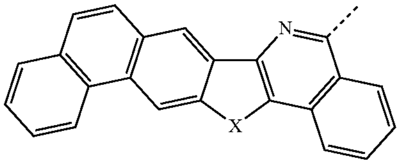
,
$A^{96}$
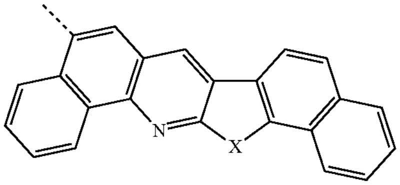
,
$A^{97}$
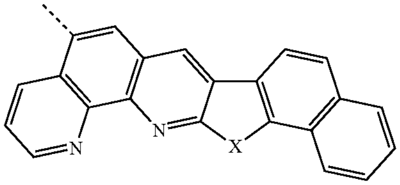
,
$A^{98}$
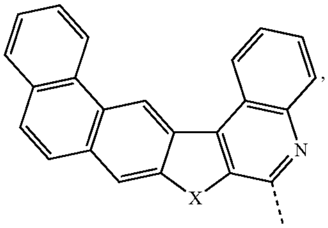
,
$A^{99}$
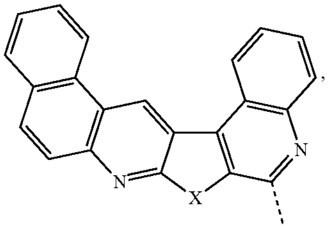
, -continued
A[100]
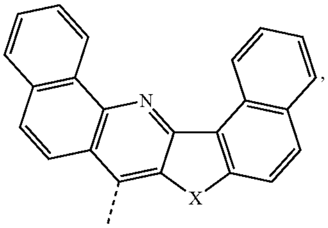
,
A[101]
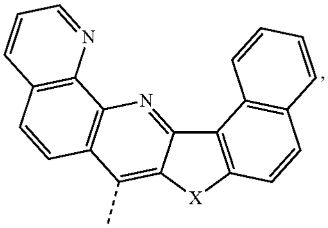
,
A[102]
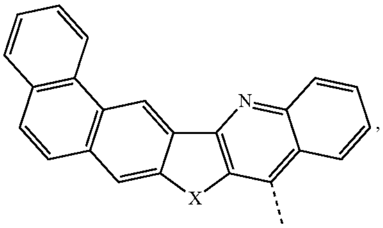
,
A[103]
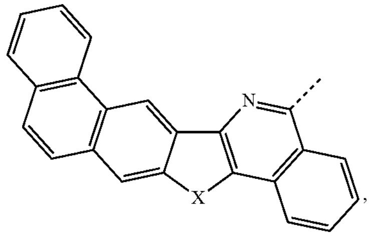
,
A[104]
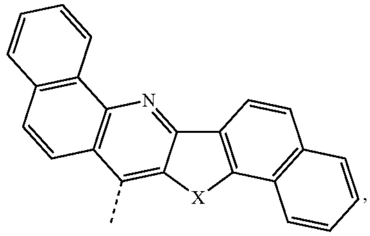
,
A[105]
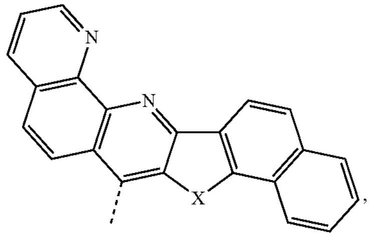
,
-continued
A[106]
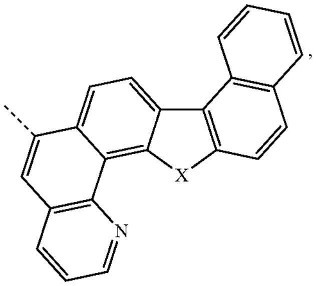
,
A[107]
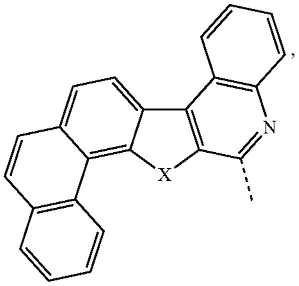
,
A[108]
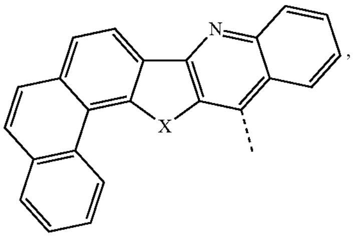
,
A[109]
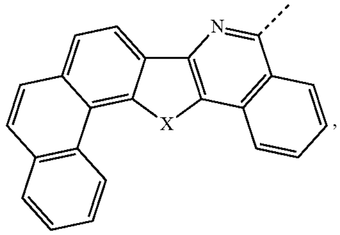
,
A[110]
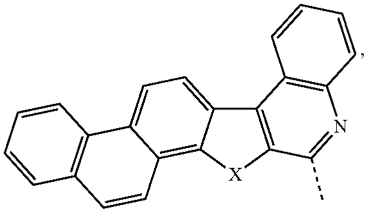
,
A[111]
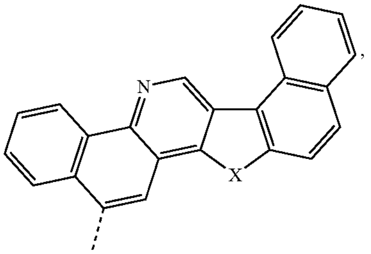
, -continued
A[112]
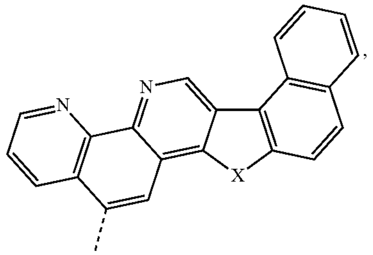,
A[113]
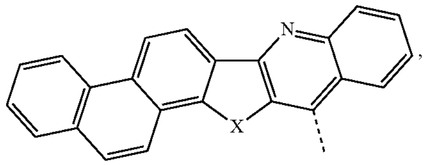,
A[114]
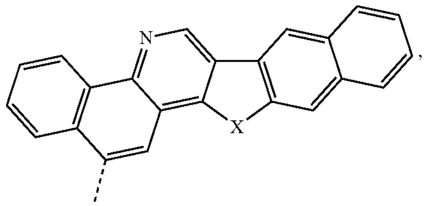,
A[115]
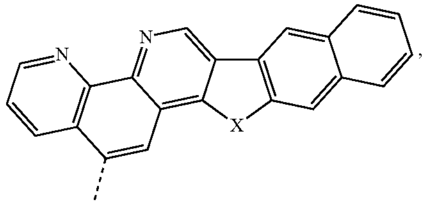,
A[116]
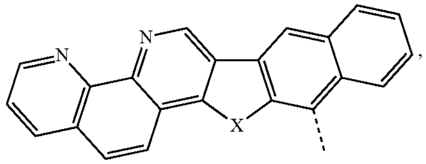,
A[117]
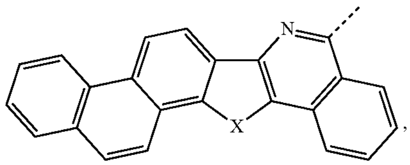,
A[118]
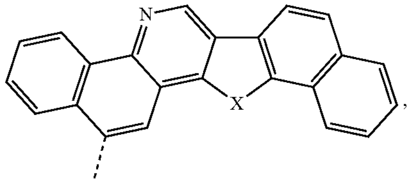,
A[119]
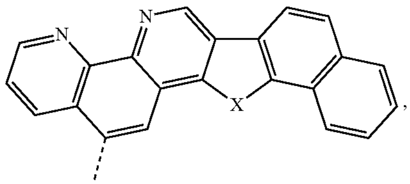,
-continued
A[120]
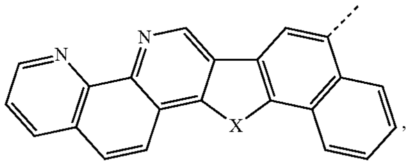,
A[121]
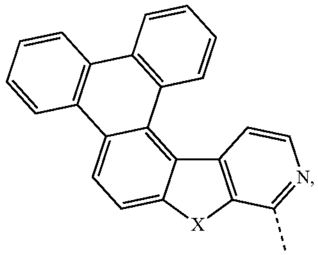,
A[122]
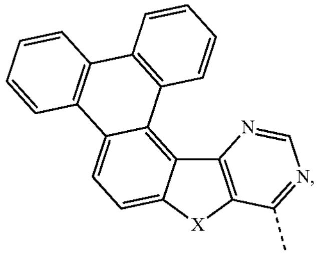,
A[123]
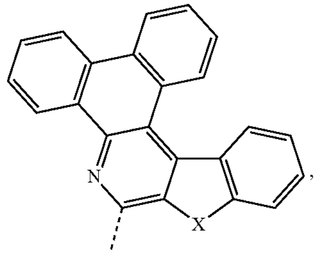,
A[124]
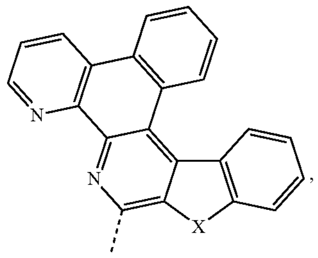,
A[125]
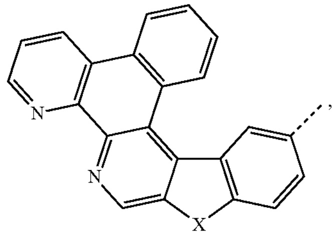, -continued
A126
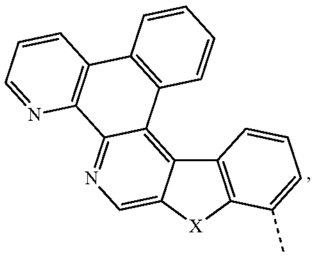
A127
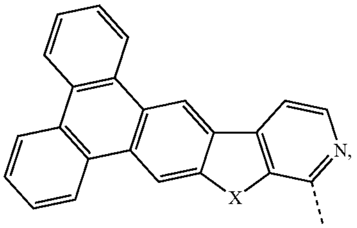
A128
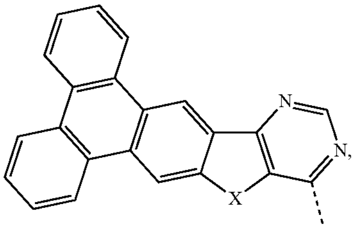
A129
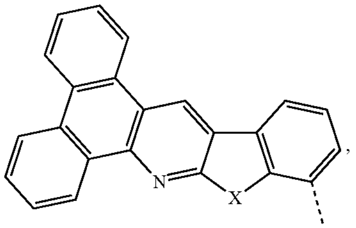
A130
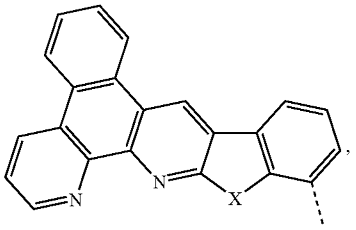
A131
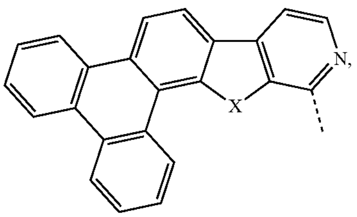
-continued
A132
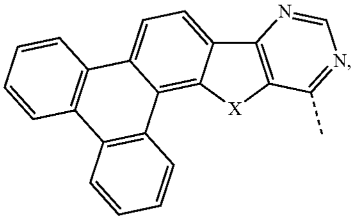
A133
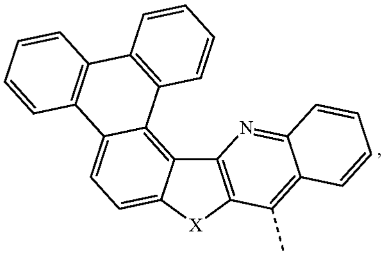
A134
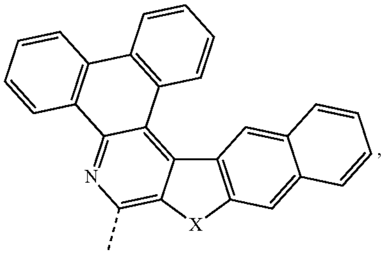
A135
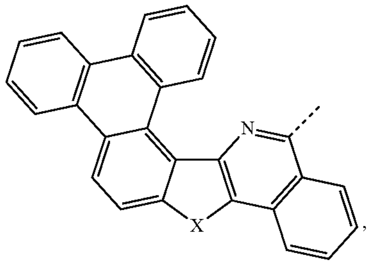
A136
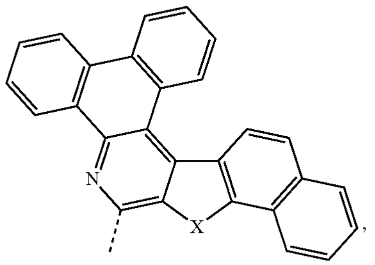
A137
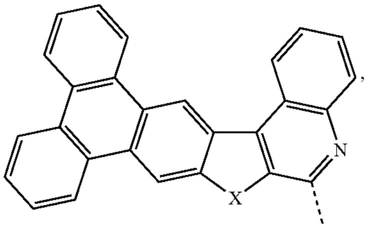

-continued
A[138]
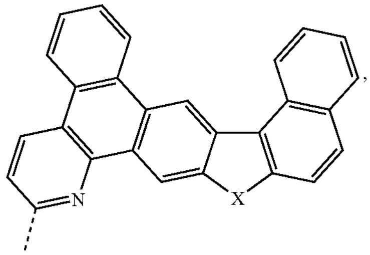,
A[139]
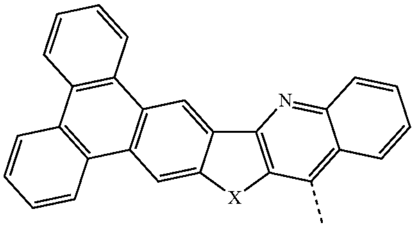,
A[140]
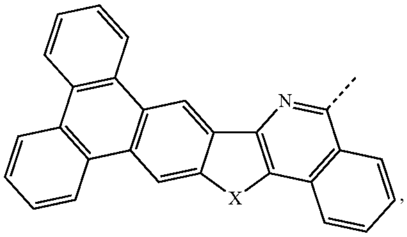,
A[141]
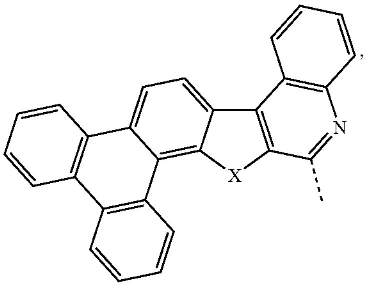,
A[142]
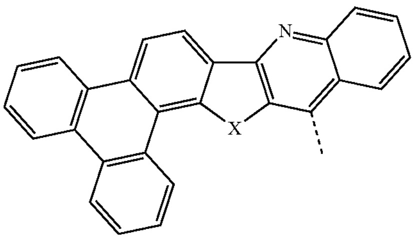,
A[143]
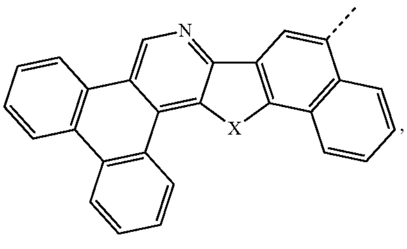, and
-continued
A[144]
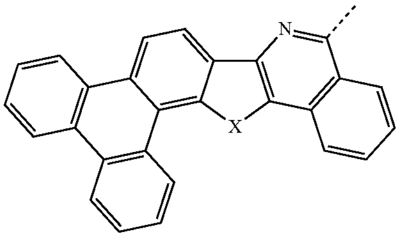,
wherein the dotted lines represent a possible substitution.
In some embodiments of the compounds $A^1$ through $A^{144}$, the compound is substituted by a group selected from the group consisting of $D^1$ through $D^{244}$ shown below:
$D^1$
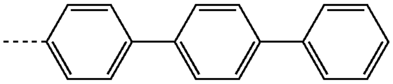,
$D^2$
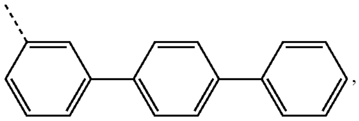,
$D^3$
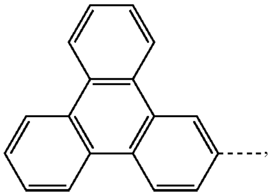,
$D^4$
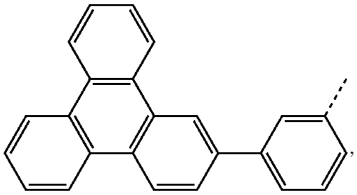,
$D^5$
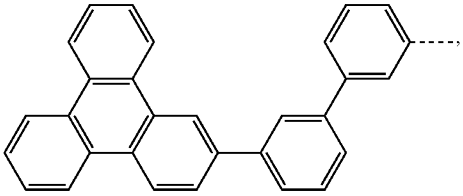,
$D^6$
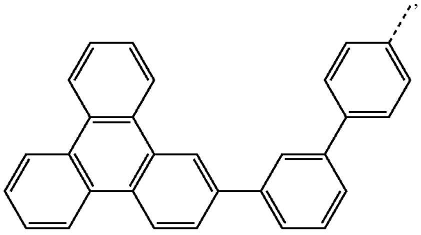

-continued
D7
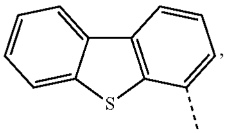
D8
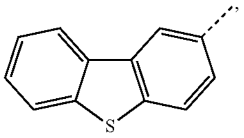
D9
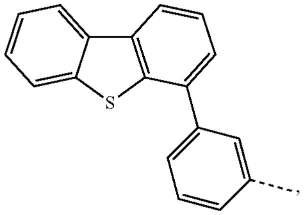
D10
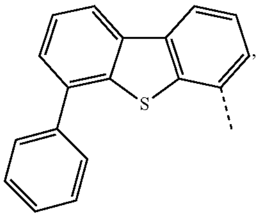
D11
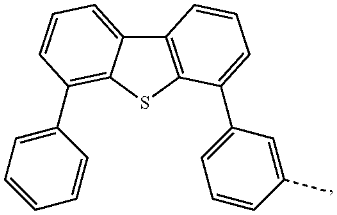
D12
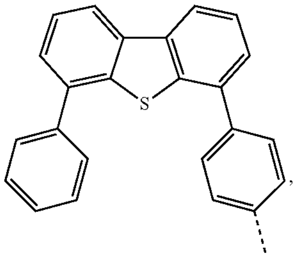
D13
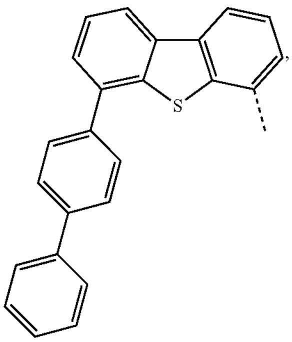
-continued
D14
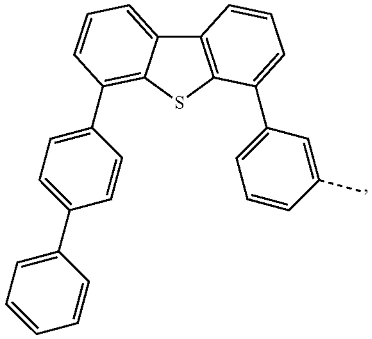
D15
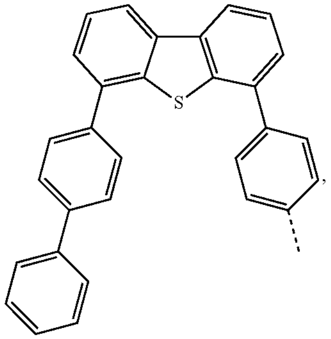
D16
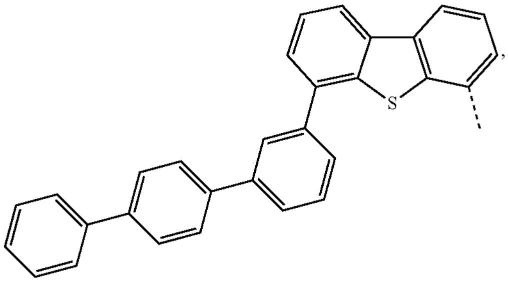
D17
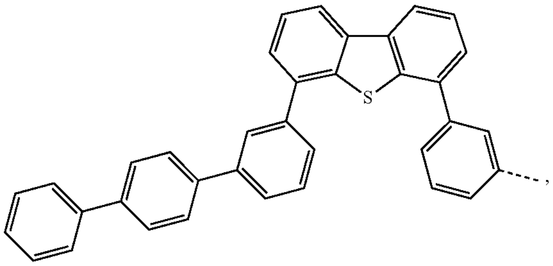
D18
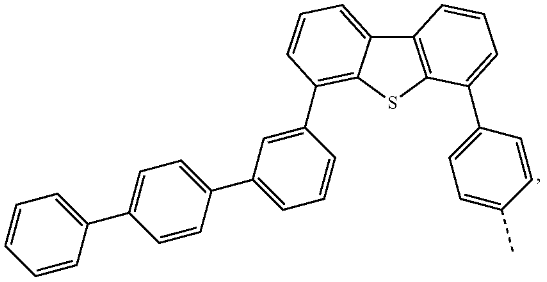

-continued
D[19]
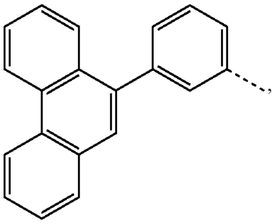
D[20]
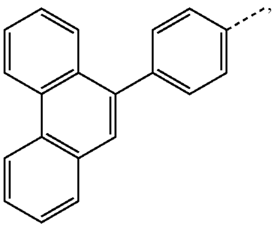
D[21]
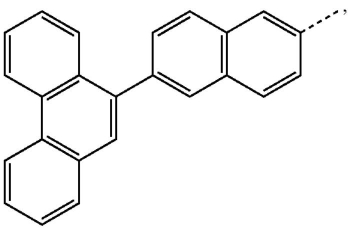
D[22]
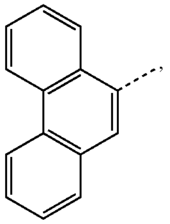
D[23]
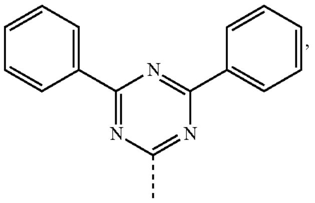
D[24]
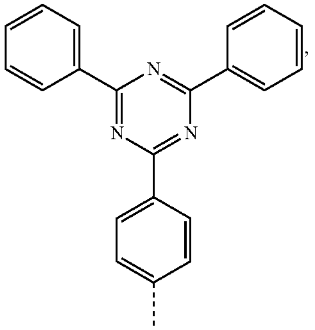
-continued
D[25]
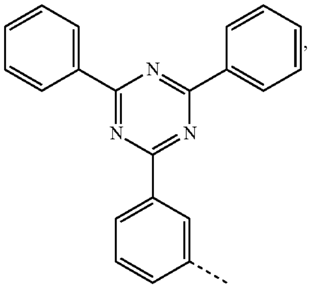
D[26]
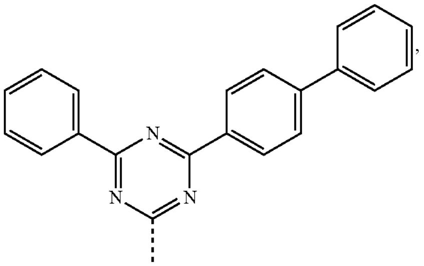
D[27]
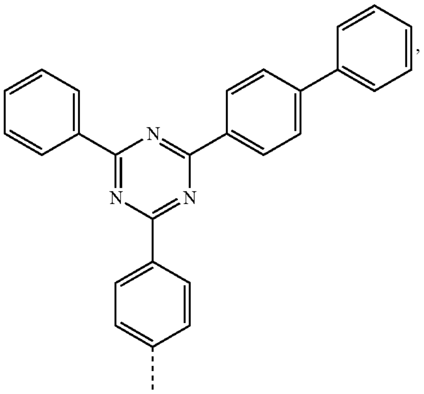
D[28]
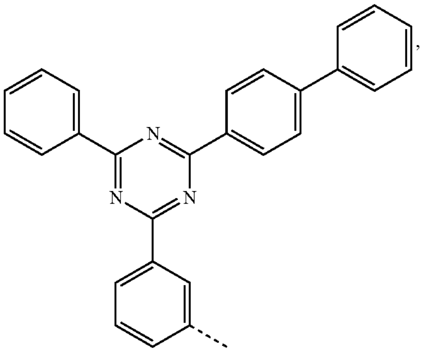
D[29]
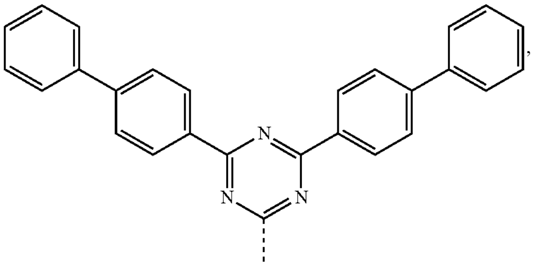

-continued
D[30]
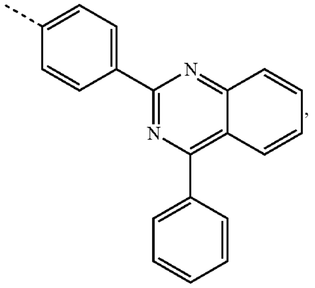
D[31]
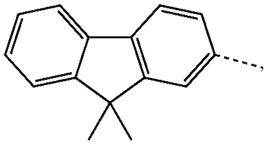
D[32]
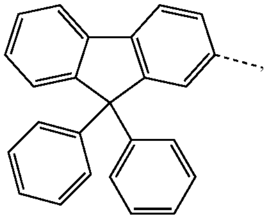
D[33]
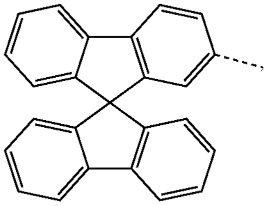
D[34]
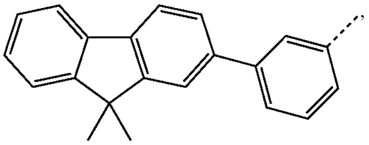
D[35]
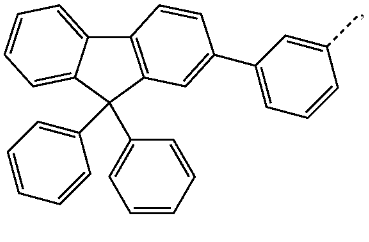
D[36]
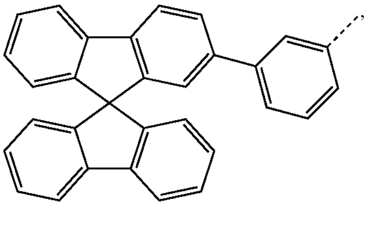
-continued
D[37]
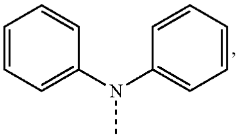
D[38]
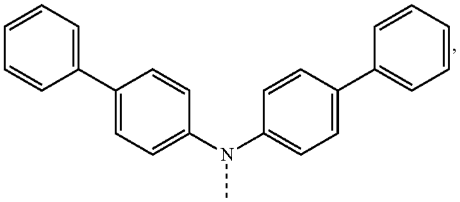
D[39]
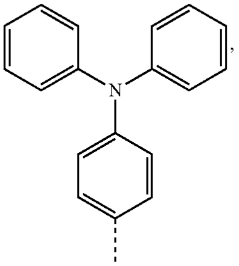
D[40]
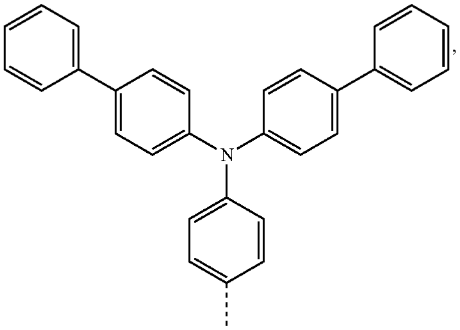
D[41]
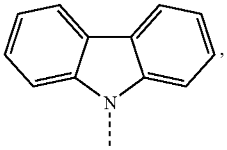
D[42]
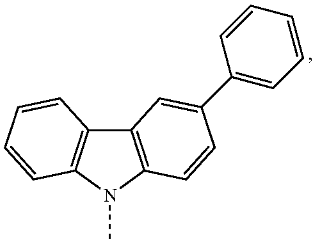

-continued
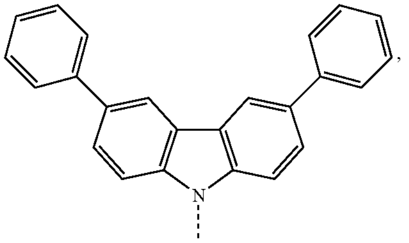
D43
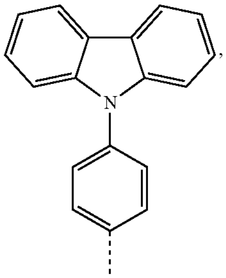
D44
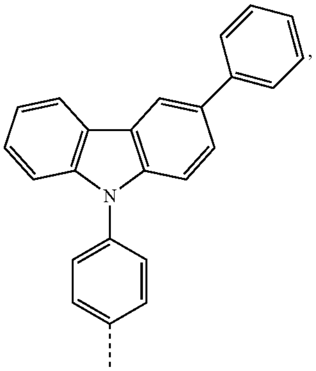
D45
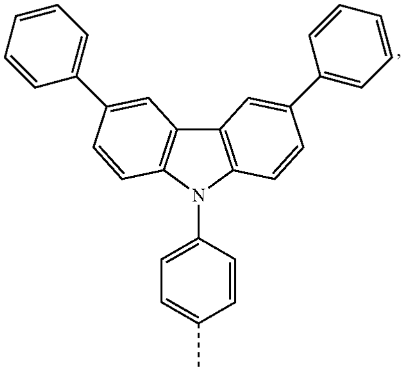
D46
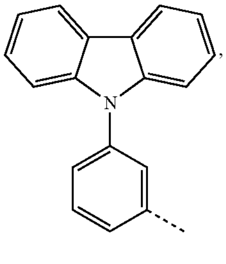
D47
-continued
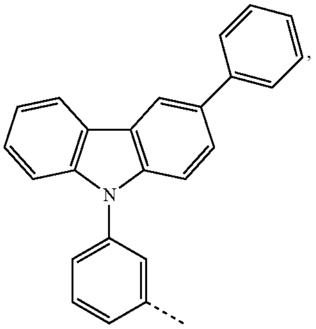
D48
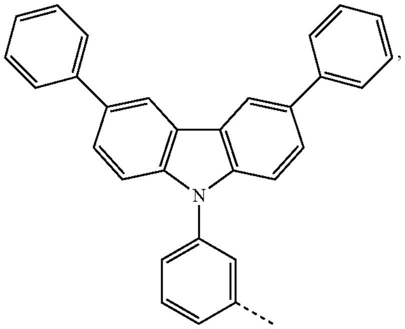
D49
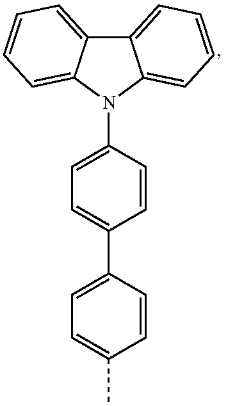
D50
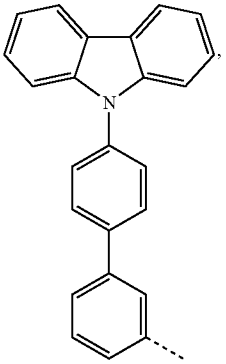
D51

D[52]
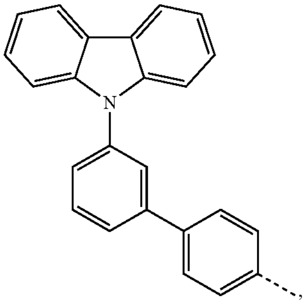
D[53]
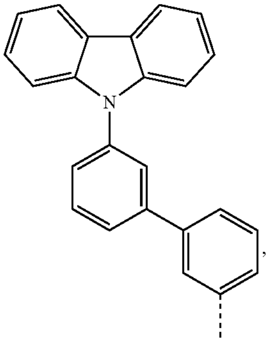
D[54]
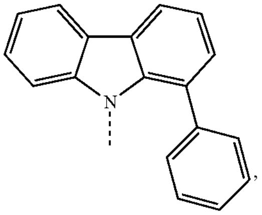
D[55]
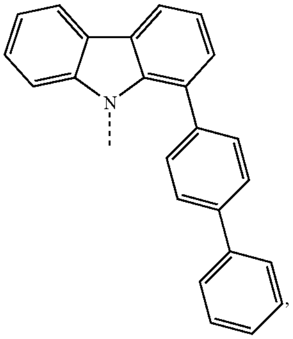
D[56]
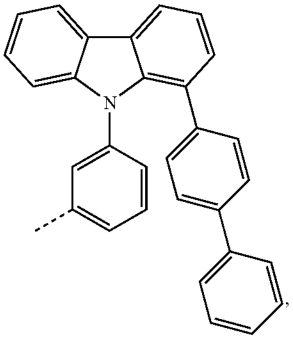
D[57]
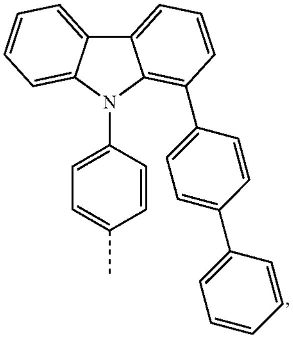
D58
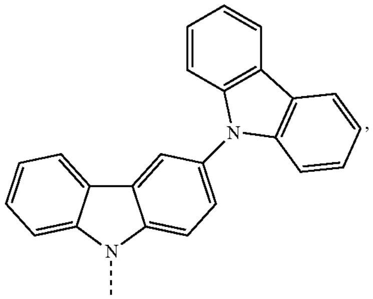
D59
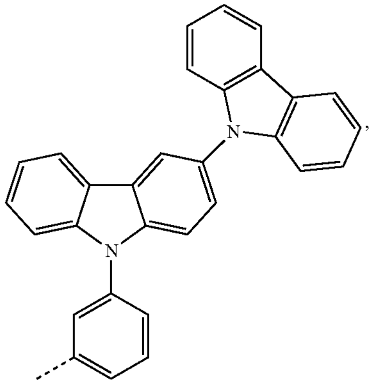
D60
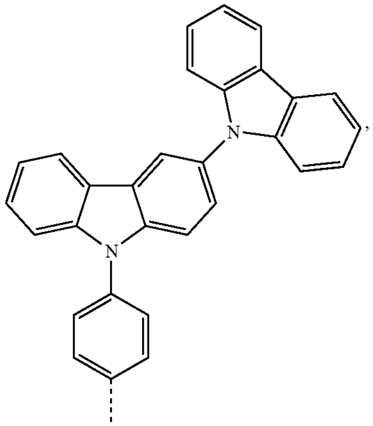

-continued
D61
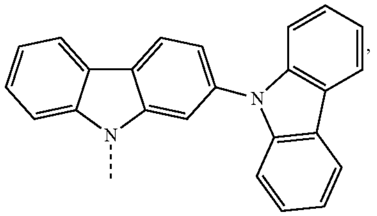
D62
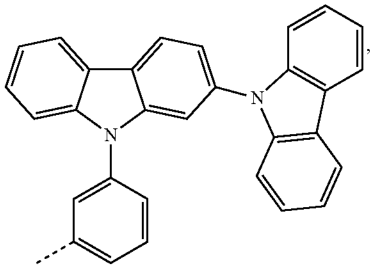
D63
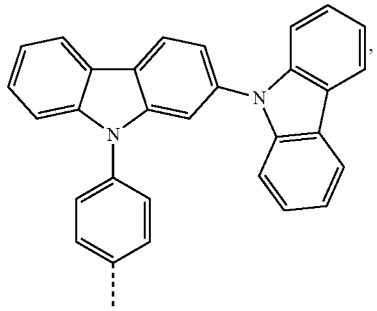
D64
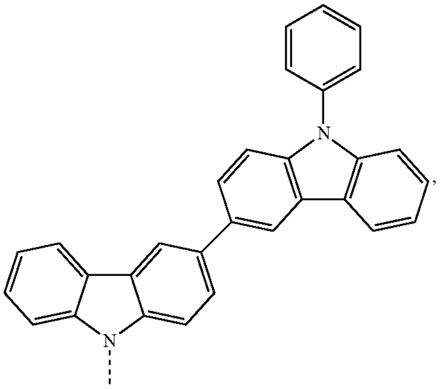
-continued
D65
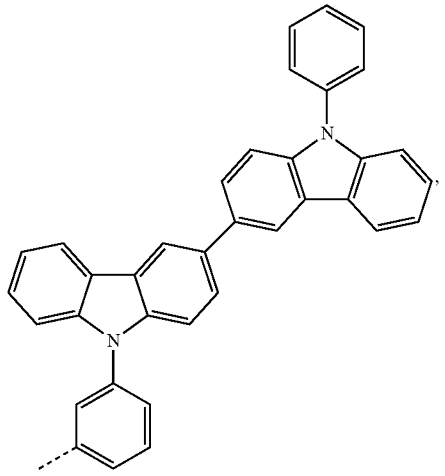
D66
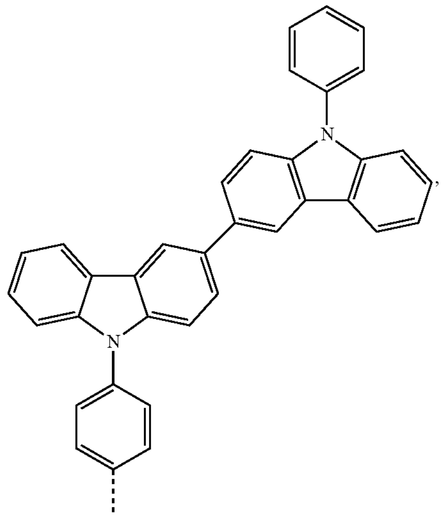
D67
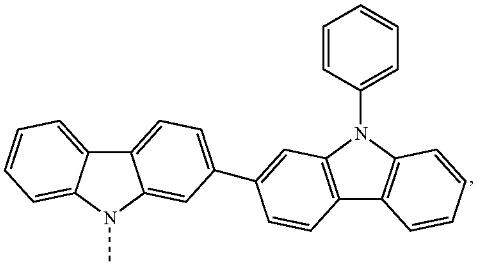
D68
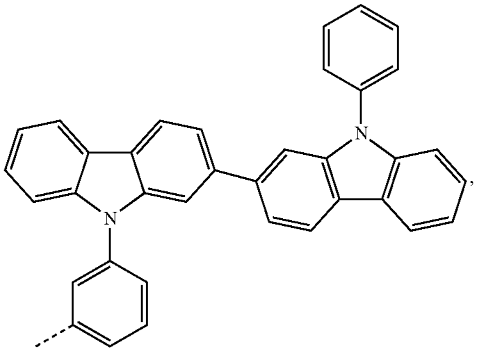

-continued
D69
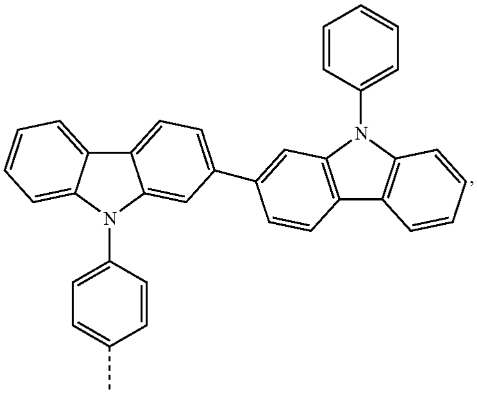
,
D70
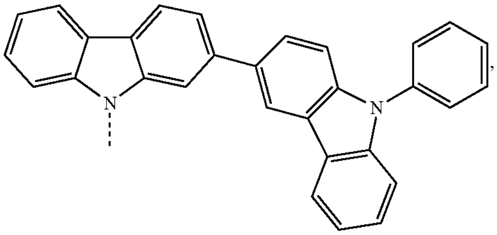
,
D71
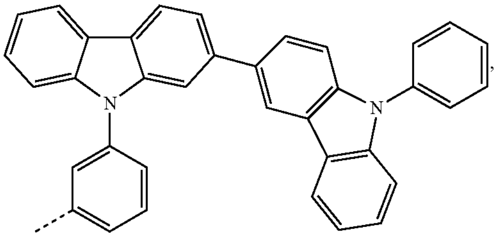
,
D72
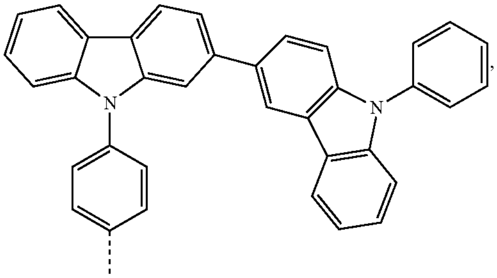
,
D73
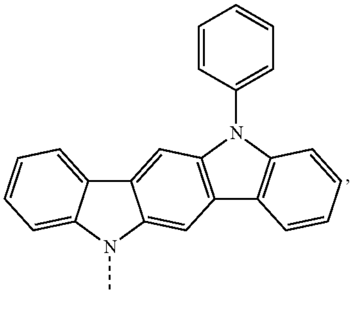
,
-continued
D74
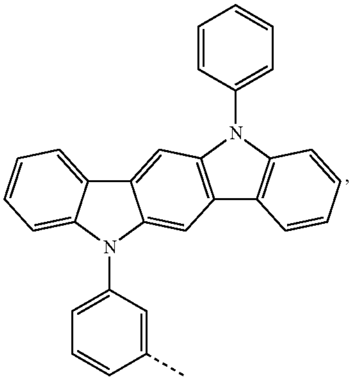
,
D75
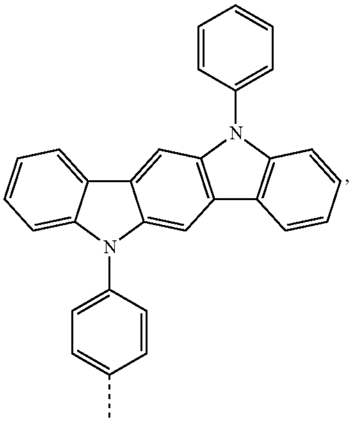
,
D76
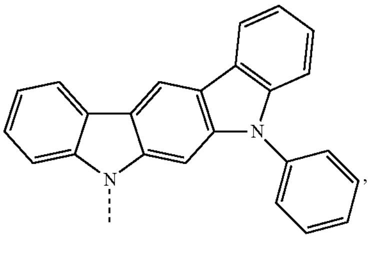
,
D77
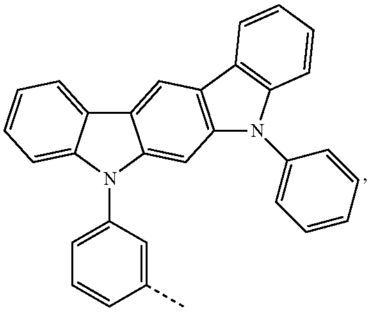
, D78
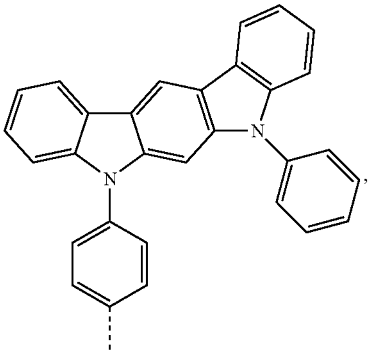,
D79
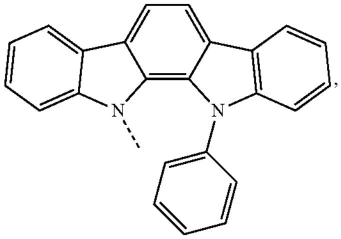,
D80
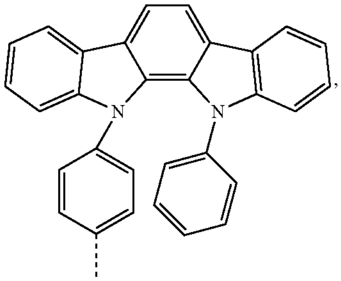,
D81
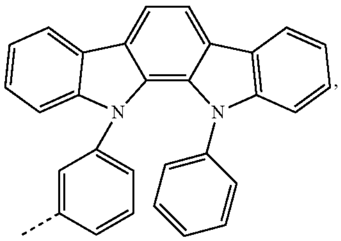,
D82
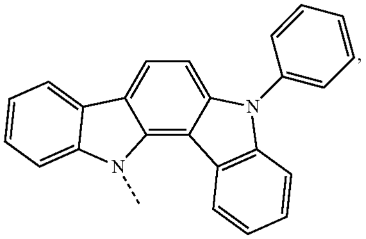,
D83
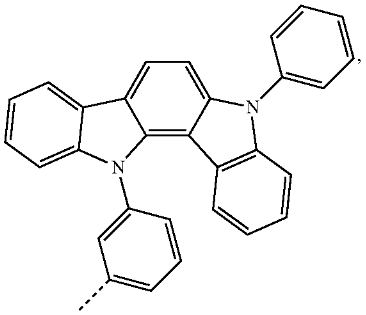,
D84
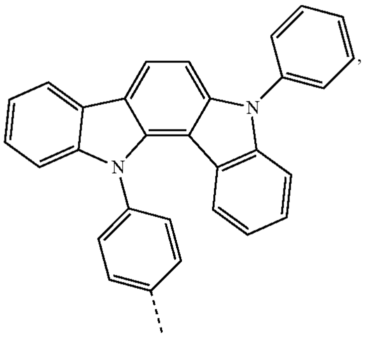,
D85
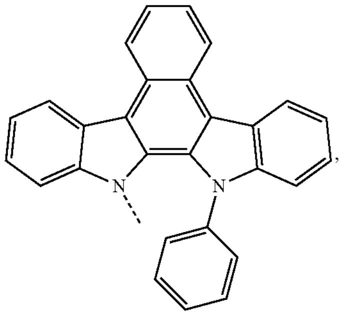,
D86
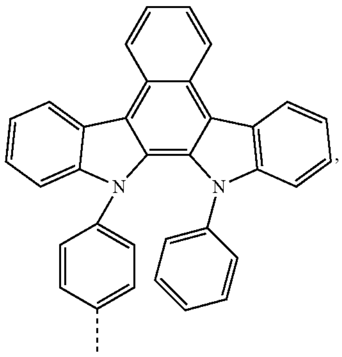, -continued
D87
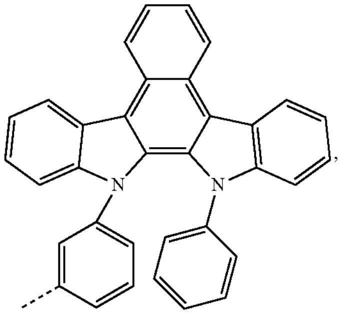
,
D88
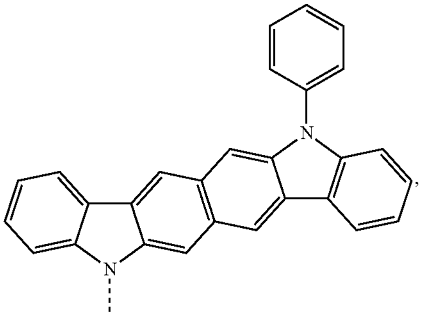
,
D89
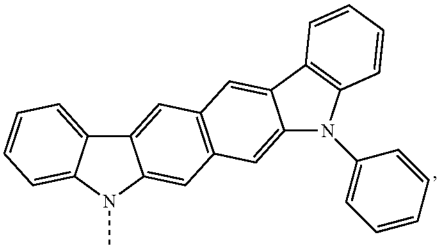
,
D90
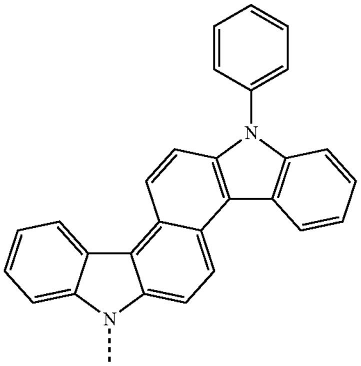
D91
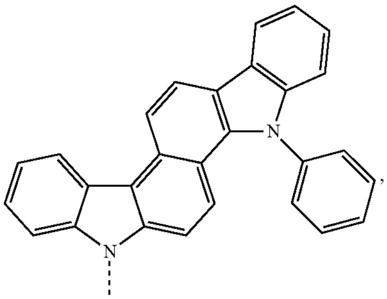
,
-continued
D92
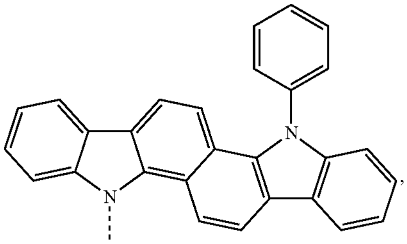
,
D93
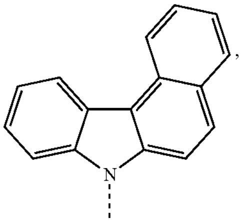
,
D94
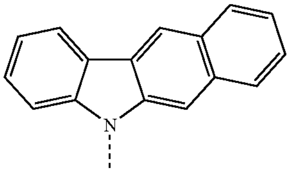
,
D95
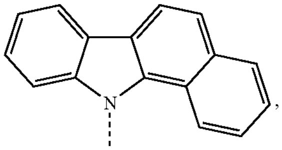
,
D96
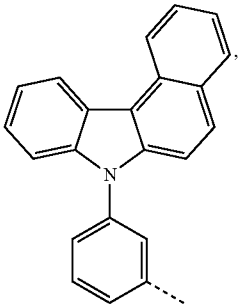
,
D97
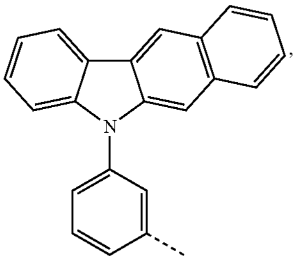
, -continued
$D^{98}$
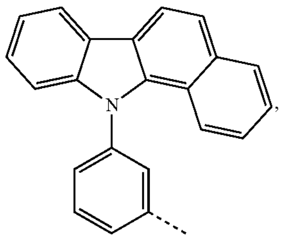
$D^{99}$
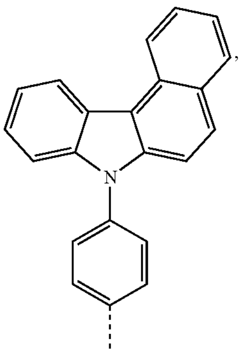
$D^{100}$
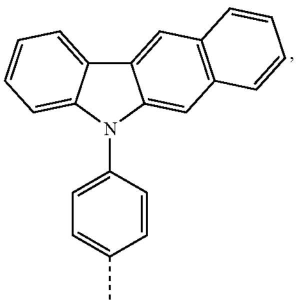
$D^{101}$
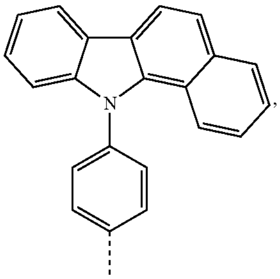
$D^{102}$
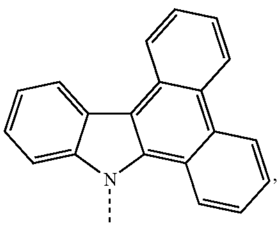
-continued
$D^{103}$
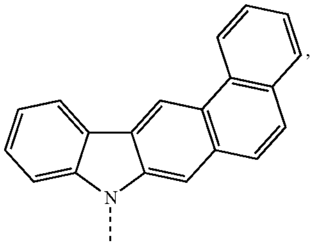
$D^{104}$
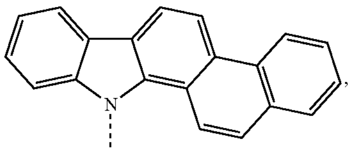
$D^{105}$
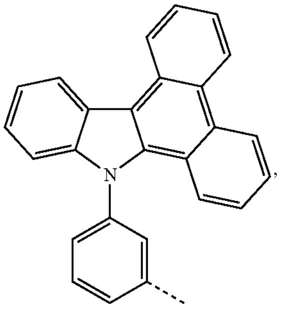
$D^{160}$
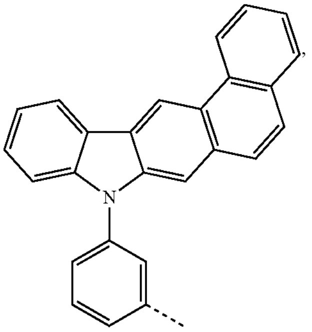
$D^{107}$
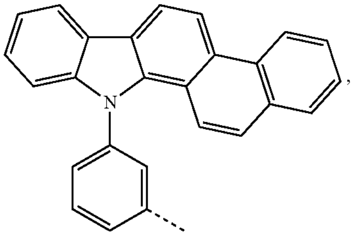

-continued
D108
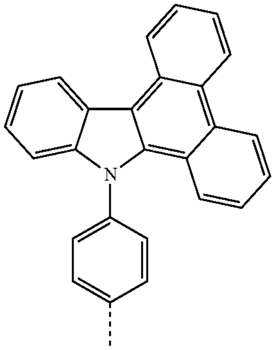
,
D109
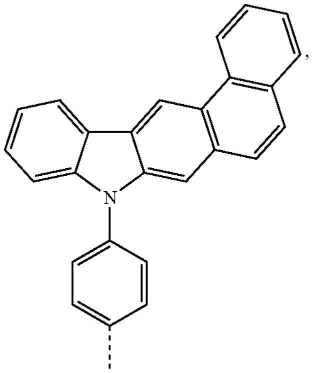
,
D110
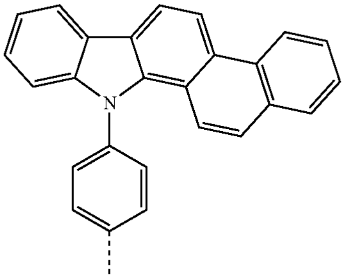
,
D111
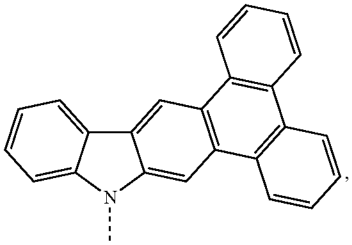
,
D112
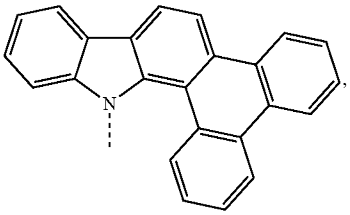
,
-continued
D113
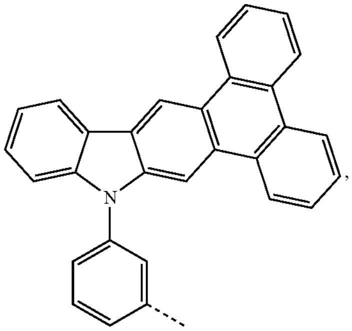
,
D114
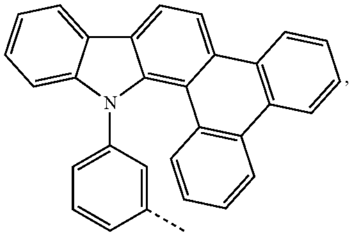
,
D115
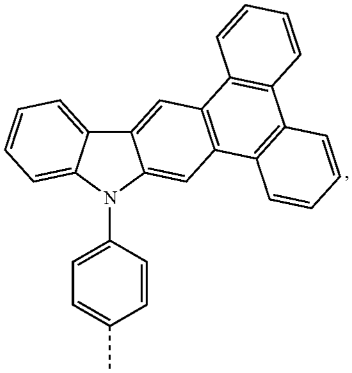
,
D116
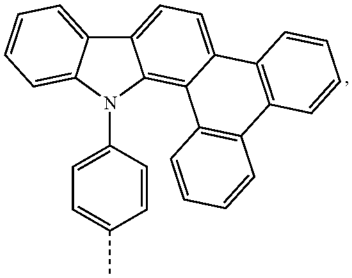
,
D117
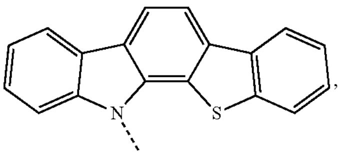
,
D118
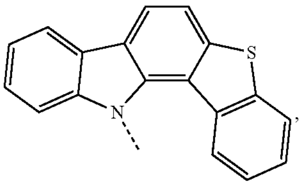
, -continued
D[119]
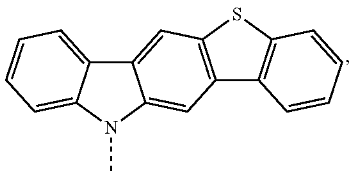
D[120]
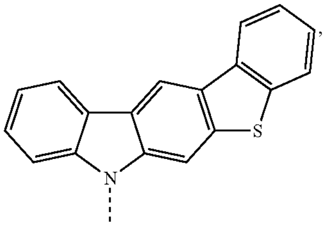
D[121]
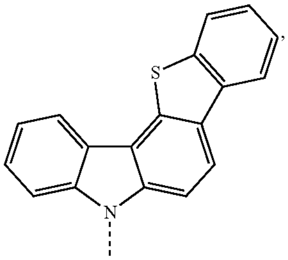
D[122]
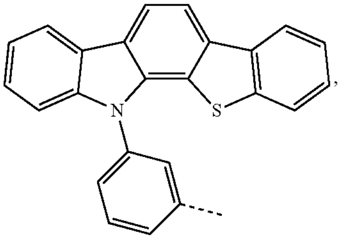
D[123]
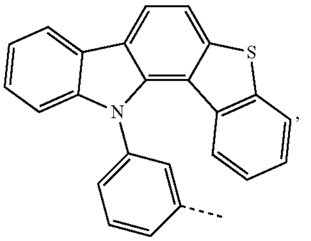
D[124]
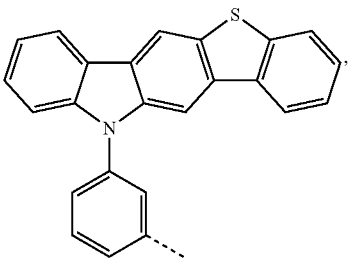
-continued
D[125]
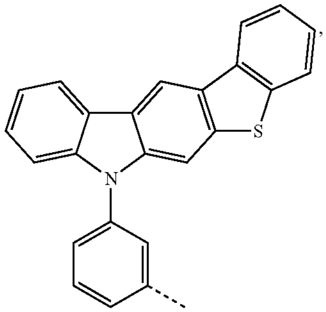
D[126]
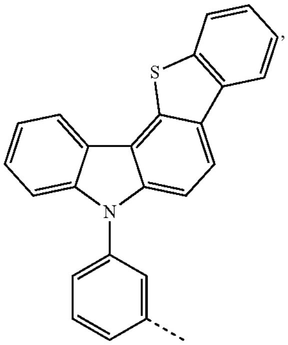
D[127]
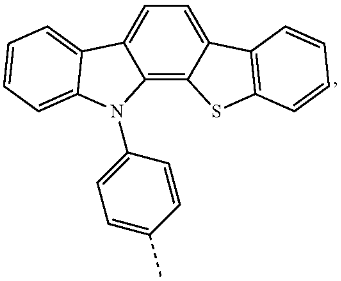
D[128]
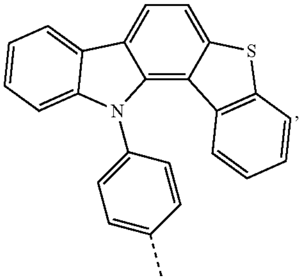
D[129]
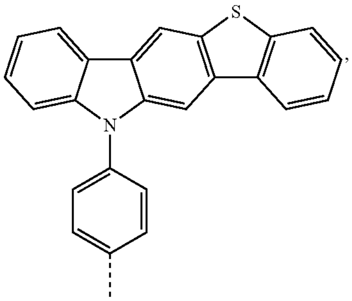

-continued
D[130]
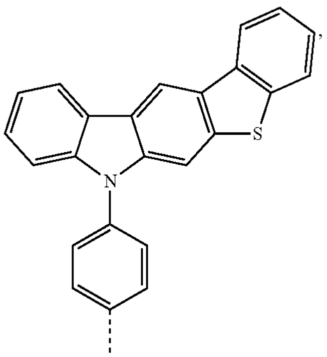
D[131]
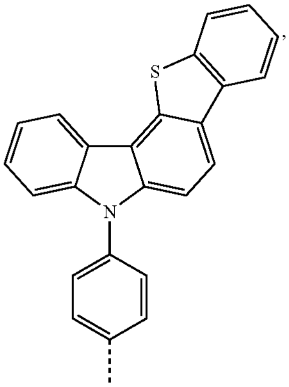
D[132]
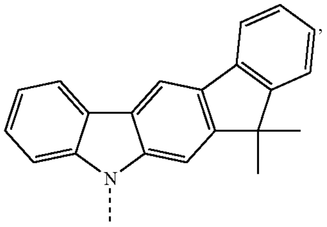
D[133]
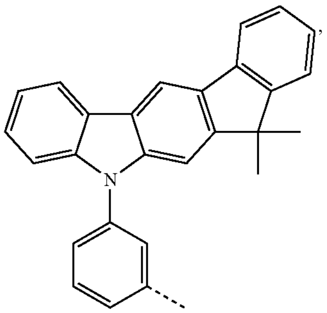
-continued
D[134]
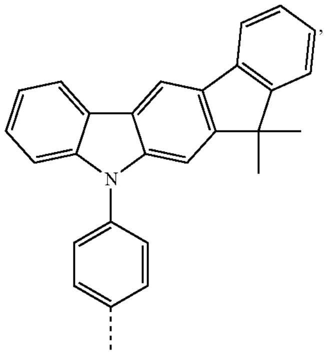
D[135]
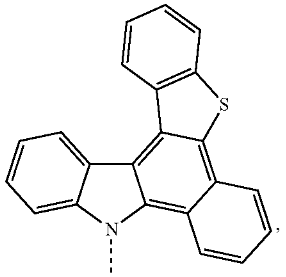
D[136]
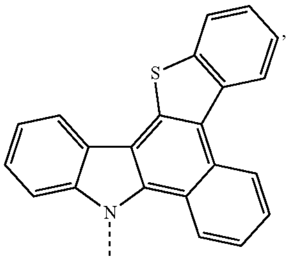
D[137]
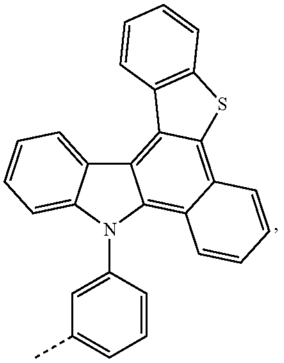
D[138]
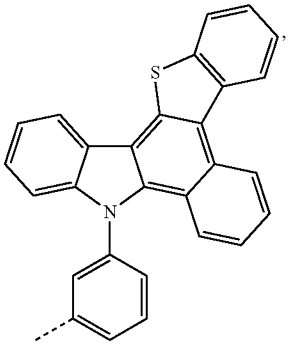

-continued
D[139]
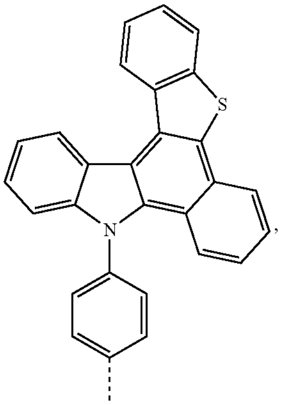
,
D[140]
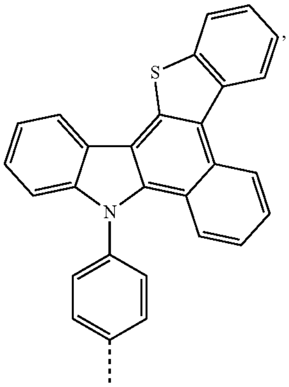
,
D[141]
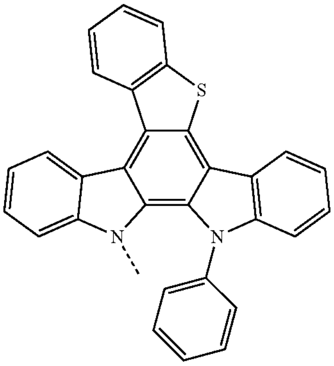
,
D[142]
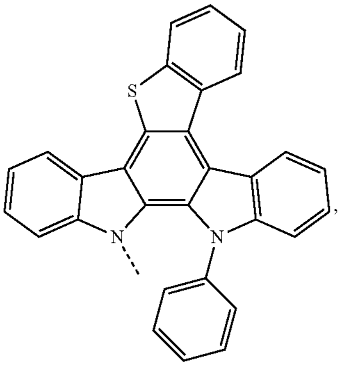
,
-continued
D[143]
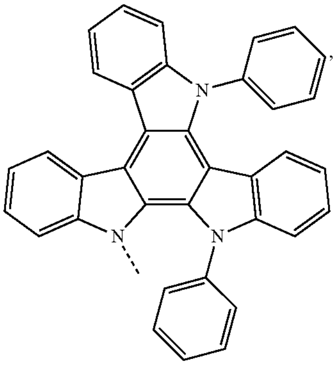
,
D[144]
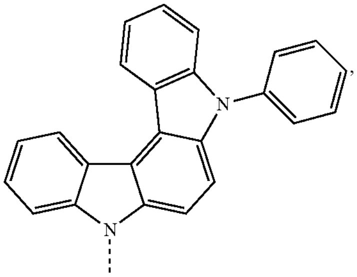
,
D[145]
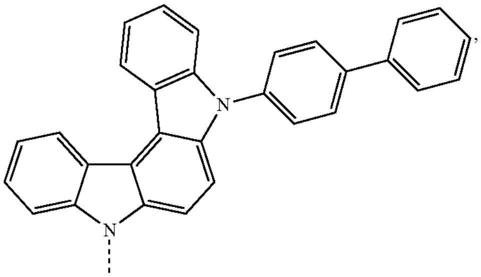
,
D[146]
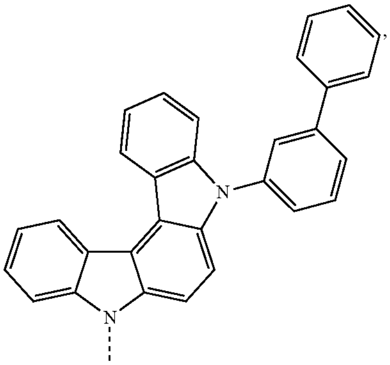
, -continued
D147
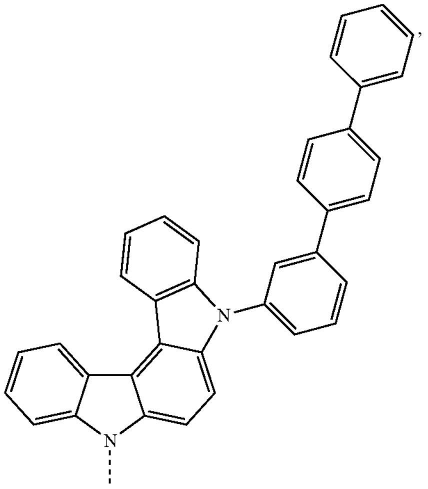
D148
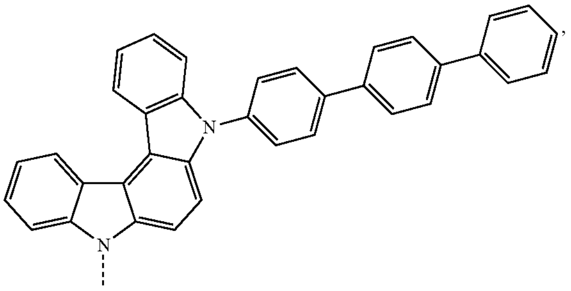
D149
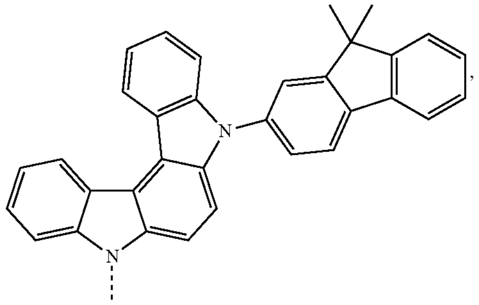
D150
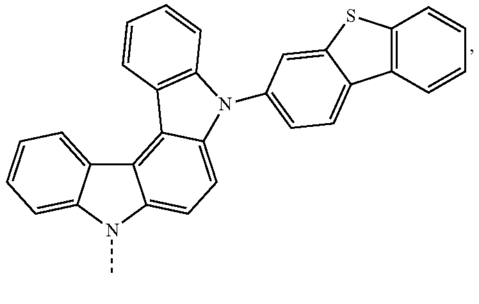
-continued
D151
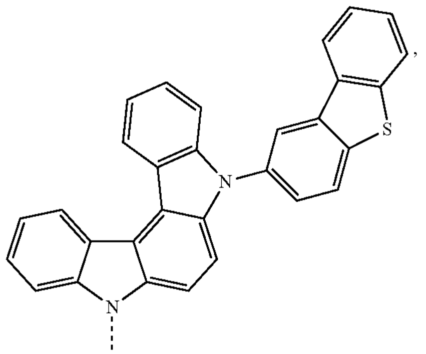
D152
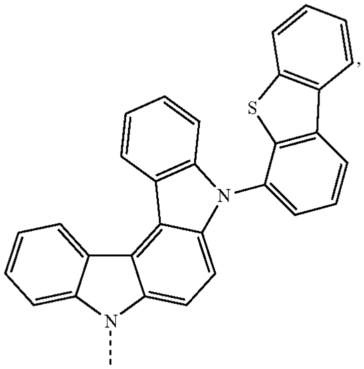
D153
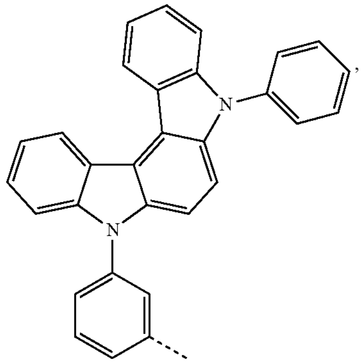
D154
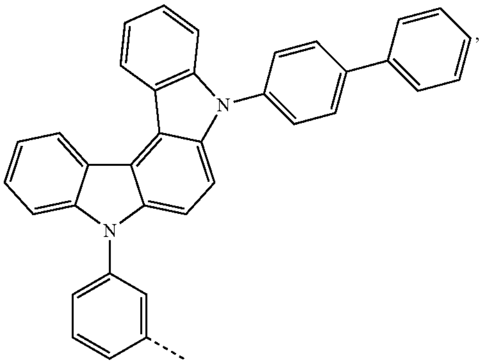

-continued
D155
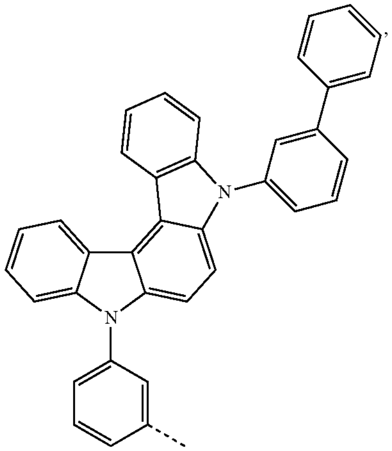
D156
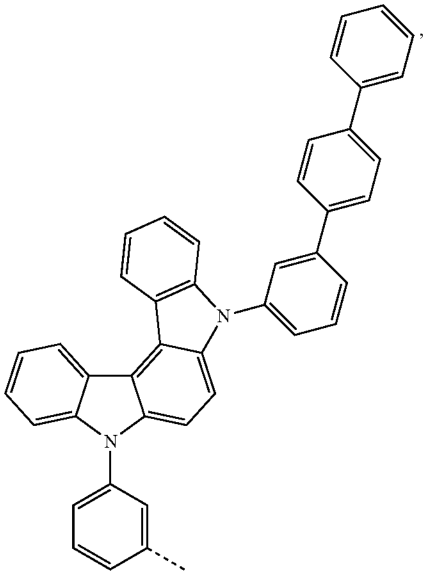
D157
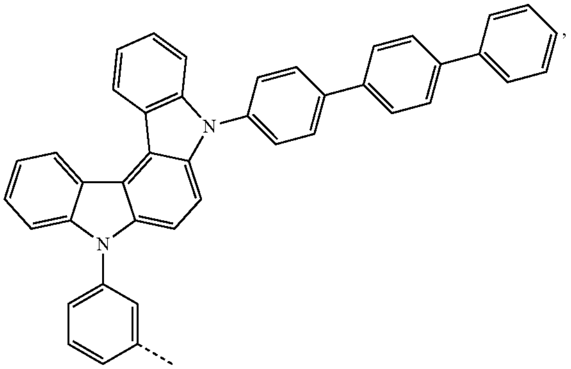
-continued
D158
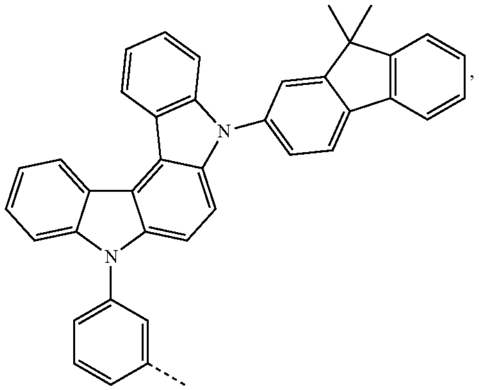
D159
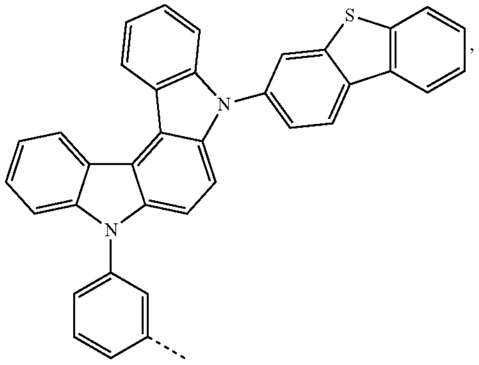
D160
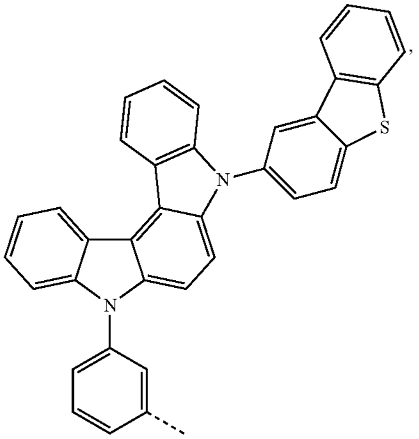

-continued
D[161]
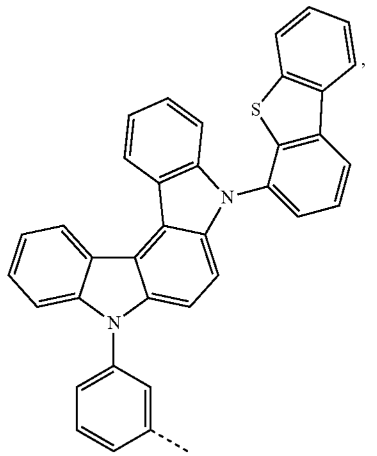
D[162]
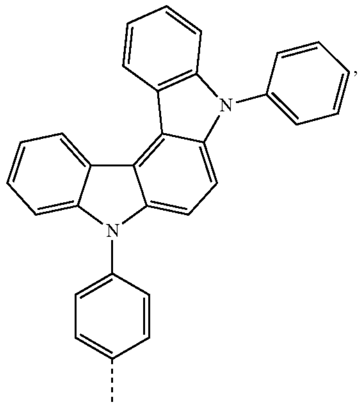
D[163]
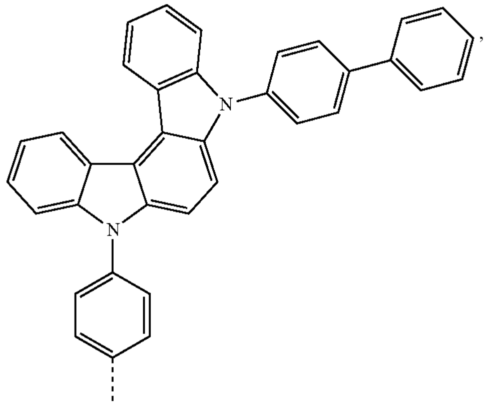
-continued
D[164]
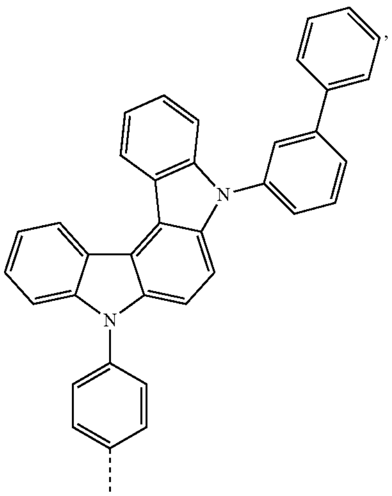
D[165]
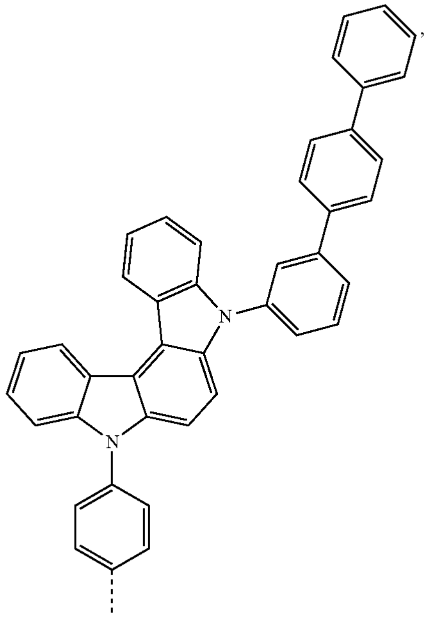
D[166]
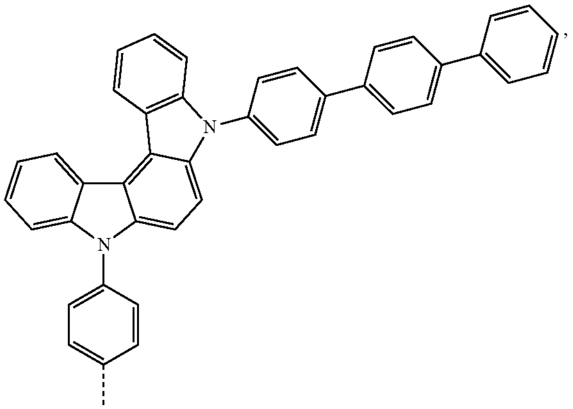

-continued
D[167]
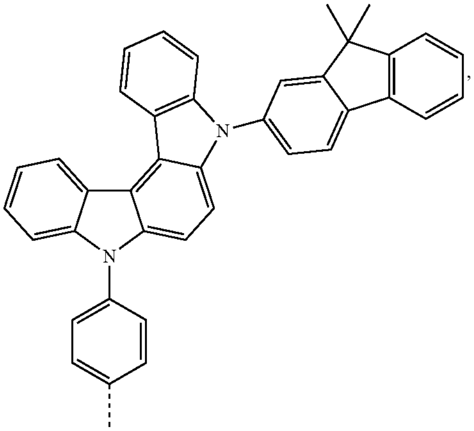
,
D[168]
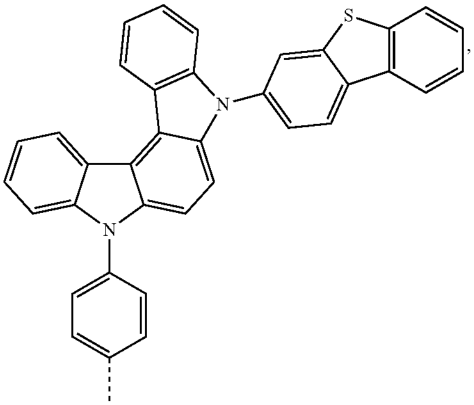
,
D[169]
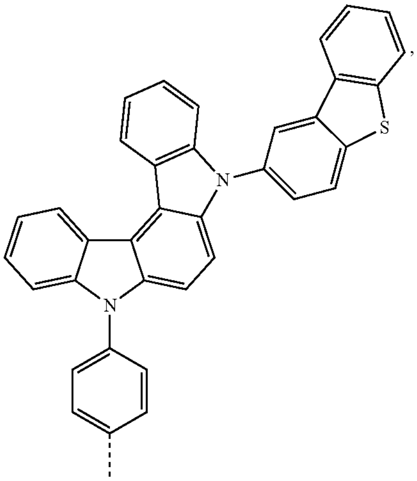
,
-continued
D[170]
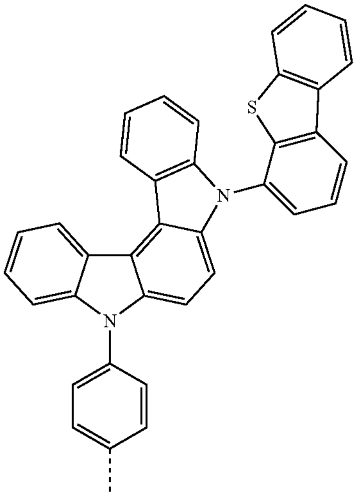
,
D[171]
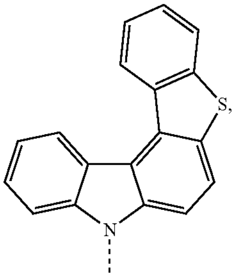
,
D[172]
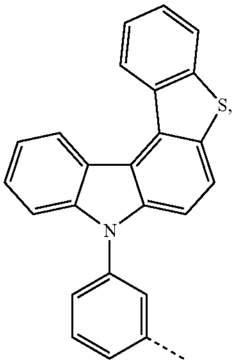
,
D[173]
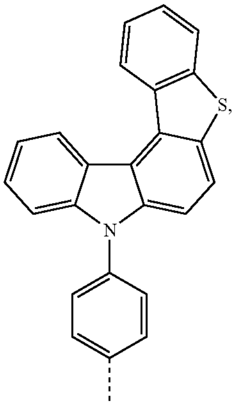
, -continued
D[174]
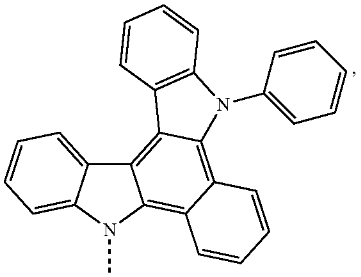
D[175]
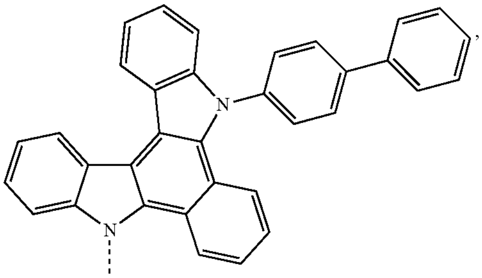
D[176]
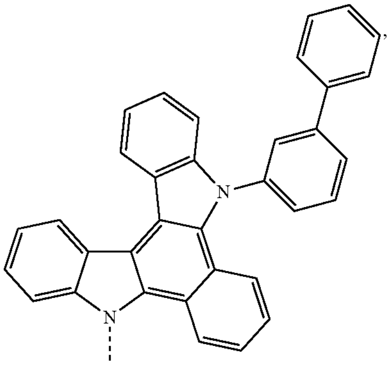
D[177]
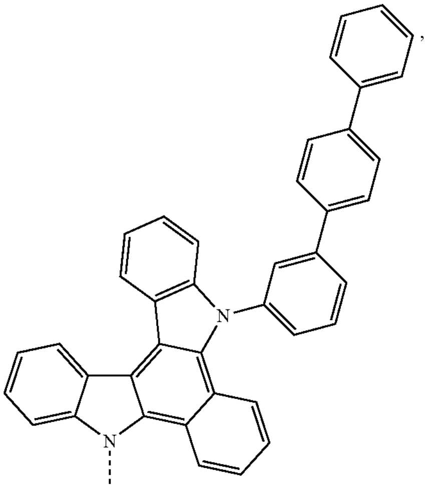
-continued
D[178]
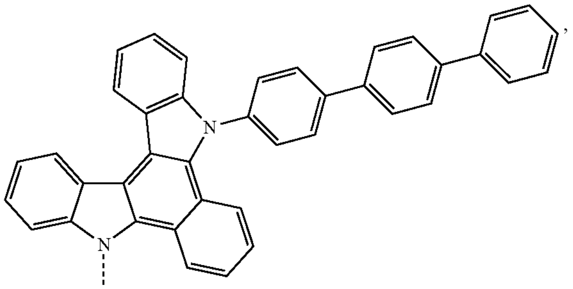
D[179]
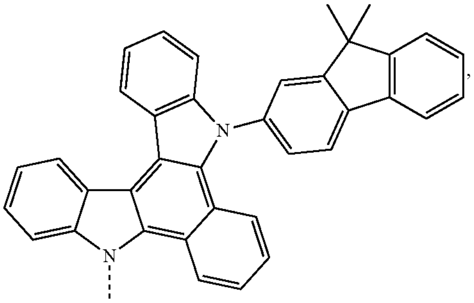
D[180]
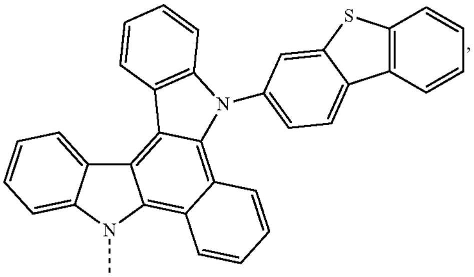
D[181]
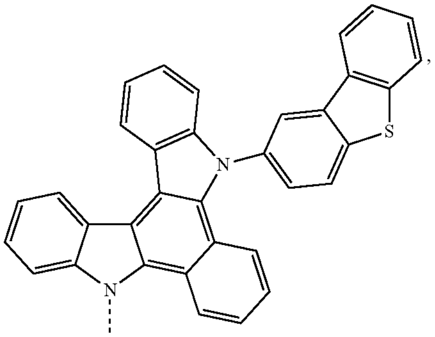
D[182]
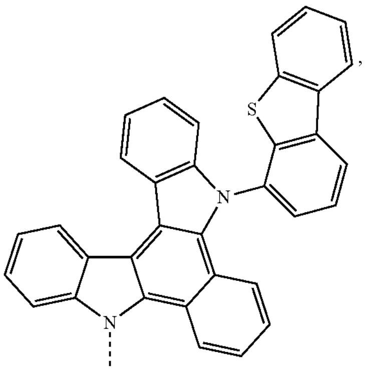

-continued
D[183]
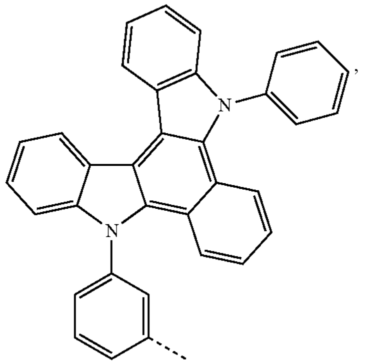
D[184]
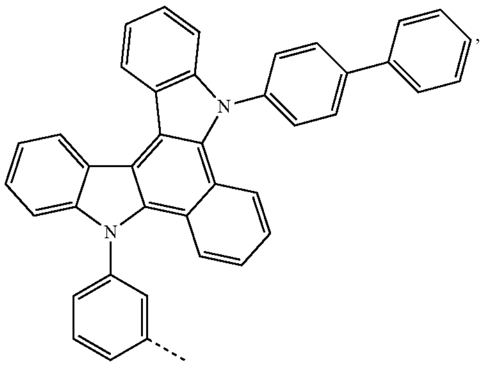
D[185]
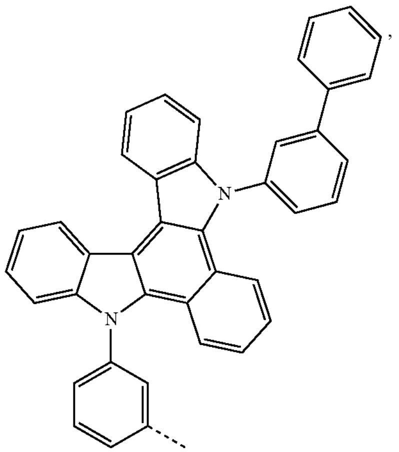
-continued
D[186]
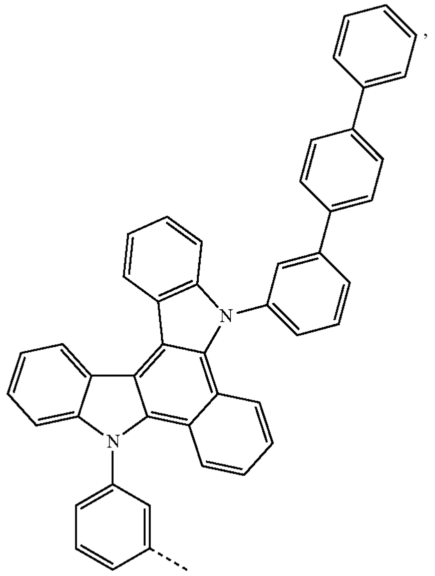
D[187]
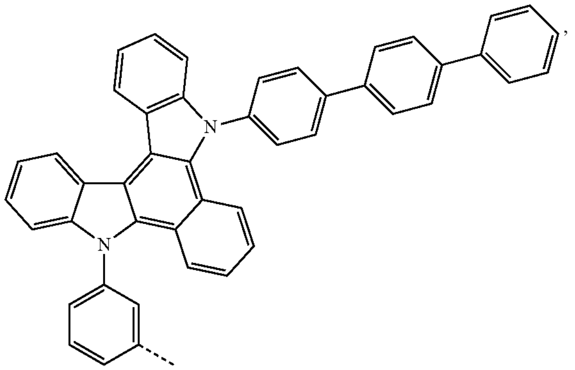
D[188]
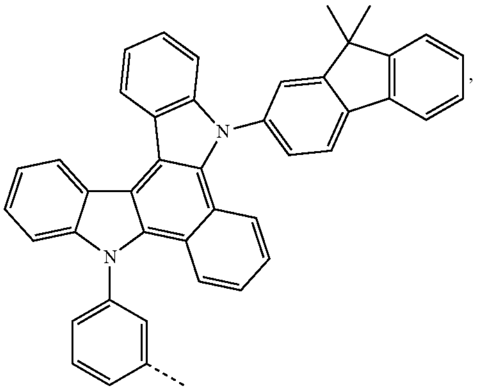

-continued
D189
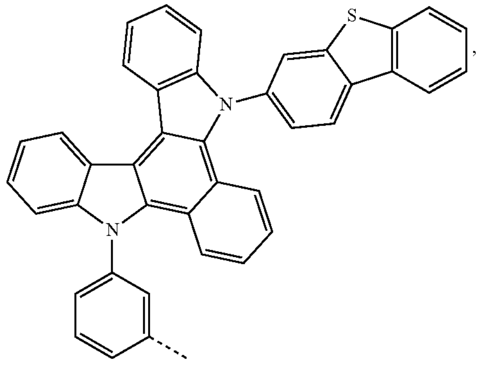
D190
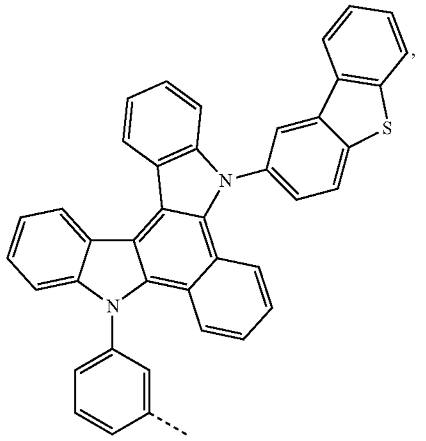
D191
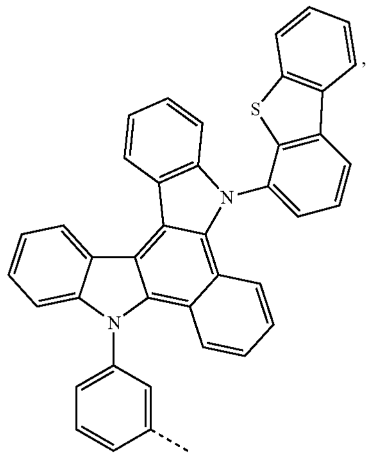
-continued
D[192]
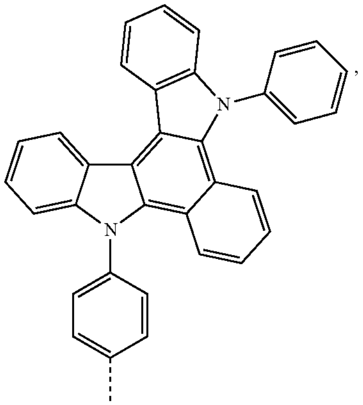
D[193]
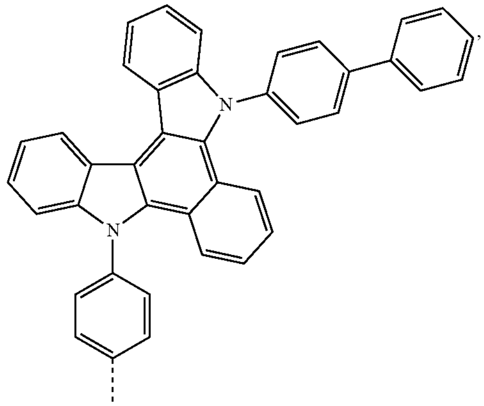
D[194]
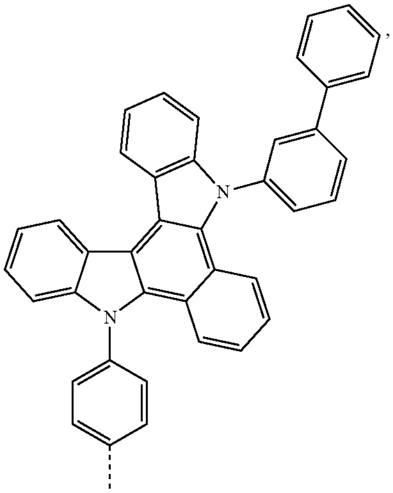

-continued
D[195]
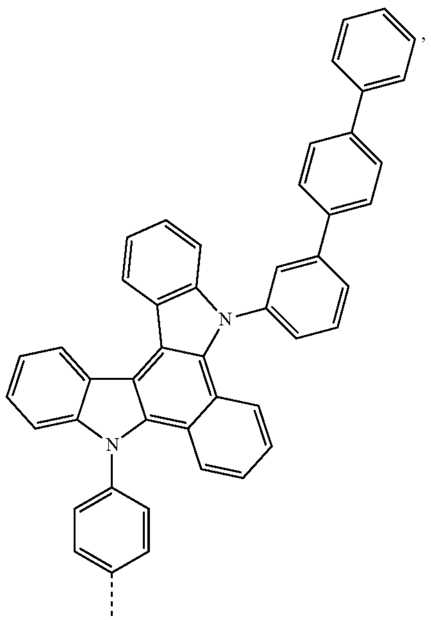
D[196]
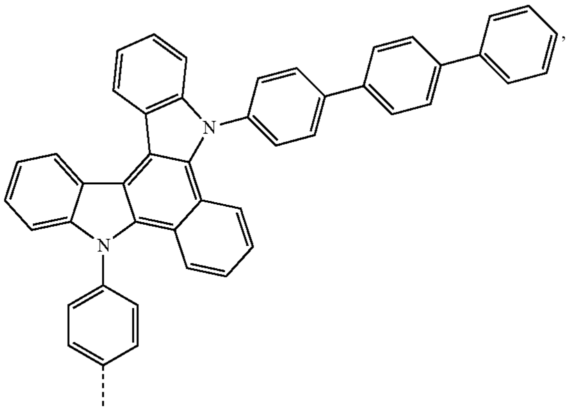
D[197]
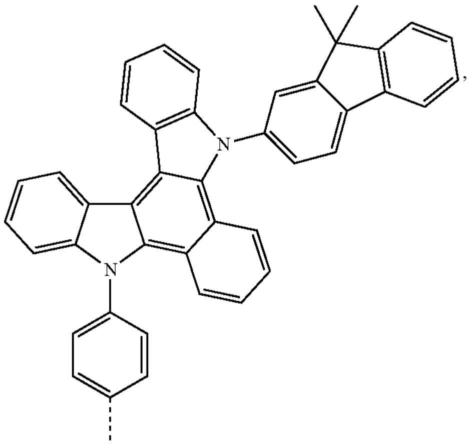
-continued
D[198]
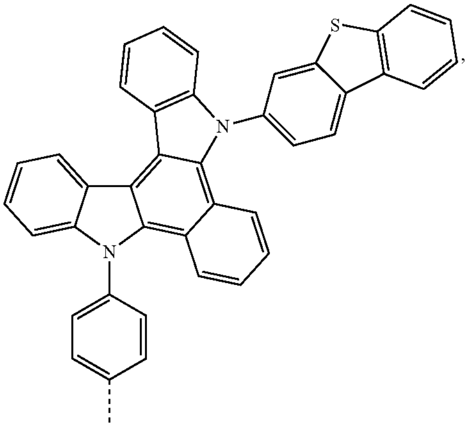
D[199]
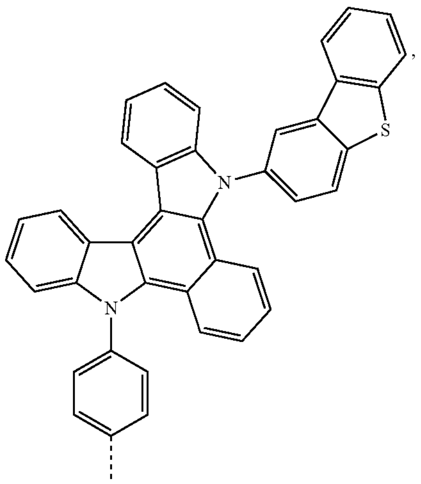
D[200]
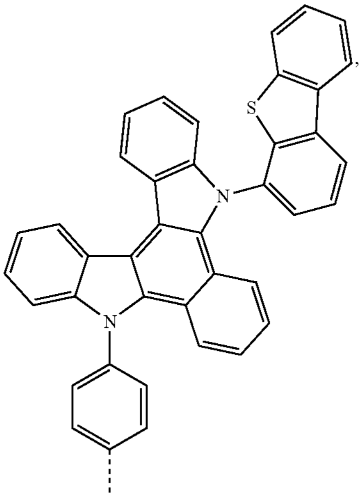
D[201]
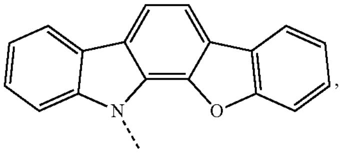
, -continued
D$^{202}$
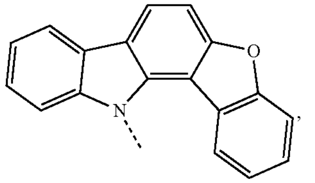
,
D$^{203}$
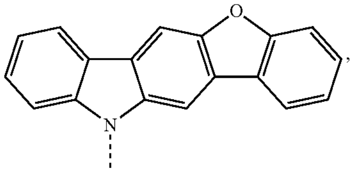
,
D$^{204}$
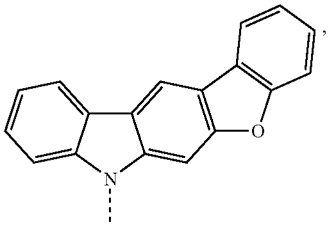
,
D$^{205}$
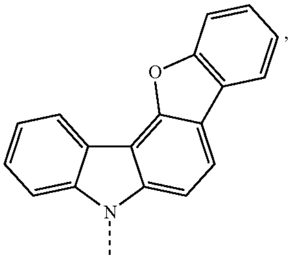
,
D$^{206}$
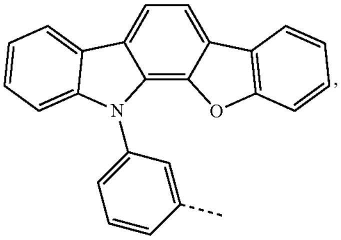
,
D$^{207}$
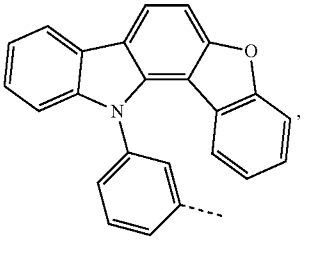
,
-continued
D$^{208}$
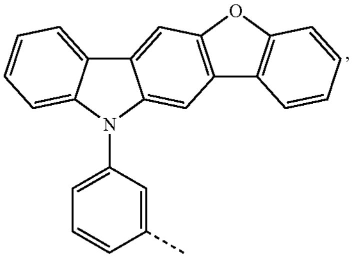
,
D$^{209}$
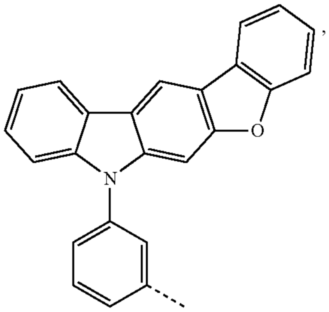
,
D$^{210}$
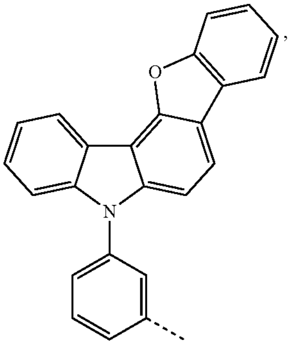
,
D$^{211}$
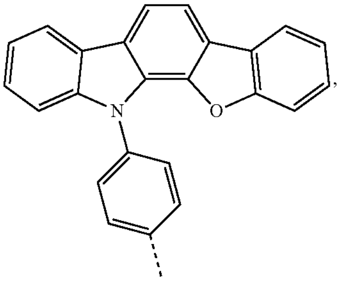
,
D$^{212}$
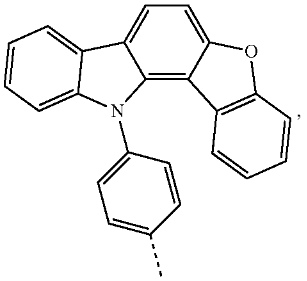
, -continued
D213
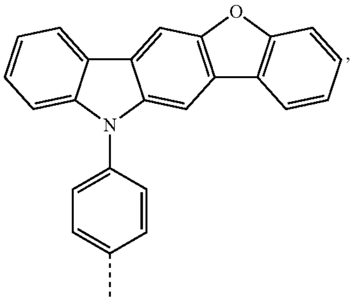
D214
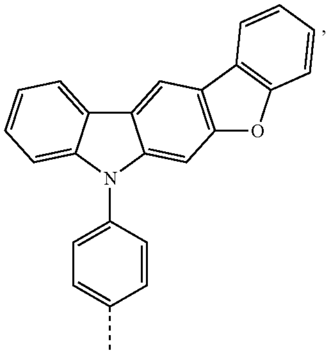
D215
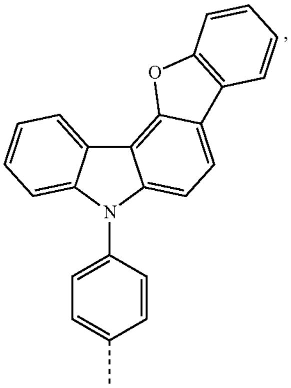
D216
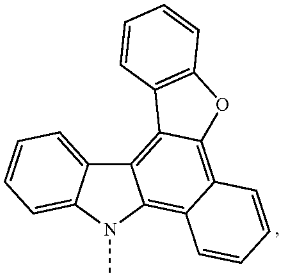
D217
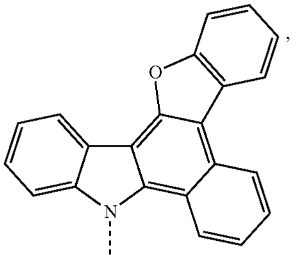
-continued
D218
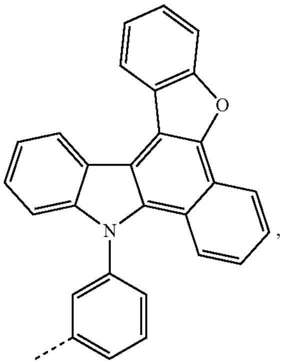
D219
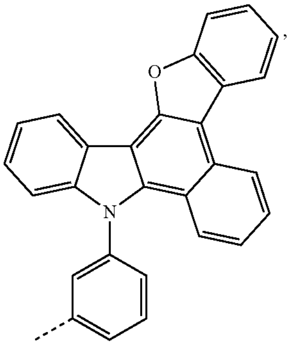
D220
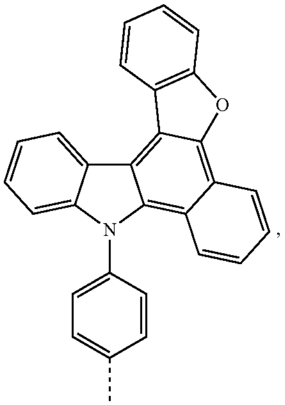
D221
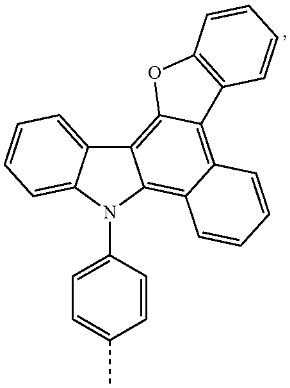

D[222]
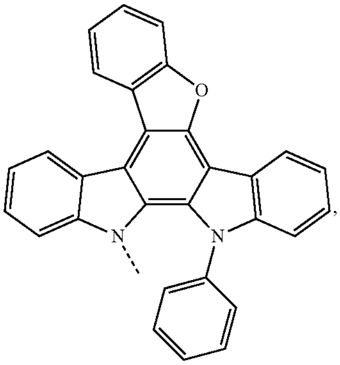,
D[223]
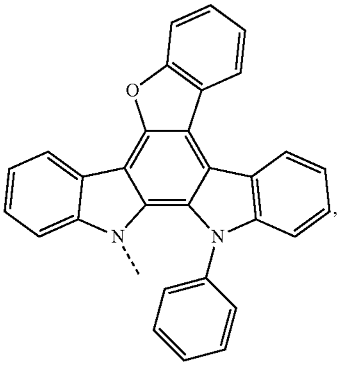,
D[224]
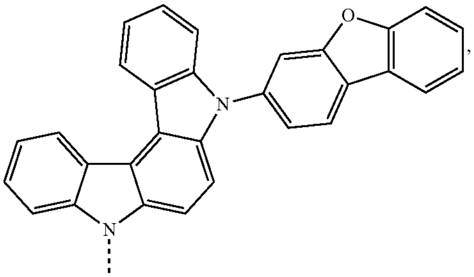,
D[225]
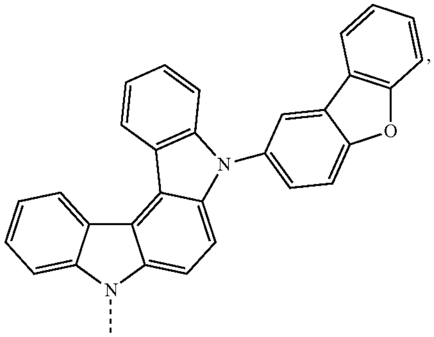,
D[226]
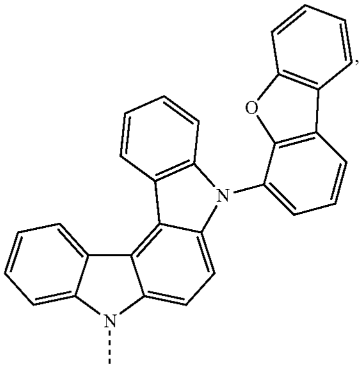,
D[227]
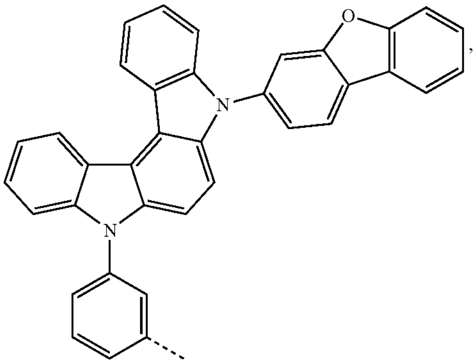,
D[228]
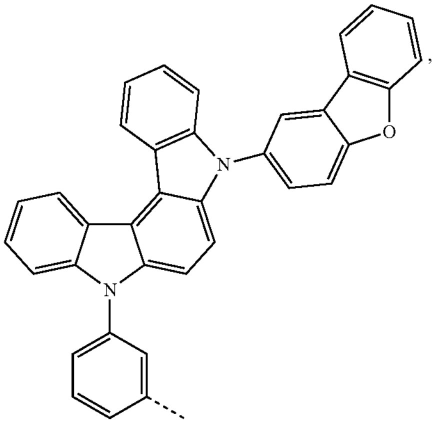,
D[229]
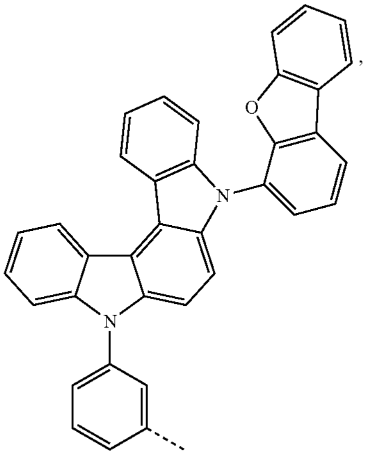, D[230]
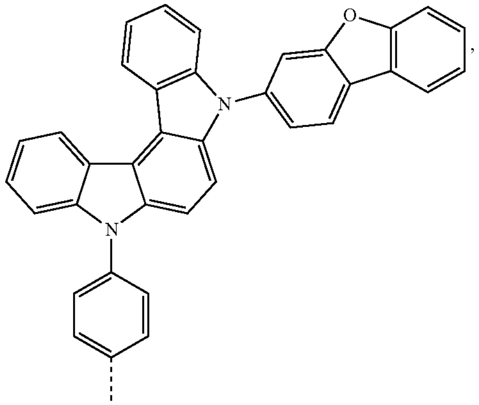
D[231]
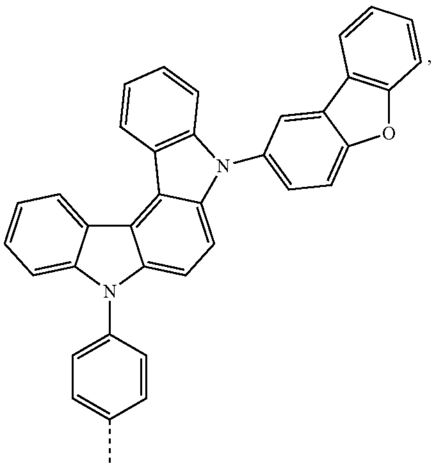
D[232]
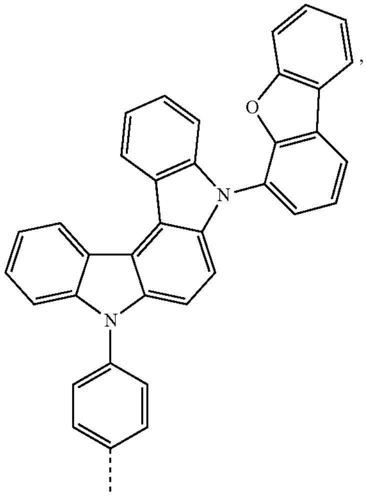
D[233]
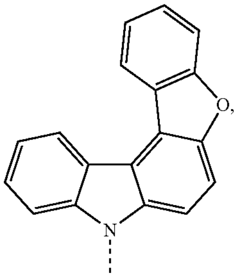
D[234]
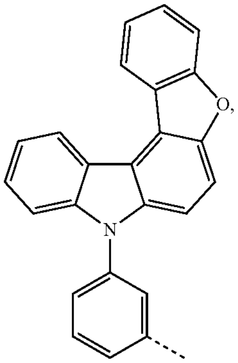
D[235]
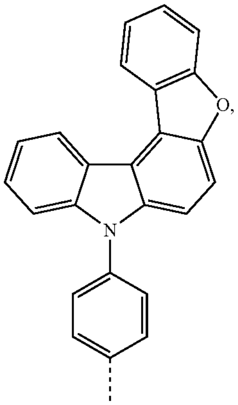
D[236]
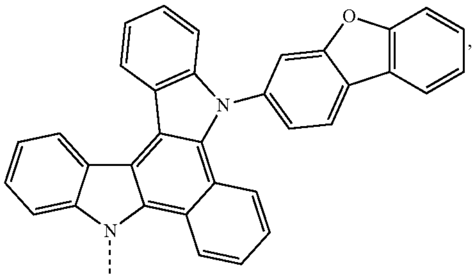

-continued
D[237]
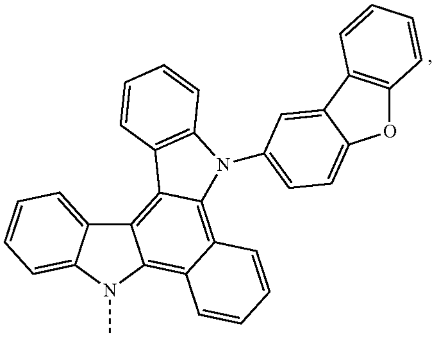
,
D[238]
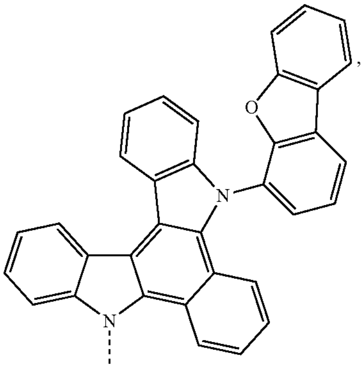
,
D[239]
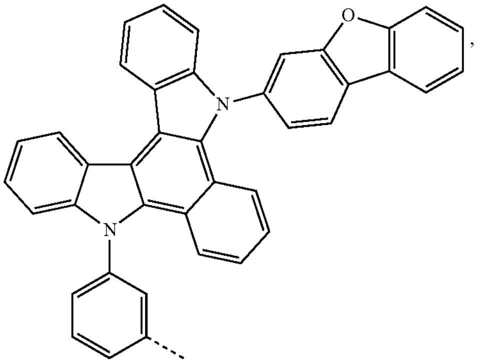
,
D[240]
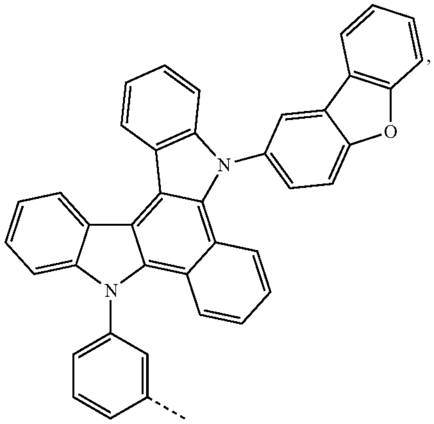
,
-continued
D[241]
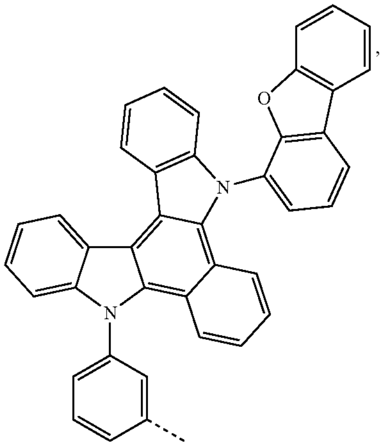
,
D[242]
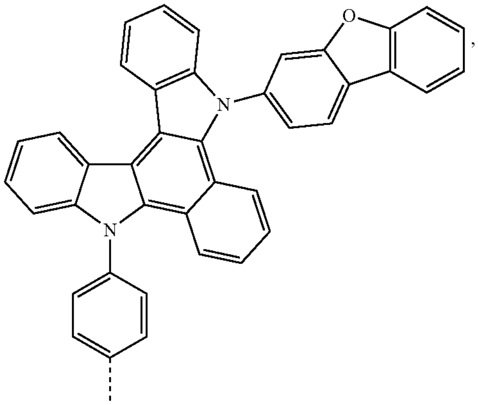
,
D[243]
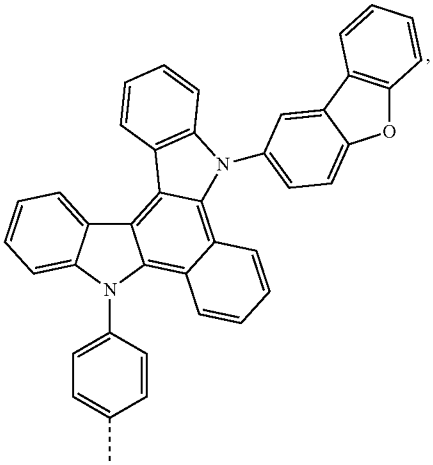
, and -continued

D244

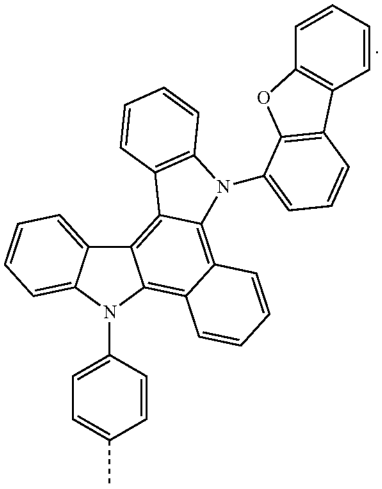

In some embodiments, the compound is Compound x(Label) having the formula $A^iD^j$; wherein x=144j+i−144, where i is an integer from 1 to 144, and j is an integer from 1 to 244; and wherein Label is the name of X atom in the corresponding N.

According to another aspect of the present disclosure, a first organic light emitting device comprising: an anode; a cathode; and an organic layer disposed between the anode and the cathode is disclosed. The organic layer comprises a compound having a formula selected from the group consisting of:

Formula 1-1

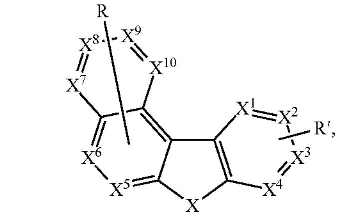

Formula 1-2

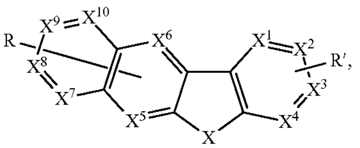

and

Formula 1-3

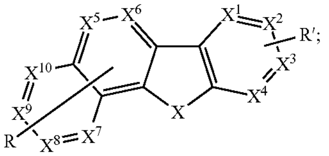

wherein X is selected from the group consisting of O, S, and Se; wherein $X^1$ to $X^{10}$ are each independently selected from the group consisting of carbon and nitrogen; wherein at least one of $X^1$ to $X^6$ is nitrogen; wherein R and R' each independently represent from mono to the possible maximum number of substitutions, or no substitution; wherein R and R' are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; wherein any adjacent substitutions on the same ring are optionally joined or fused into a ring; and wherein at least one of R and R' is not hydrogen or deuterium;

provided that when adjacent subsitutions on $X^5$ and $X^6$ in Formula I-1 and I-3 fuse into a six-member ring, this ring and the ring having $X^7$ to $X^{10}$ can not be pyridine at the same time.

In some embodiments of the first organic light emitting device, the organic layer is an emissive layer and the compound is a host.

In some embodiments of the first organic light emitting device, the organic layer further comprises a phosphorescent emissive dopant; wherein the emissive dopant is a transition metal complex having at least one ligand or part of the ligand if the ligand is more than bidentate, selected from the group consisting of:

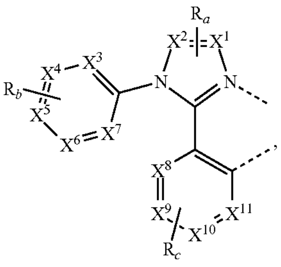

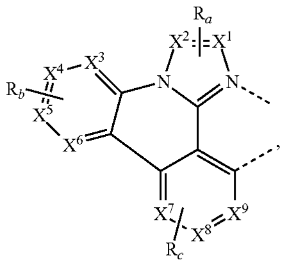

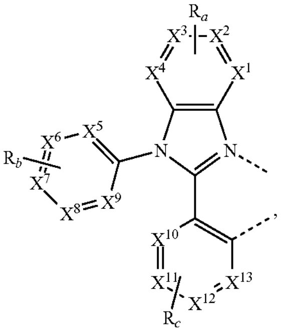

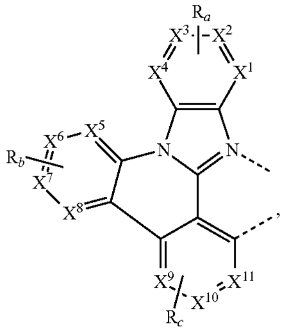

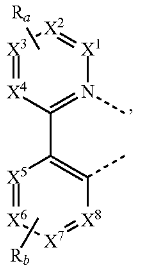

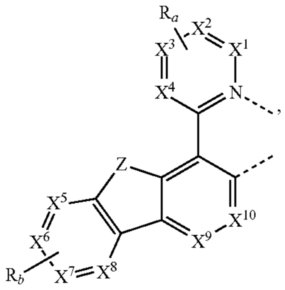

-continued

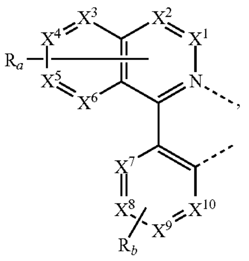

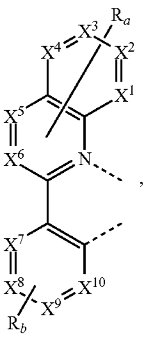

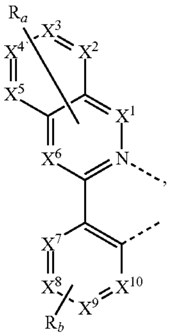

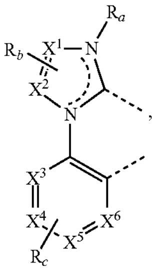

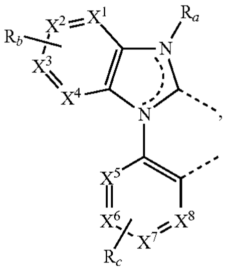

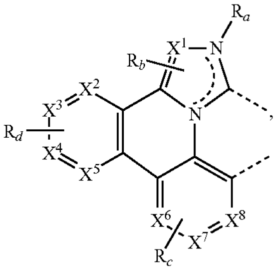

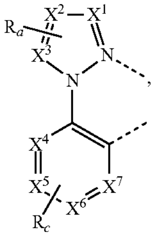

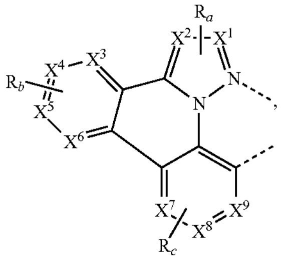

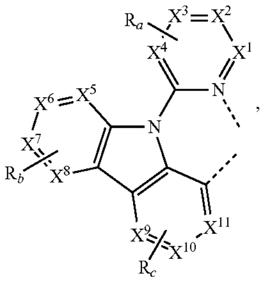

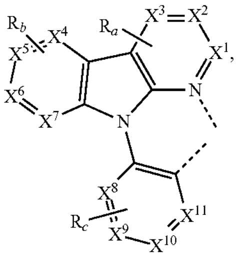

and

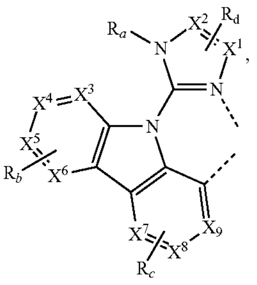

wherein each $X^1$ to $X^{13}$ are independently selected from the group consisting of carbon and nitrogen;

wherein Z is selected from the group consisting of BR', NR', PR', O, S, Se, C═O, S═O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

In some embodiments of the first organic light emitting device, the organic layer is a charge carrier blocking layer and the compound is a charge carrier blocking material in the organic layer.

In some embodiments of the first organic light emitting device, the organic layer is a charge carrier transporting layer and the compound is a charge carrier transporting material in the organic layer.

In some embodiments of the first organic light emitting device, the device can be incorporated into a consumer product, an electronic component module, an organic light-emitting device, or a lighting panel.

In some embodiments of the first organic light emitting device, the organic layer is an emissive layer and the compound is an emitter.

In some embodiments of the first organic light emitting device where the compound is an emitter in the emissive layer, the first organic light emitting device emits a luminescent radiation at room temperature when a voltage is applied across the first organic light emitting device, and the luminescent radiation comprises a delayed fluorescence process.

In some embodiments of the first organic light emitting device where the compound is an emitter in the emissive layer, the emissive layer further comprises a host material.

In some embodiments of the first organic light emitting device where the compound is an emitter in the emissive layer, the emissive layer further comprises a first phosphorescent emitting material. In some embodiments, the emissive layer further comprises a second phosphorescent emitting material.

In some embodiments where the compound is an emitter in the emissive layer and the emissive layer further comprises a first phosphorescent emitting material, the first organic light emitting device emits a white light at room temperature when a voltage is applied across the organic light emitting device. In some embodiments of the white light emitting device, the compound emits a blue light with a peak wavelength of about 400 nm to about 500 nm. In some embodiments of the white light emitting device, the compound emits a yellow light with a peak wavelength of about 530 nm to about 580 nm.

In another aspect of the present disclosure, a formulation comprising a compound having a formula selected from the group consisting of:

Formula 1-1

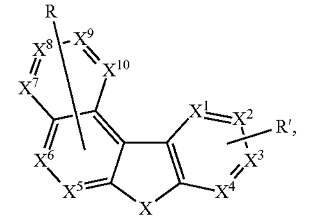

Formula 1-2

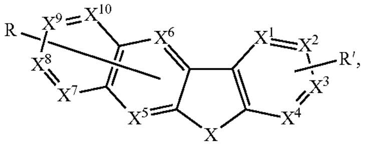

and

Formula 1-3

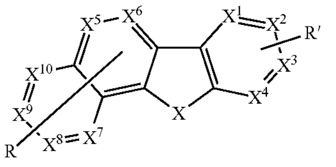

is disclosed.

In Formula 1-1, Formula 1-2, and Formula 1-3,

X is selected from the group consisting of O, S, and Se;

wherein $X^1$ to $X^{10}$ are each independently selected from the group consisting of carbon and nitrogen;

wherein at least one of $X^1$ to $X^6$ is nitrogen;

wherein R and R' each independently represent from mono to the possible maximum number of substitutions, or no substitution;

wherein R and R' are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein any adjacent substitutions on the same ring are optionally joined or fused into a ring; and wherein at least one of R and R' is not hydrogen or deuterium;

provided that when adjacent subsitutions on $X^5$ and $X^6$ in Formula I-1 and I-3 fuse into a six-member ring, this ring and the ring having $X^7$ to $X^{10}$ can not be pyridine at the same time.

In yet another aspect of the present disclosure, a formulation that comprises the first compound of the present disclosure is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

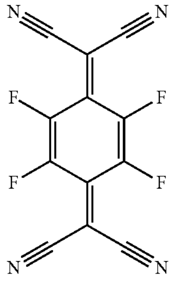

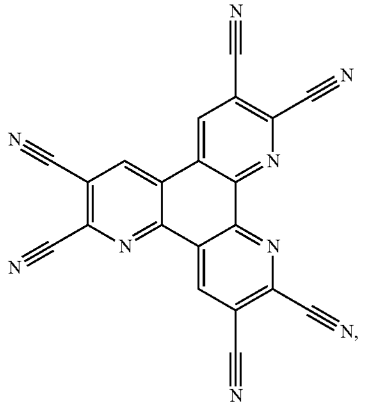

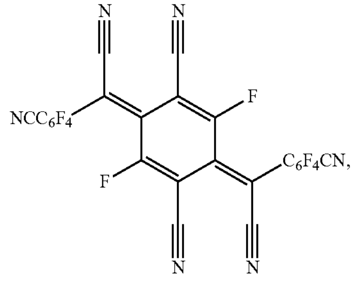

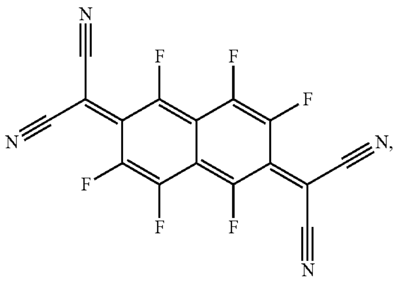

-continued

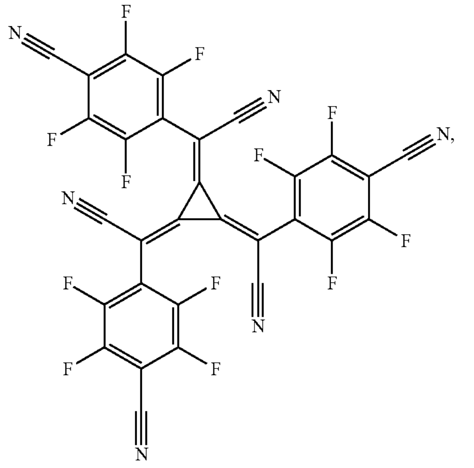

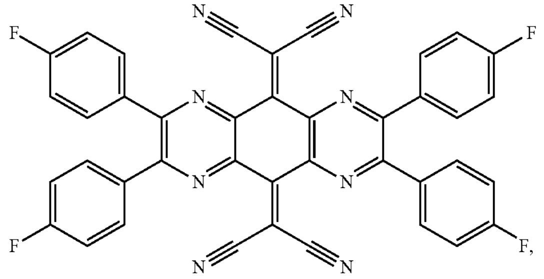

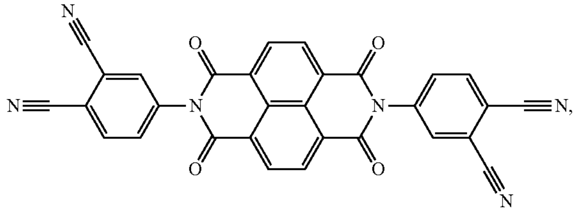

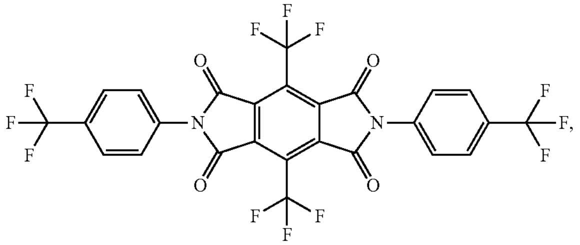

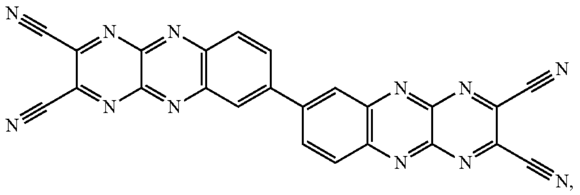

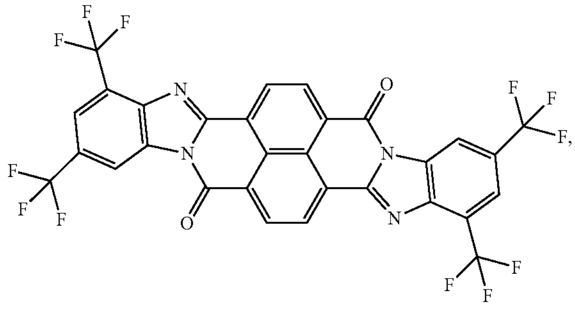

-continued

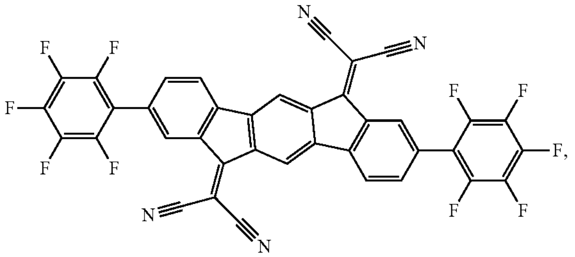

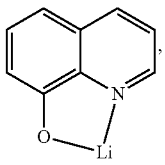

, and

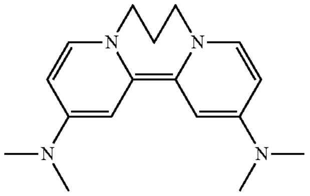

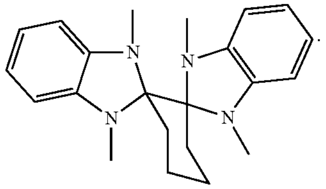

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

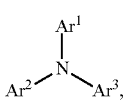

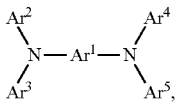

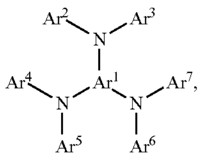

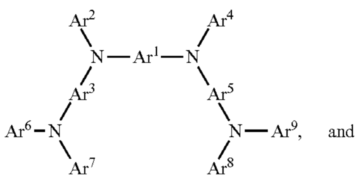

and

-continued

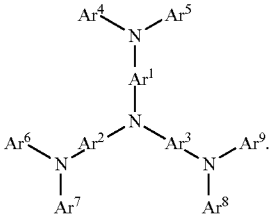

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

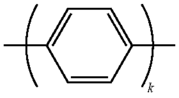,
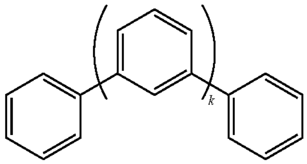,
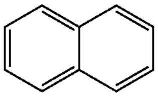,
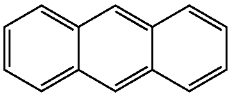,
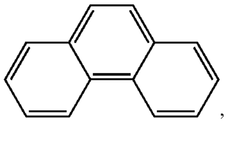,
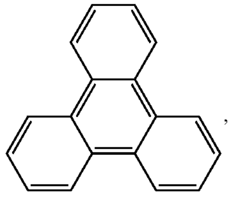,

-continued

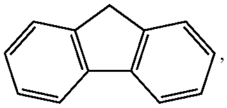, and 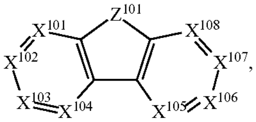, wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

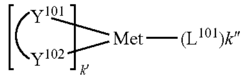

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018,

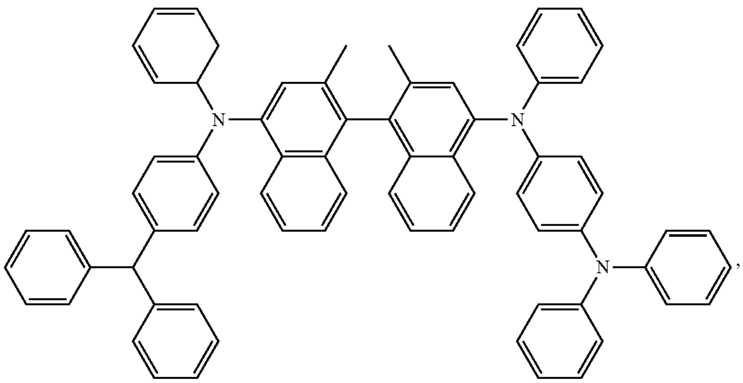
,
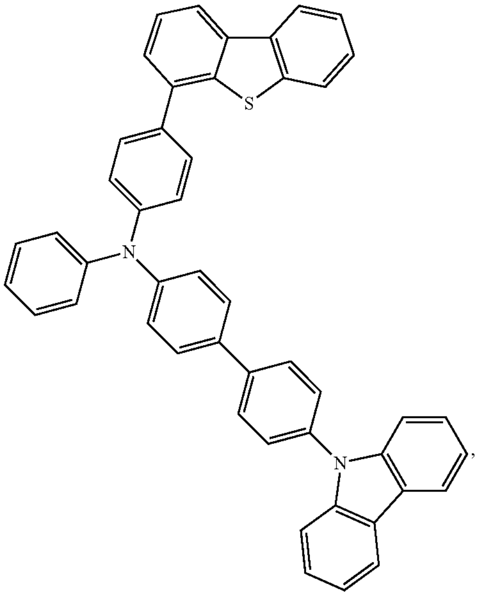
,
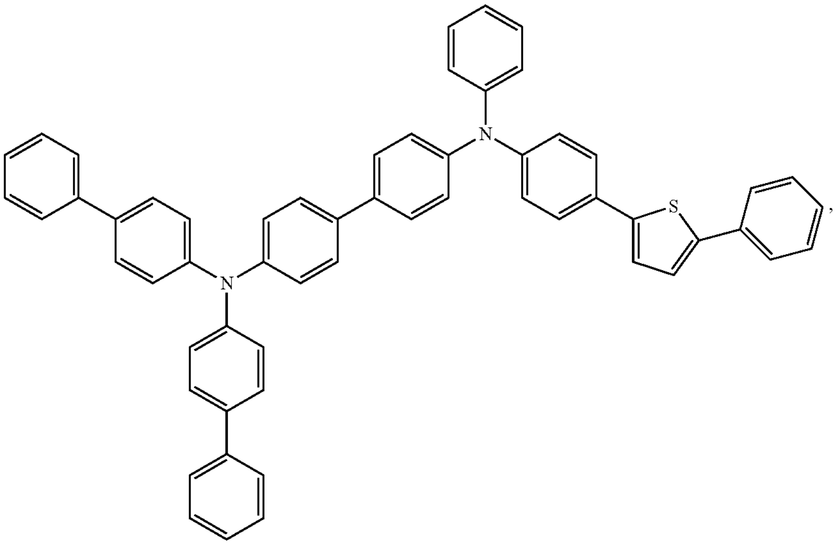
,

-continued
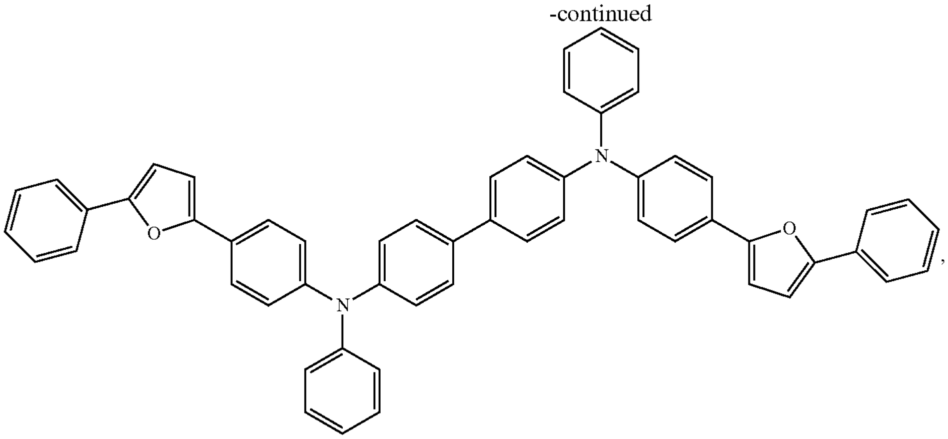
,
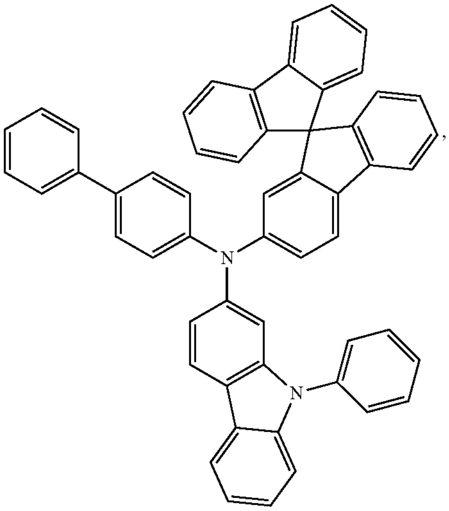
,
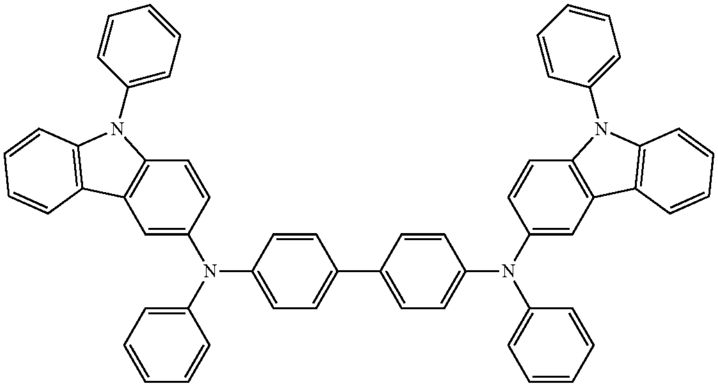
,
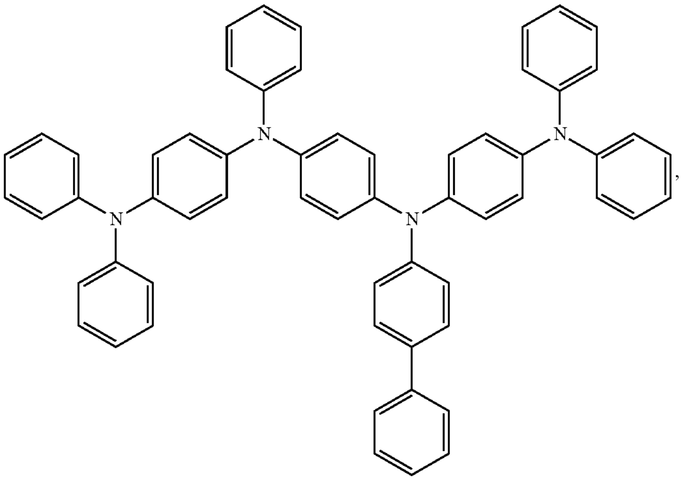
,

-continued
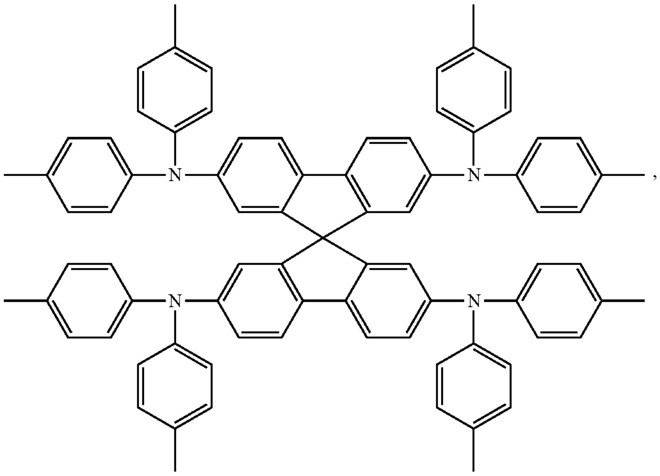
,
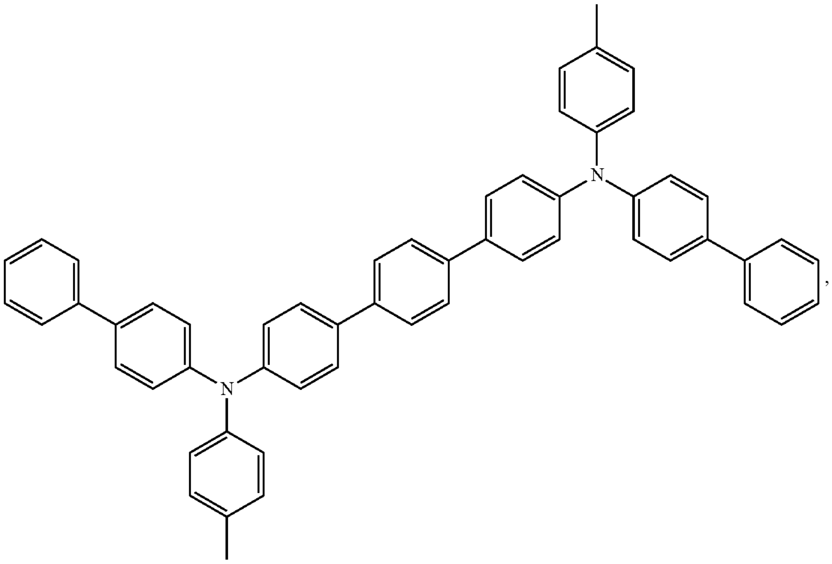
,
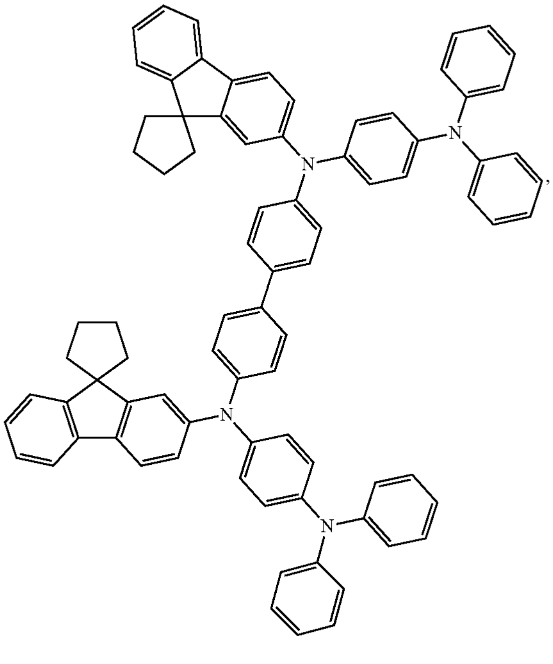
,

-continued
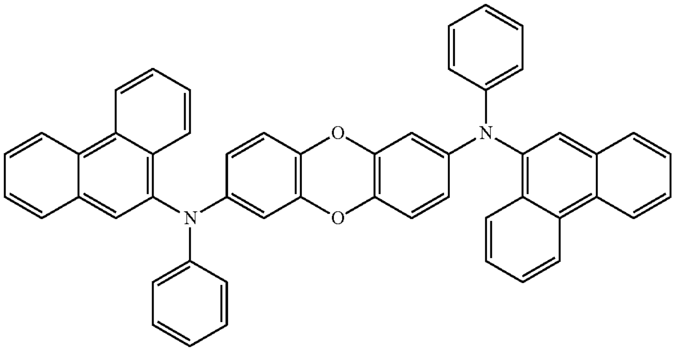,
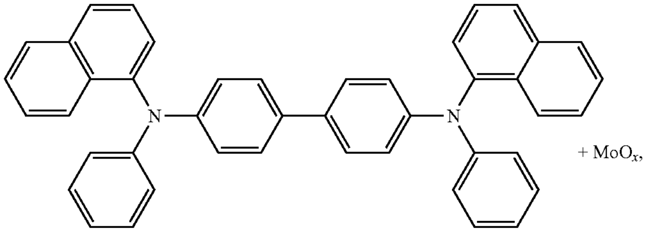
+ $MoO_x$,
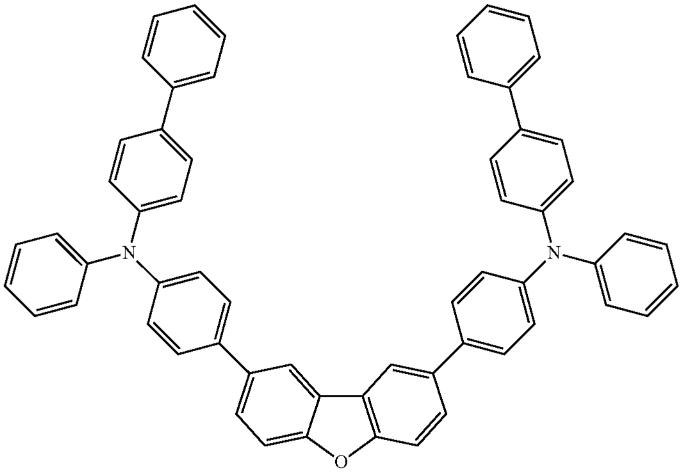,
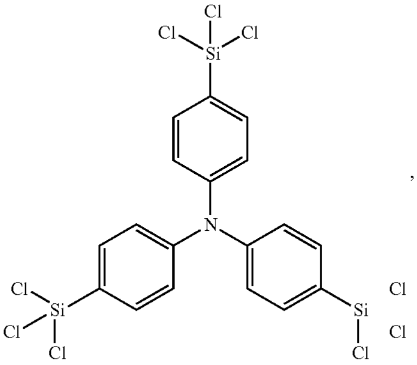,
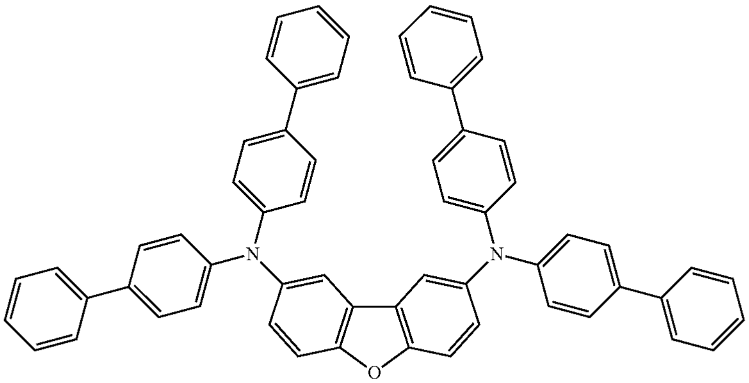,
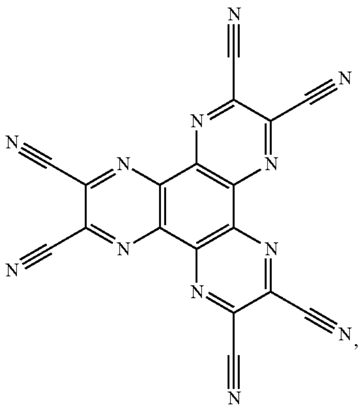, -continued
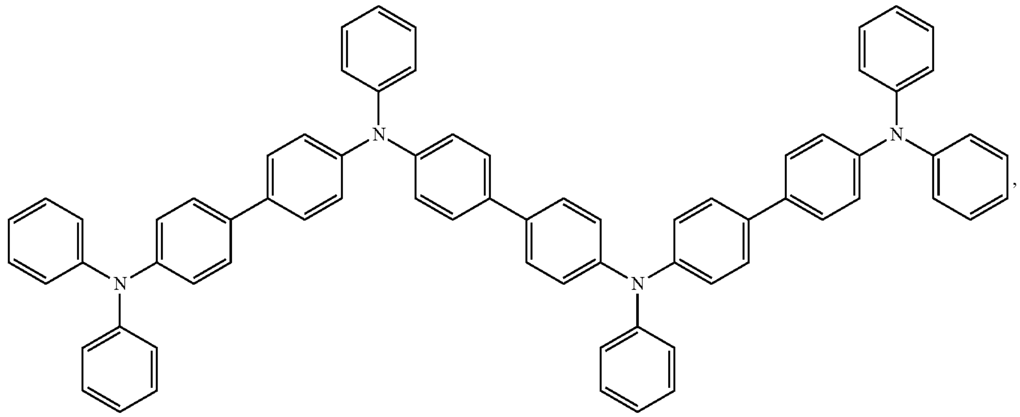
,
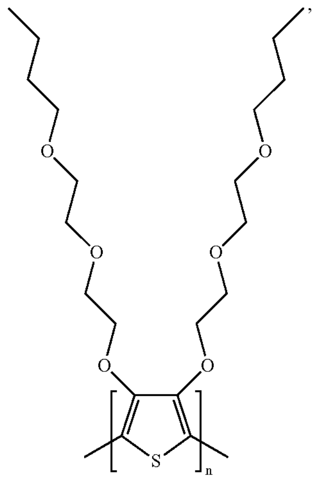
,
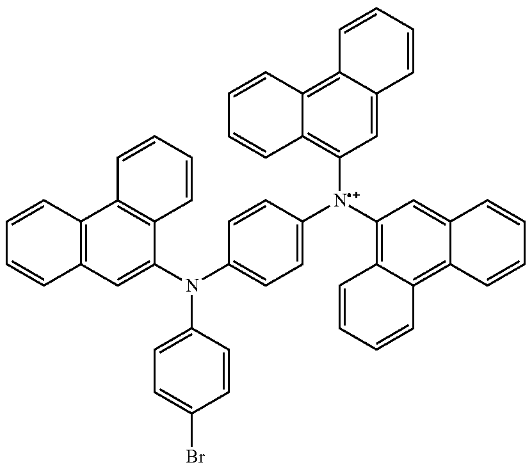
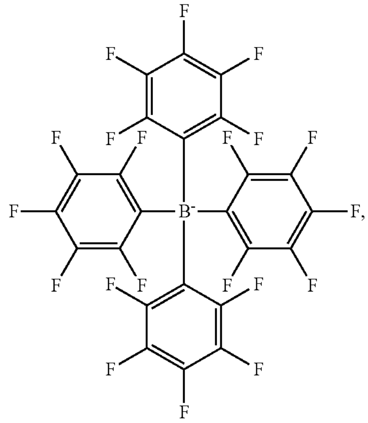
,
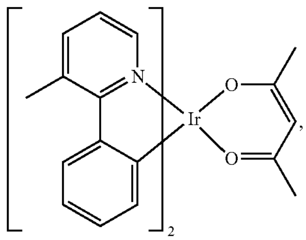
, -continued
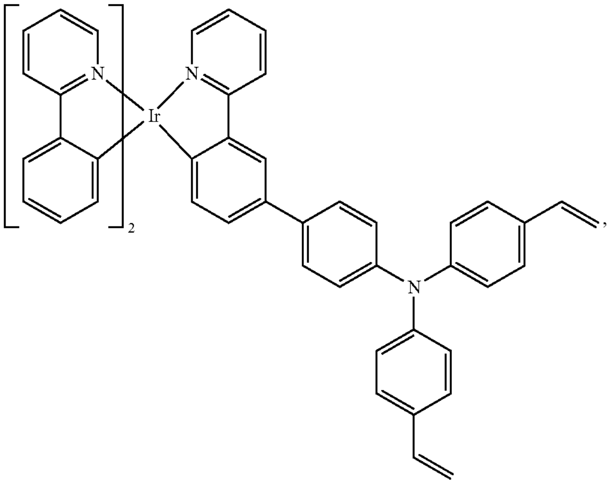
,
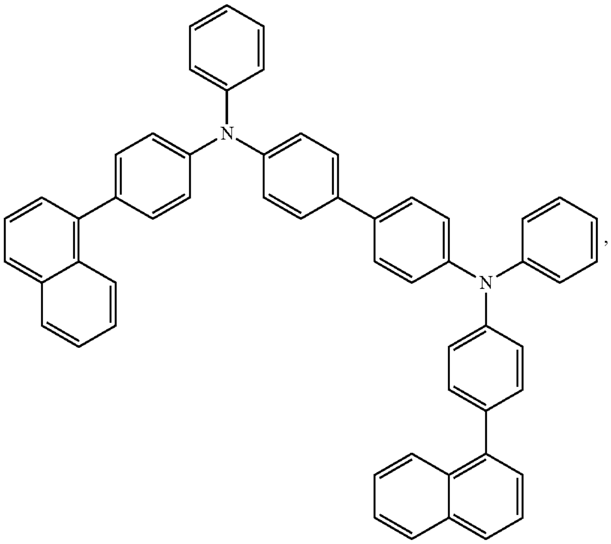
,
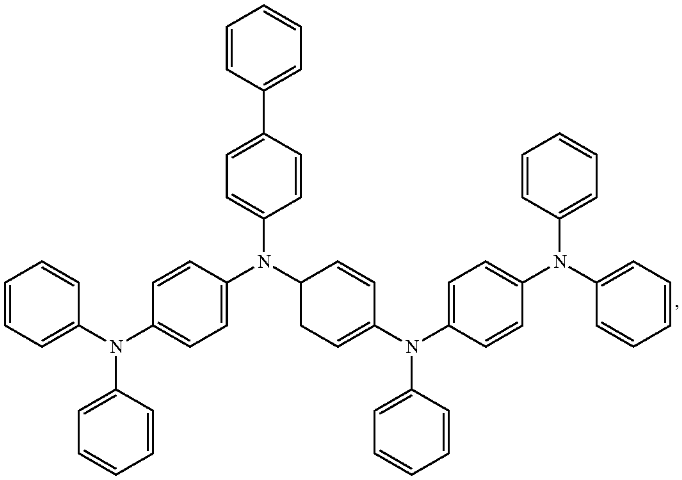
, -continued
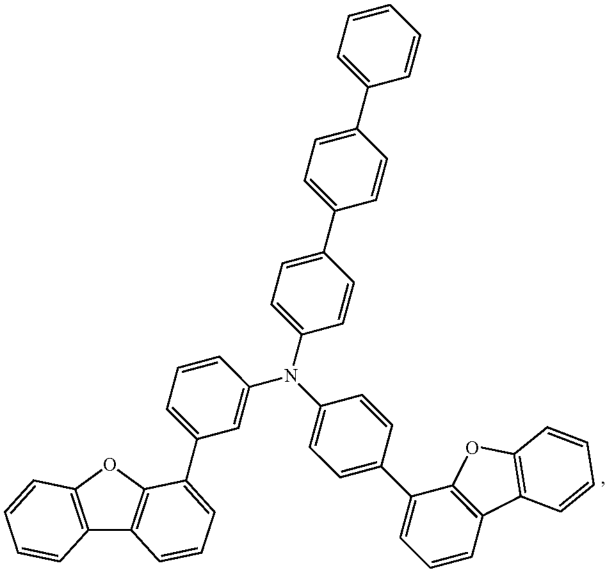
,
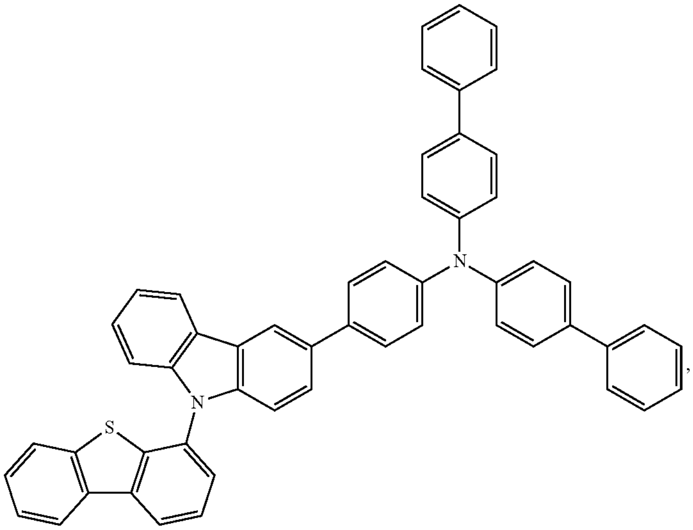
,
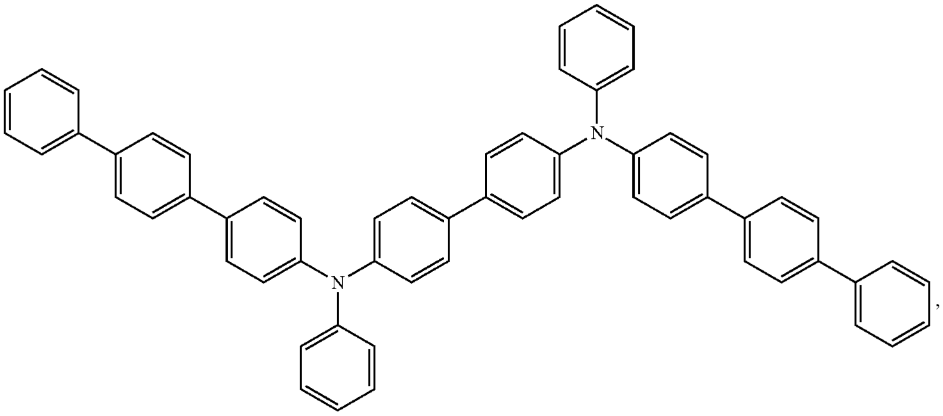
, -continued
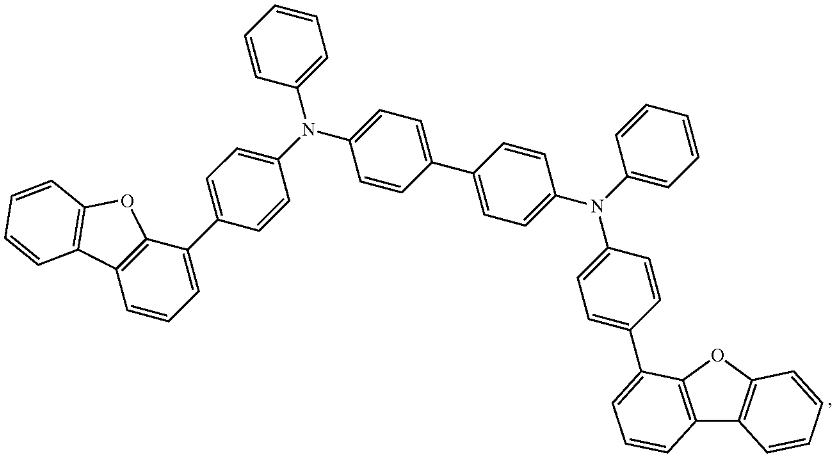
,
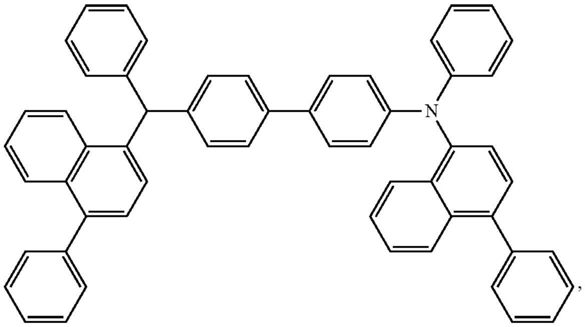
,
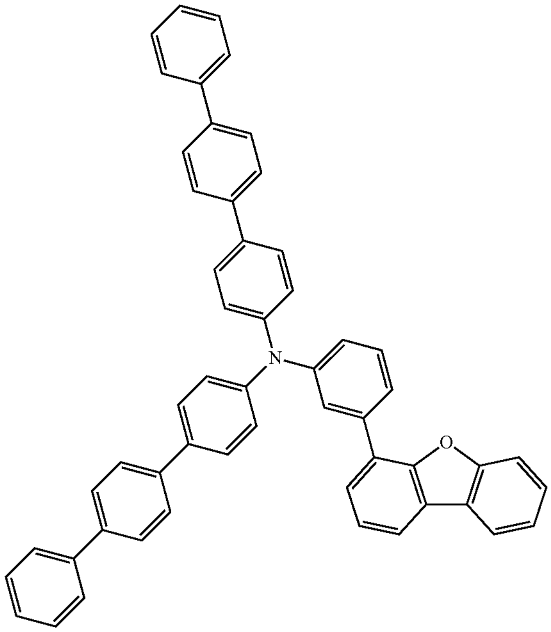
,
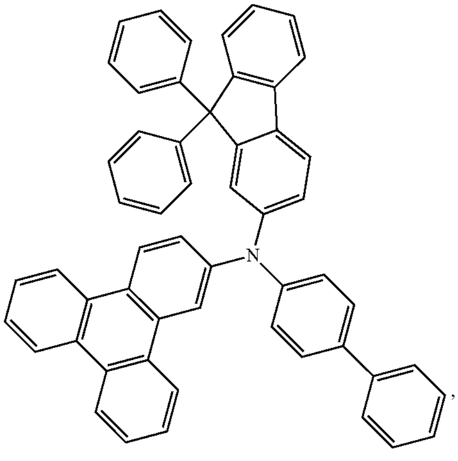
,
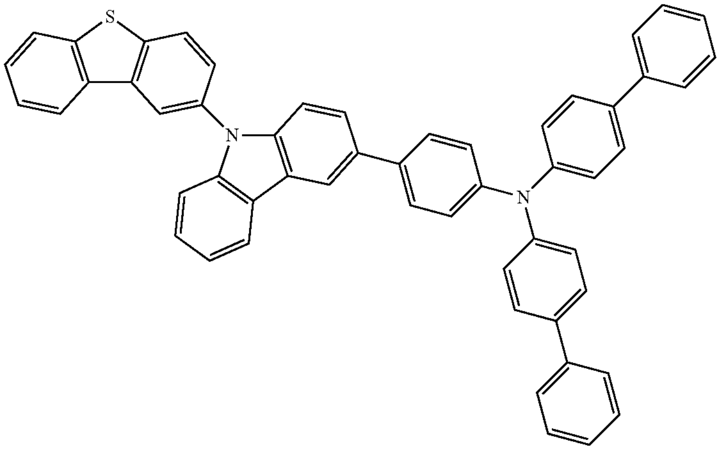
, -continued
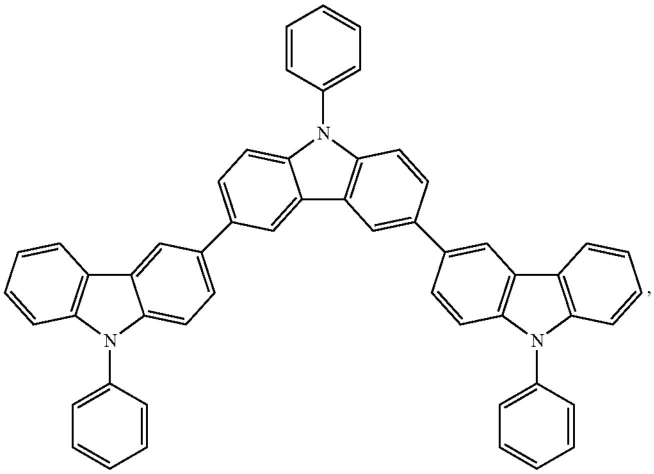,
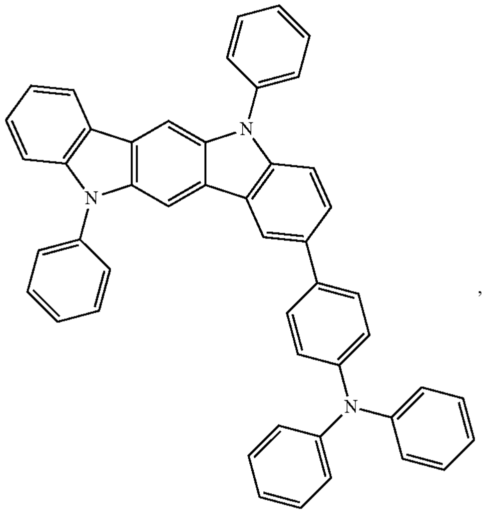,
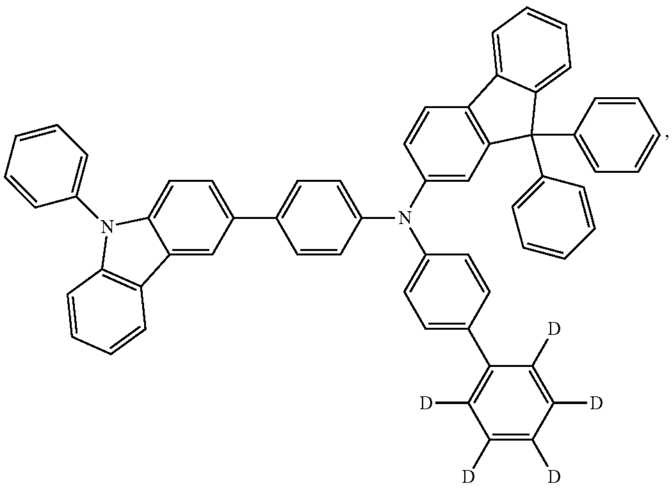,
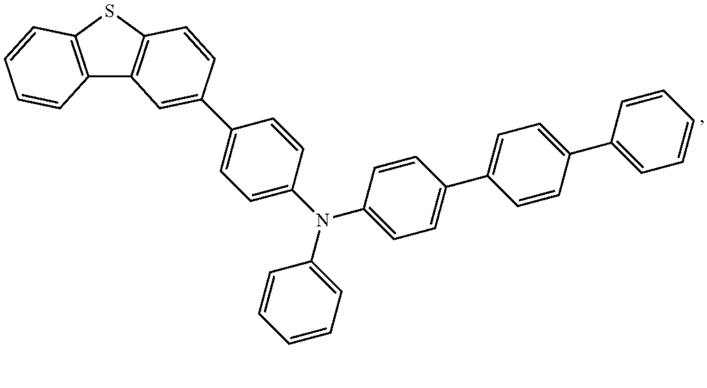, -continued
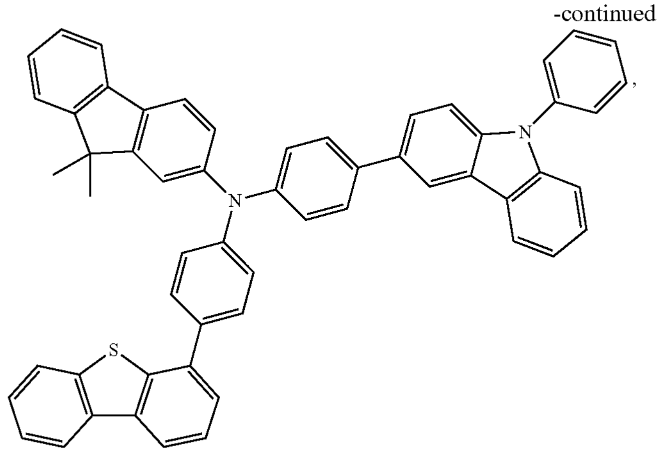
,
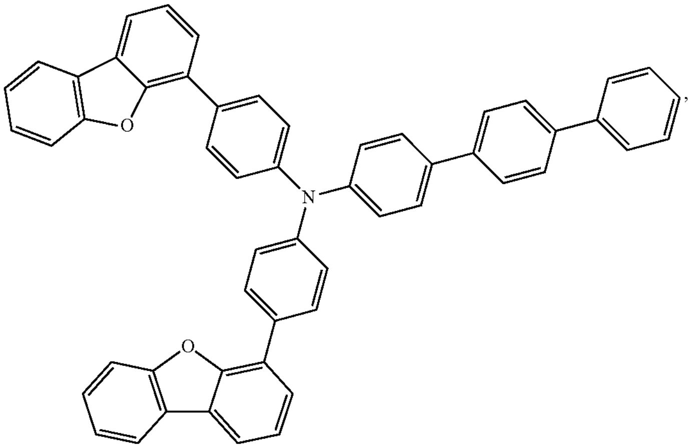
,
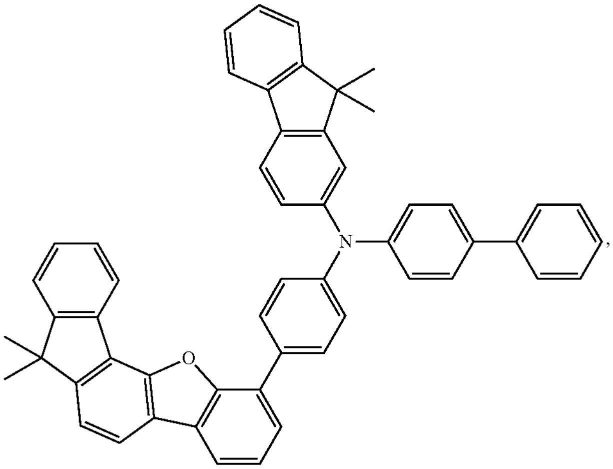
,
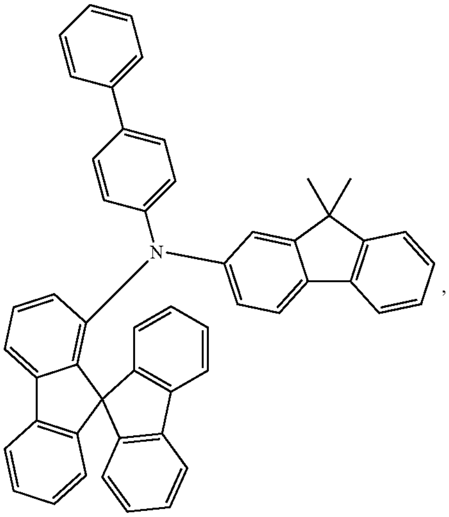
, -continued
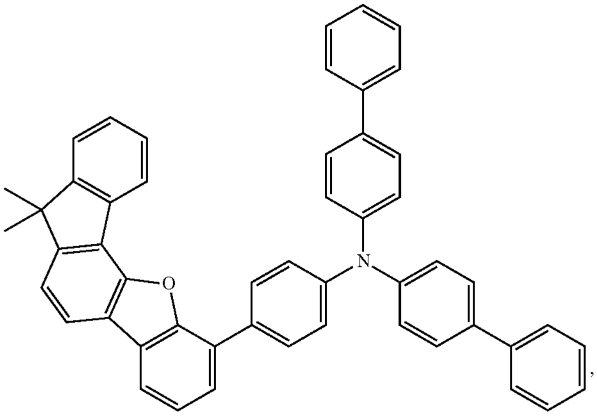
,
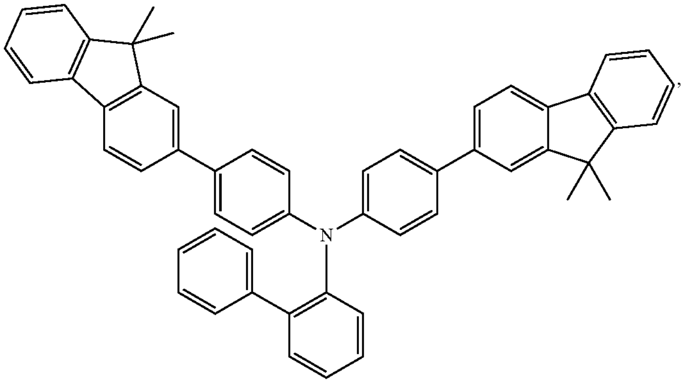
,
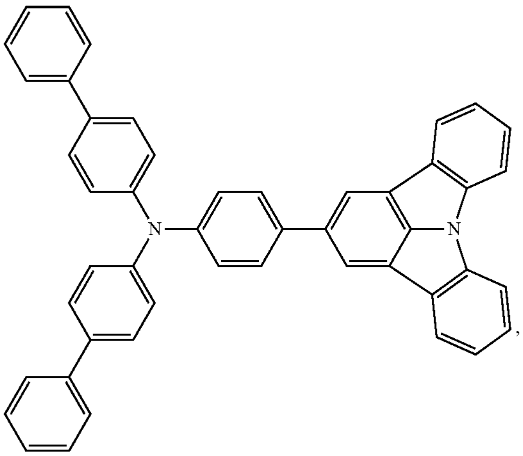
,
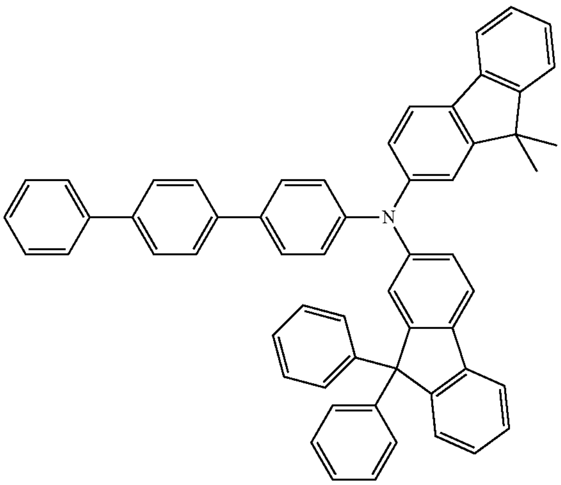
, -continued
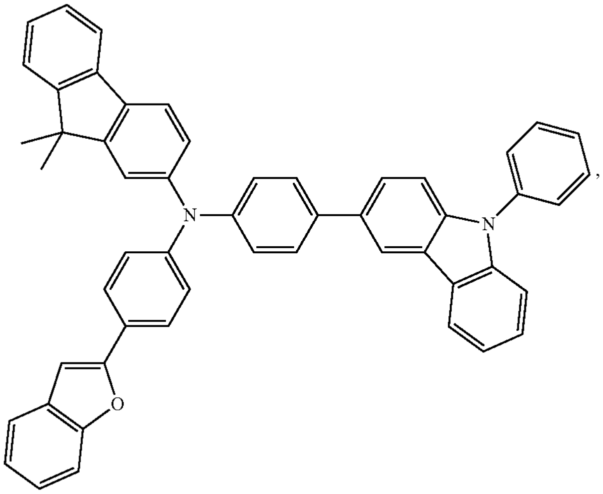,
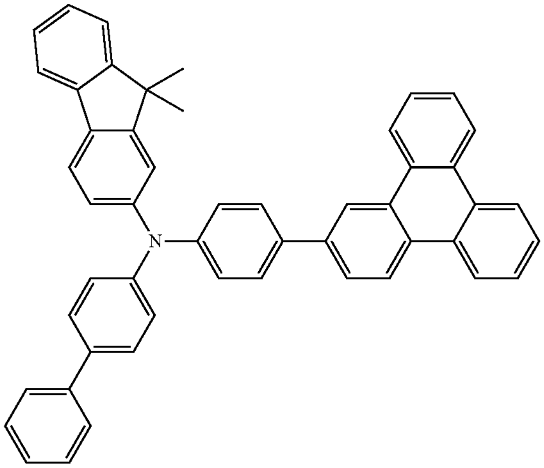,
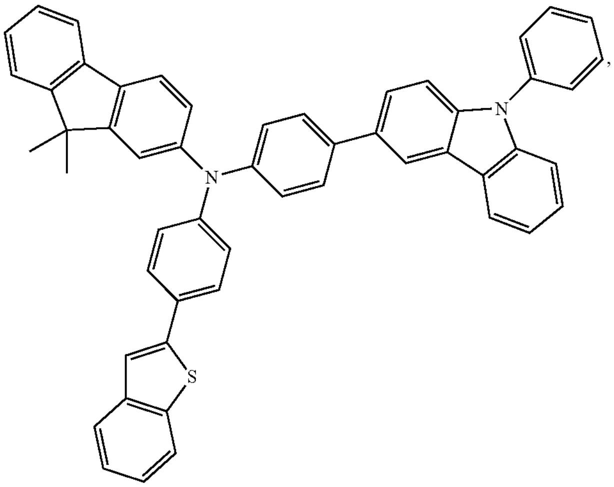,
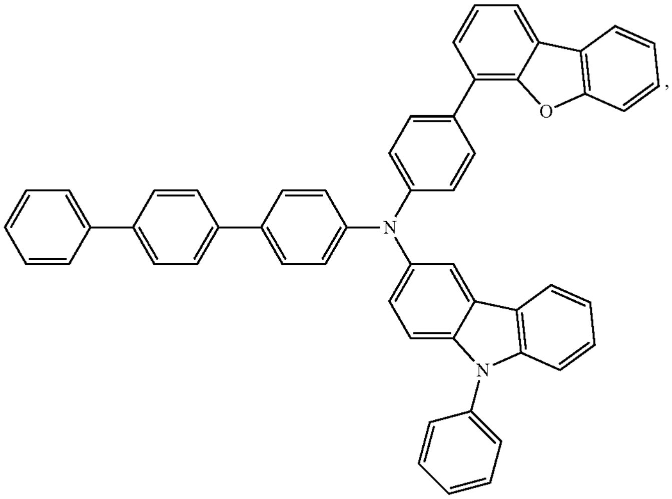, -continued
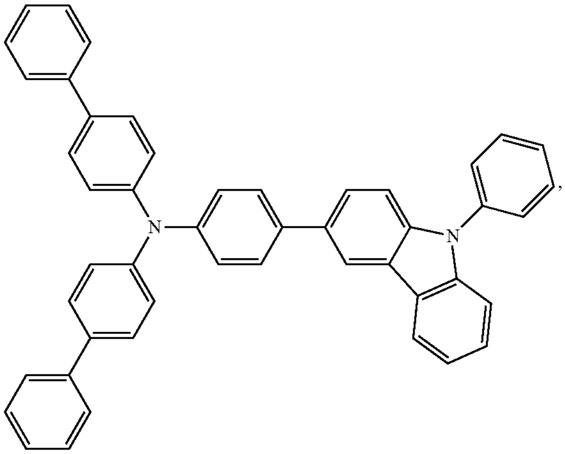
,
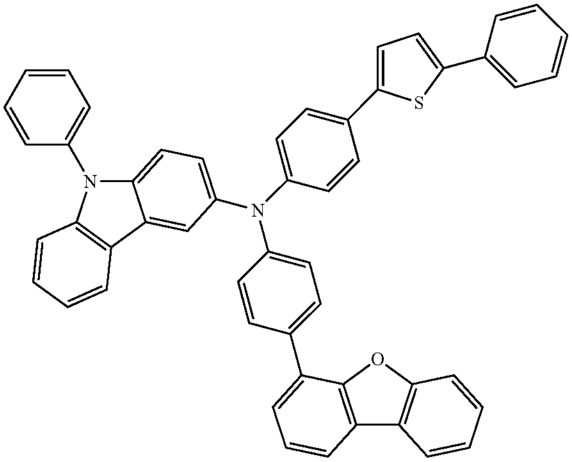
,
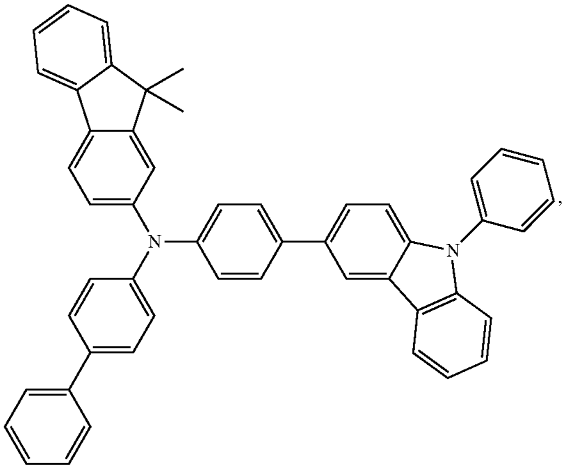
,
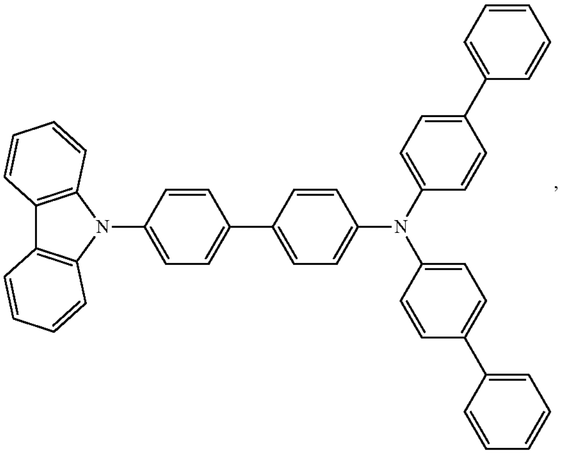
,
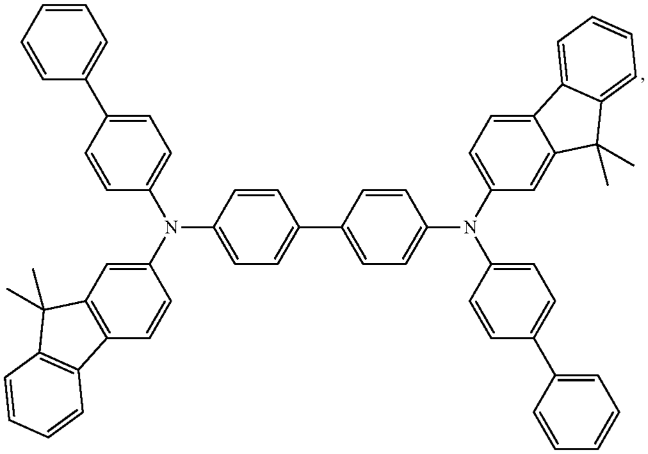
, -continued
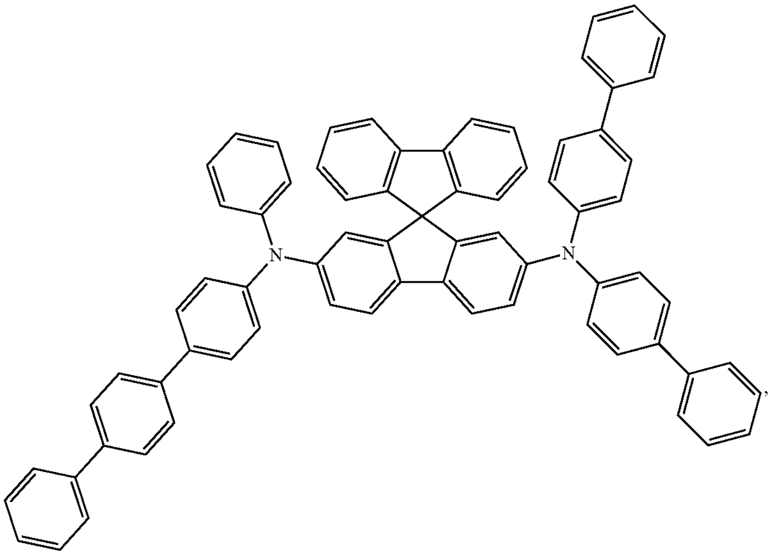
,
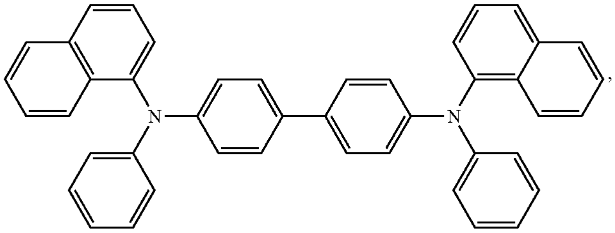
,
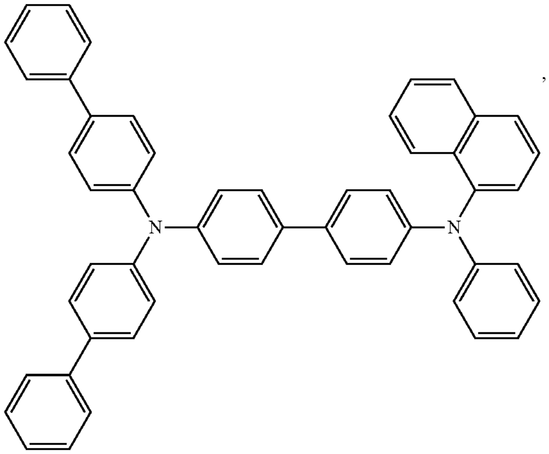
,
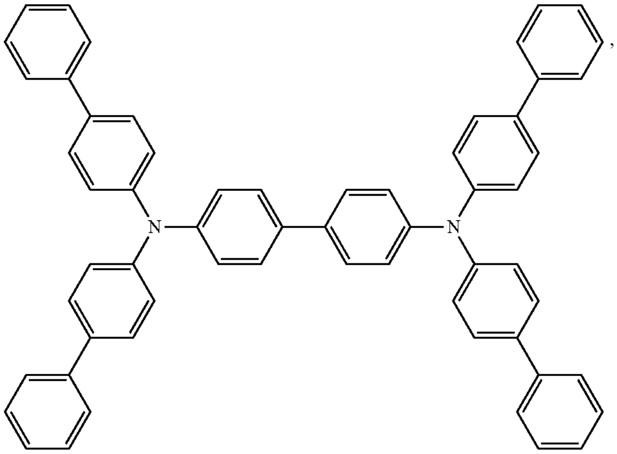
, -continued
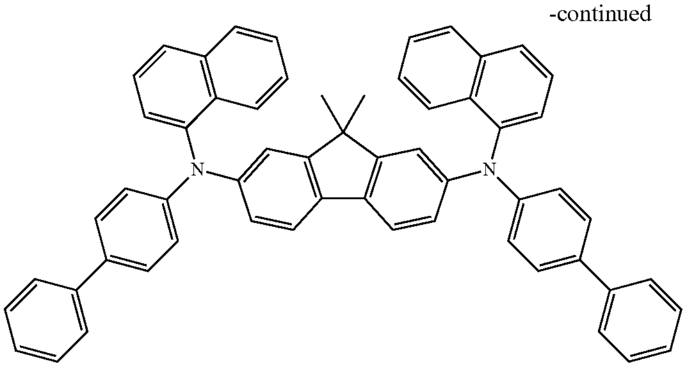
,
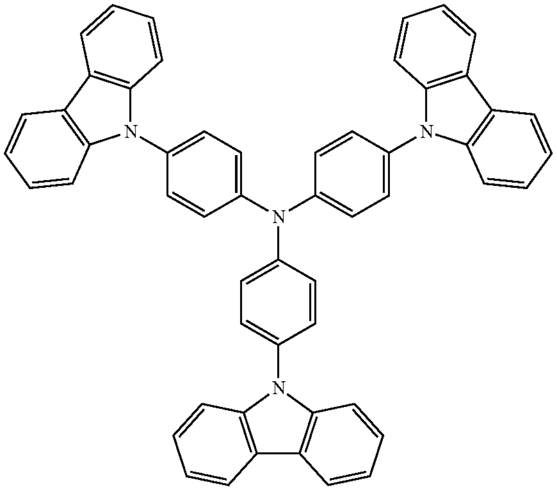
,
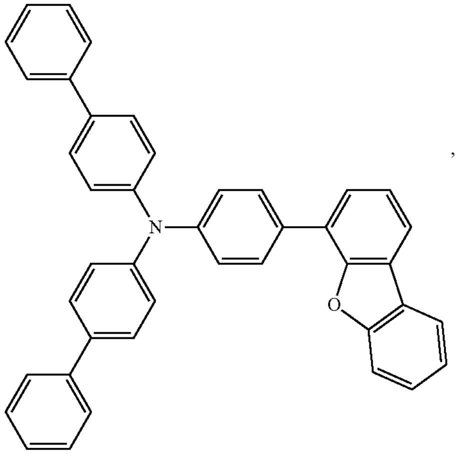
,
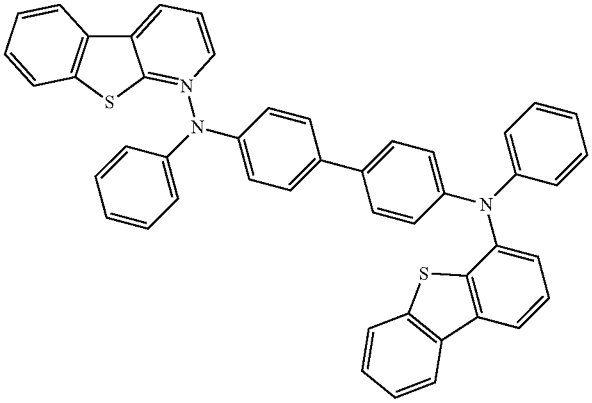
,
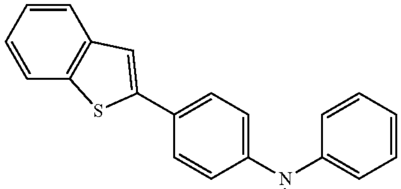
,
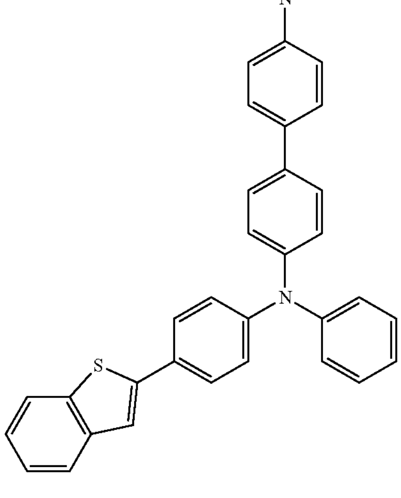
, and -continued

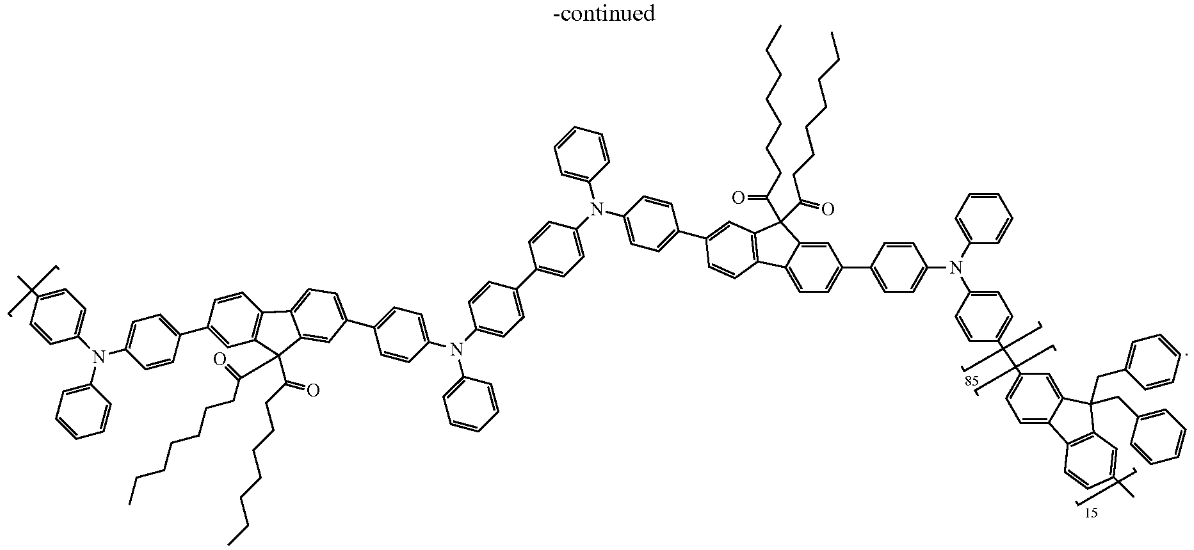

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting dopant material, and may contain one or more additional host materials using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

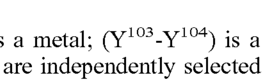

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

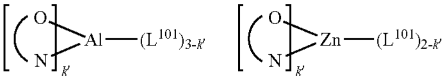

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of other organic compounds used as additional host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

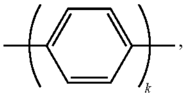
,
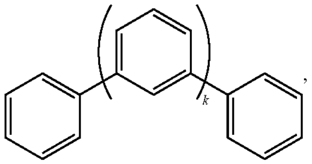
,
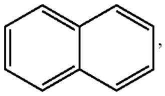
,
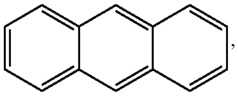
,
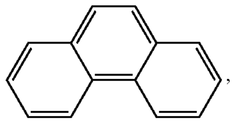
,
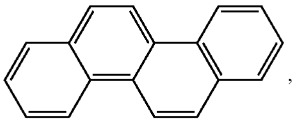
,
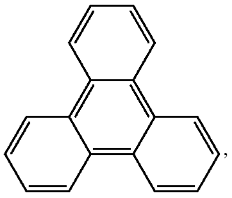
,
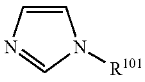
,
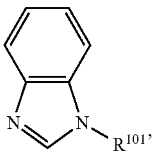
,
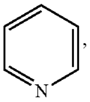
,
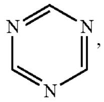
,
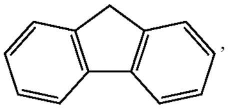
,
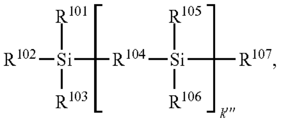
,
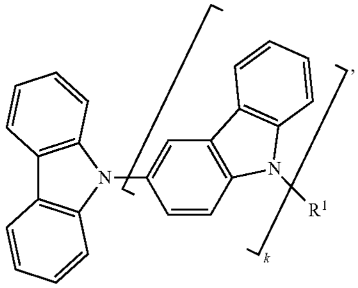
,
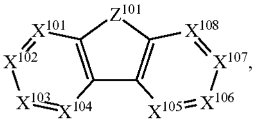
,
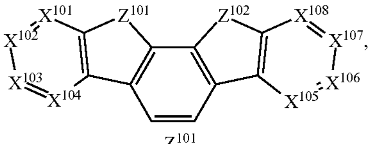
,
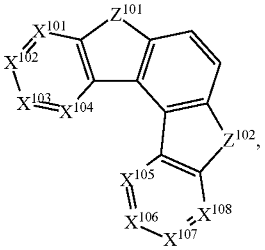
, -continued

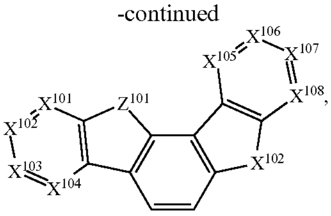
,
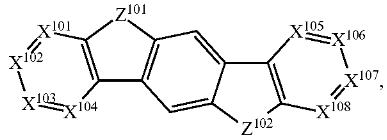
, and
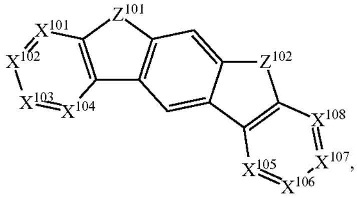
, wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.

$Z^{101}$ and $L^{102}$ is selected from $NR^{101}$, O, or S.

Non-limiting examples of the additional host materials that may be used in an OLED in combination with the host compound disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO02011081431, WO2011086863, WO2012128298, WO2012133644, WO2012133649, WO2013024872, WO2013035275, WO2013081315, WO2013191404, WO2014142472,

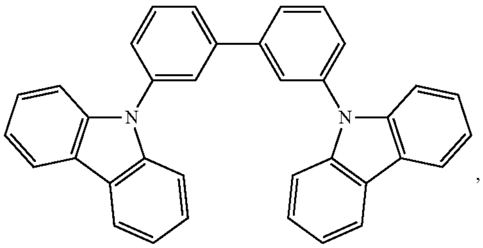
,
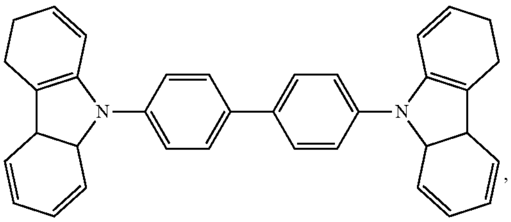
,
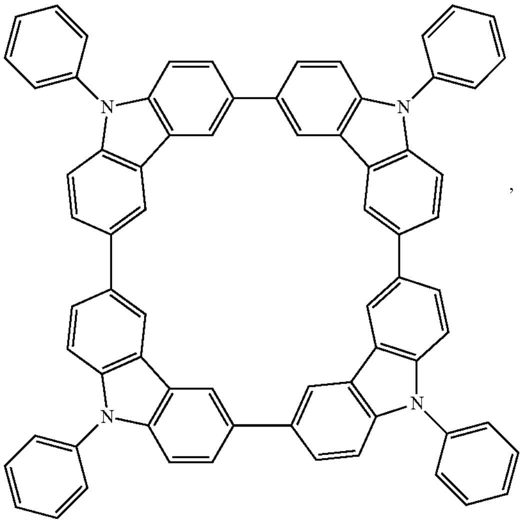
,
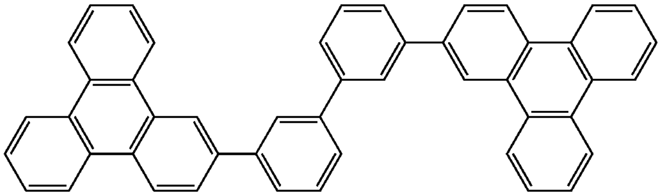
,
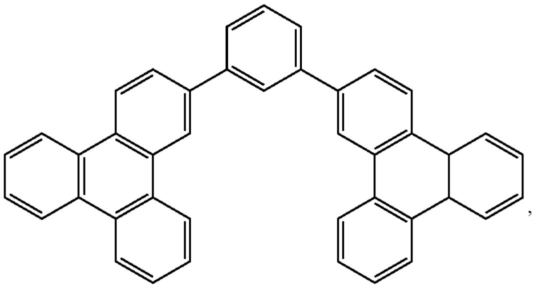
,
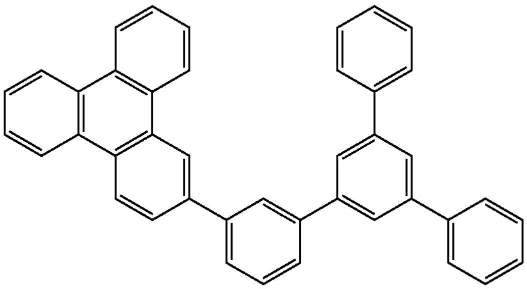
,
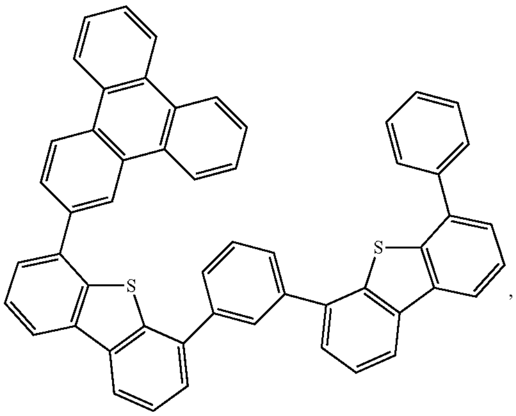
,
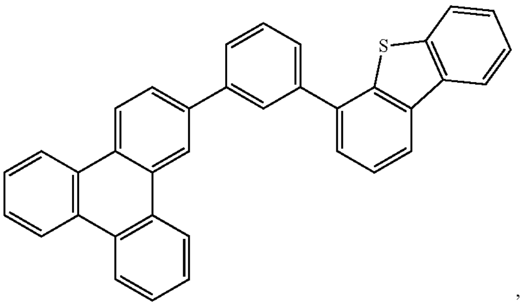
, -continued
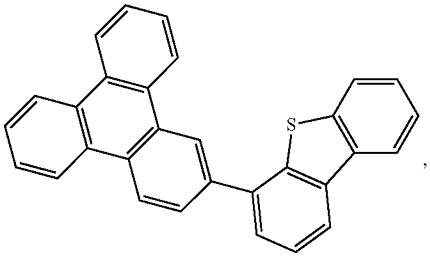
,
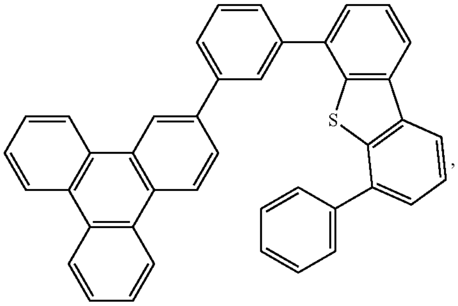
,
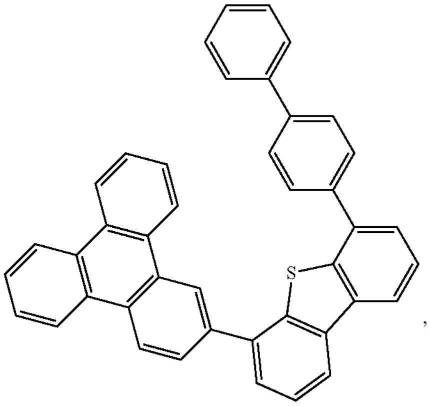
,
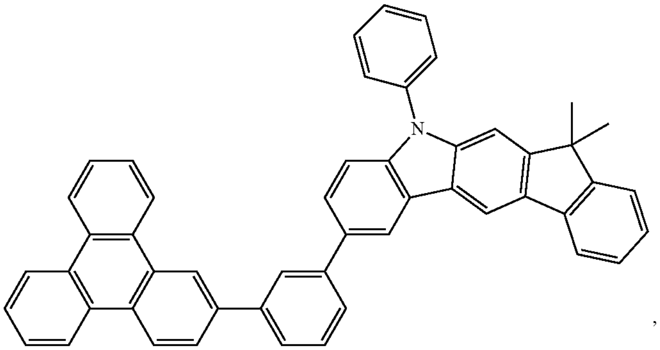
,
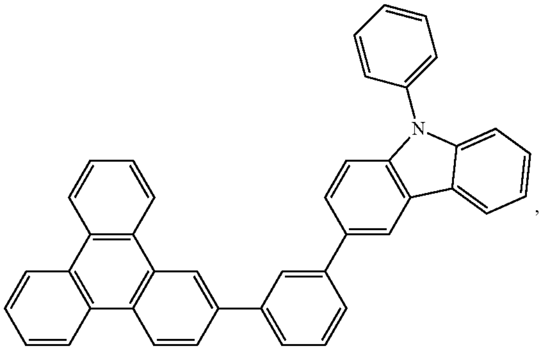
,
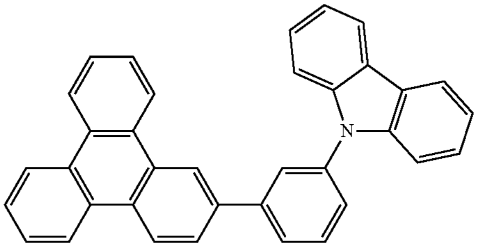
,
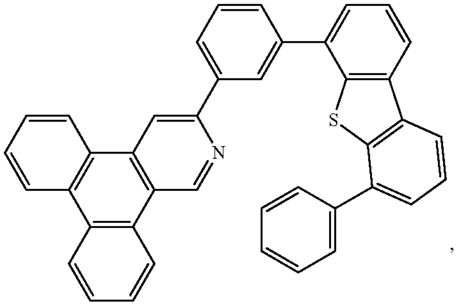
,
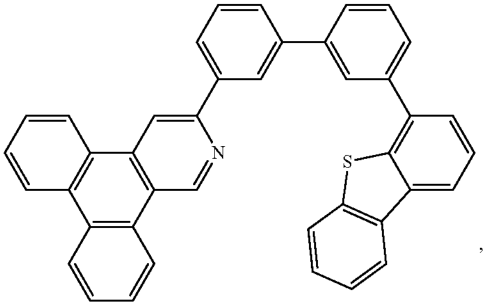
,
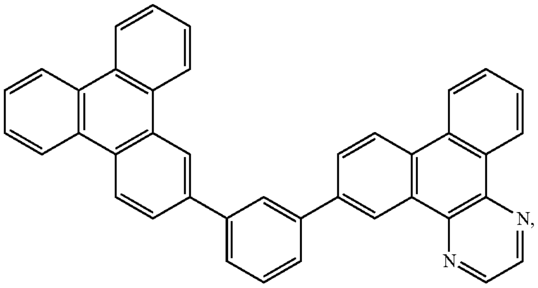
,
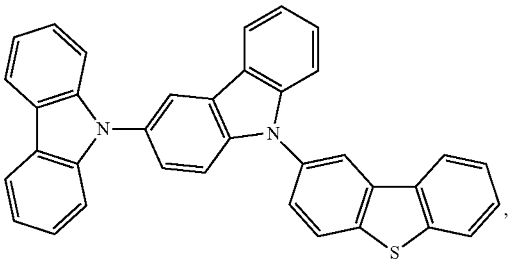
, -continued
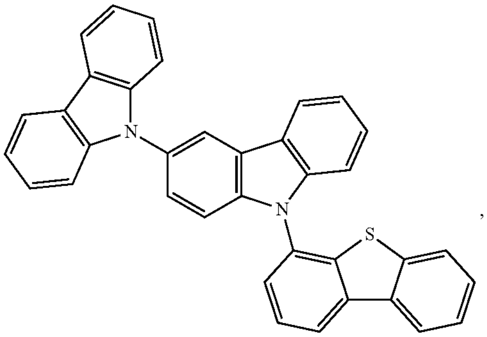
,
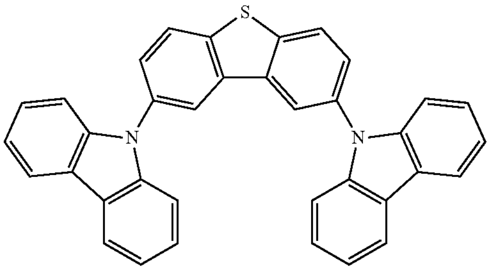
,
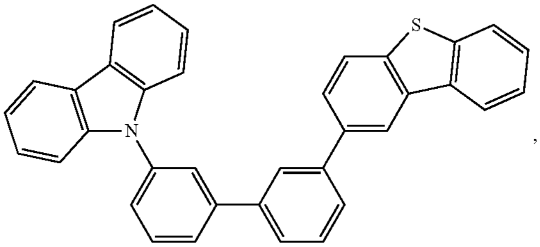
,
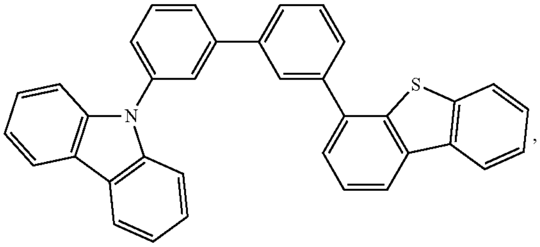
,
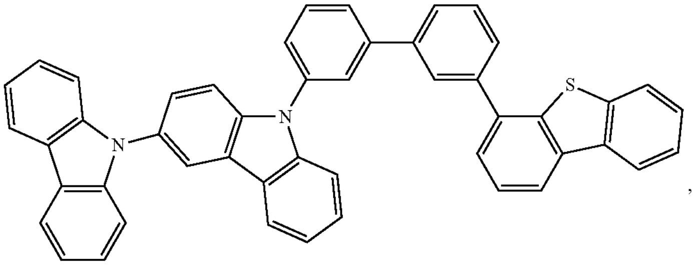
,
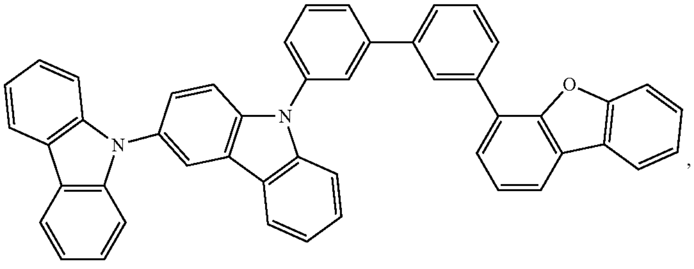
,
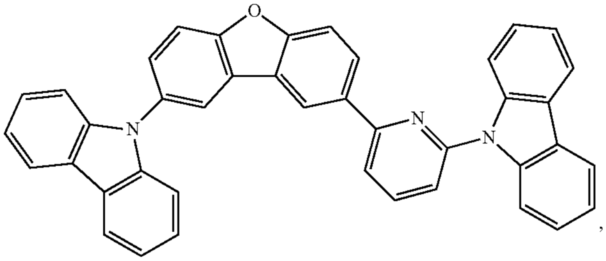
,
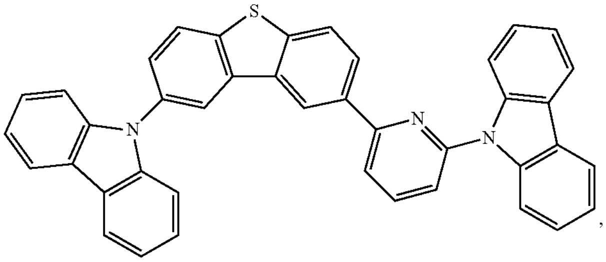
, -continued
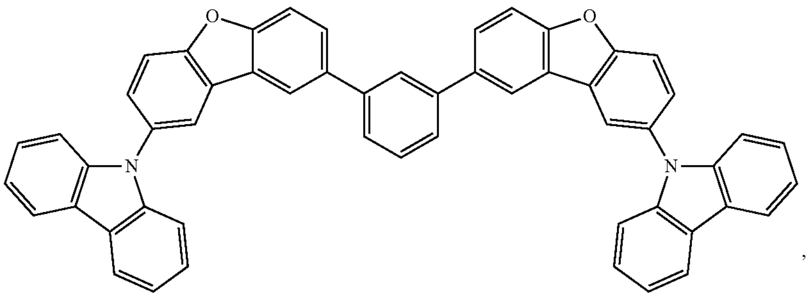
,
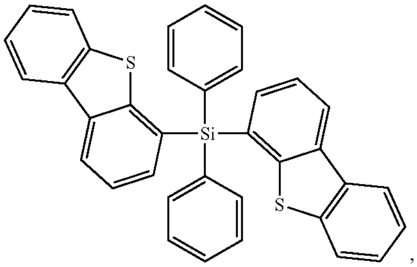
,
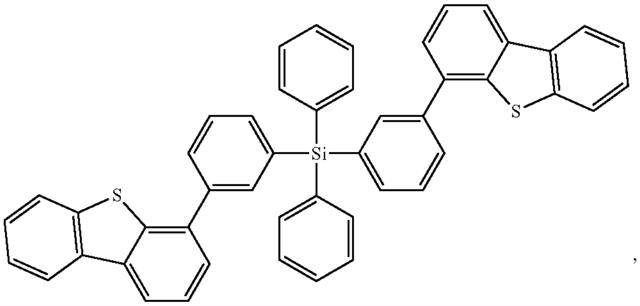
,
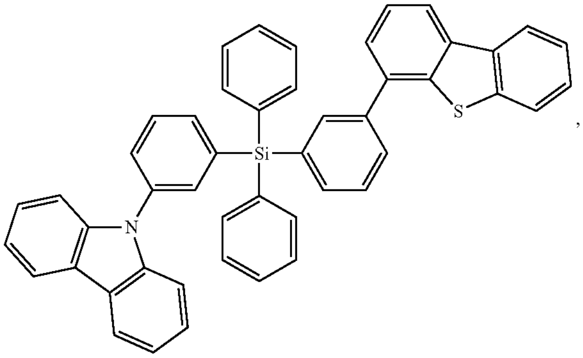
,
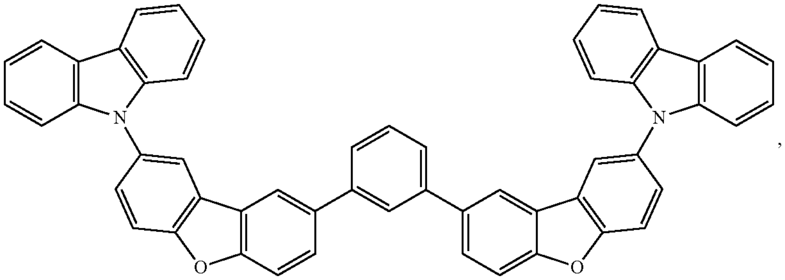
,
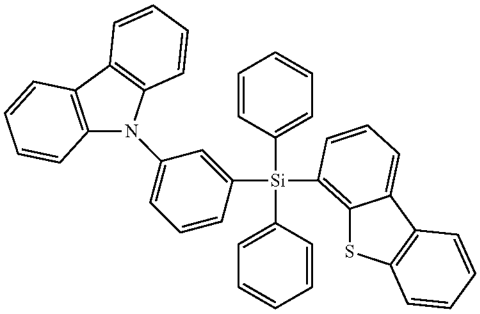
,
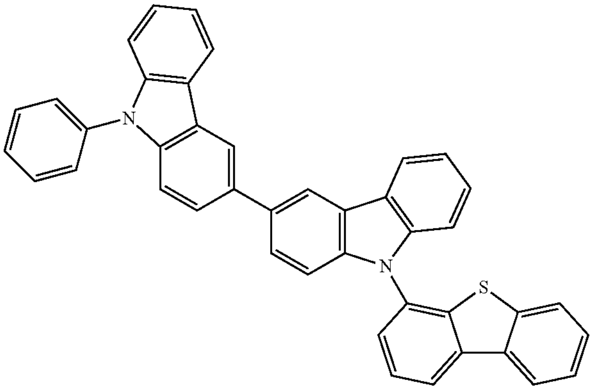
, -continued
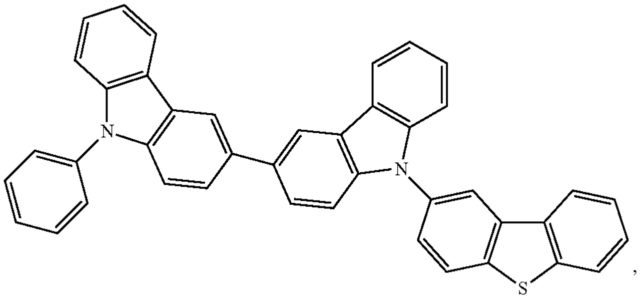
,
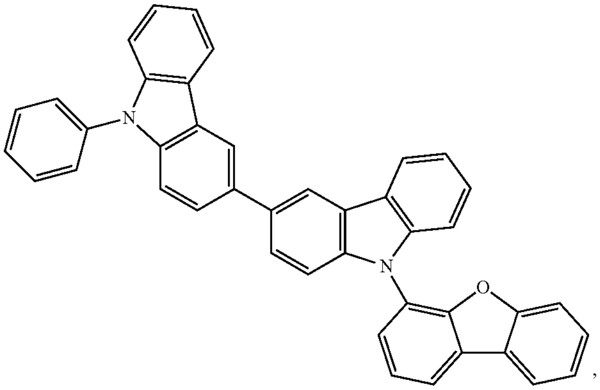
,
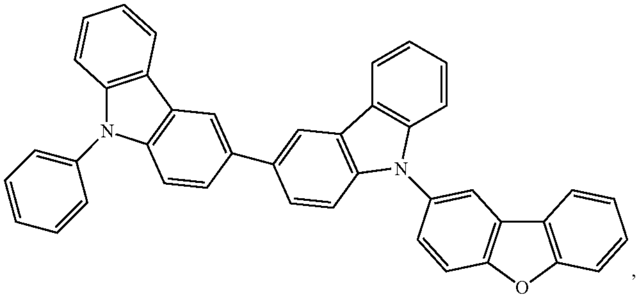
,
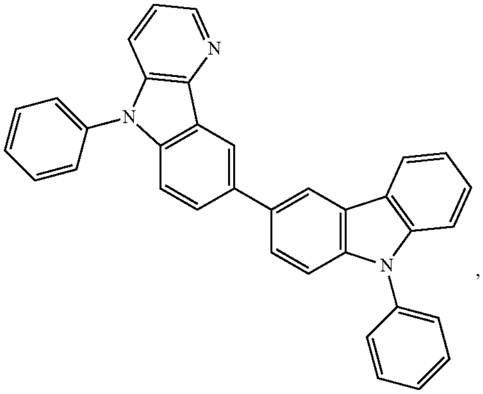
,
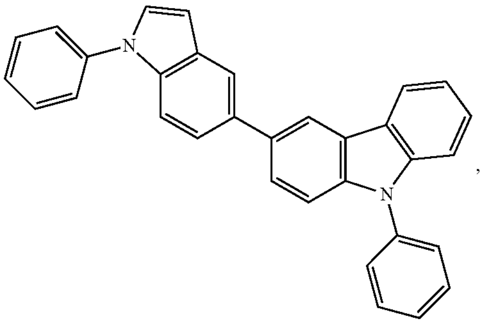
,
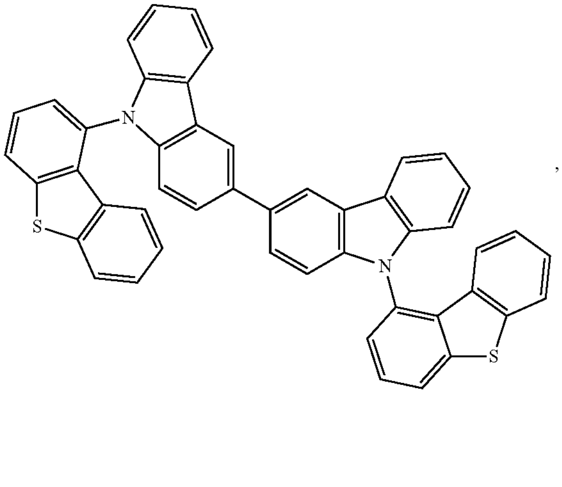
, -continued
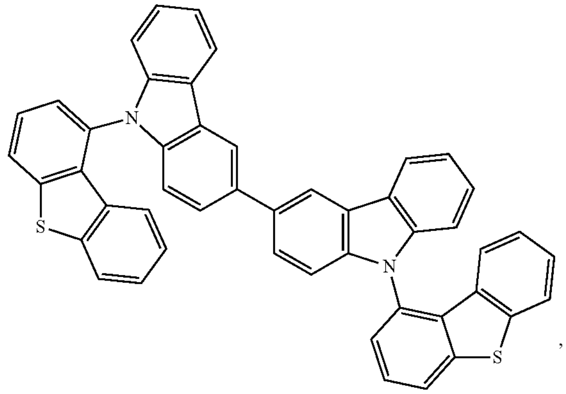
,
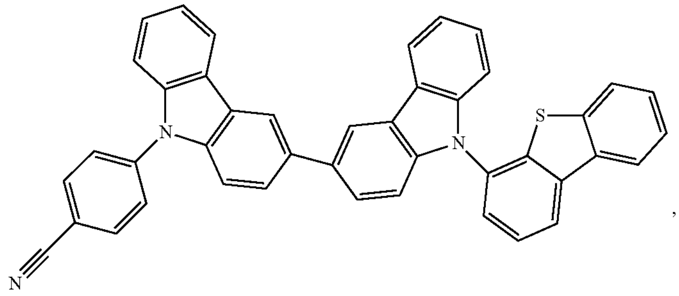
,
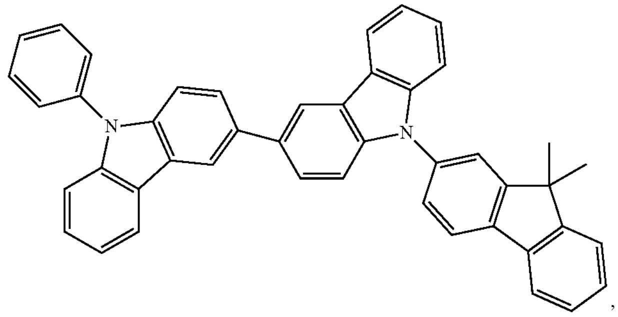
,
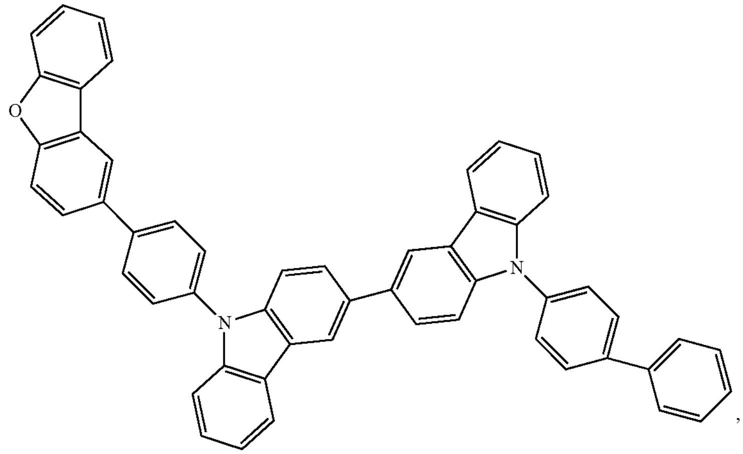
, -continued
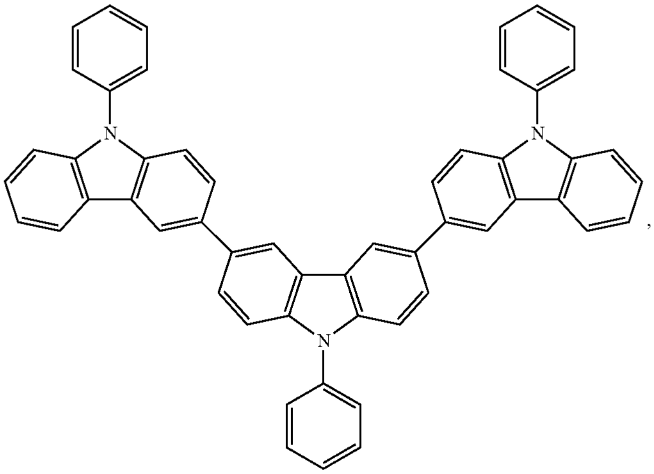
,
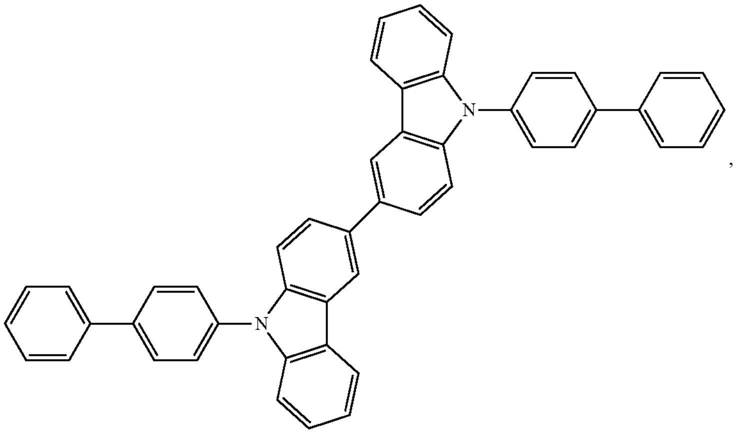
,
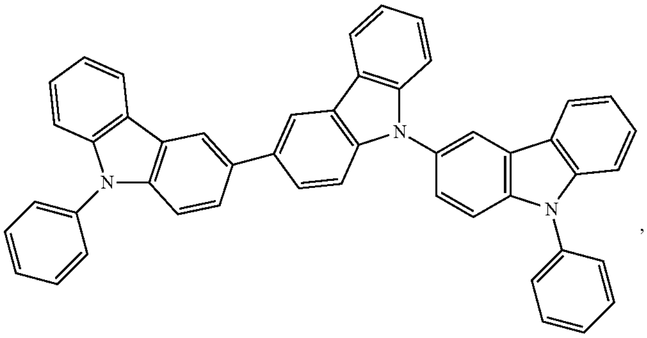
,
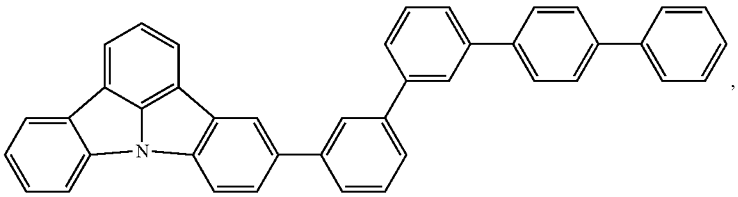
, -continued
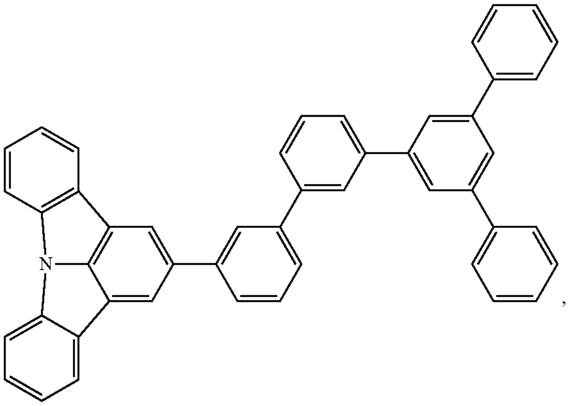
,
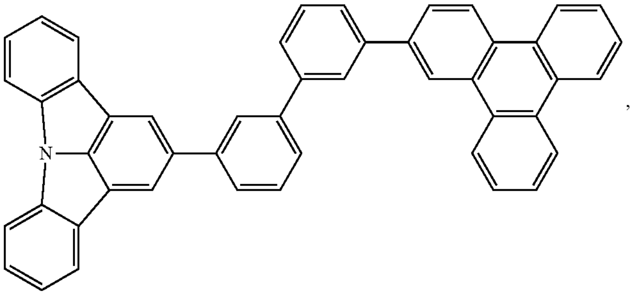
,
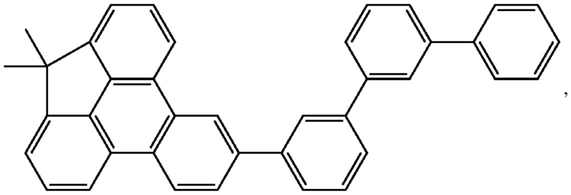
,
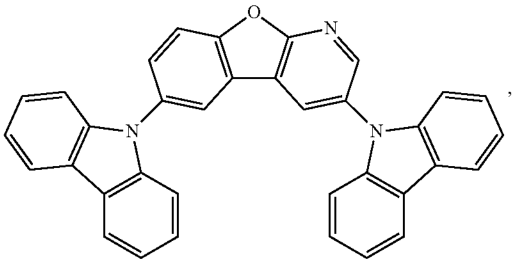
,
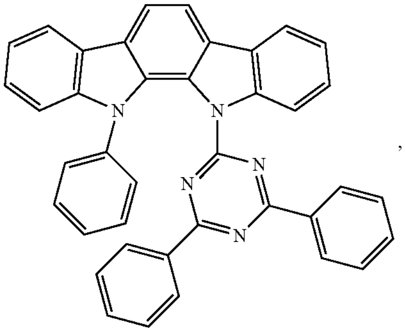
,
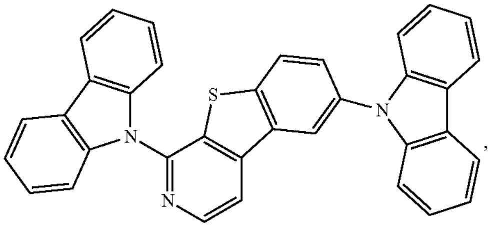
,
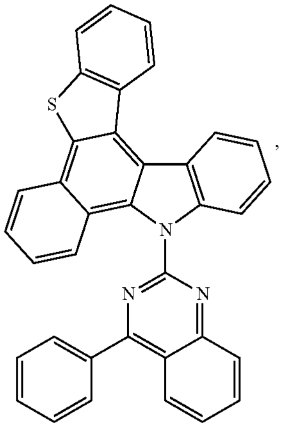
, -continued
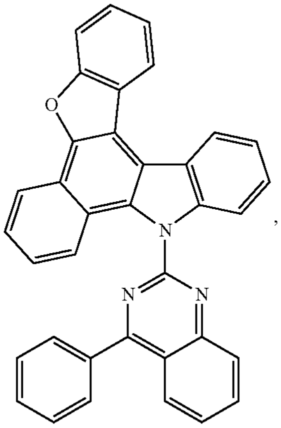
,
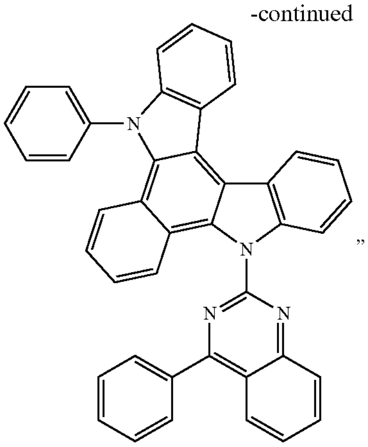
,,
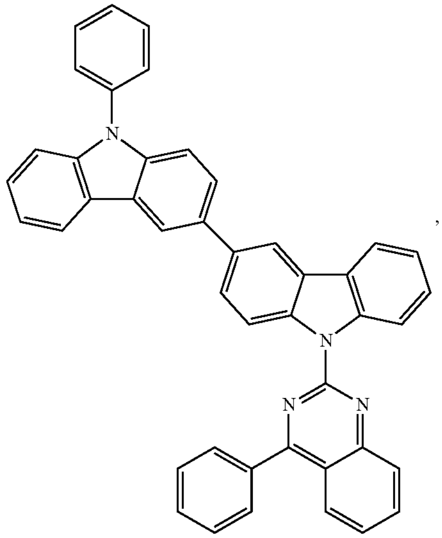
,
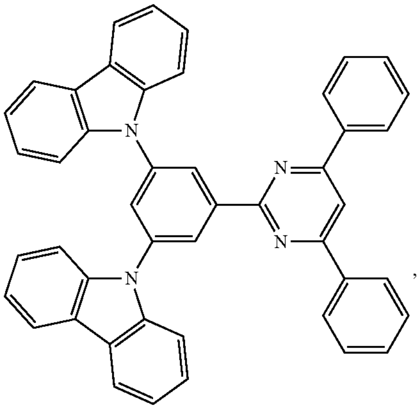
,
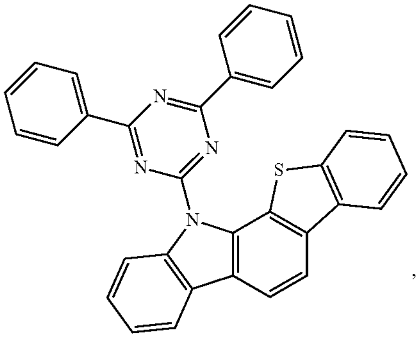
,
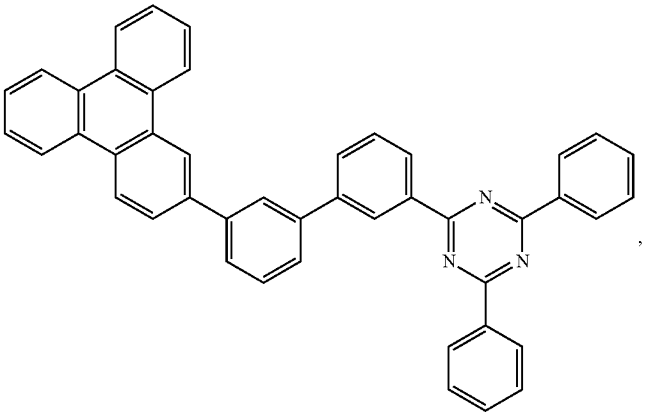
,
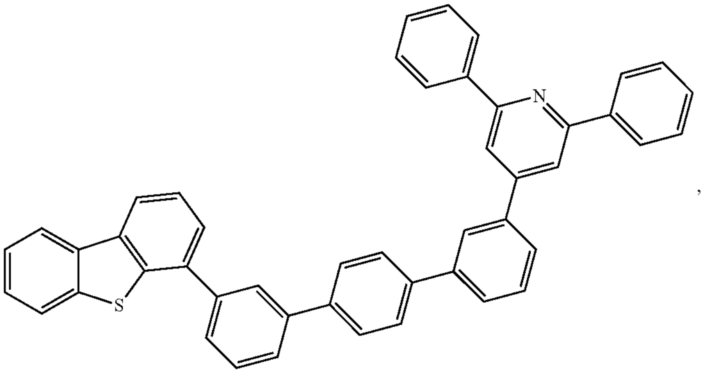
, -continued
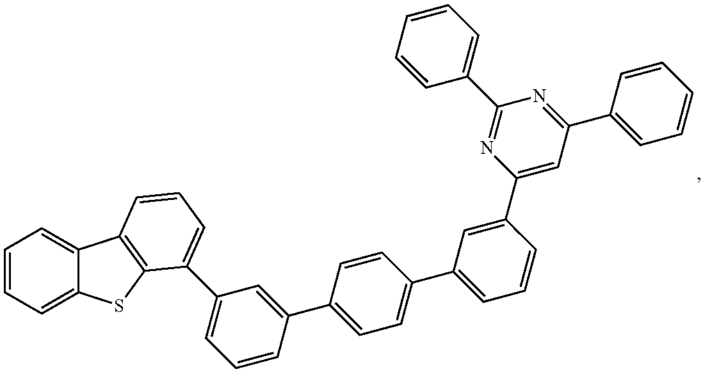
,
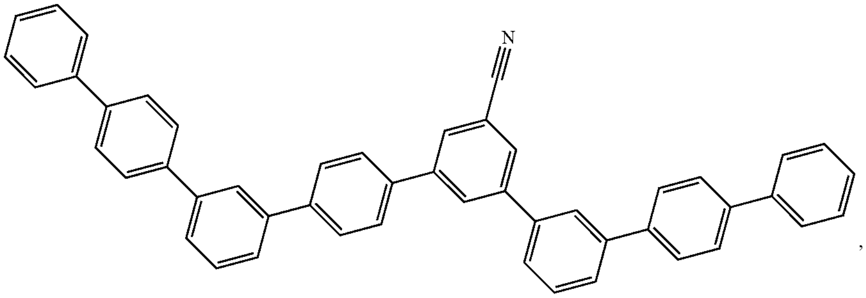
,
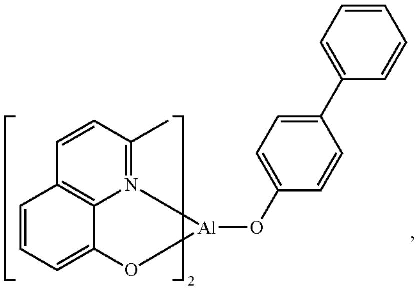
,
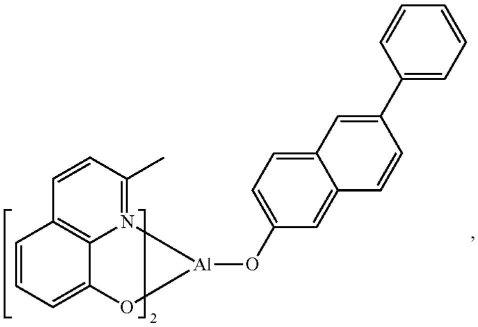
,
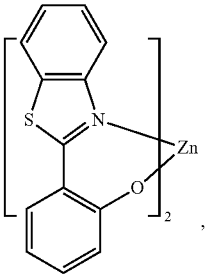
,
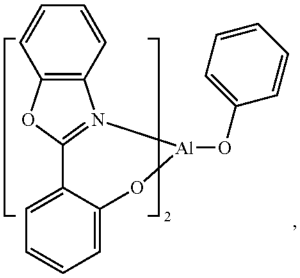
,
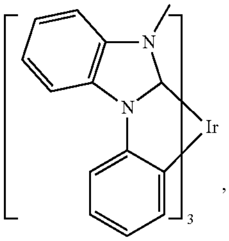
,
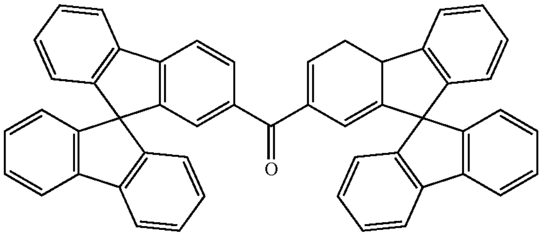
,
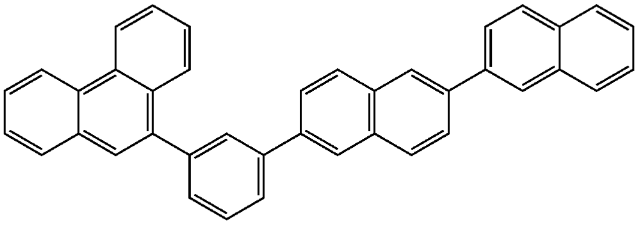
, -continued

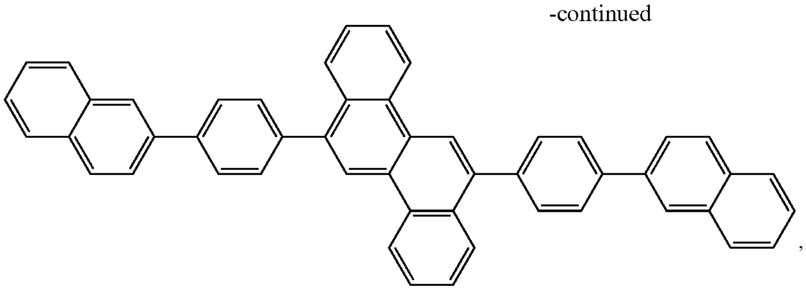

, and

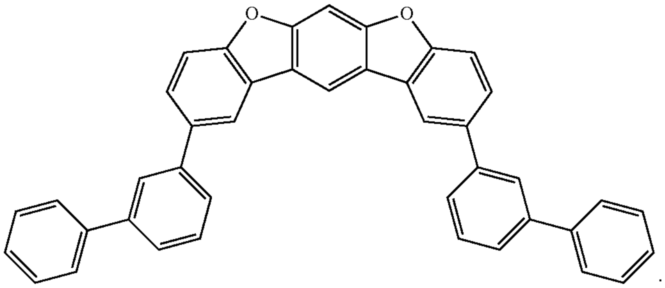

.

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450,

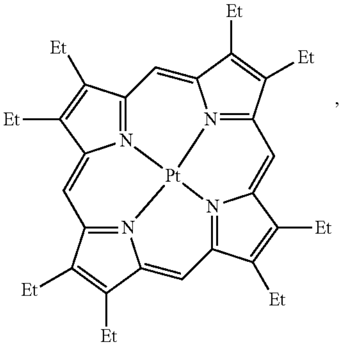

,

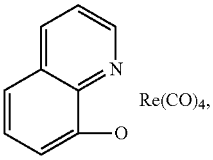

,

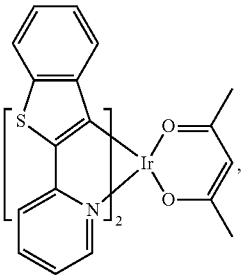

,

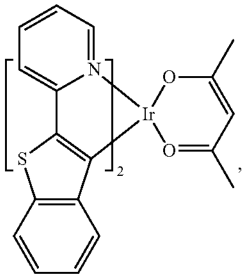

,

-continued
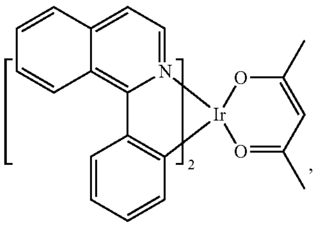,
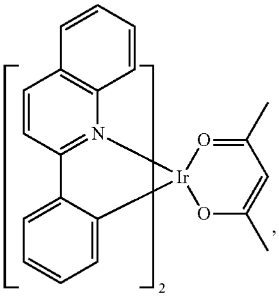,
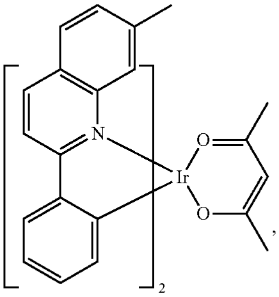,
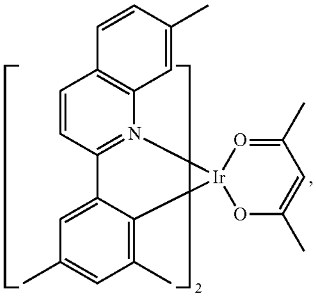,
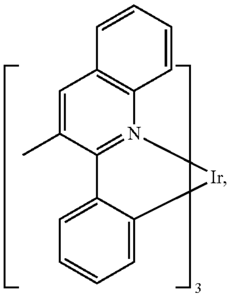
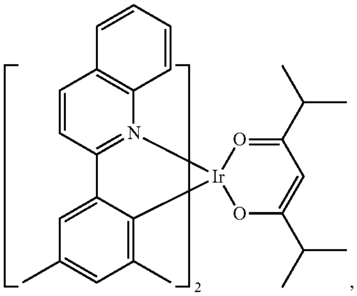,
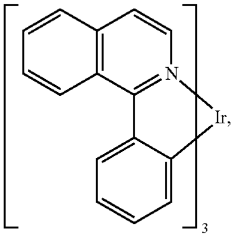
-continued
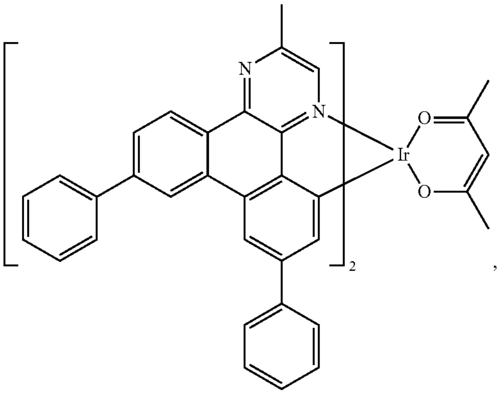,
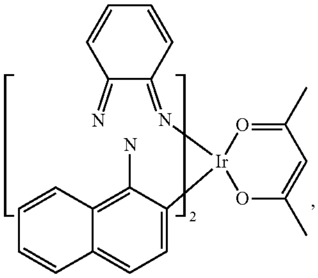,
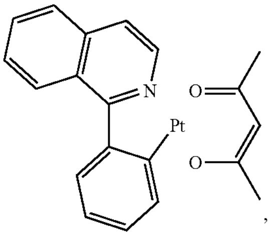,
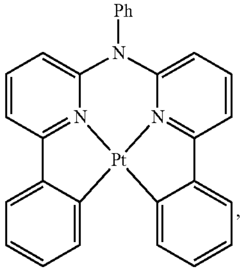,
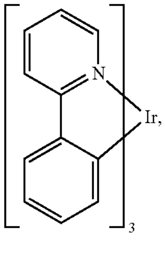
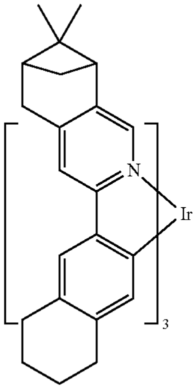,
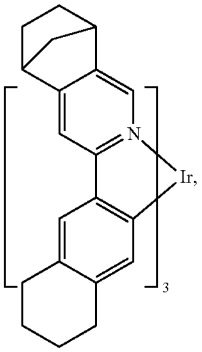

-continued
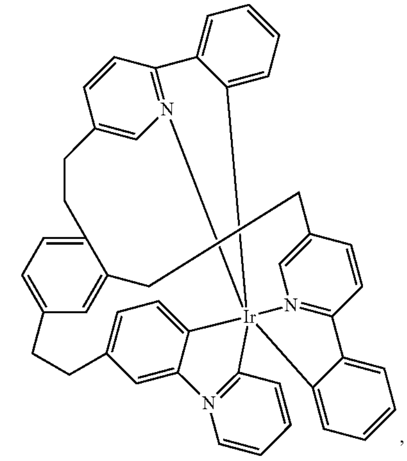
,
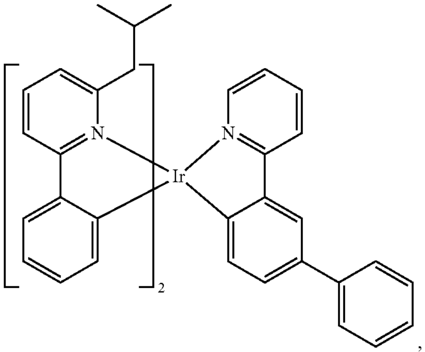
,
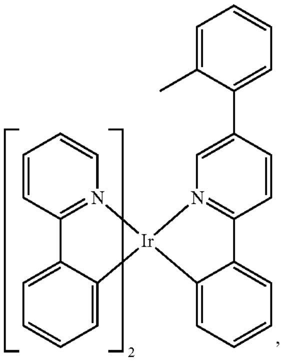
,
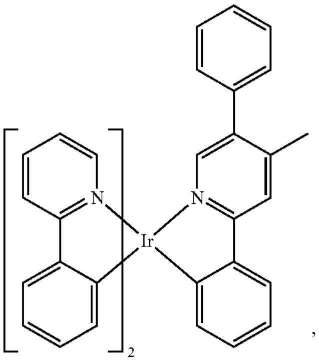
,
-continued
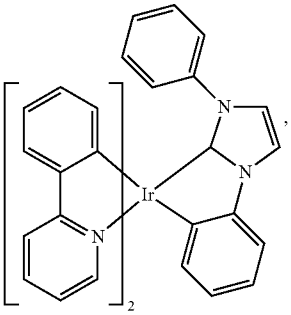
,
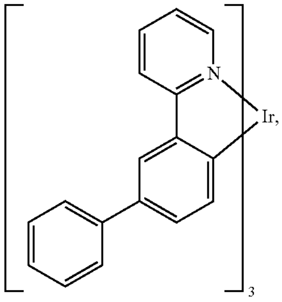
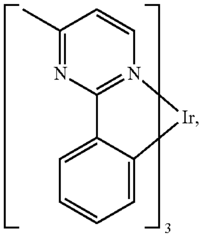
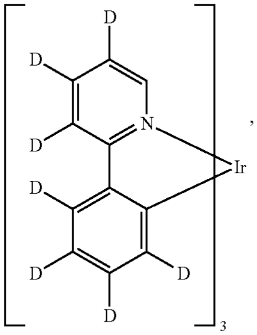
,
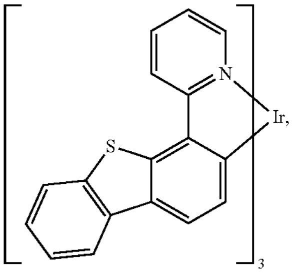
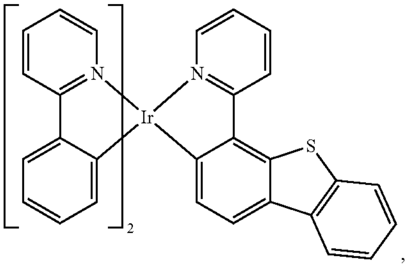
,
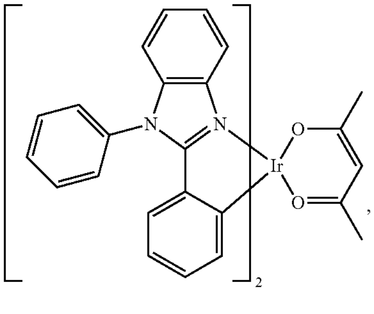
, -continued
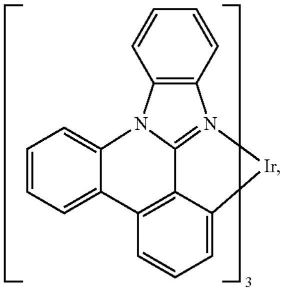
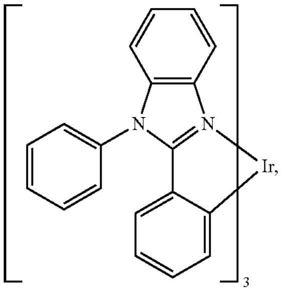
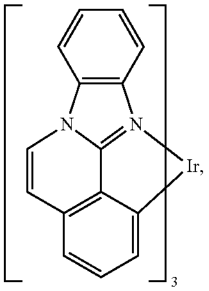
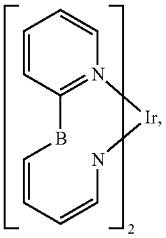
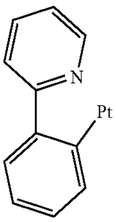
,
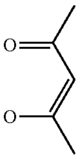
,
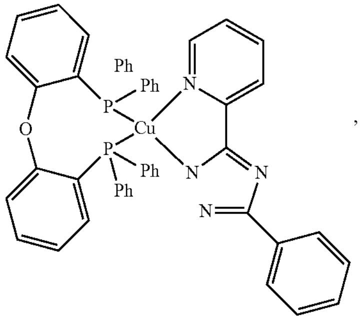
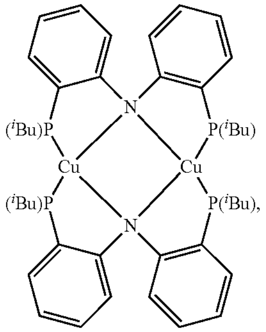
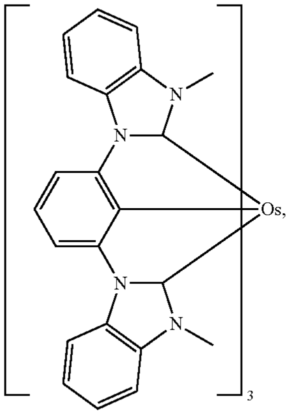
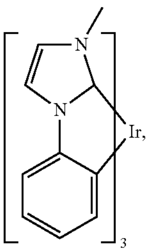
-continued
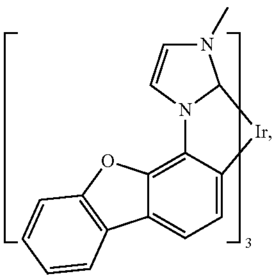
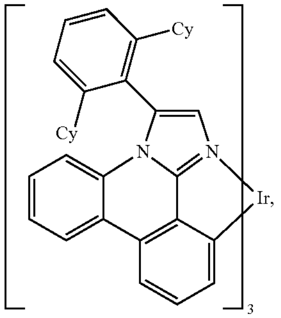
,
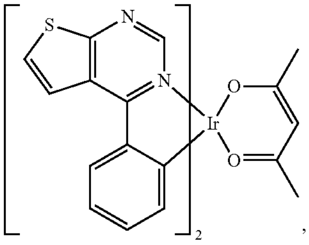
,
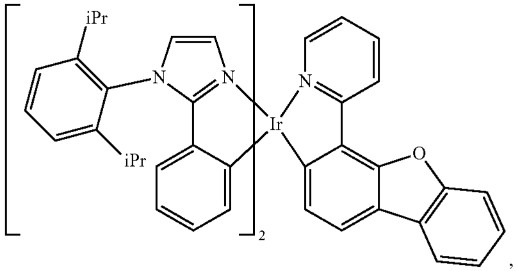
,
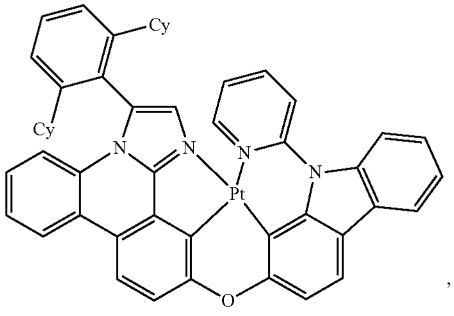
,
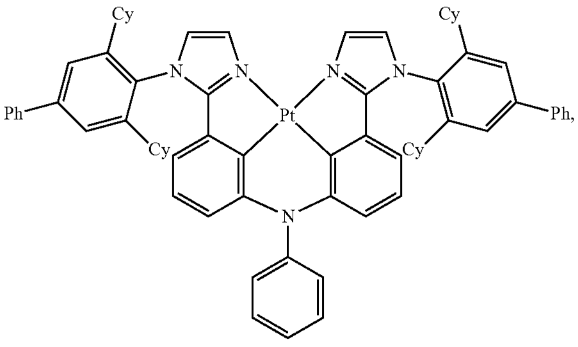

-continued
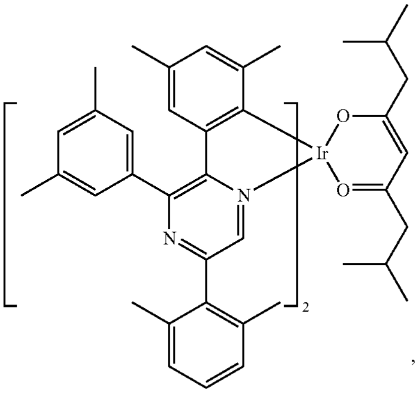
,
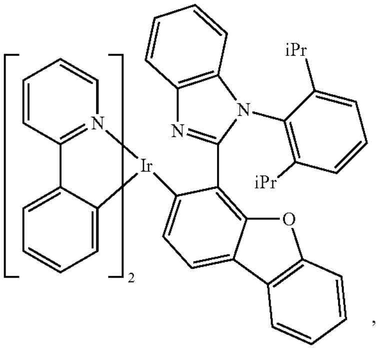
,
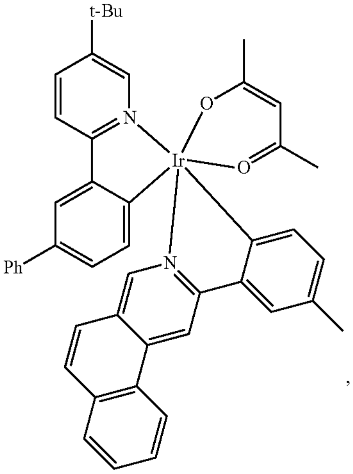
,
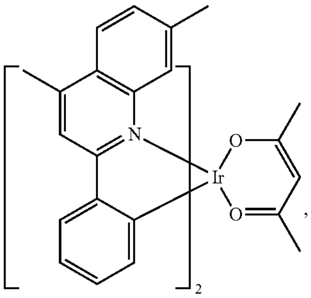
,
-continued
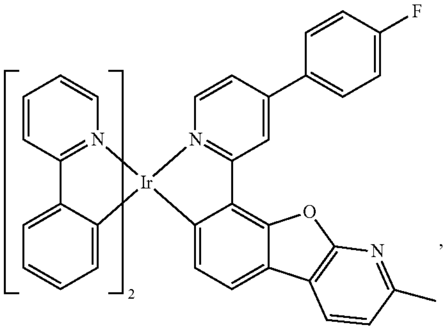
,
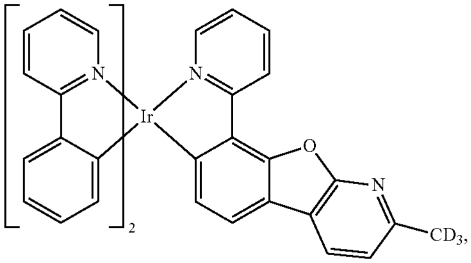
,
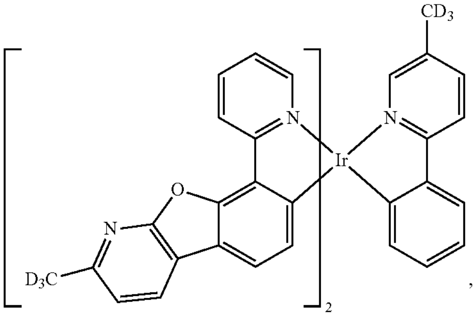
,
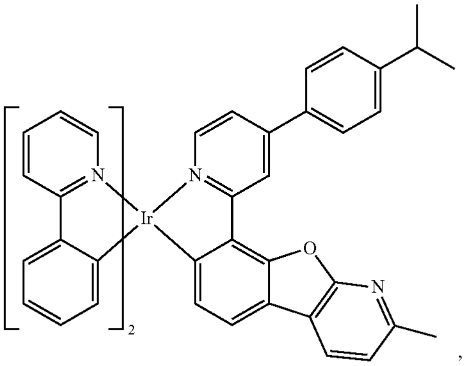
,
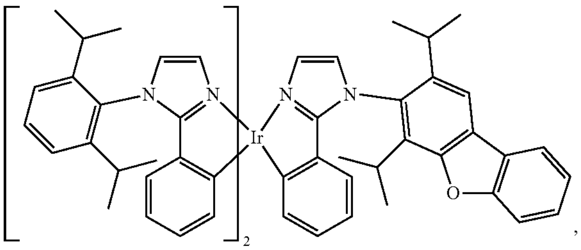
, -continued
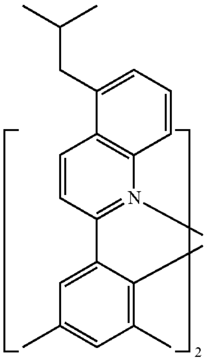
,
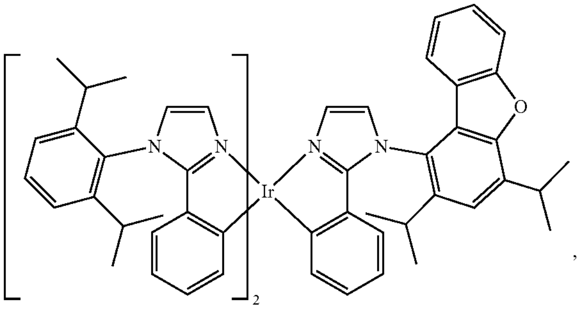
,
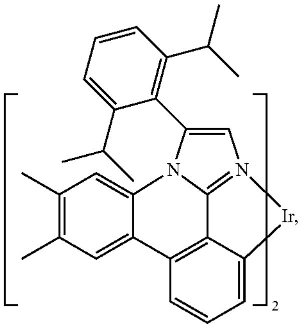
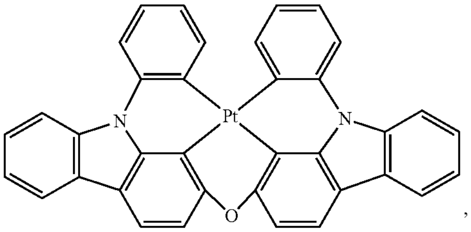
,
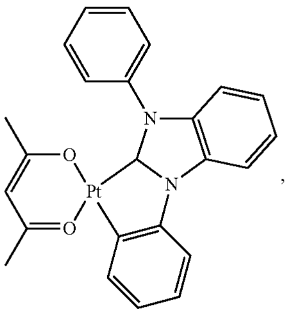
,
-continued
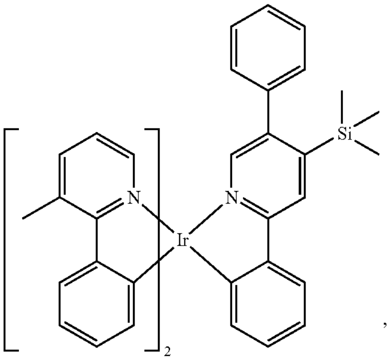
,
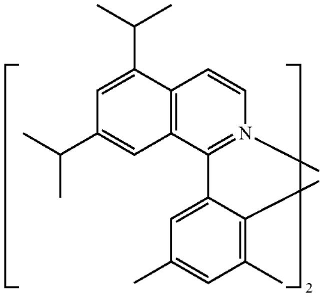
,
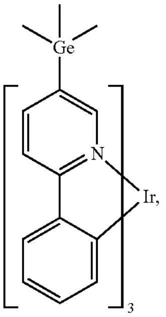
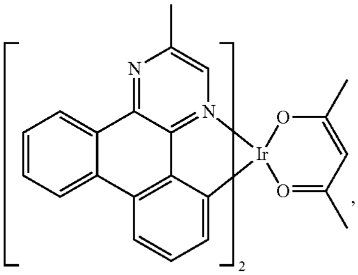
,
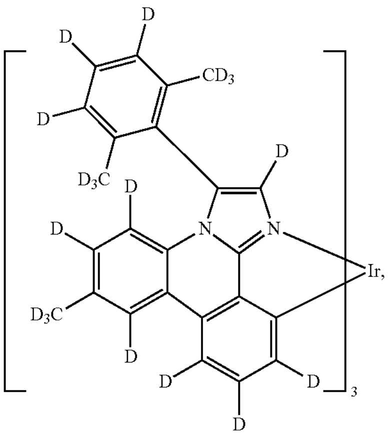

-continued
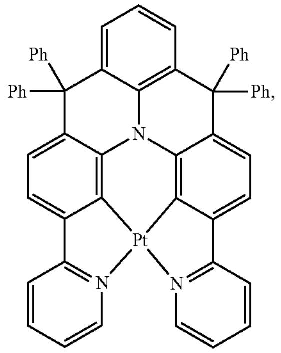
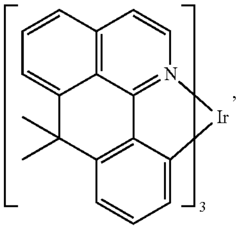
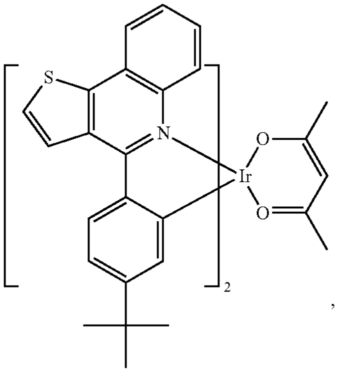
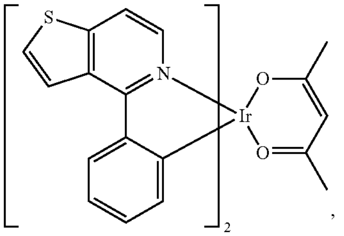
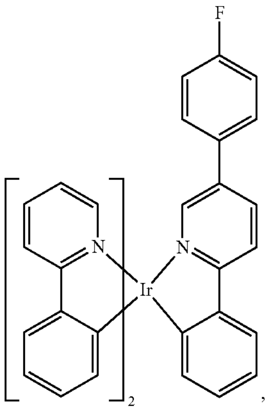
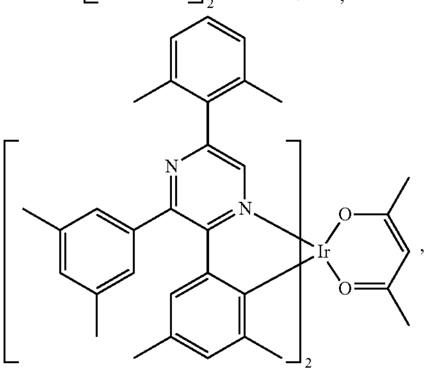
-continued
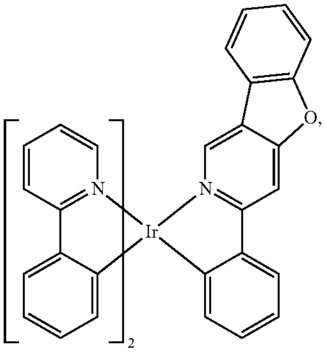
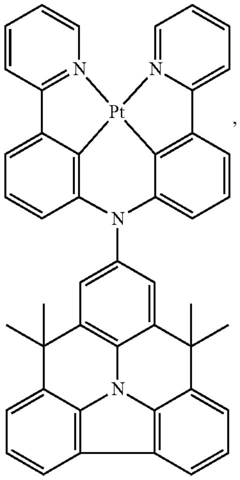
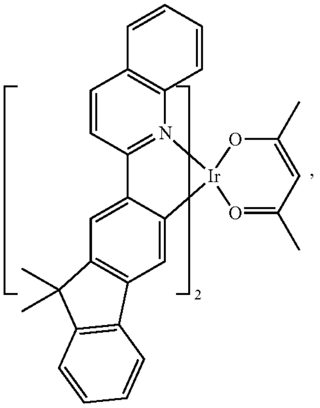
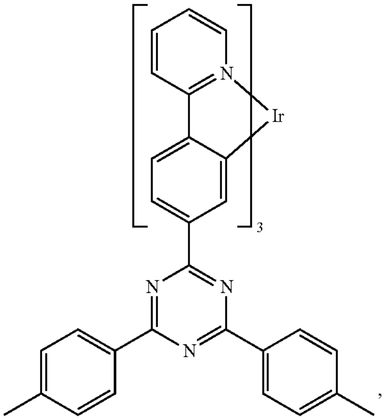
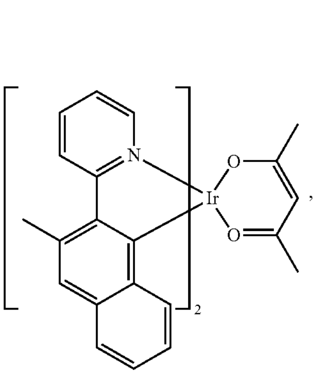

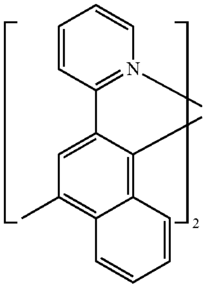
,
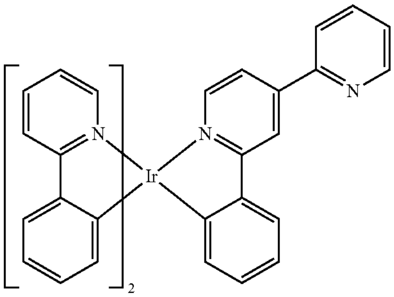
,
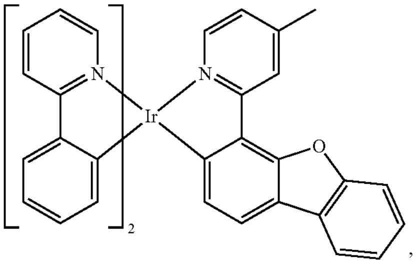
,
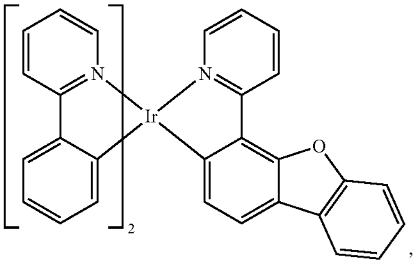
,
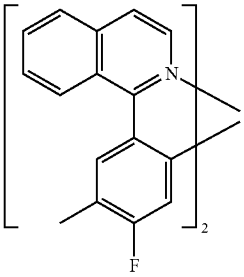
,
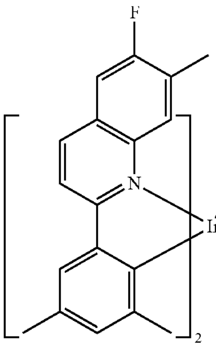
,
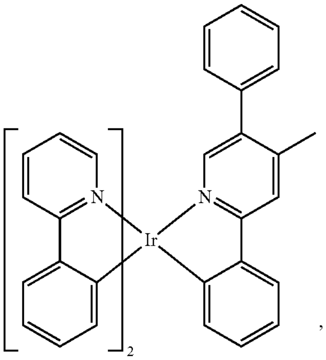
,
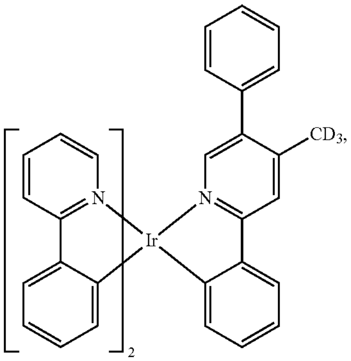
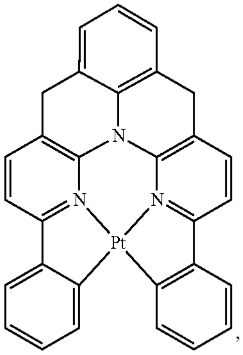
,
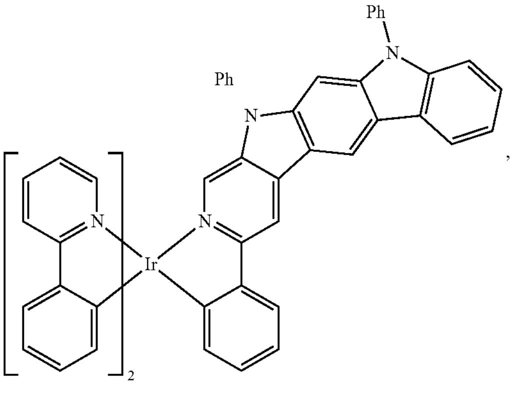
, -continued
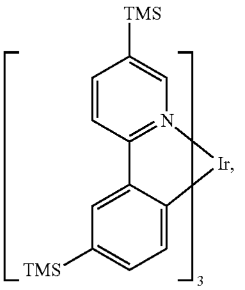
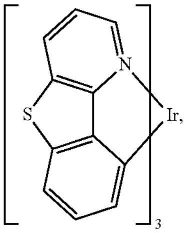
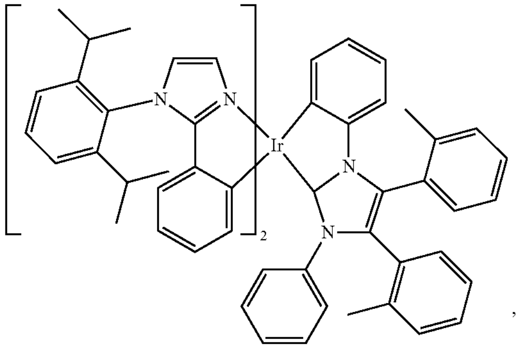
,
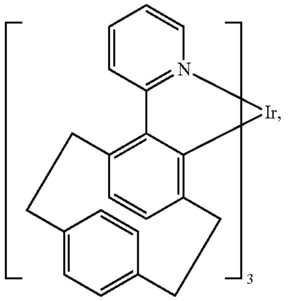
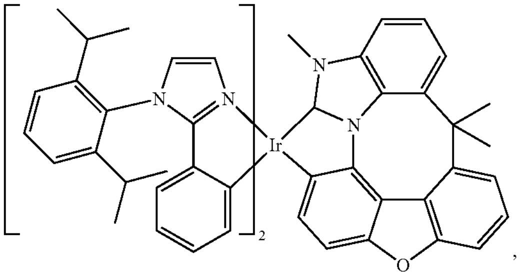
,
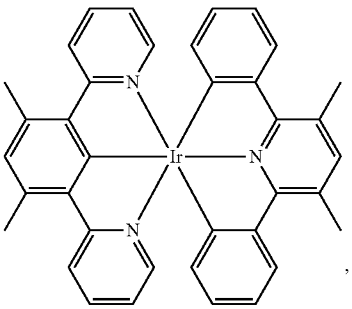
,
-continued
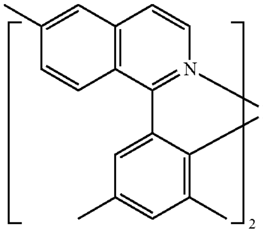
,
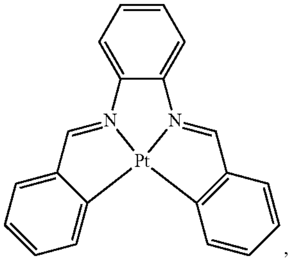
,
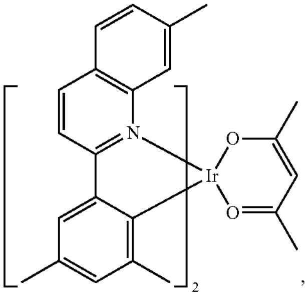
,
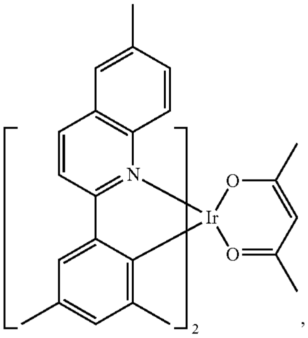
,
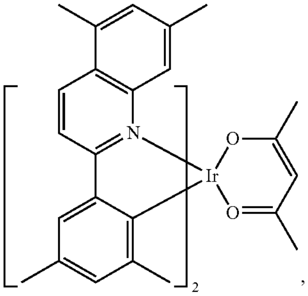
,
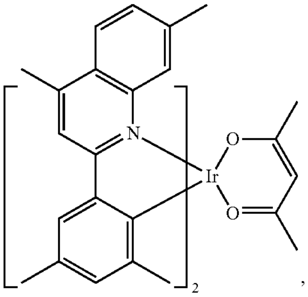
, -continued
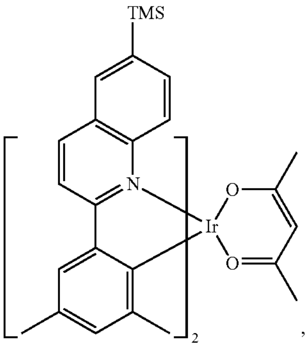
,
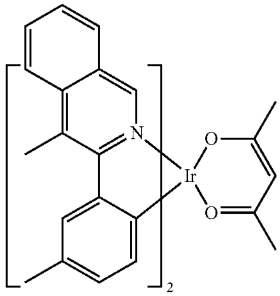
,
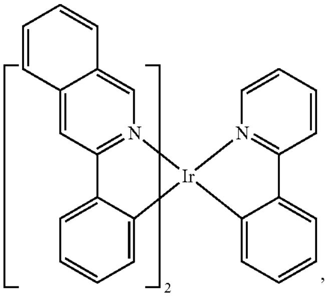
,
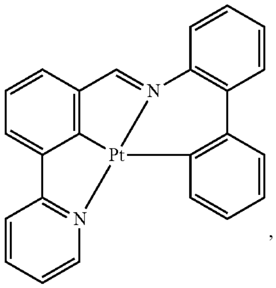
,
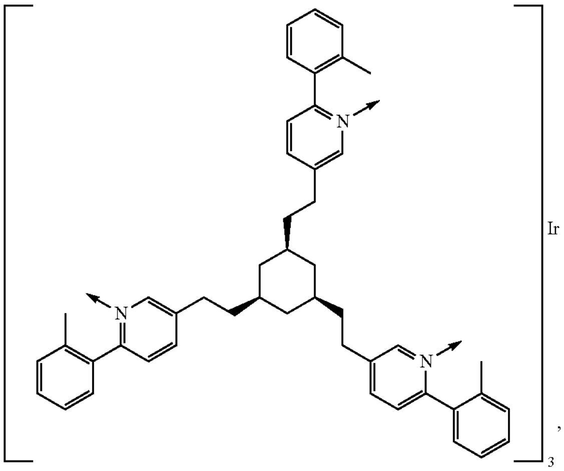
,
-continued
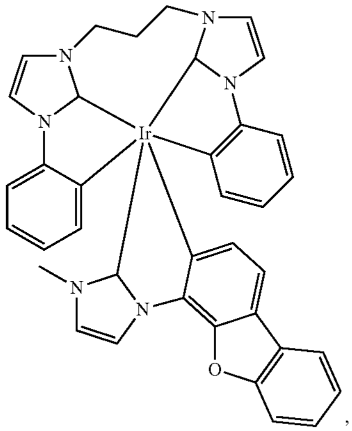
,
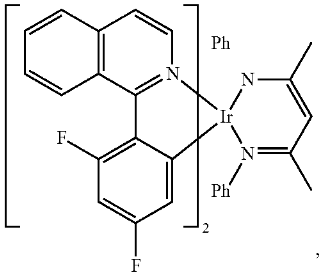
,
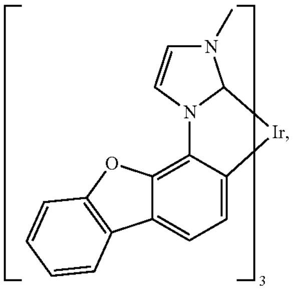
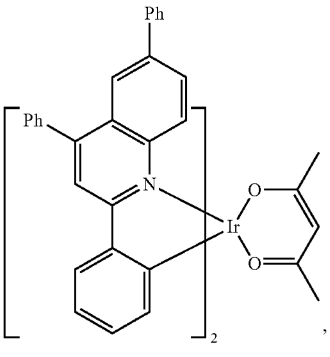
,
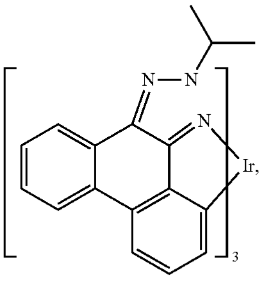
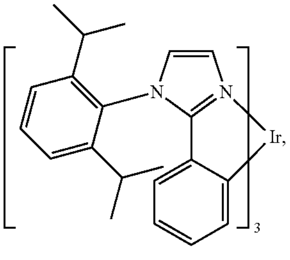

-continued

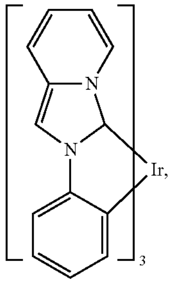

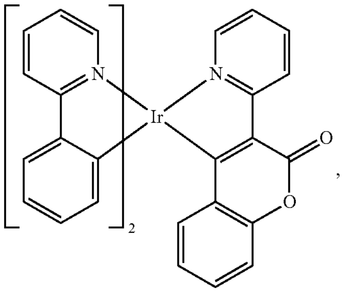

,

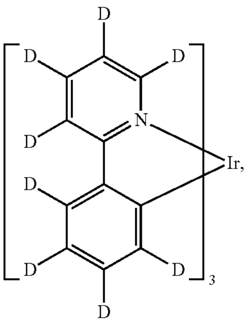

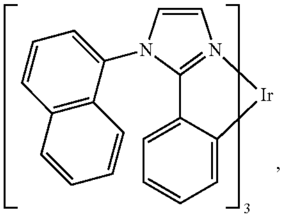

,

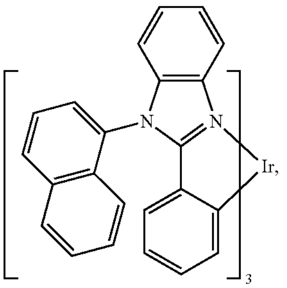

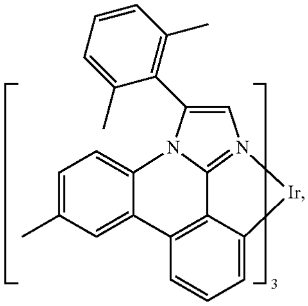

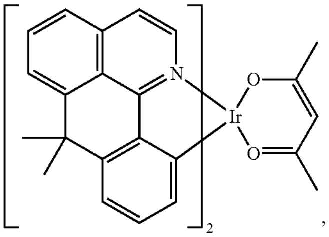

,

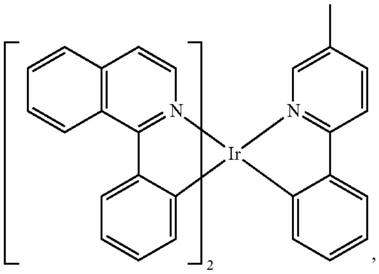

,

-continued

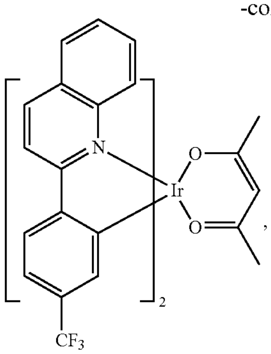

,

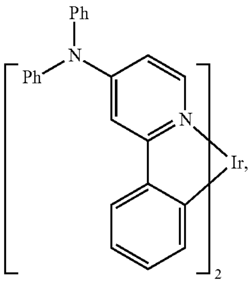

and

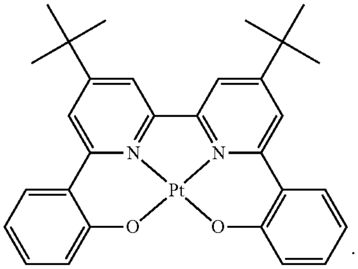

.

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

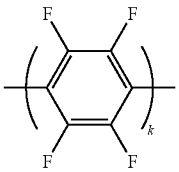

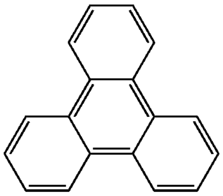

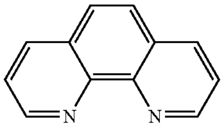

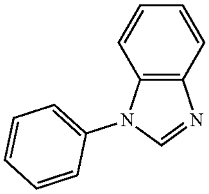

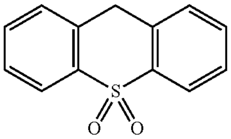

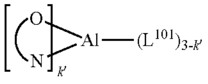

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

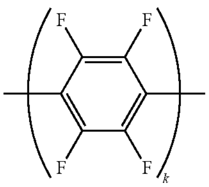
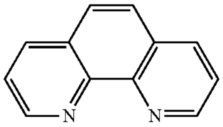
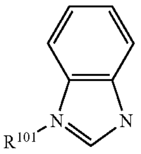
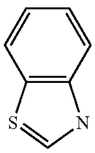
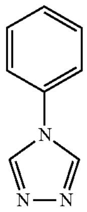
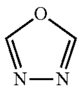
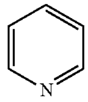
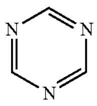
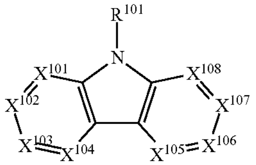
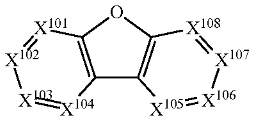
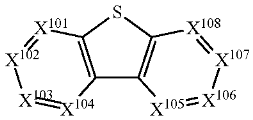
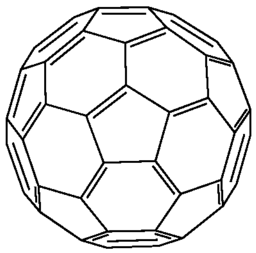
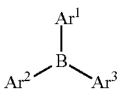

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

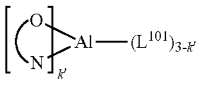
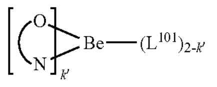

-continued

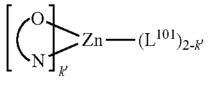
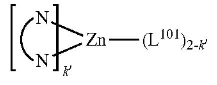

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

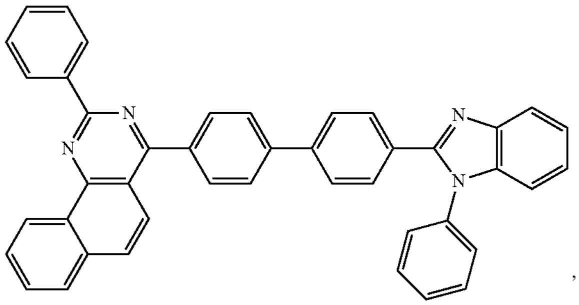
,

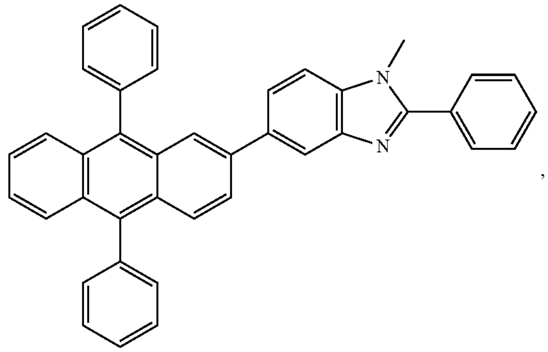
,

-continued
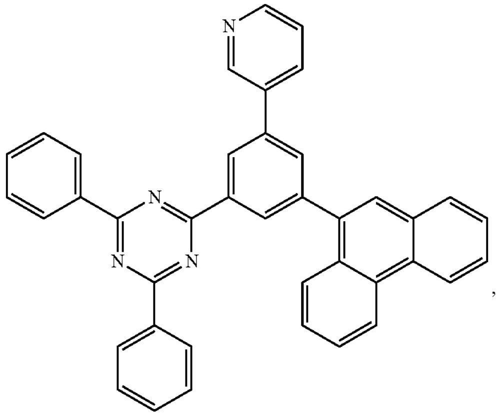
,
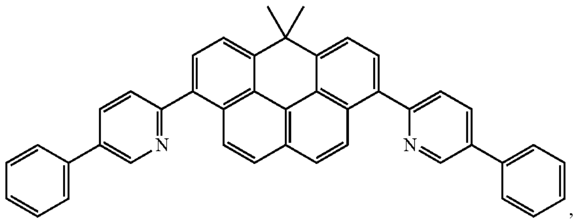
,
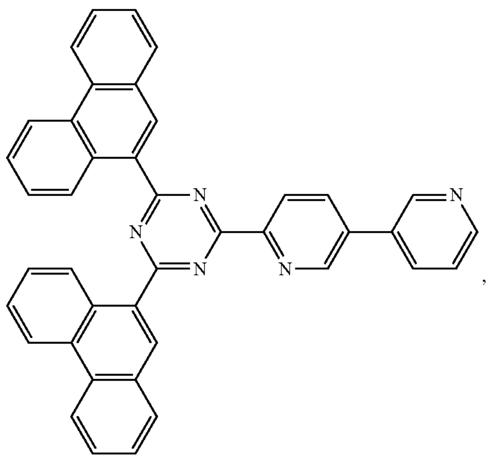
,
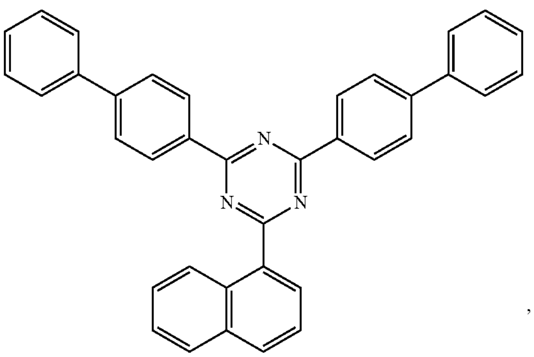
,
-continued
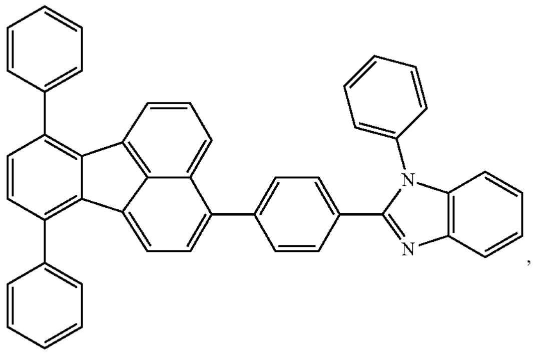
,
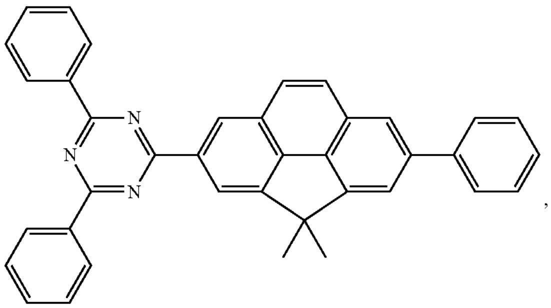
,
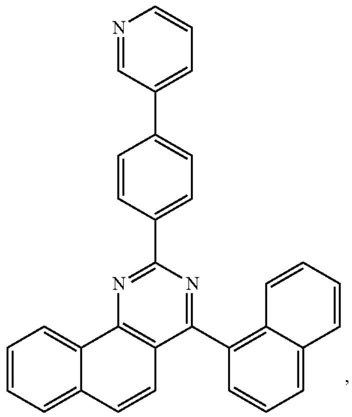
,
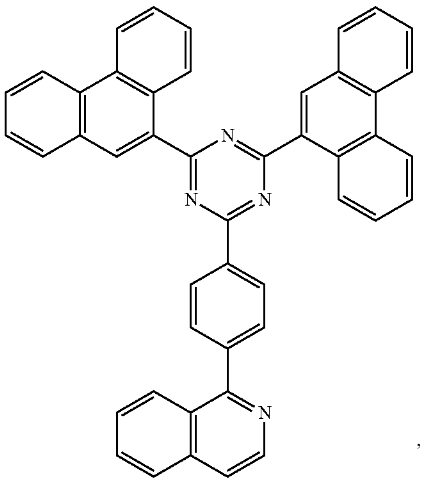
,

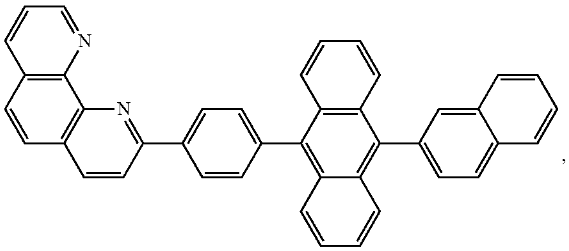
,
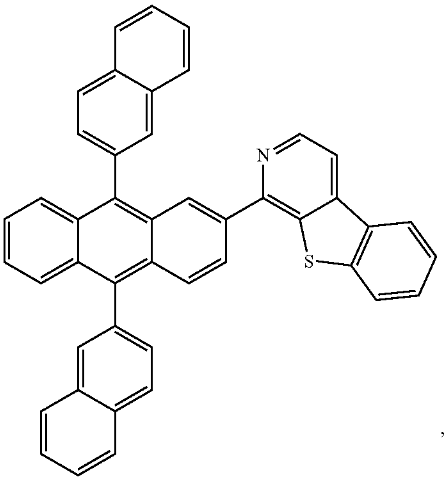
,
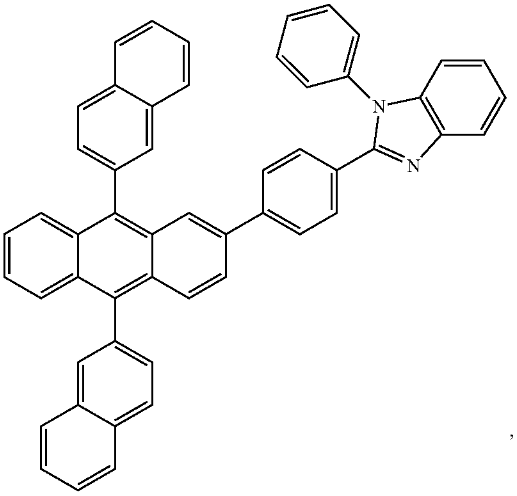
,
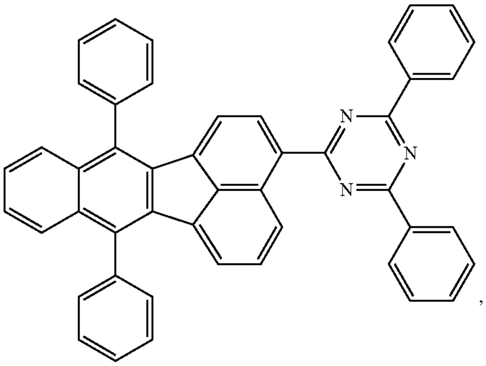
,
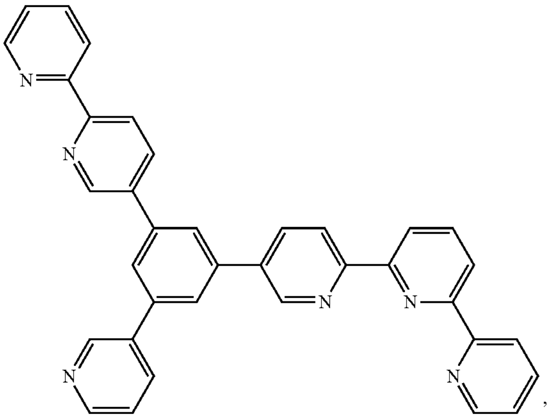
,
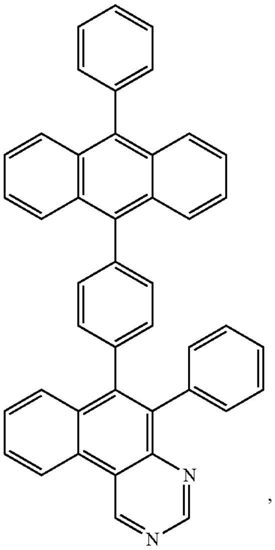
,
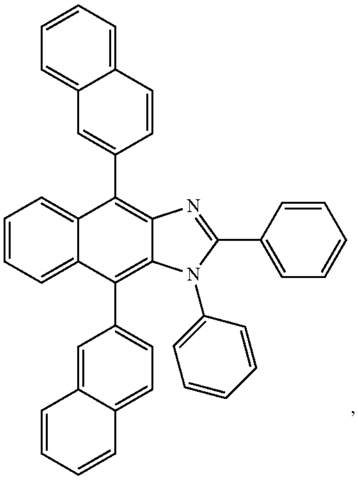
, -continued
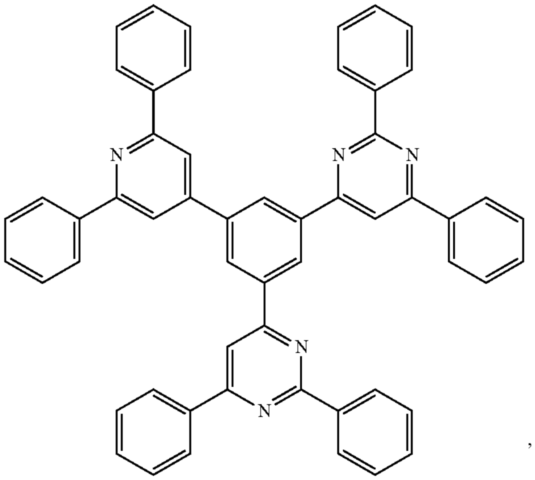
,
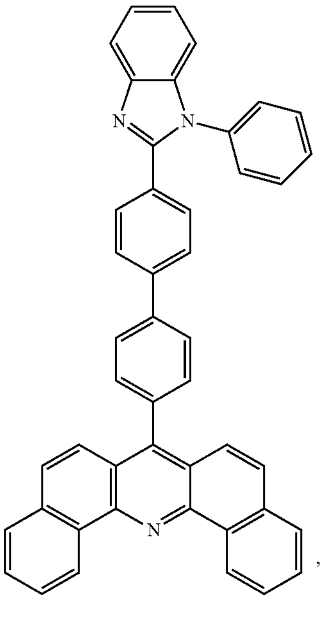
,
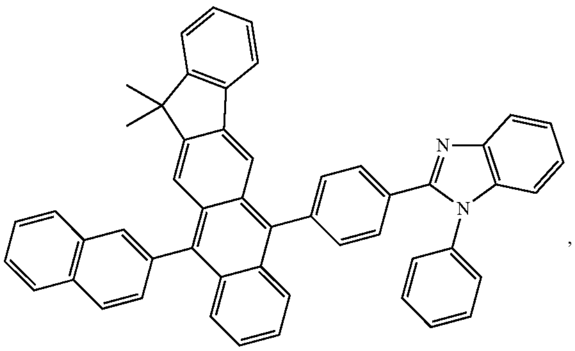
,
-continued
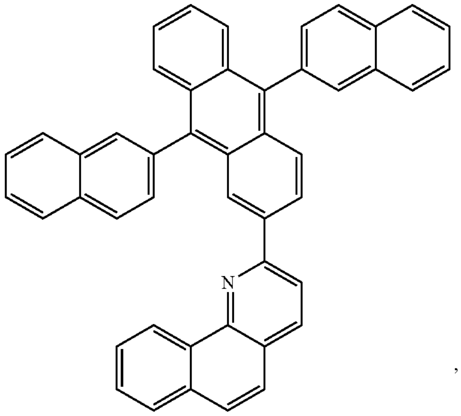
,
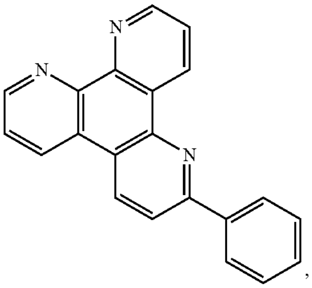
,
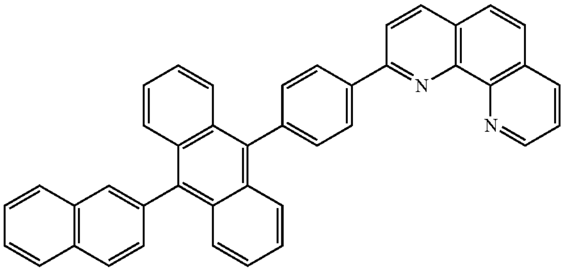
,
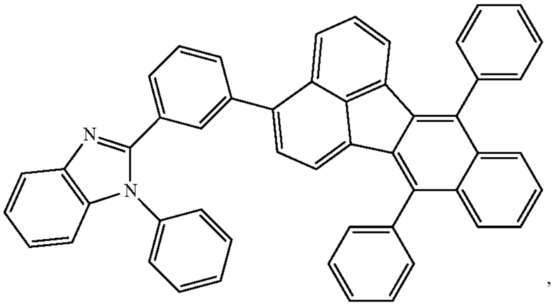
, -continued
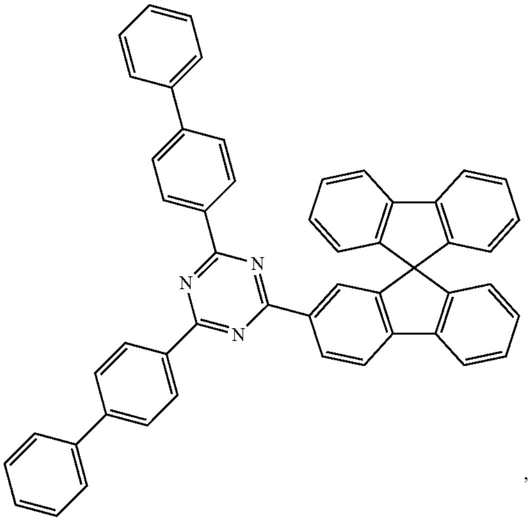
,
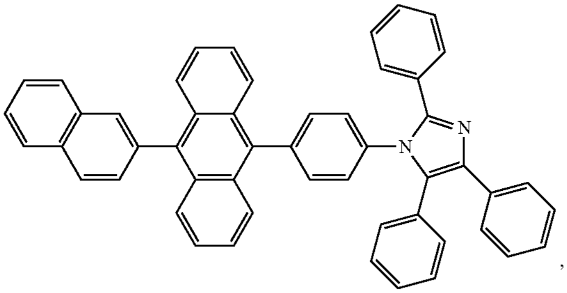
,
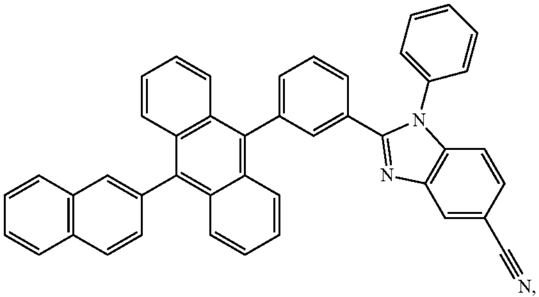
,
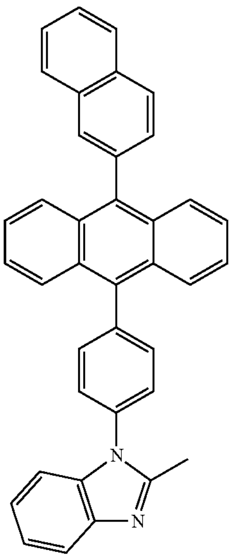
,
-continued
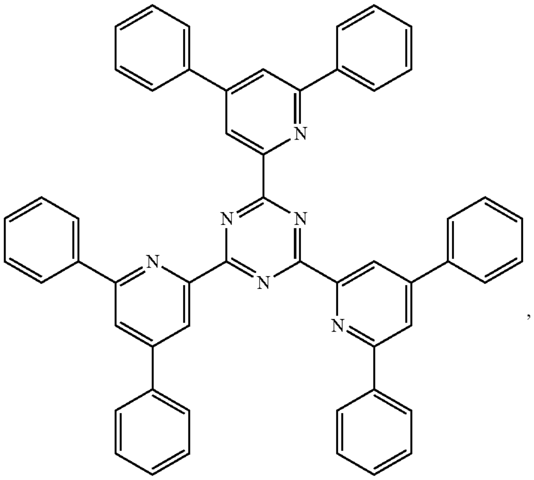
,
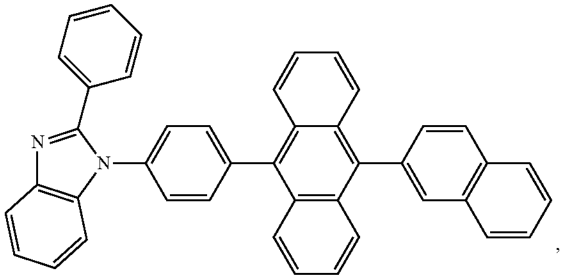
,
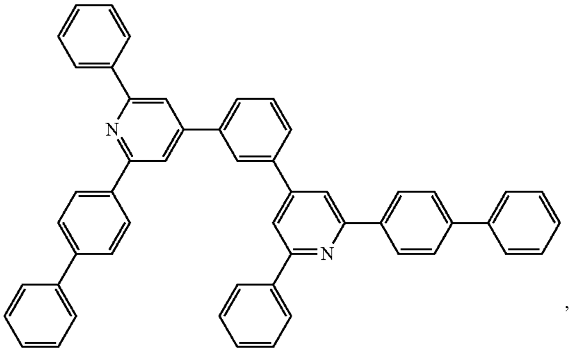
,
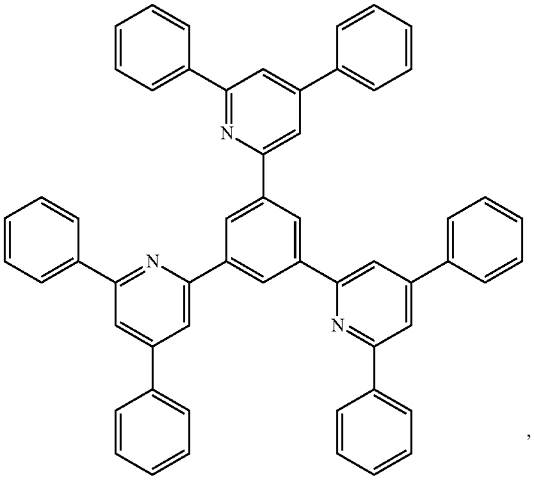
, -continued

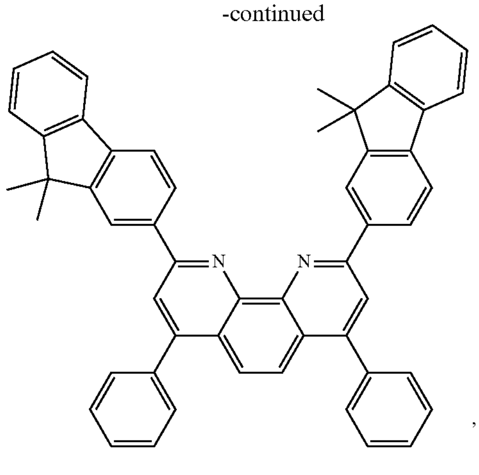

, and

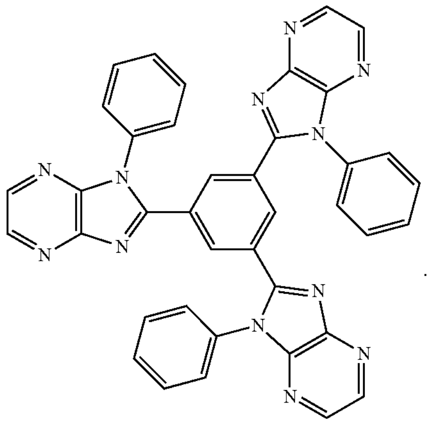 [SMILES: c1ccc(-n2c(-c3cc(-c4nc5nccnc5n4-c4ccccc4)cc(-c4nc5nccnc5n4-c4ccccc4)c3)nc3nccnc32)cc1]

.

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof Material Synthesis:

Chemical abbreviations used throughout this document are as follows: $Pd_2(dba)_3$ is tri(dibenzylideneacetone) dipalladium(0); SPhos is dicyclohexyl(2',6'-dimethoxy-[1,1'-biphenyl]-2-yl)phosphine; and DCM is dichloromethane.

Synthesis of Compound 9073(S)

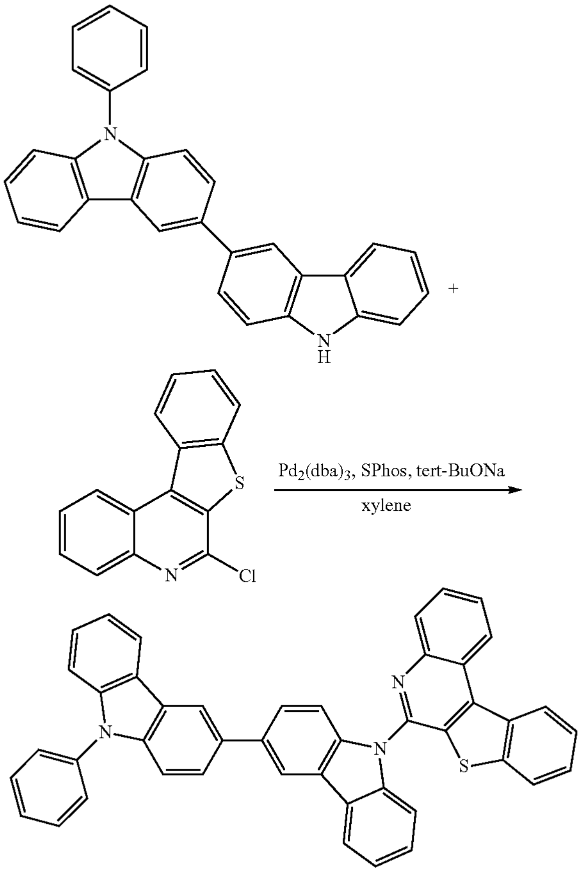

A solution of 9-phenyl-9H,9'H-3,3'-bicarbazole (3.5 g, 8.57 mmol), 6-chlorobenzo[4,5]thieno[2,3-c]quinoline (3.47 g, 12.85 mmol), sodium tert-butoxide (2.059 g, 21.42 mmol) in o-xylene (200 ml) was degassed for 20 mins. $Pd_2(dba)_3$ (0.392 g, 0.428 mmol), SPhos (0.352 g, 0.857 mmol) were added. The mixture was heated to reflux under nitrogen for 16 hours. After cooling to room temperature, the solid was removed by filtration and the solvent was evaporated. The residue was purified by column chromatography on silica gel with heptane/DCM (7/3 to 6/4, v/v) as eluent and recrystallization from heptane to yield Compound 9073(S) (4.0 g, 73%) as a yellow solid.

Synthesis of Compound 9195(S)

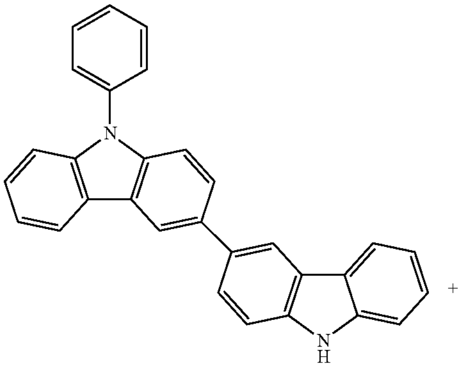

-continued

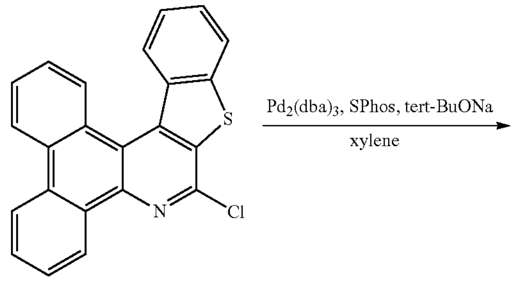

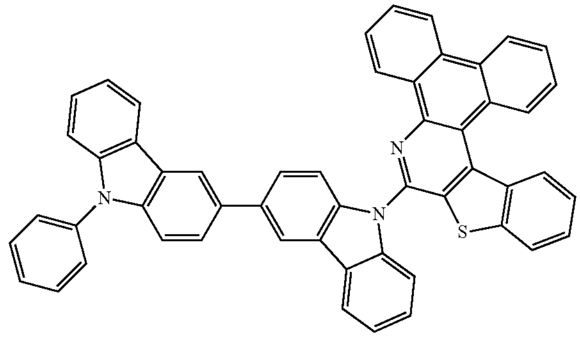

A solution of 9-phenyl-9H,9'H-3,3'-bicarbazole (3.15 g, 7.71 mmol), 6-chlorodibenzo[f,h]benzo[4,5]thieno[2,3-c]quinoline (3.42 g, 9.25 mmol), $Pd_2(dba)_3$ (0.282 g, 0.308 mmol), SPhos (0.8 g, 1.951 mmol) and sodium tert-butoxide (1.703 g, 17.74 mmol), in o-xylene (200 ml) was degased and refluxed under nitrogen for 24 hours. After cooling to room temperature, the solid was removed by filtration and the solvent was evaporated. The residue was purified by column chromatography on silica gel with heptane/DCM (7/3 to 1/99, v/v) as eluent and trituration with ethanol to yield Compound 9195(S) as a yellow solid.

Synthesis of Compound 20737(S)

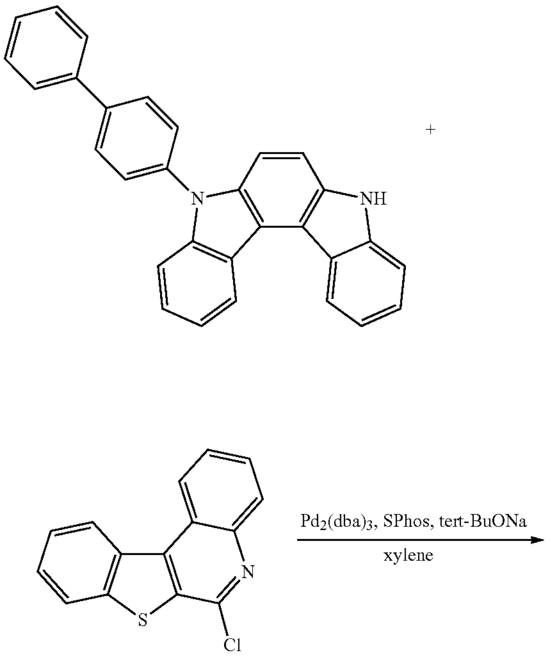

-continued

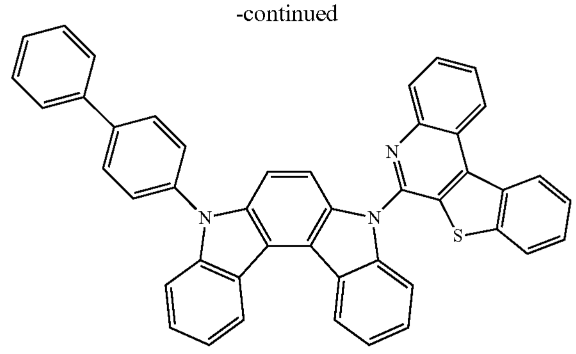

A solution of 6-chlorobenzo[4,5]thieno[2,3-c]quinoline (2.87 g, 10.65 mmol) and 5-([1,1'-biphenyl]-4-yl)-5,8-dihydroindolo[2,3-c]carbazole (2.9 g, 7.10 mmol), sodium tert-butoxide (1.706 g, 17.75 mmol) in o-xylene (20 ml) was degassed for 20 mins. $Pd_2(dba)_3$ (0.325 g, 0.355 mmol), SPhos (0.291 g, 0.710 mmol) were added. The mixture was heated to reflux under nitrogen for 3 h. After coling to room temperature, the reaction mixture was filtered through a short plug of silica gel. Upon evaporation off the solvent, the residue was triturated successively with ethanol, ethyl acetate, toluene, DCM and toluene to yield Compound 20737(S) (2.3 g, 50%) as a yellow solid.

EXPERIMENTAL

Application in OLED: All devices were fabricated by high vacuum (~$10^{-7}$ Torr) thermal evaporation. The anode electrode was 120 nm of indium tin oxide (ITO). The cathode electrode consisted of 1 nm of LiF followed by 100 nm of Al. All devices were encapsulated with a glass lid sealed with an epoxy resin in a nitrogen glove box (<1 ppm of $H_2O$ and $O_2$) immediately after fabrication, and a moisture getter was incorporated inside the package.

Device Examples: A first set of device examples have organic stacks consisting of, sequentially, from the ITO surface, 10 nm of LG101 (from LG Chem) as the hole injection layer (HIL), 40 nm of PPh-TPD as the hole-transport layer (HTL), 40 nm of emissive layer (EML), followed by 35 nm of aDBT-ADN with LiQ as the electron-transport layer (ETL). The EML has two components, 97 wt % of invented compounds (Compounds 9073(S), or 20737 (S)) or comparative compounds (CC-1, CC-2 or CC-3) as the host, and 3 wt % of RD as the emitter. The structure of the compounds used are shown below:

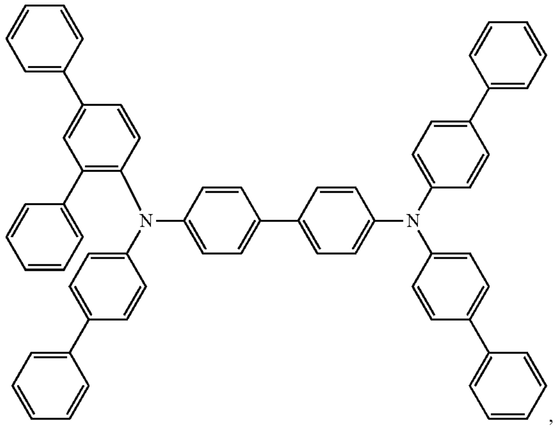
,

PPh-TPD

-continued

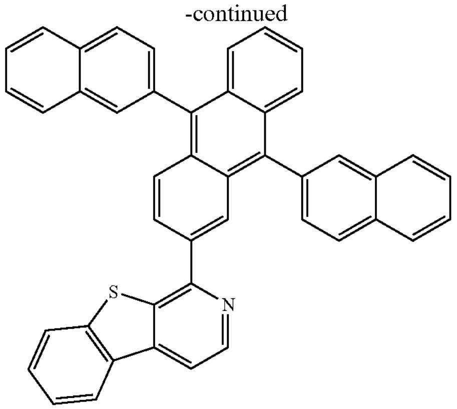, aDBT-ADN

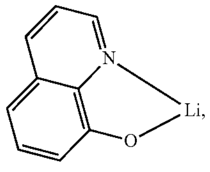

LiQ

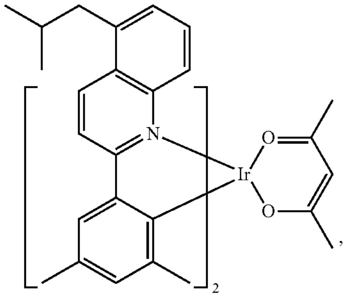,

RD

Compound 9073(S)

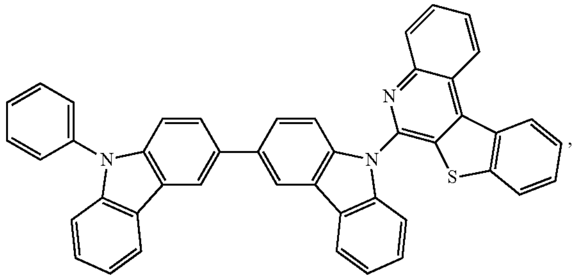,

Compound 20737(S)

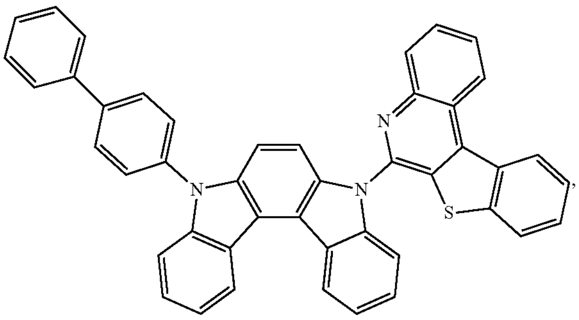,

CC-1

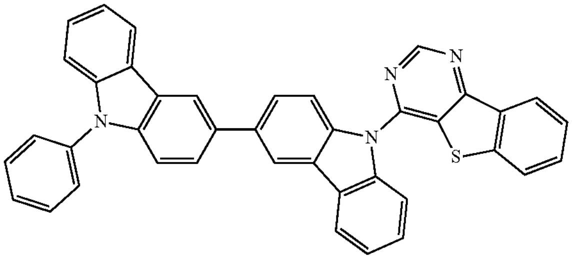,

-continued

CC-2

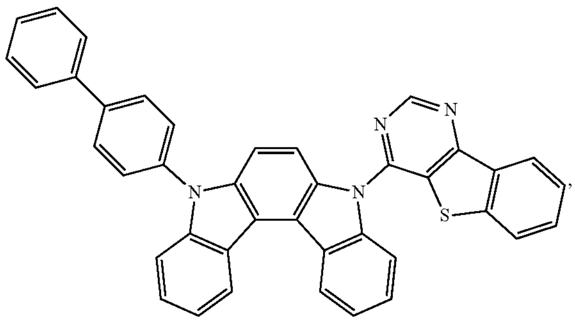,

CC-2

CC-3

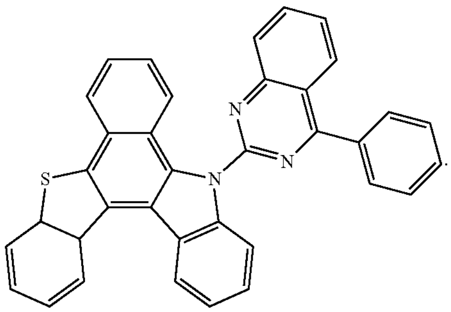.

CC-3

Table D1, below, is a summary of the device data, emission color and external quantum efficiency (EQE), recorded at 1000 nits for the devices.

| Device ID | Host | Emission Color | EQE [%] |
|---|---|---|---|
| Device-1 | Compound 9073(S) | Red | 24.4 |
| Device-2 | Compound 20737(S) | Red | 23.9 |
| Device-C1 | CC-1 | Red | 10.2 |
| Device-C2 | CC-2 | Red | 11.6 |
| Device-C3 | CC-3 | Red | 21.2 |

The data in Table D1 shows that OLEDs (Device-1 and Device-2) using inventive compounds as the host in the EML are much more efficient than their conterparts using comparative compounds (CC-1, CC-2 and CC-3) as the host. The superior performance of the inventice compounds are attributable to their unique chemical structures containing benzo-fused aza-dibenzothiophene that might have facilitated charge transport to achieve a more balanced charge carrier fluxes inside the devices, which is critical to enhance OLED device performance.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having a formula selected from the group consisting of:

Formula 1-1

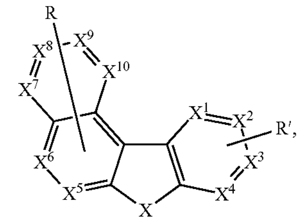

Formula 1-2

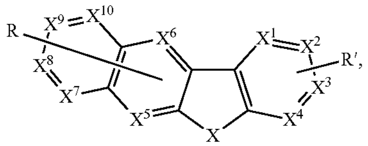

and

Formula 1-3

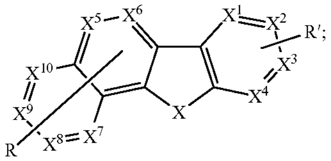

wherein X is selected from the group consisting of O, S, and Se;

wherein $X^1$ to $X^{10}$ are each independently selected from the group consisting of carbon and nitrogen;

wherein at least one of $X^1$ to $X^6$ is nitrogen;

wherein R and R' each independently represent from mono to the possible maximum number of substitutions, or no substitution;

wherein R and R' are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein at least one of $X^4$ and $X^5$ is carbon, which is substituted by a $D^j$ selected from the group consisting of:

$D^7$

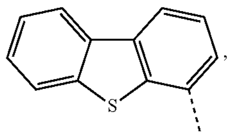

$D^8$

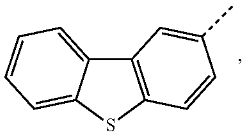

-continued $D^{10}$

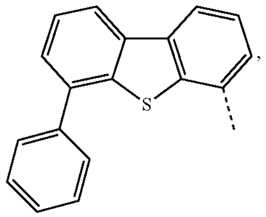

$D^{11}$

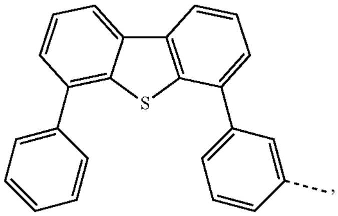

$D^{12}$

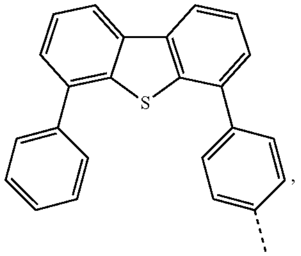

$D^{13}$

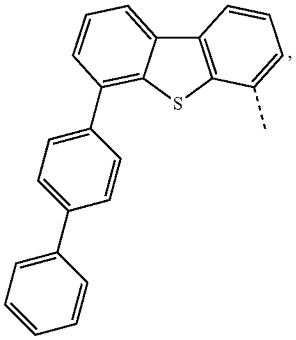

$D^{14}$

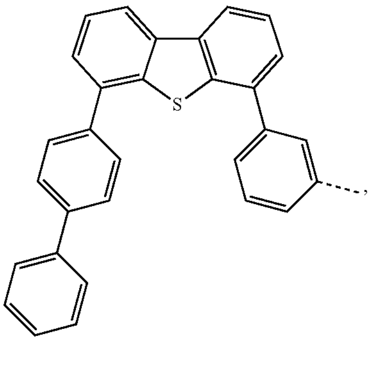

-continued
D15
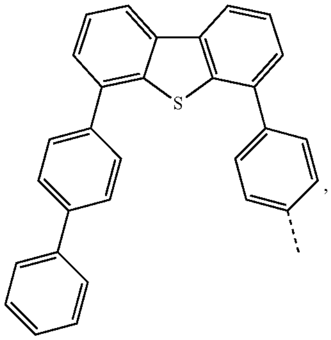
D16
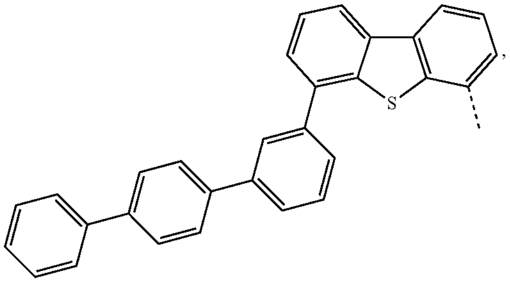
D17
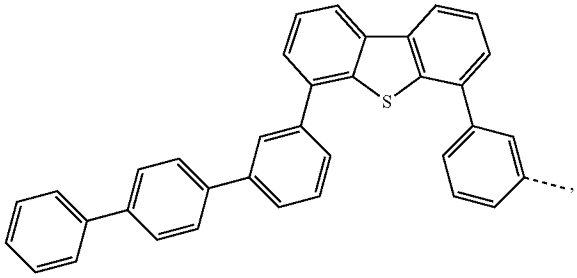
D18
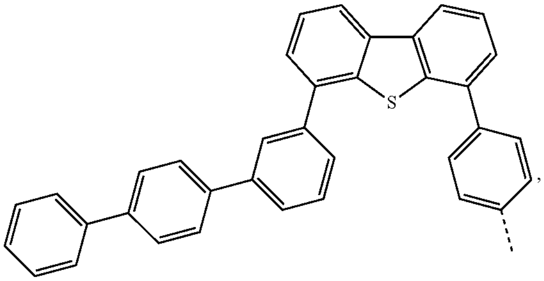
D19
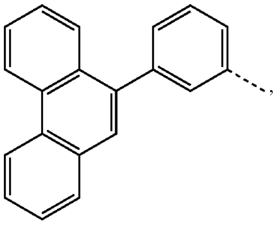
-continued
D20
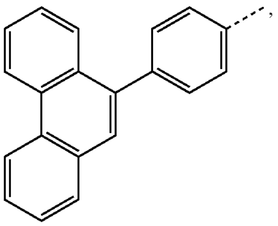
D21
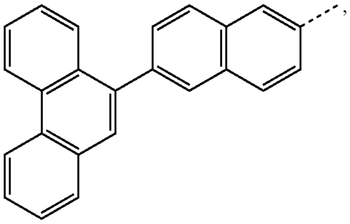
D22
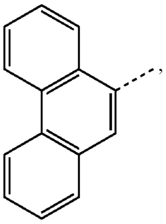
D23
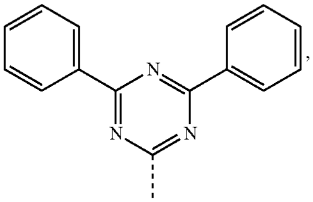
D24
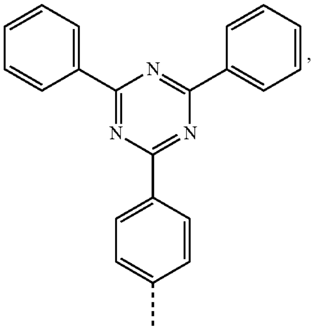
D25
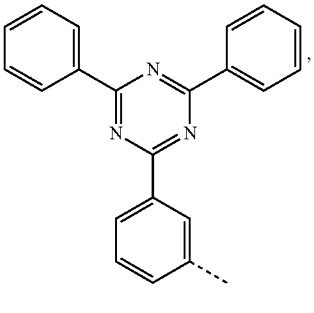

-continued
D[26]
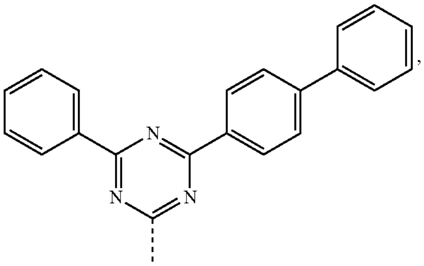
D[27]
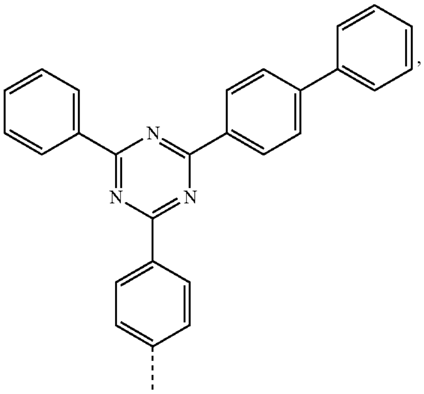
D[28]
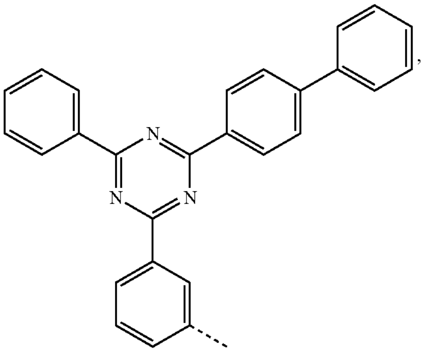
D[29]
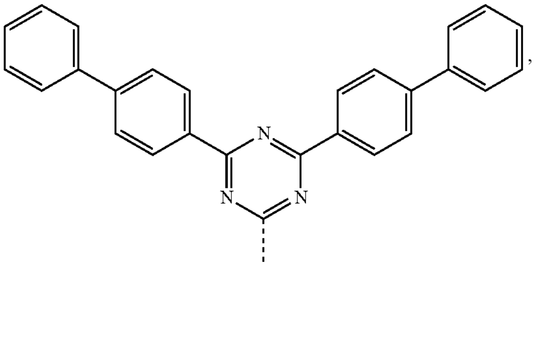
D[31]
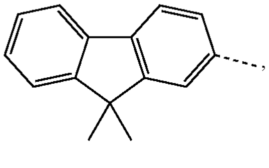
-continued
D[32]
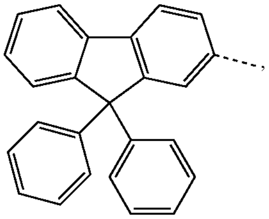
D[33]
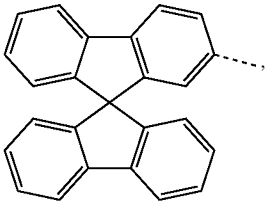
D[36]
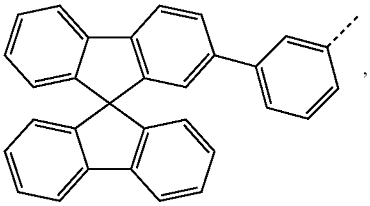
D[41]
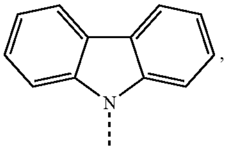
D[42]
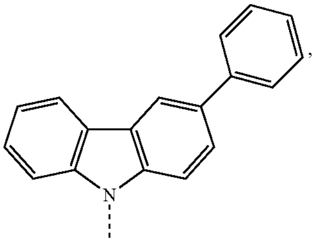
D[43]
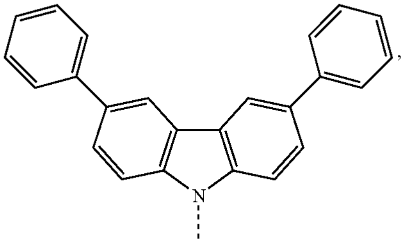

D45
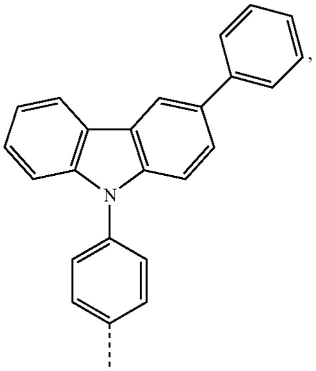,
D46
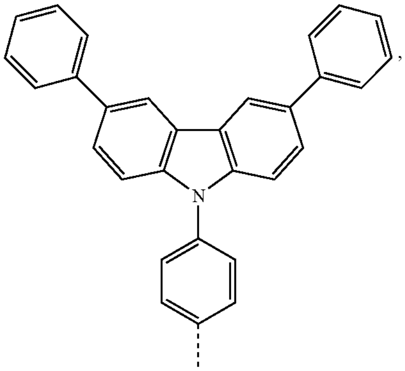,
D47
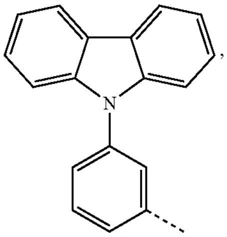,
D48
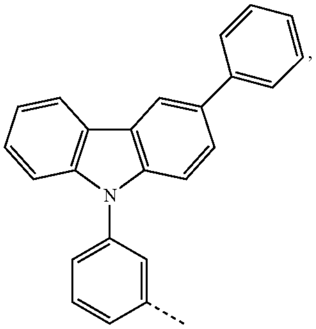,
D49
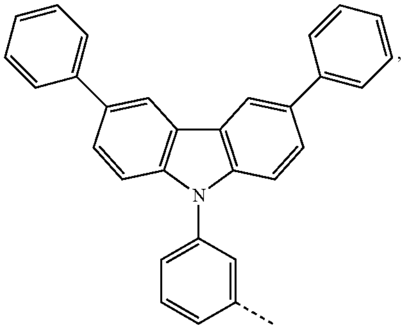,
D54
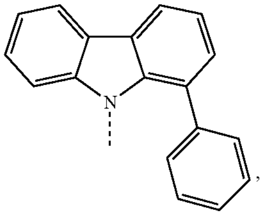,
D55
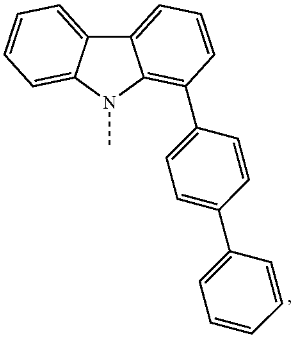,
D56
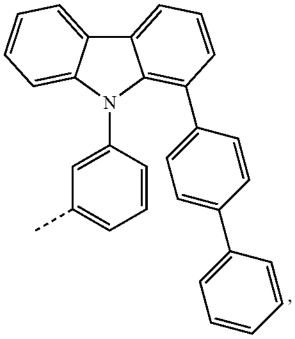,
D57
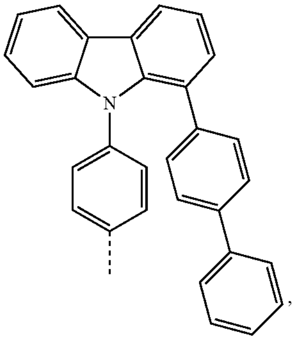, -continued
D[58]
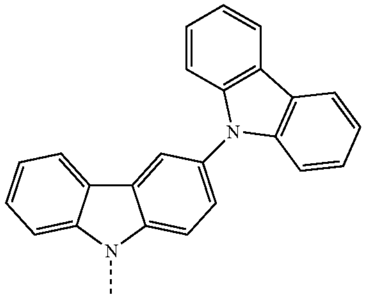,
D[61]
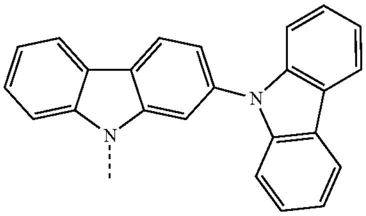,
D[64]
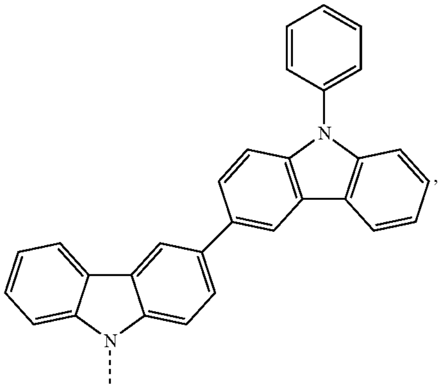,
D[65]
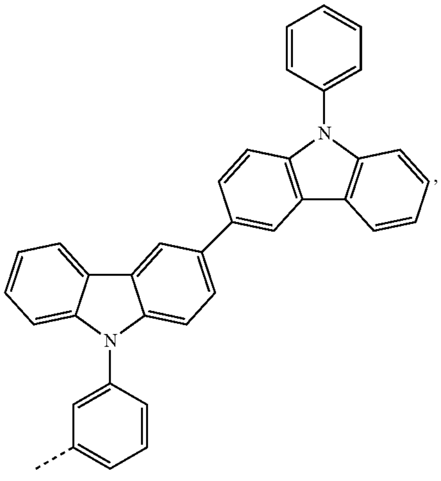,
-continued
D[66]
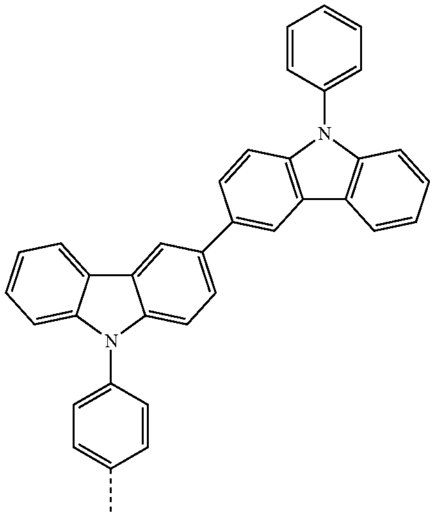,
D[67]
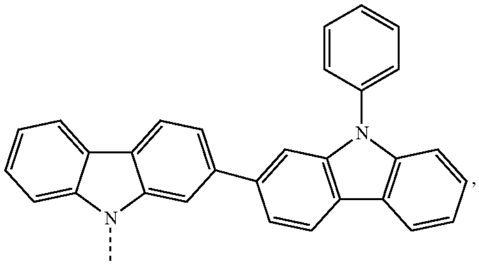,
D[68]
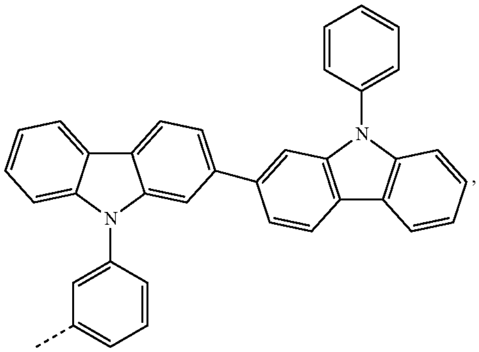,
D[69]
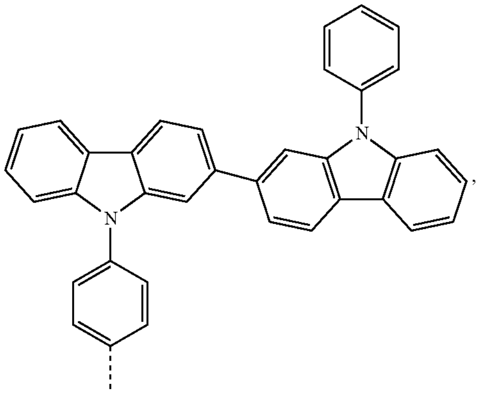, -continued
D[70]
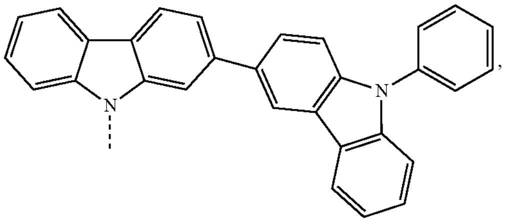
D[71]
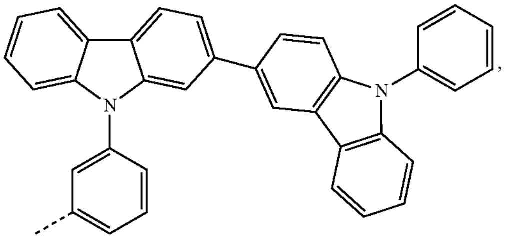
D[72]
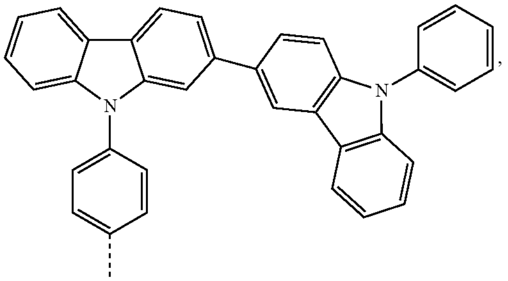
D[73]
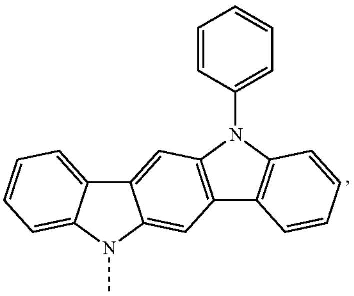
D[74]
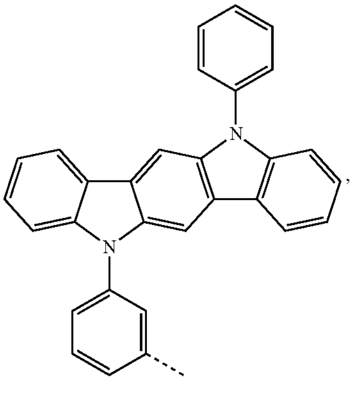
-continued
D[75]
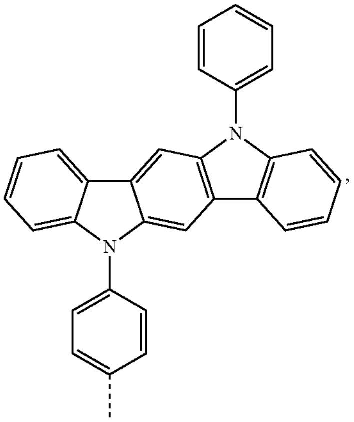
D[76]
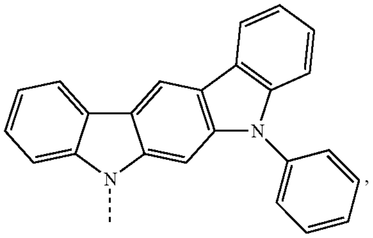
D[79]
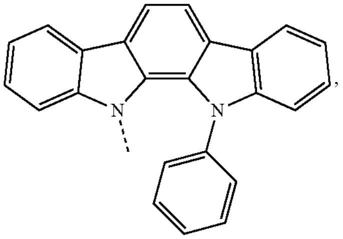
D[80]
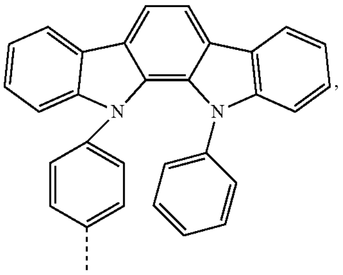
D[81]
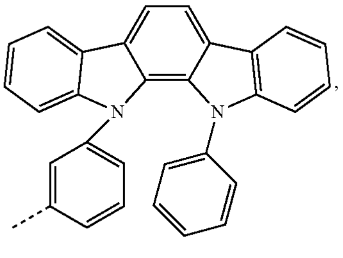

-continued
D[82]
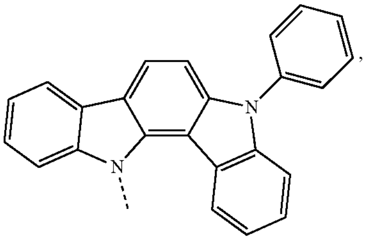
,
D[83]
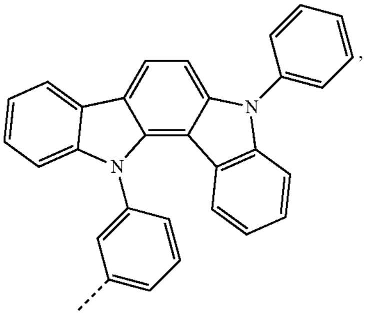
,
D[84]
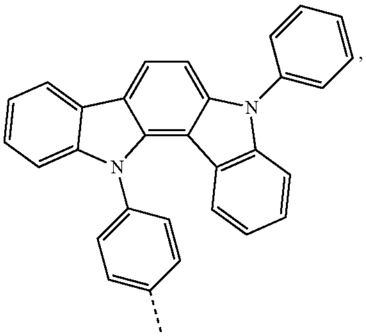
,
D[85]
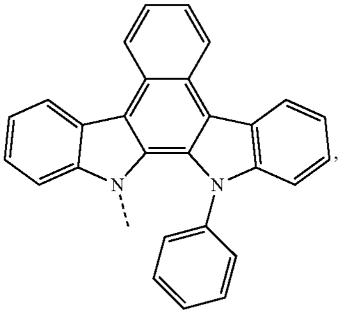
,
D[86]
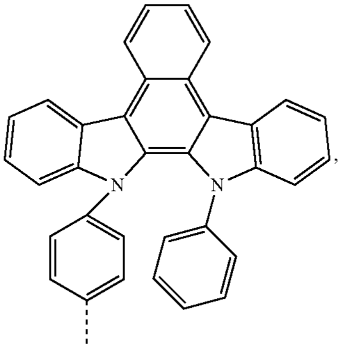
,
-continued
D[87]
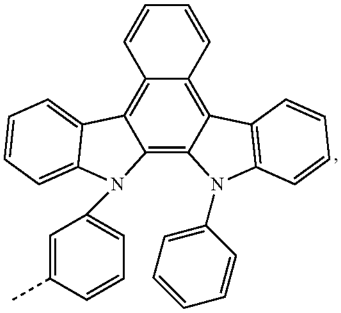
,
D[88]
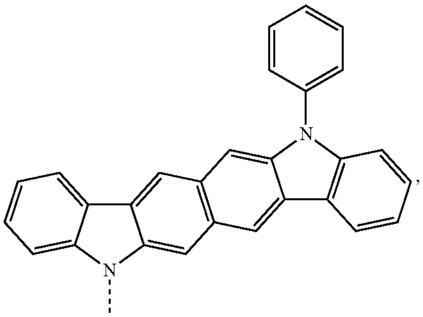
,
D[89]
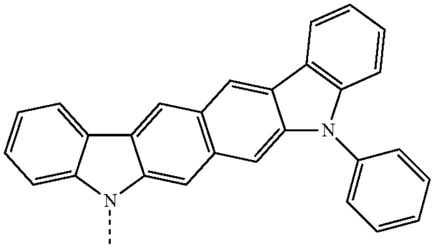
,
D[90]
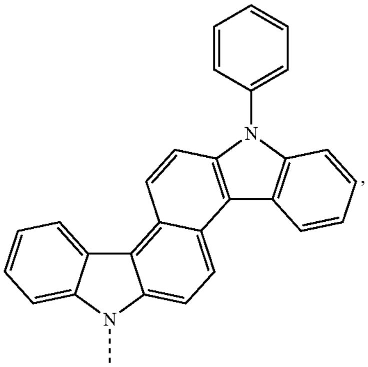
,
D[91]
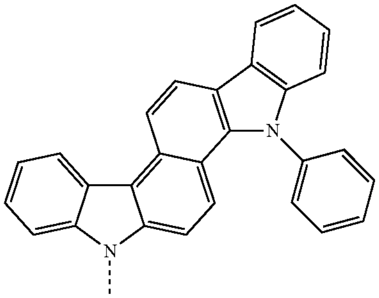
, -continued
D[92]
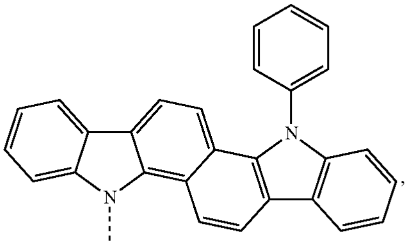
D[93]
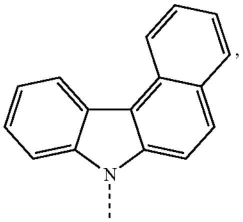
D[94]
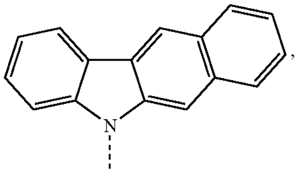
D[95]
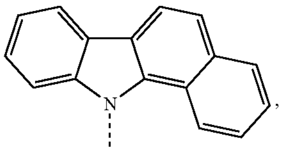
D[96]
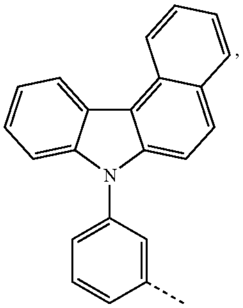
D[97]
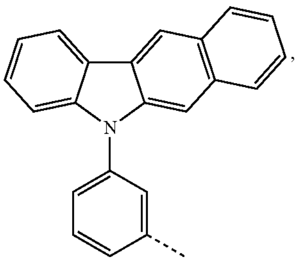
-continued
D[98]
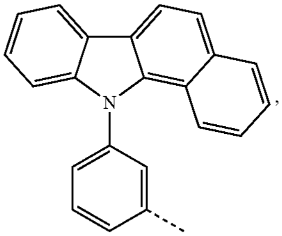
D[99]
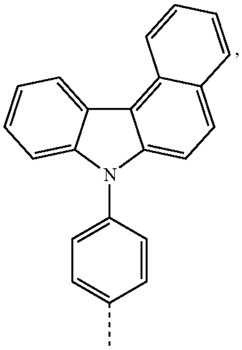
D[100]
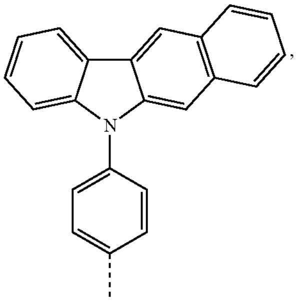
D[101]
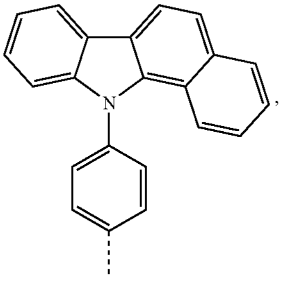
D[102]
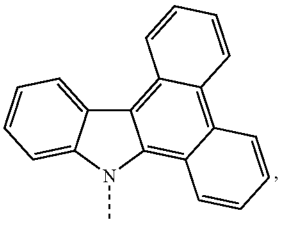

-continued
D103
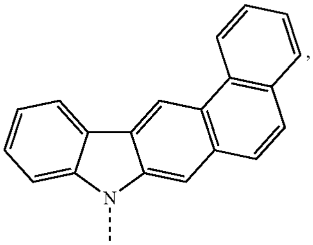,
D104
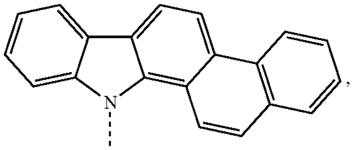,
D105
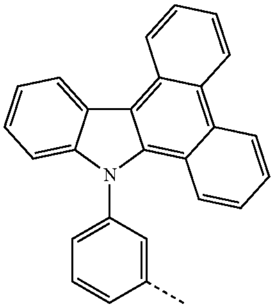,
D106
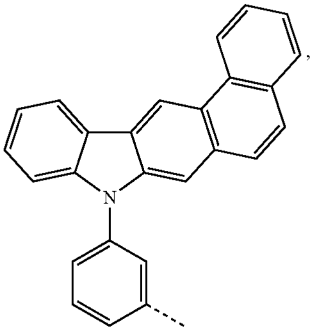,
D107
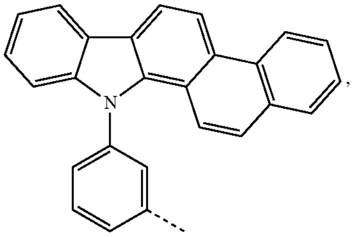,
-continued
D108
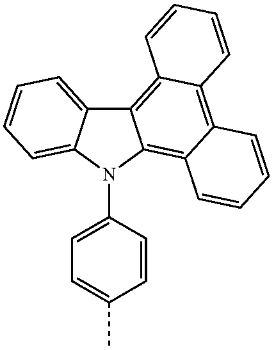,
D109
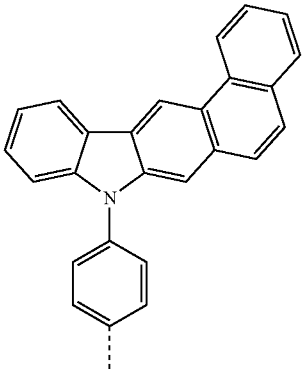,
D110
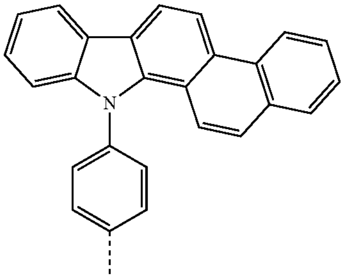,
D111
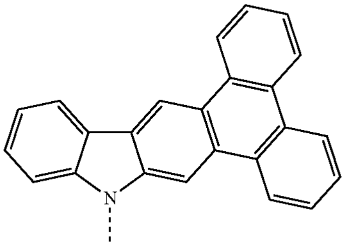,
D112
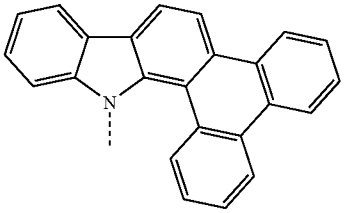, -continued
D[113]
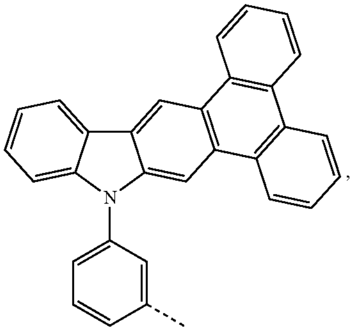
D[114]
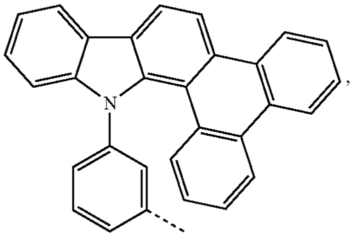
D[115]
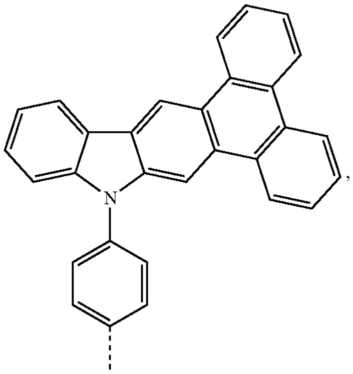
D[116]
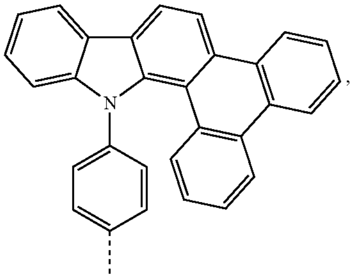
D[117]
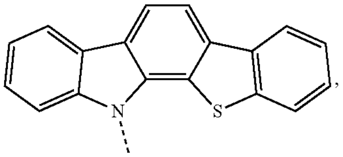
D[118]
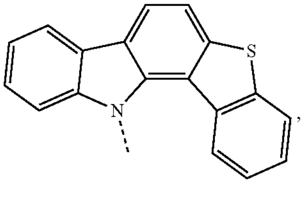
-continued
D[119]
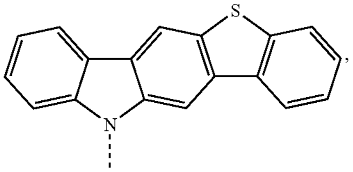
D[120]
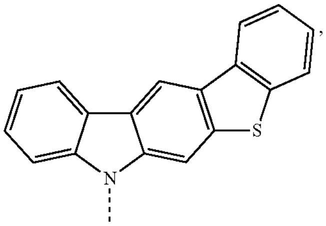
D[121]
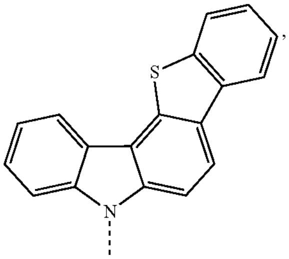
D[122]
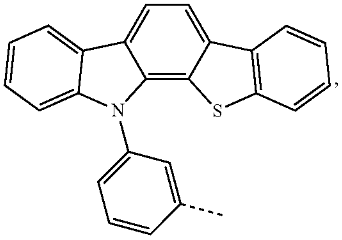
D[123]
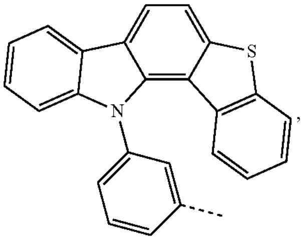
D[124]
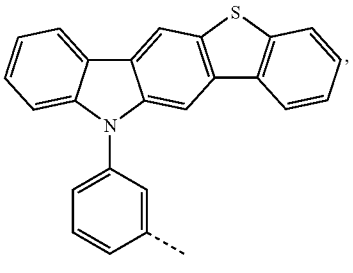

-continued
D[125]
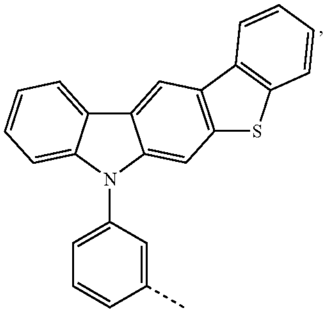
D[126]
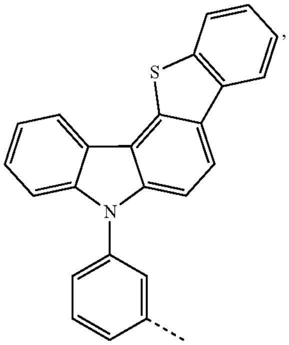
D[127]
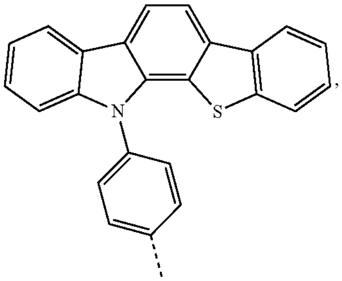
D[128]
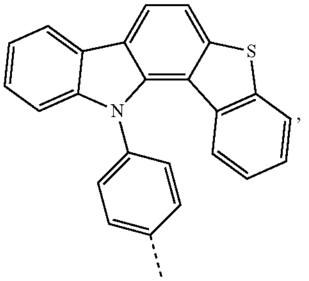
D[129]
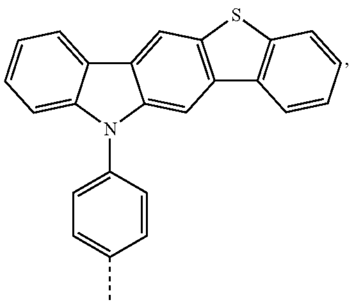
-continued
D[130]
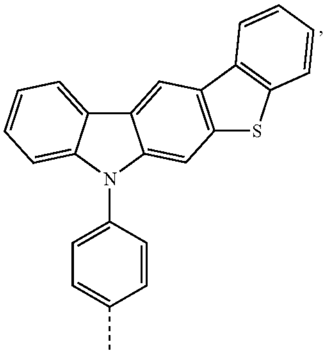
D[131]
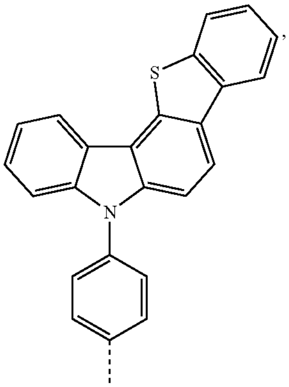
D[132]
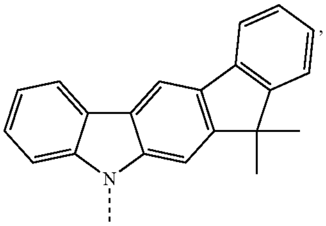
D[133]
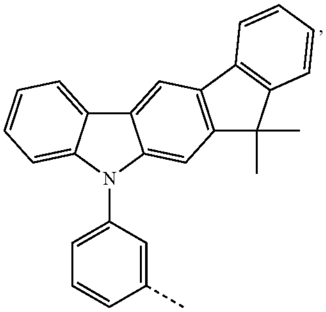

-continued
D[134]
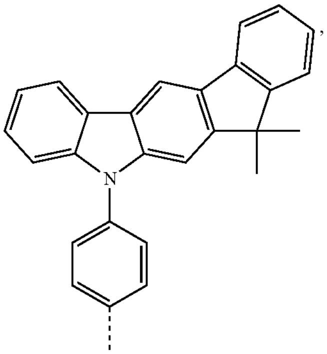
,
D[135]
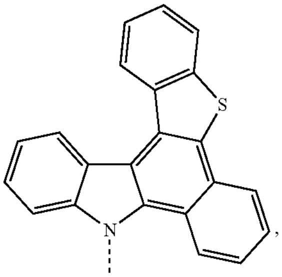
,
D[136]
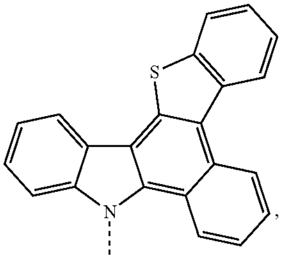
,
D[137]
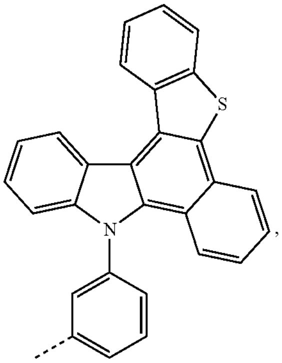
,
D[138]
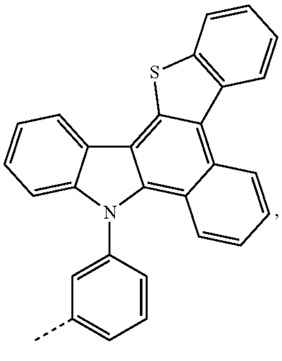
,
-continued
D[139]
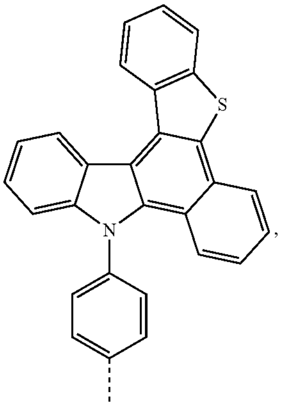
,
D[140]
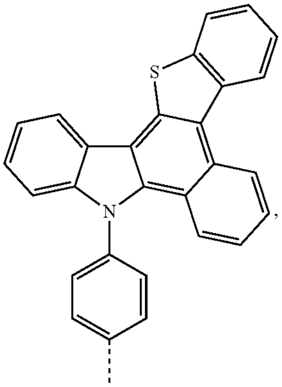
,
D[141]
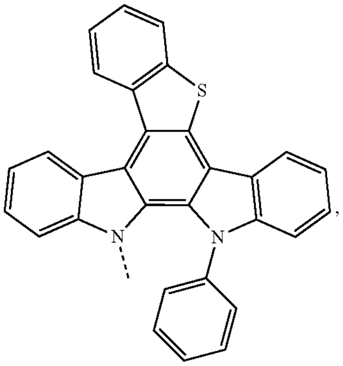
,
D[142]
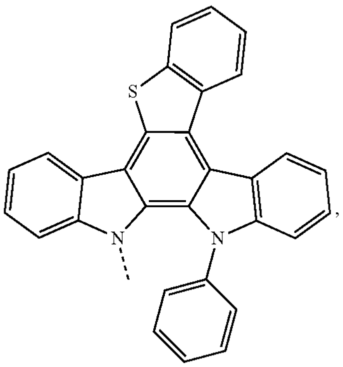
, -continued
D[143]
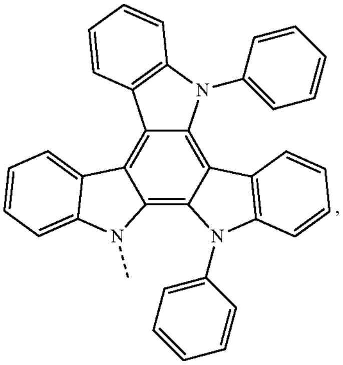
D[144]
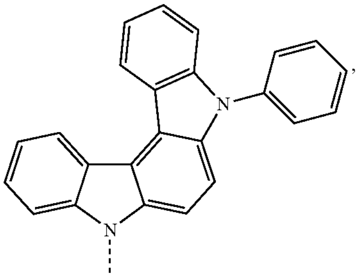
D[145]
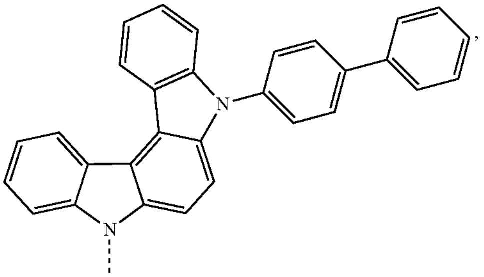
D[146]
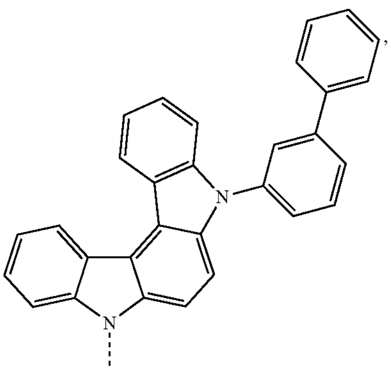
-continued
D[147]
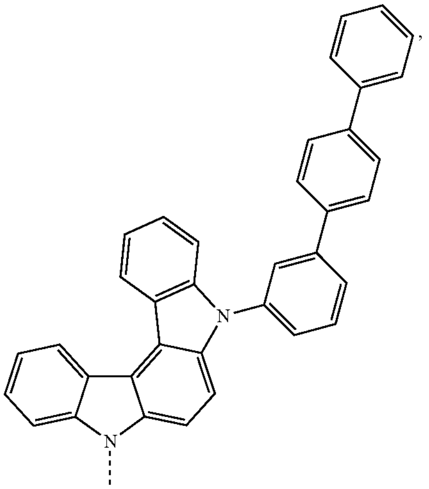
D[148]
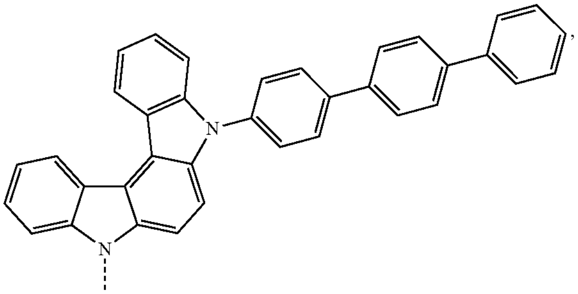
D[149]
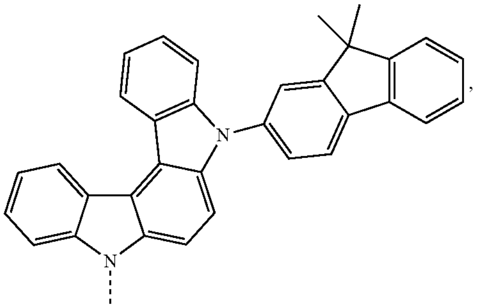
D[150]
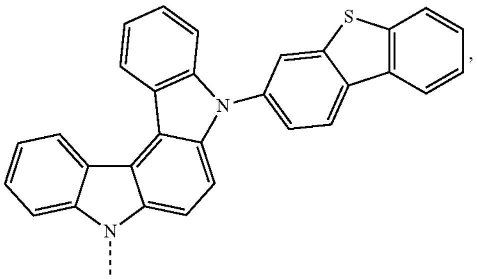

-continued
D[151]
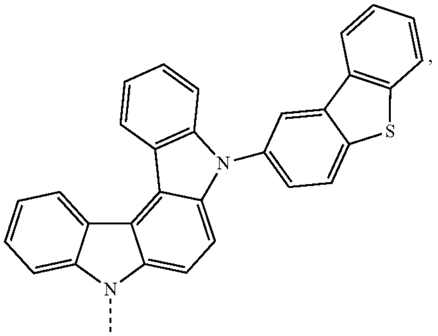
D[152]
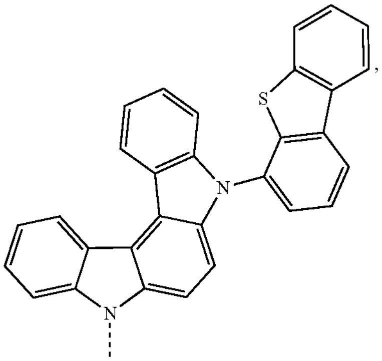
D[153]
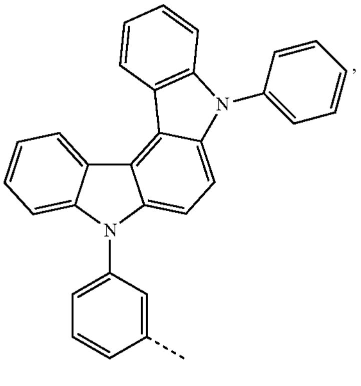
D[154]
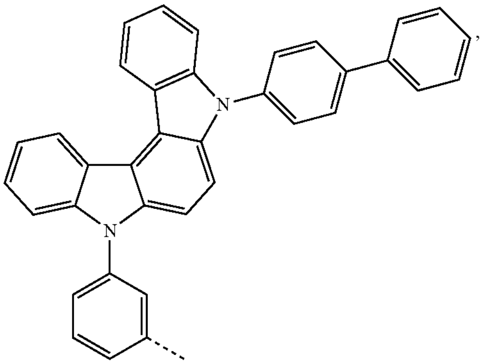
-continued
D[155]
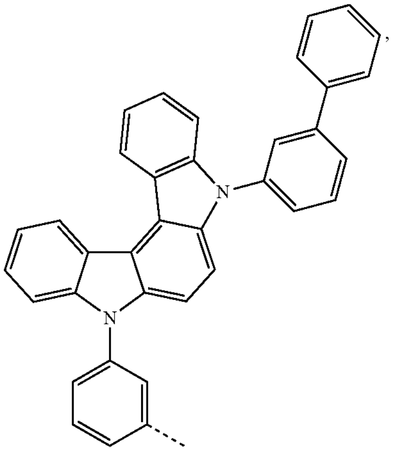
D[156]
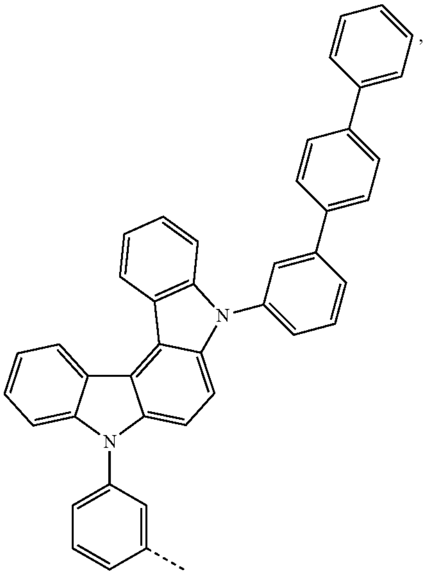
D[157]
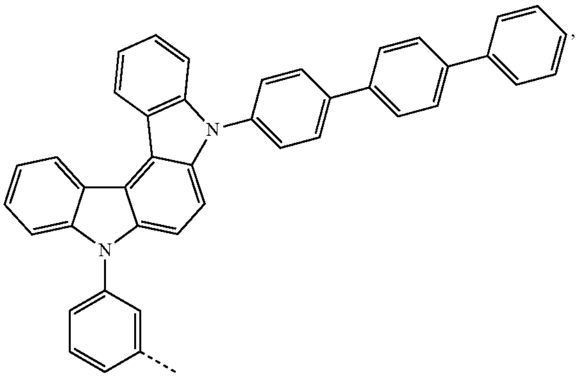

-continued
D158
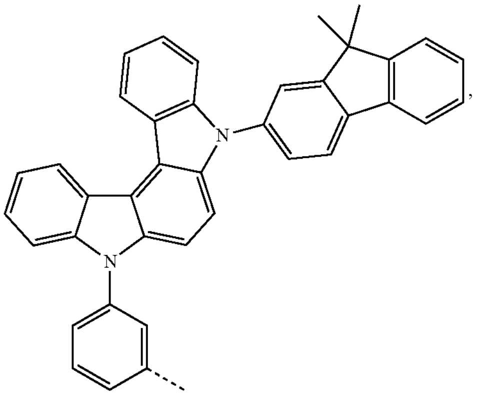
D159
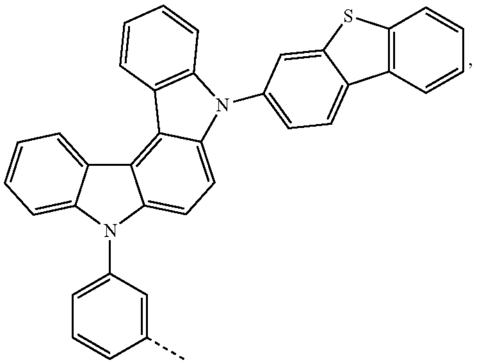
D160
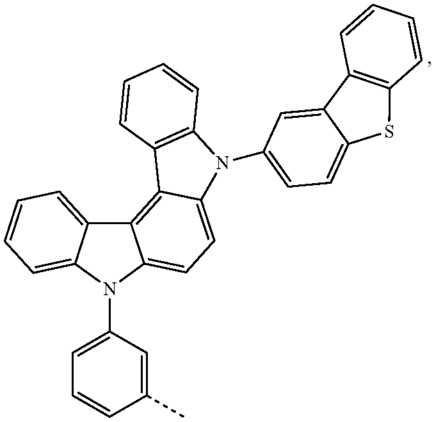
D161
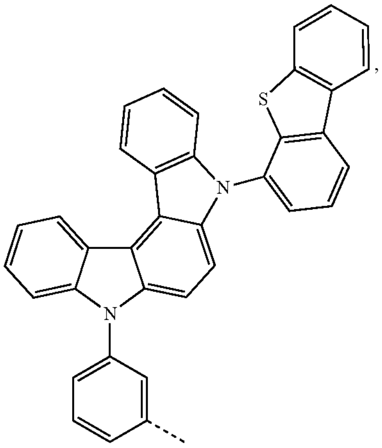
-continued
D162
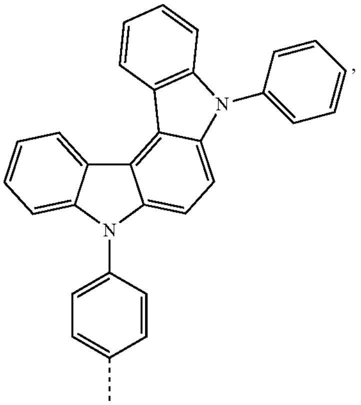
D163
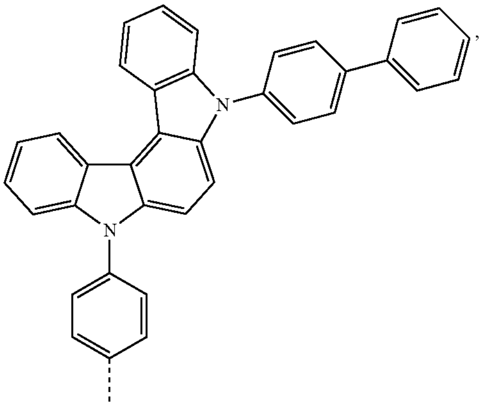
D164
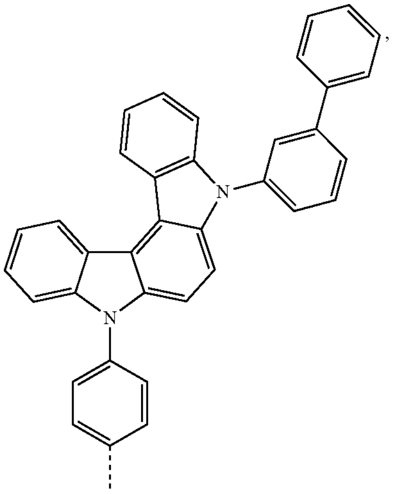

-continued
D[165]
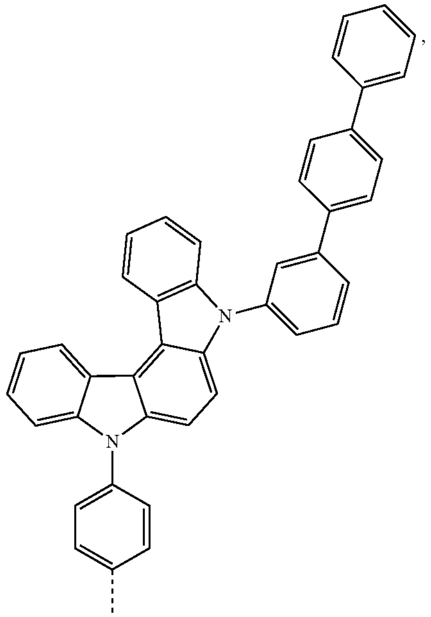
D[166]
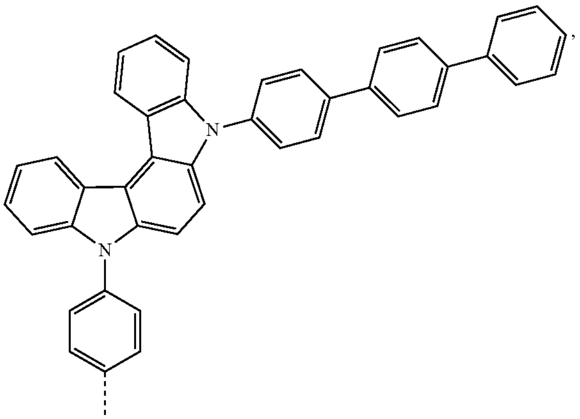
D[167]
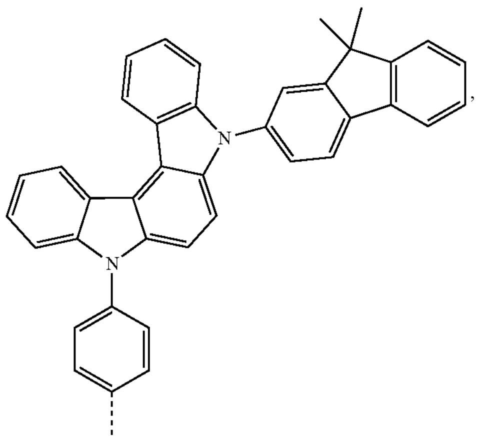
-continued
D[168]
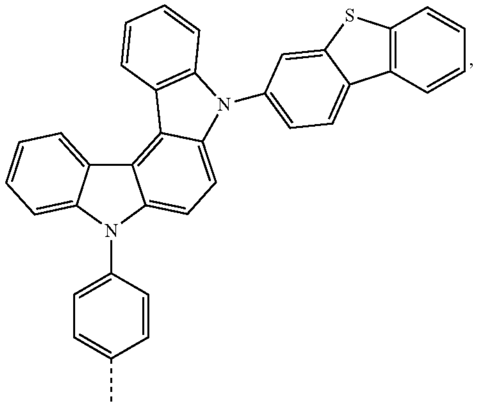
D[169]
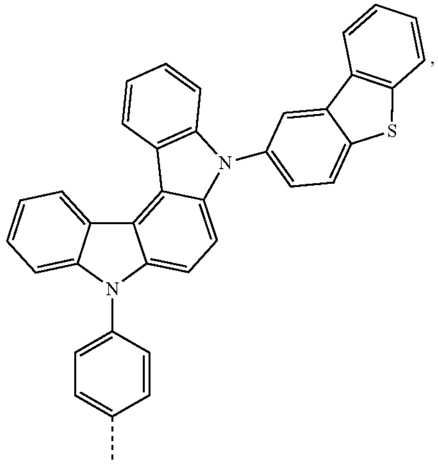
D[170]
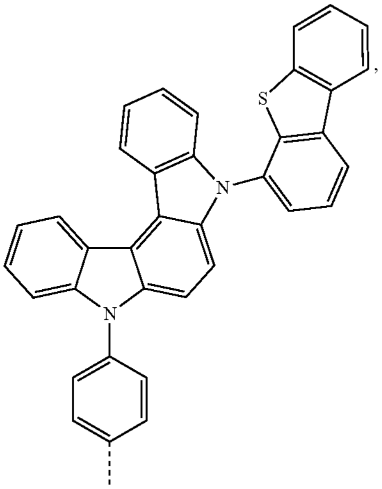

-continued
D[171]
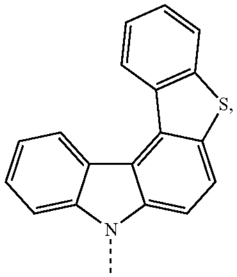
D[172]
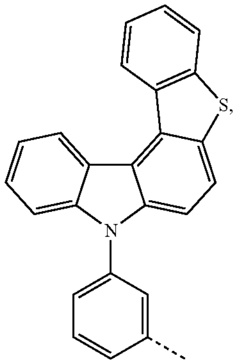
D[173]
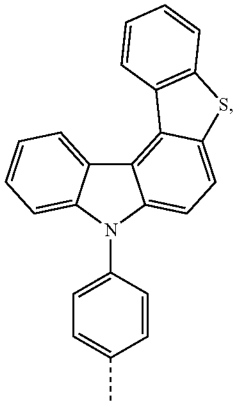
D[174]
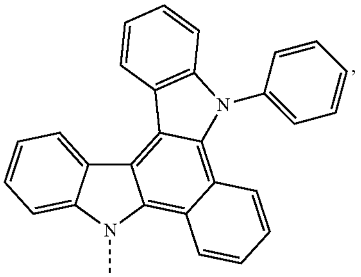
D[175]
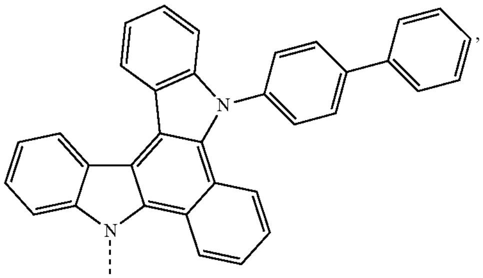
-continued
D[176]
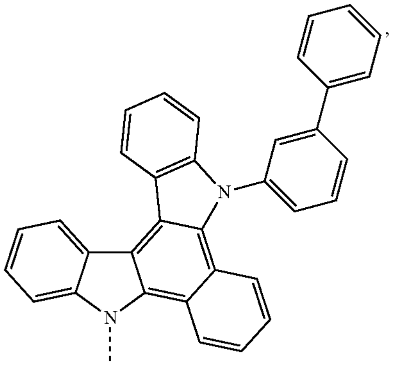
D[177]
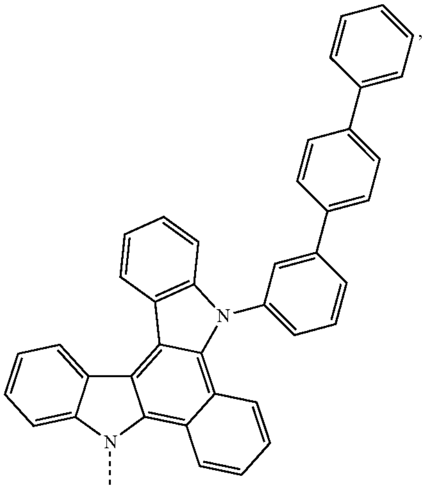
D[178]
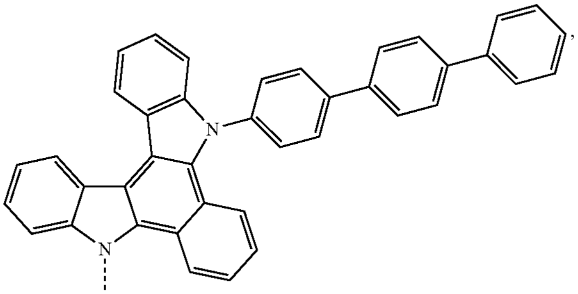
D[179]
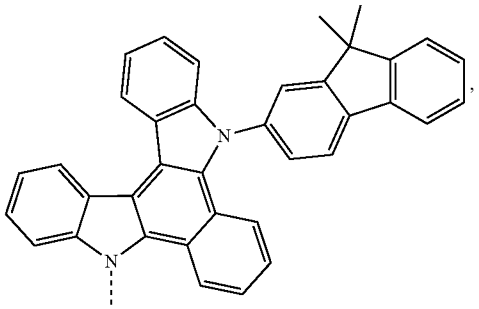

D[180]
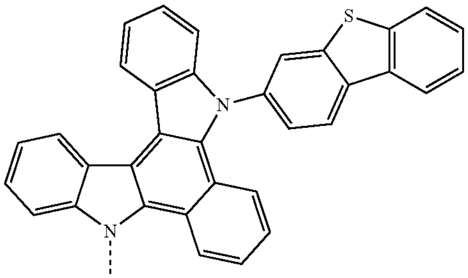
,
D[181]
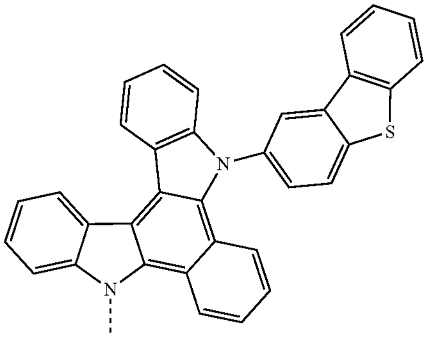
,
D[182]
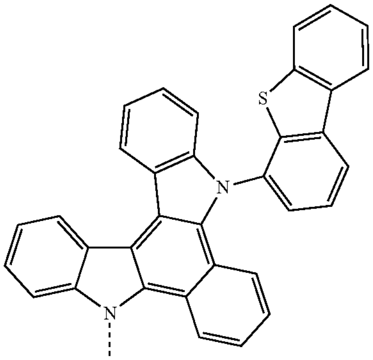
,
D[183]
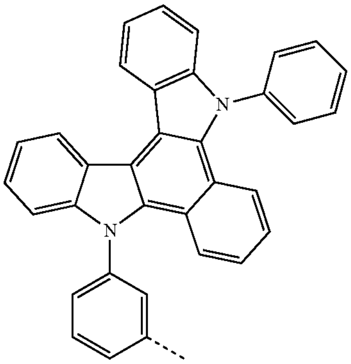
,
D[184]
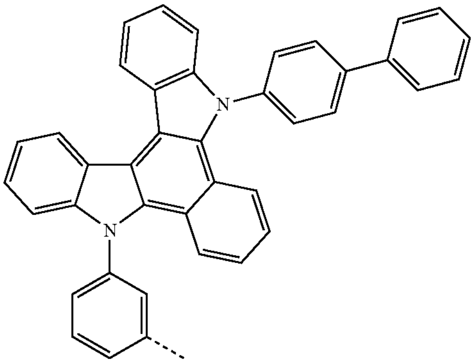
,
D[185]
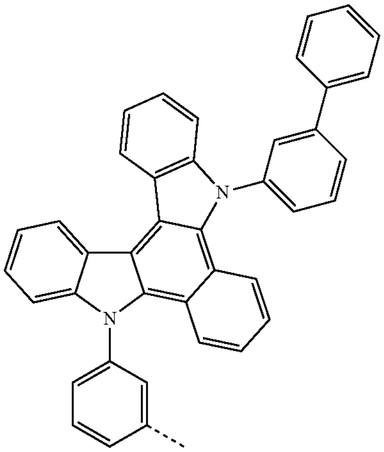
,
D[186]
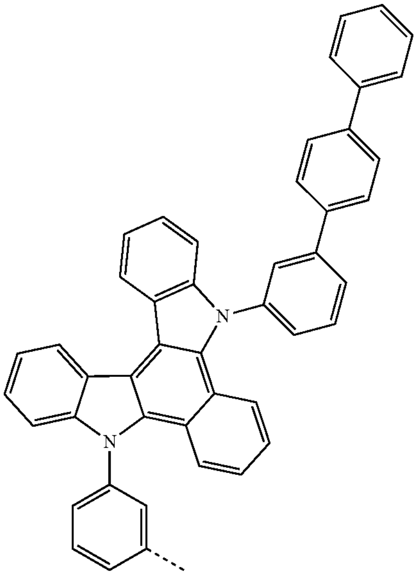
, D[187]
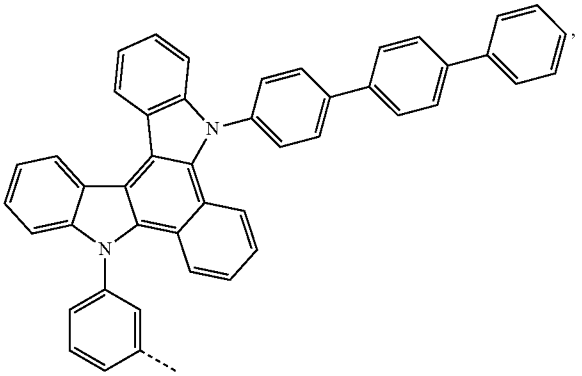
D[188]
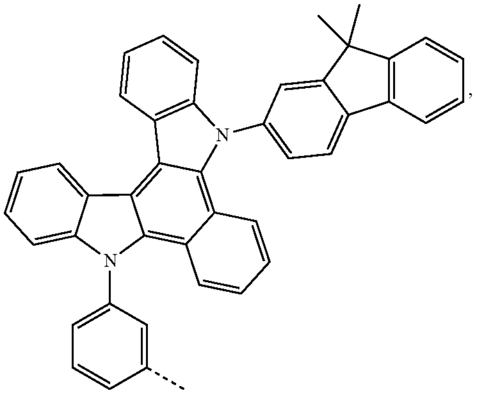
D[189]
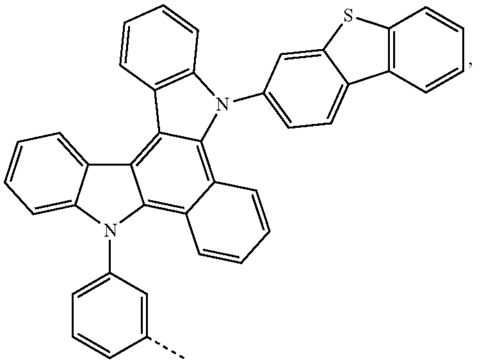
D[190]
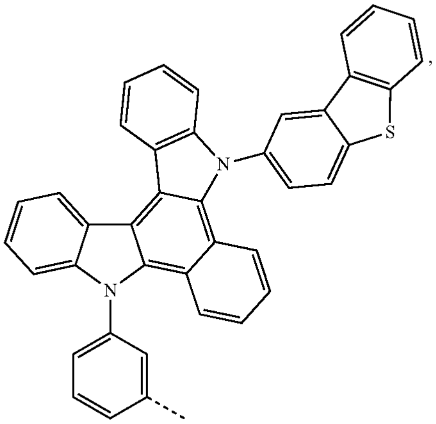
D[191]
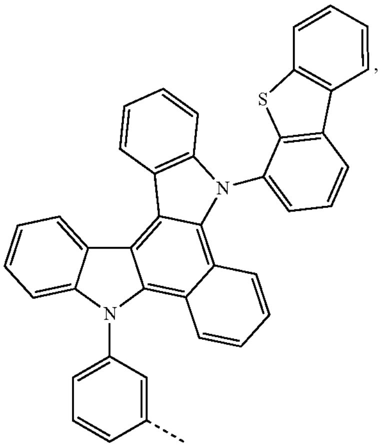
D[192]
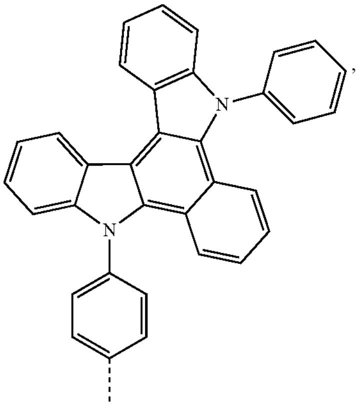
D[193]
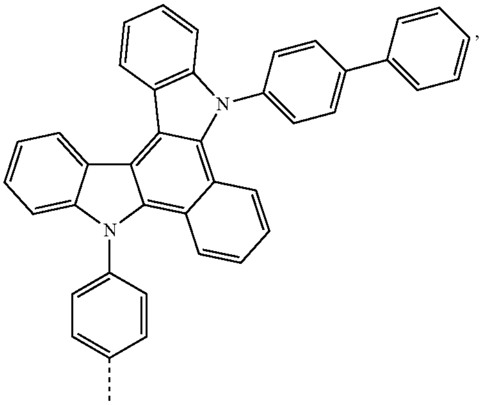

-continued
D[194]
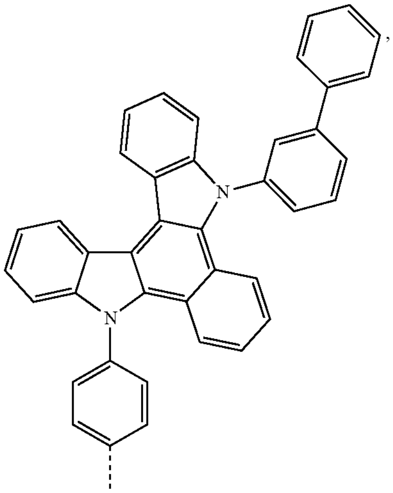
,
D[195]
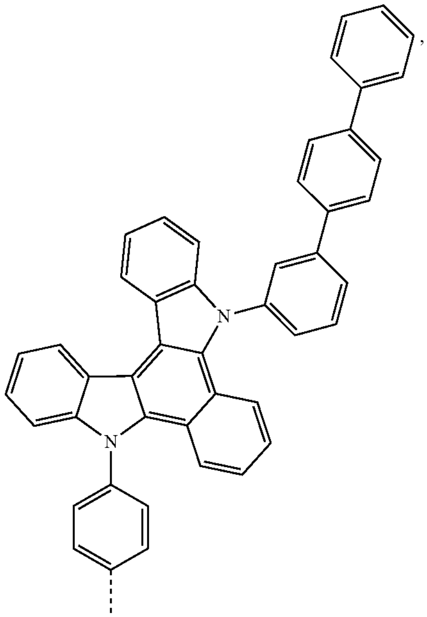
,
D[196]
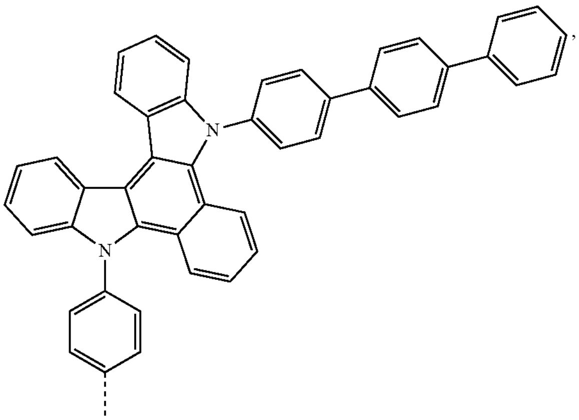
,
-continued
D[197]
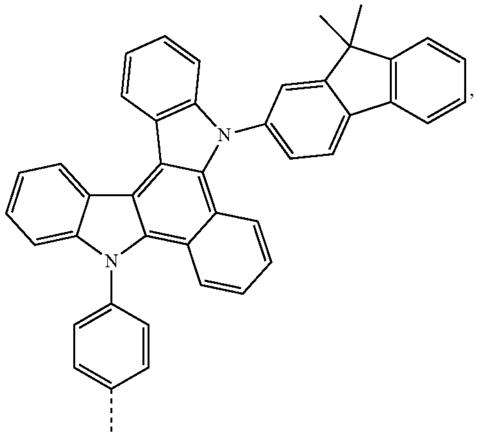
,
D[198]
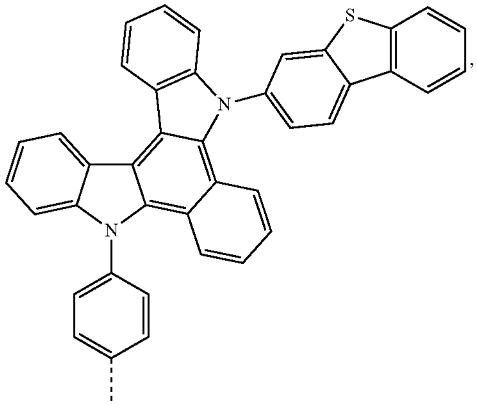
,
D[199]
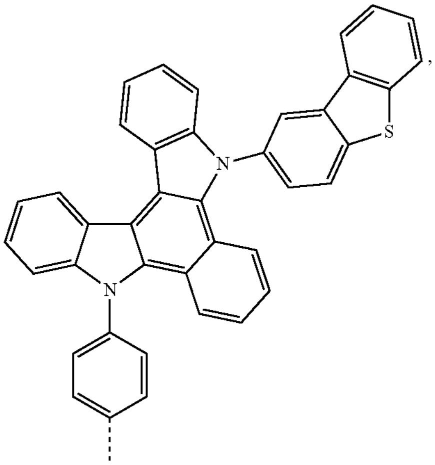
, -continued
$D^{200}$
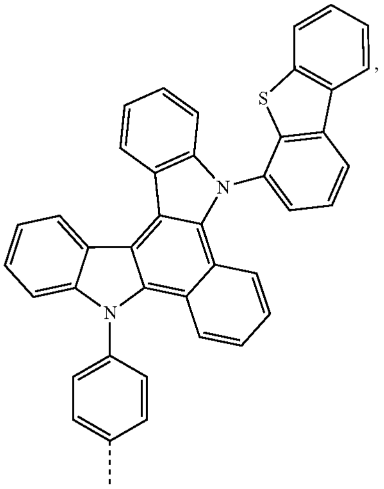
$D^{201}$
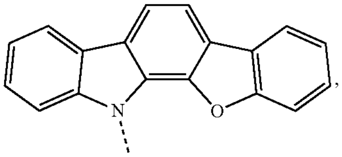
$D^{202}$
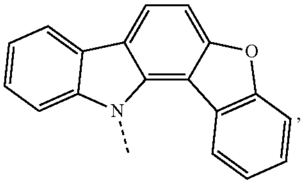
$D^{203}$
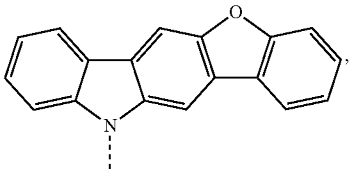
$D^{204}$
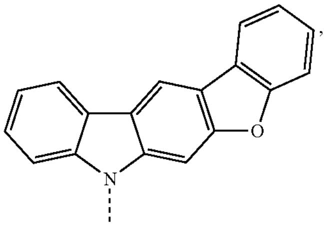
$D^{205}$
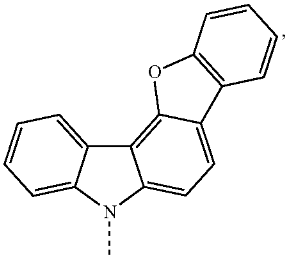
-continued
$D^{206}$
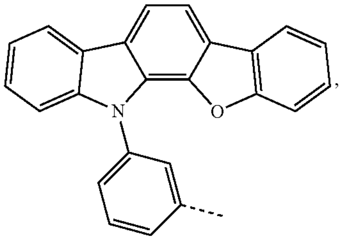
$D^{207}$
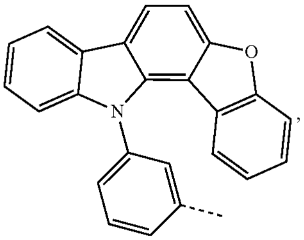
$D^{208}$
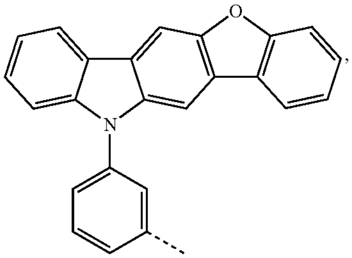
$D^{209}$
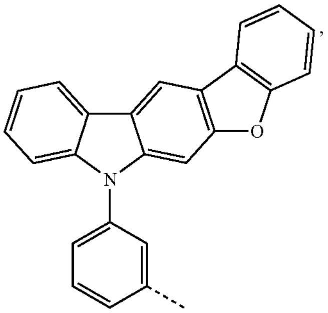
$D^{210}$
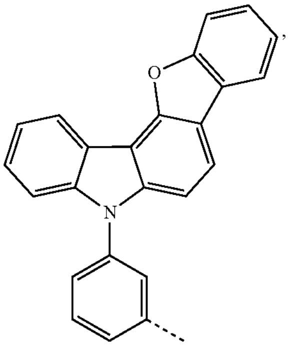

-continued
D[211]
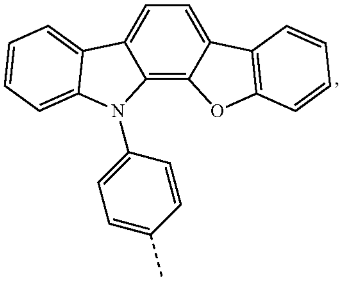
D[212]
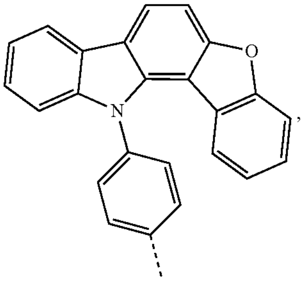
D[213]
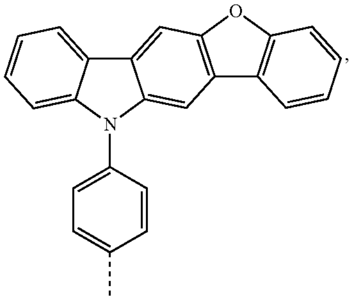
D[214]
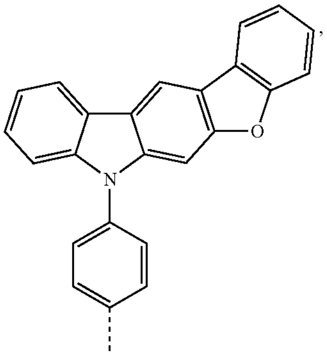
D[215]
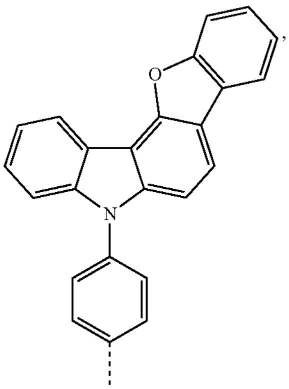
-continued
D[216]
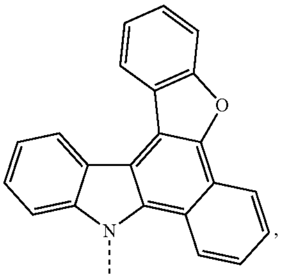
D[217]
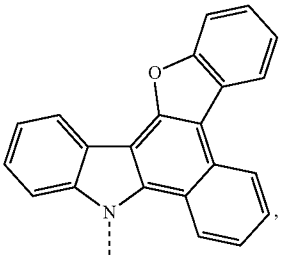
D[218]
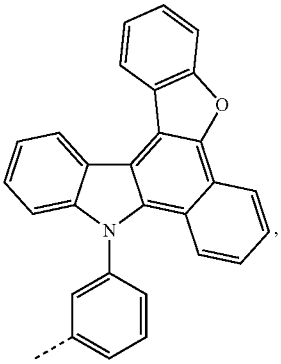
D[219]
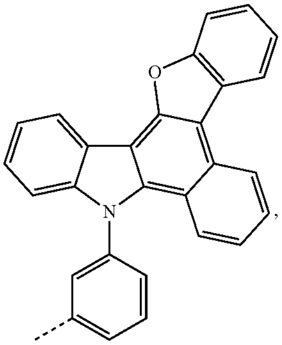

-continued
D[220]
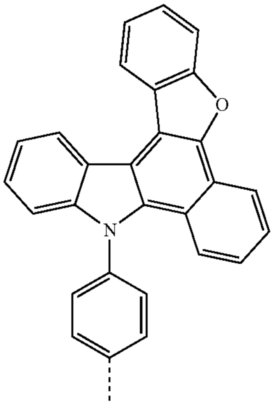
,
D[221]
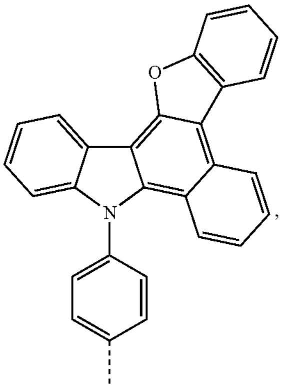
,
D[222]
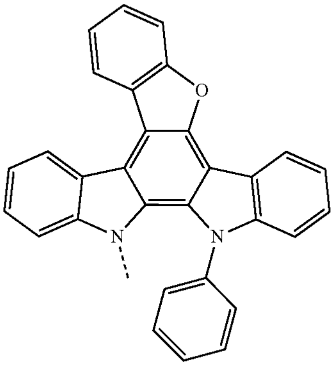
,
D[223]
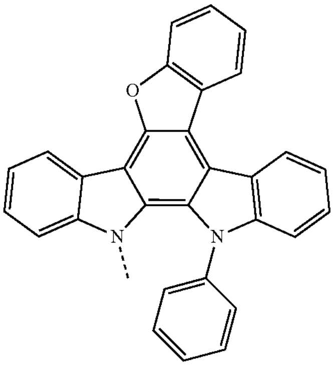
,
-continued
D[224]
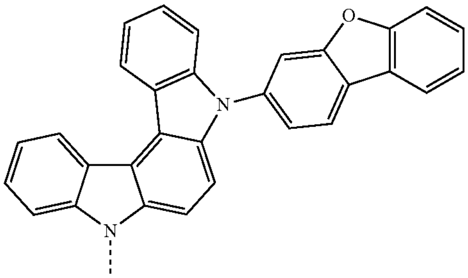
,
D[225]
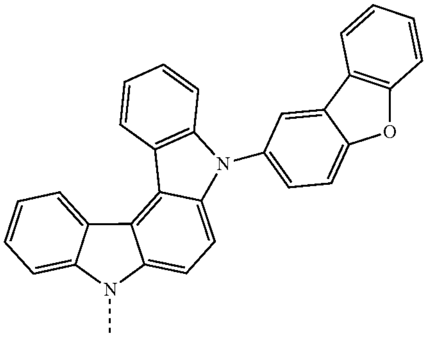
,
D[226]
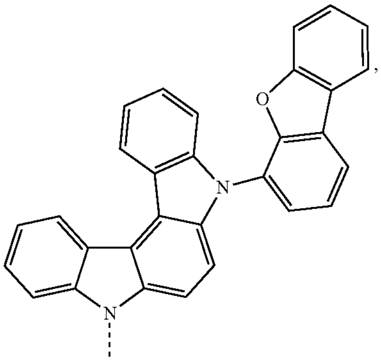
,
D[227]
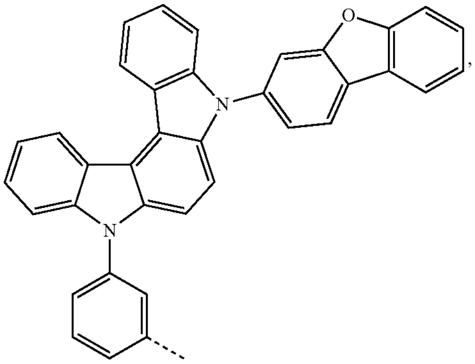
, D[228]
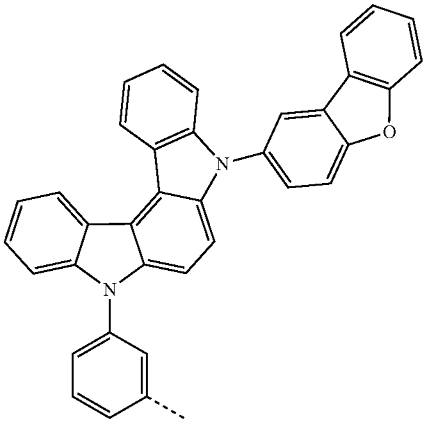
,
D[229]
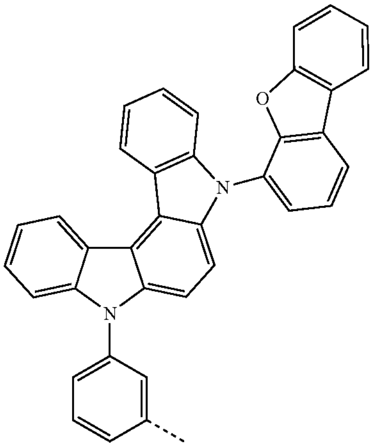
,
D[230]
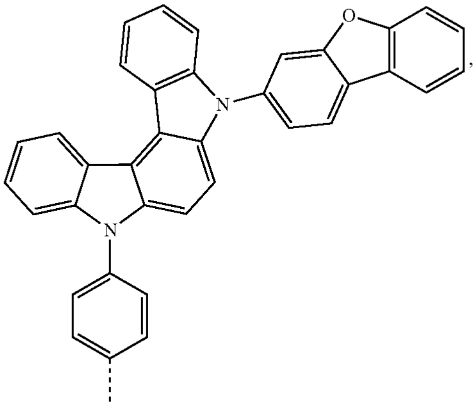
,
D[231]
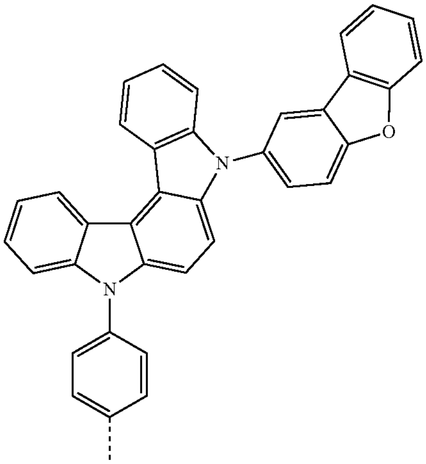
,
D[232]
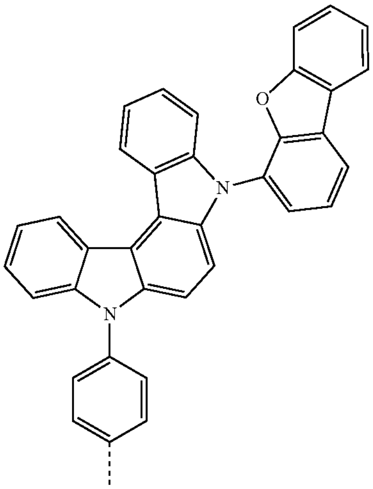
,
D[233]
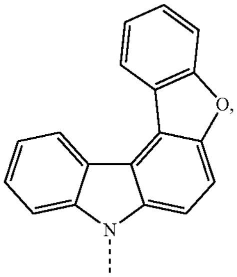
,
D[234]
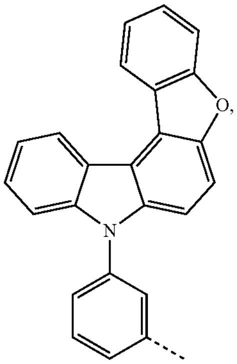
, -continued
D[235]
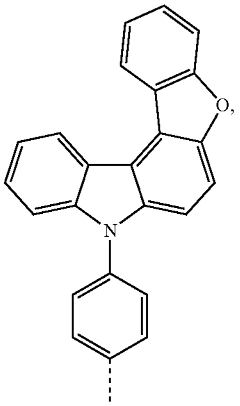
D[236]
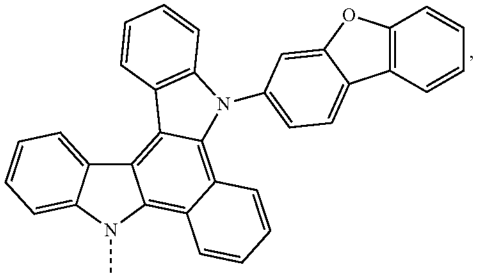
D[237]
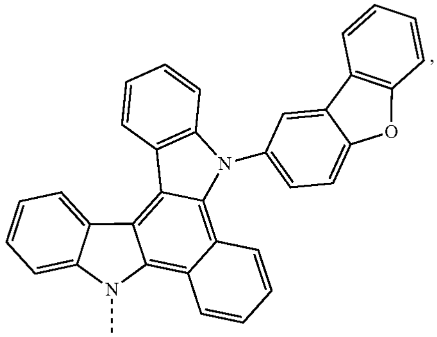
D[238]
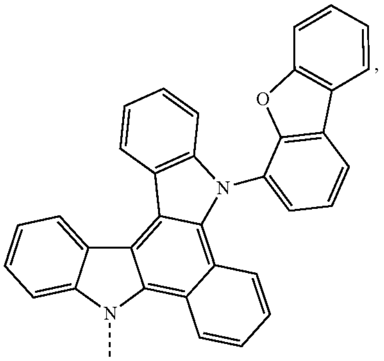
-continued
D[239]
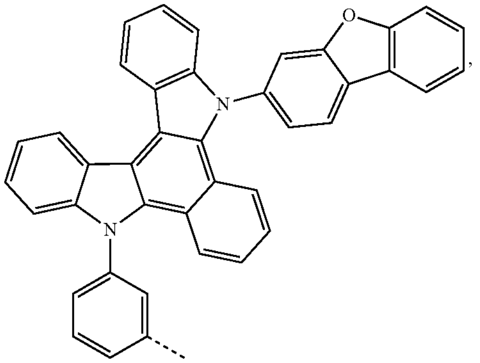
D[240]
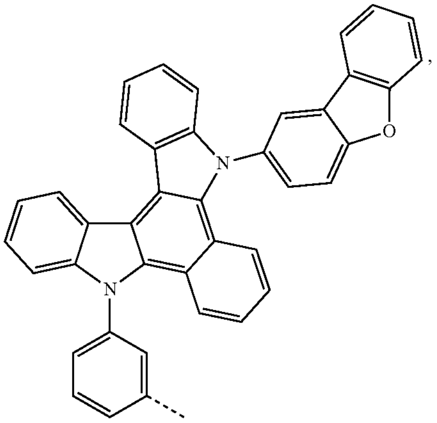
D[241]
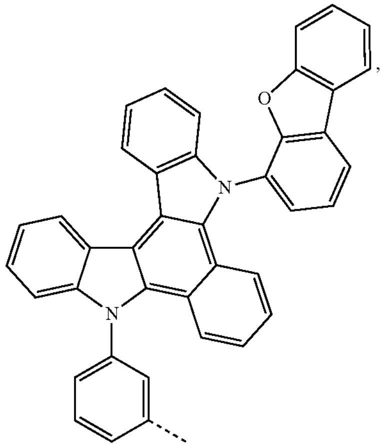

-continued

D242

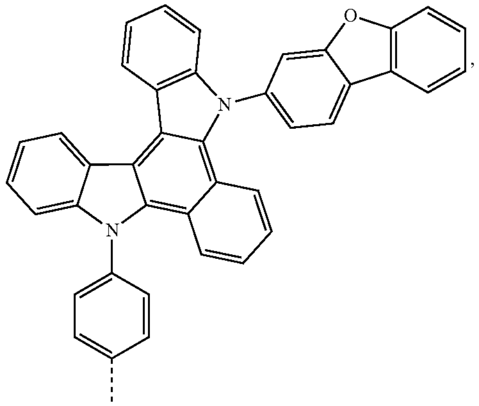

D243

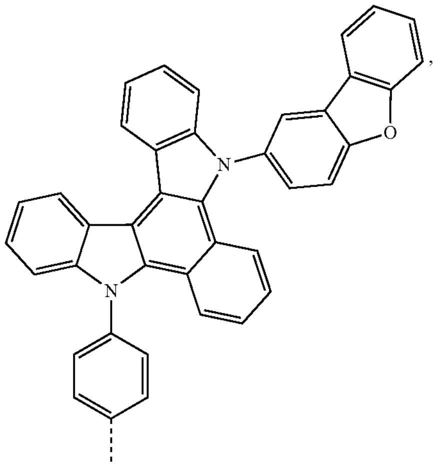

, and

D244

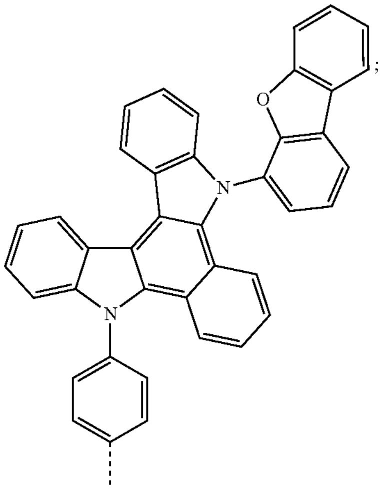

wherein any adjacent substitutions on the same ring are optionally joined or fused into a ring; and wherein at least one of the following is true: (i) at least one of $X^5$ and $X^6$ is N, (ii) at least one of $X^7$ to $X^{10}$ is N, (iii) each of $X^1$ to $X^4$ is carbon;

provided that when adjacent substitutions on $X^5$ and $X^6$ in Formula I-1 and I-3 fuse into a six-member ring, this ring and the ring having $X^7$ to $X^{10}$ cannot be pyridine at the same time.

2. The compound of claim 1, wherein at least one of $X^5$ and $X^6$ is nitrogen.

3. The compound of claim 1, wherein the adjacent substitutions on $X^5$ and $X^6$ are not joined or fused into a ring.

4. The compound of claim 1, wherein $X^1$ to $X^4$ are all carbon.

5. The compound of claim 1, wherein at least one of $X^1$ to $X^4$ is nitrogen, and at least one of $X^5$ and $X^6$ is nitrogen.

6. The compound of claim 1, wherein the compound has at least five aromatic rings fused together.

7. The compound of claim 1, wherein the compound is selected from the group consisting of:

Formula 2-1

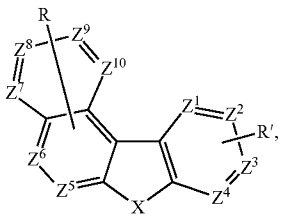

Formula 2-2

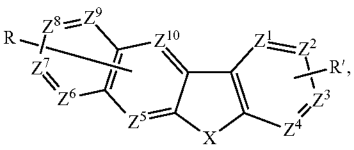

Formula 2-3

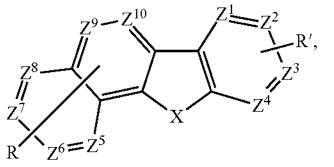

Formula 2-4

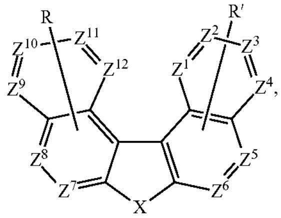

Formula 2-5

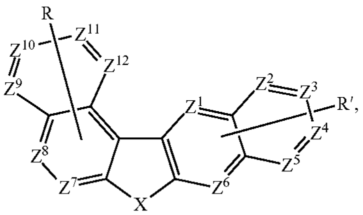

Formula 2-6

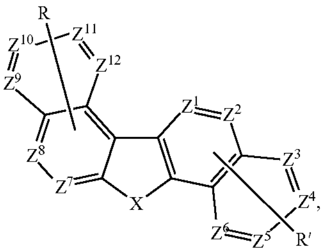

-continued
Formula 2-7
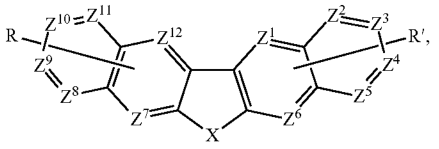
Formula 2-8
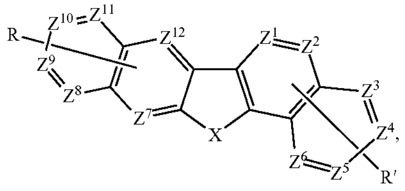
Formula 2-9
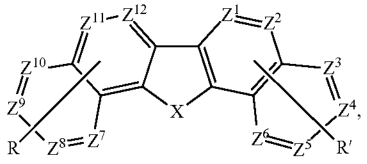
Formula 2-10
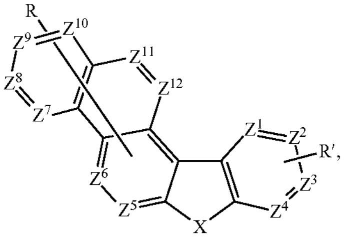
Formula 2-11
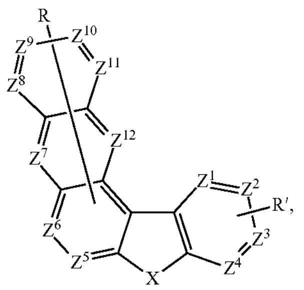
Formula 2-12
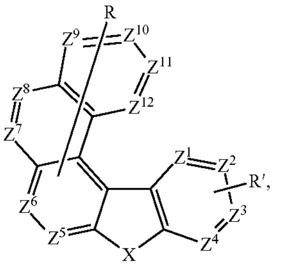
Formula 2-13
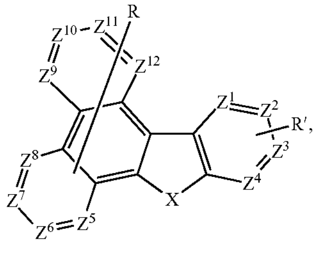
-continued
Formula 2-14
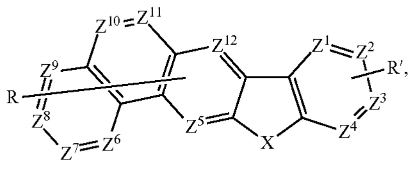
Formula 2-15
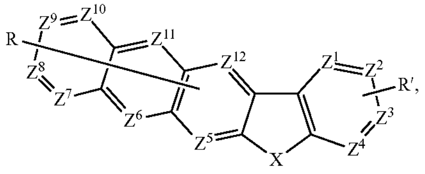
Formula 2-16
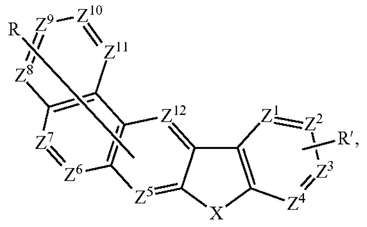
Formula 2-17
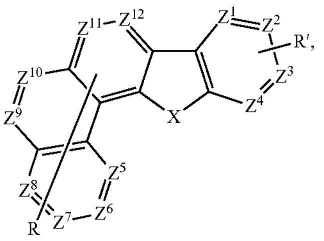
Formula 2-18
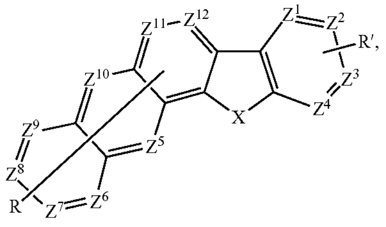
Formula 2-19
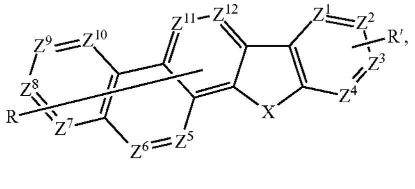
Formula 2-20
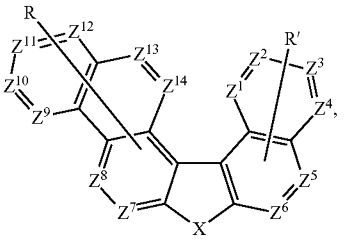

-continued
Formula 2-21
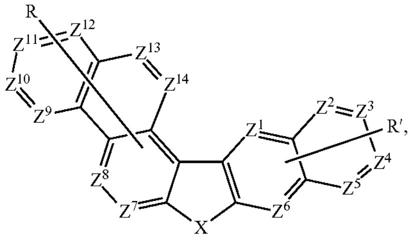
Formula 2-22
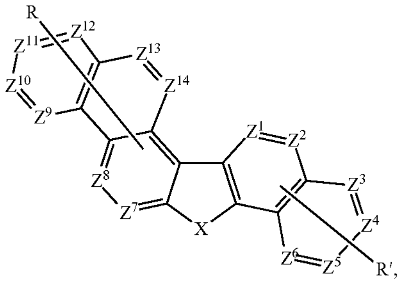
Formula 2-23
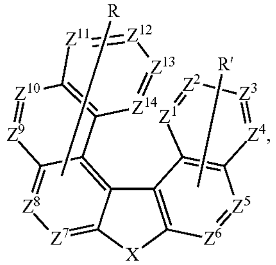
Formula 2-24
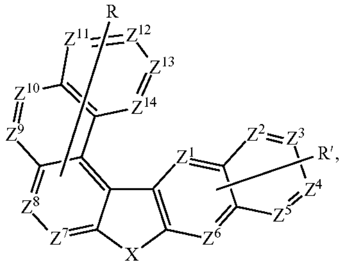
Formula 2-25
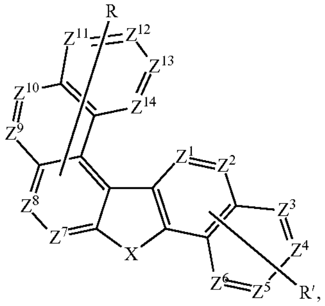
Formula 2-26
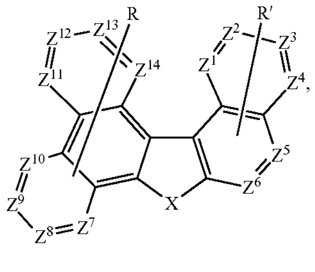
-continued
Formula 2-27
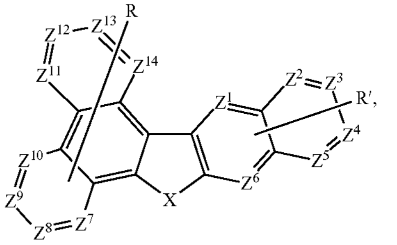
Formula 2-28
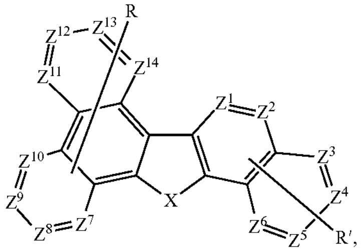
Formula 2-29
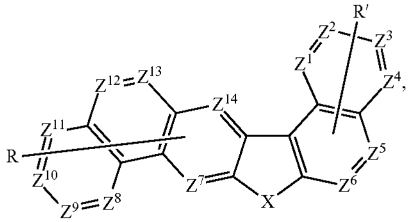
Formula 2-30
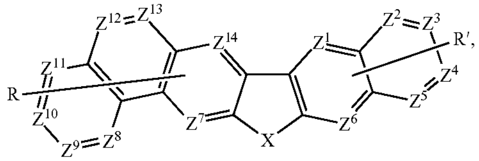
Formula 2-31
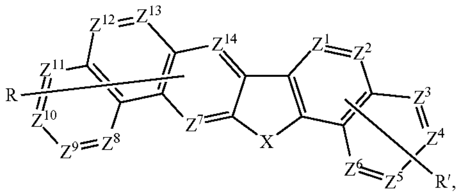
Formula 2-32
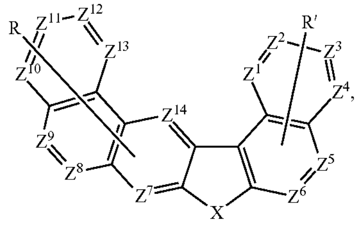
Formula 2-33
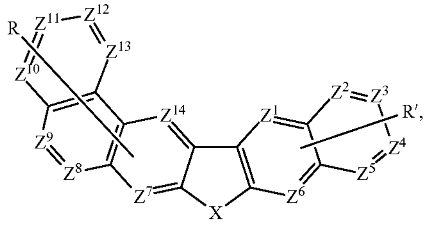

-continued
Formula 2-34
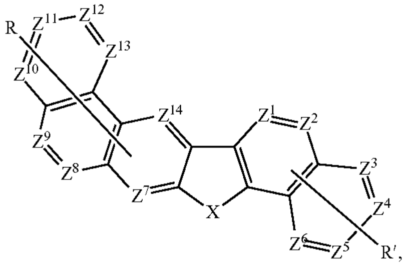
Formula 2-35
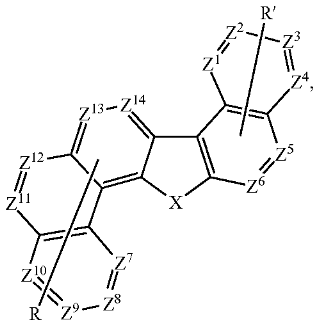
Formula 2-36
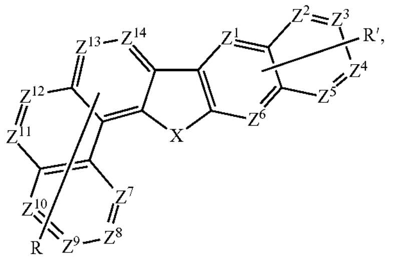
Formula 2-37
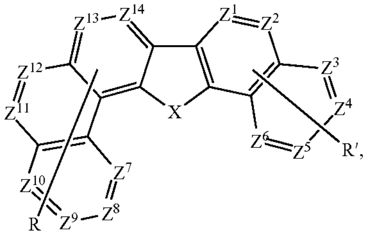
Formula 2-38
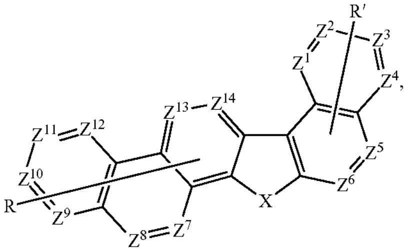
Formula 2-39
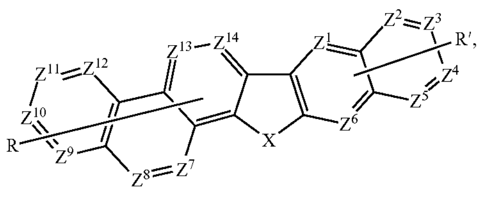
-continued
Formula 2-40
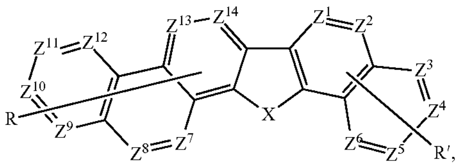
Formula 2-41
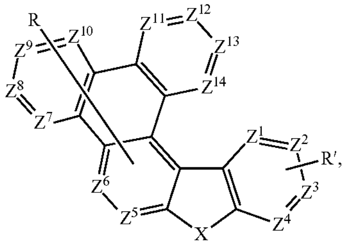
Formula 2-42
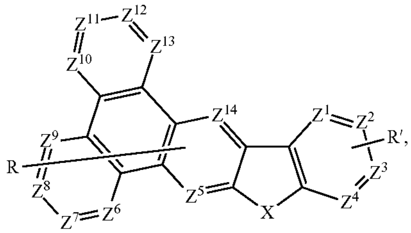
Formula 2-43
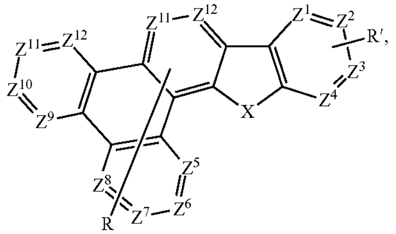
Formula 2-44
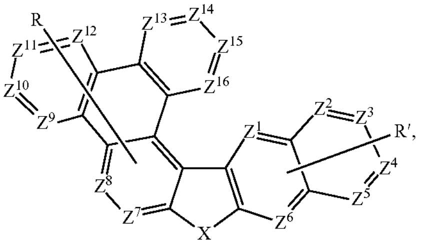
Formula 2-45
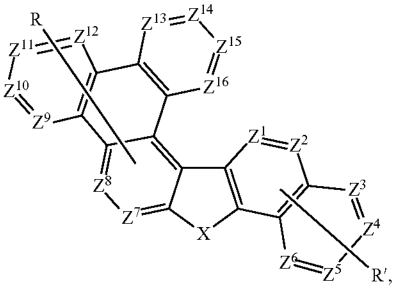

-continued
Formula 2-46
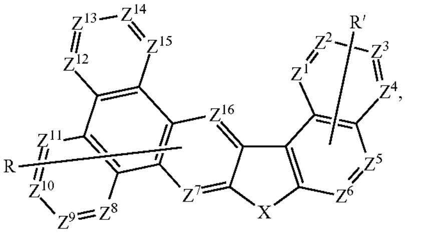
Formula 2-47
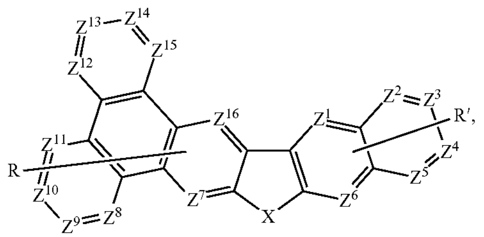
Formula 2-48
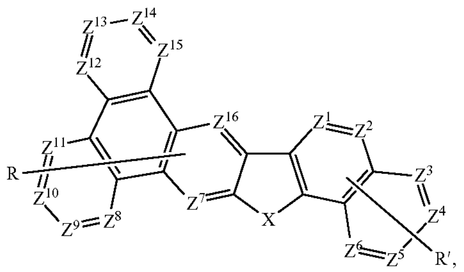
Formula 2-49
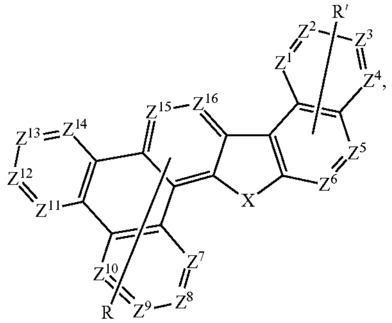
Formula 2-50
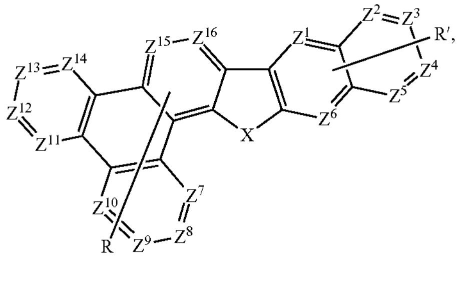
and
-continued
Formula 2-51
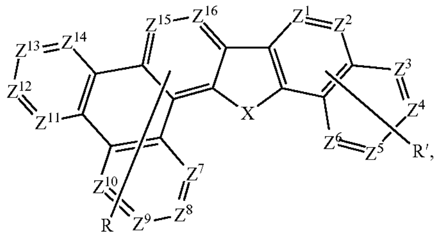
wherein $Z^1$ to $Z^{16}$ are each independently selected from the group consisting of carbon and nitrogen.
8. The compound of claim 1, wherein the compound comprises a group selected from the group consisting of:
$A^1$
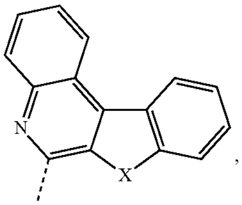
,
$A^3$
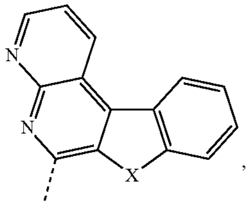
,
$A^4$
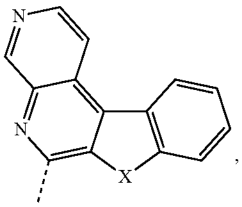
,
$A^5$
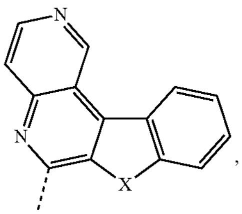
,
$A^6$
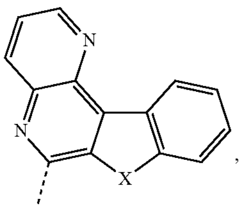
, -continued
A[7]
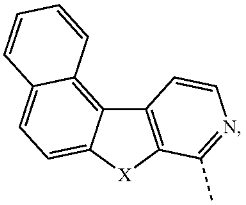
A[8]
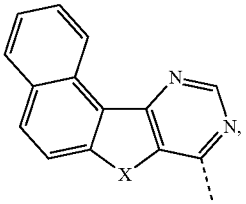
A[8]
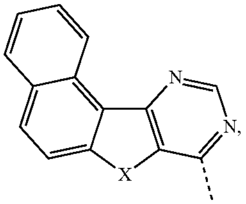
A[10]
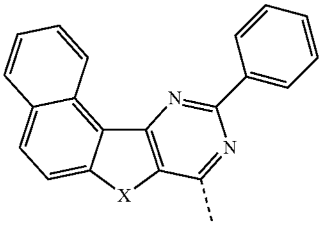
,
A[12]
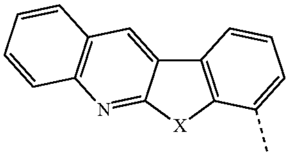
,
A[14]
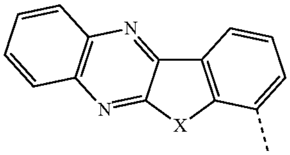
,
A[16]
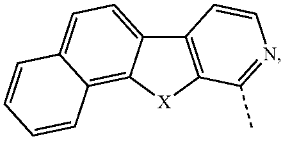
A[17]
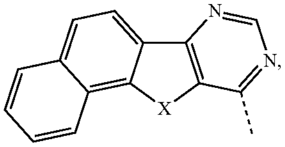
-continued
A[18]
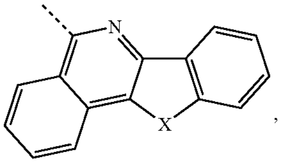
,
A[19]
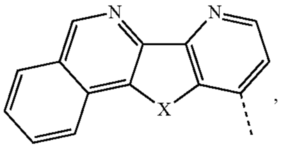
,
A[20]
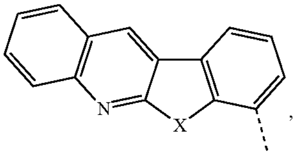
,
A[21]
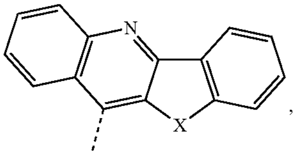
,
A[22]
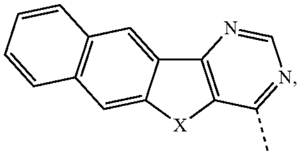
A[23]
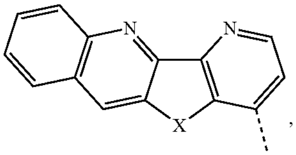
,
A[24]
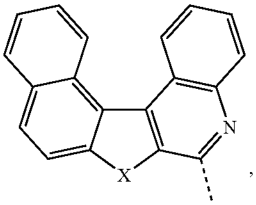
,
A[25]
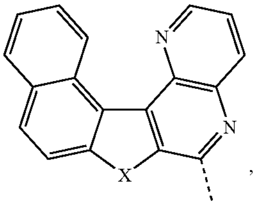
, -continued
A[26]
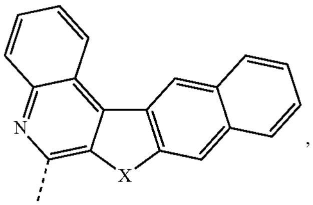,
A[27]
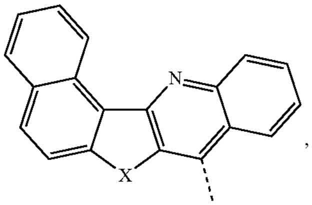,
A[28]
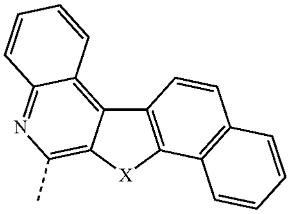,
A[29]
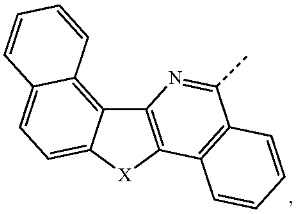,
A[30]
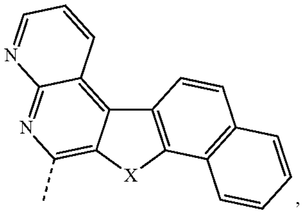,
A[31]
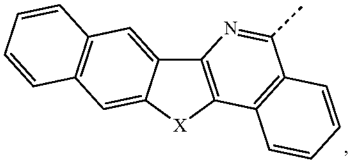,
A[32]
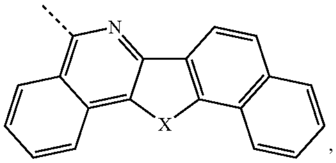,
-continued
A[33]
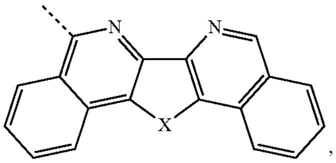,
A[34]
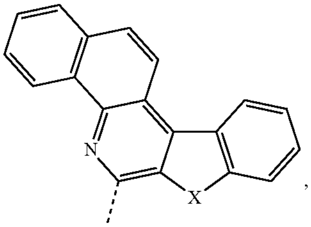,
A[35]
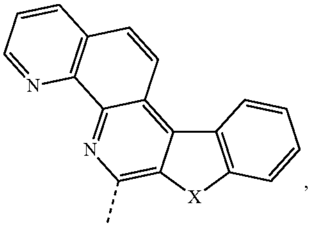,
A[36]
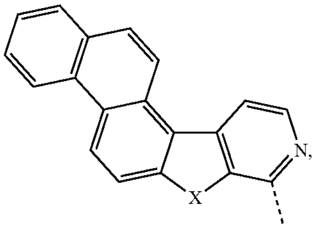
A[37]
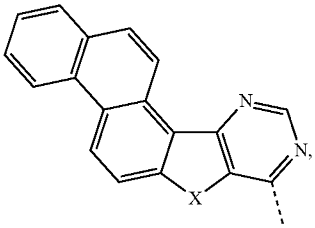
A[40]
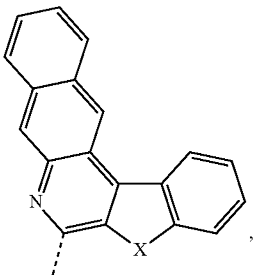, -continued
A42
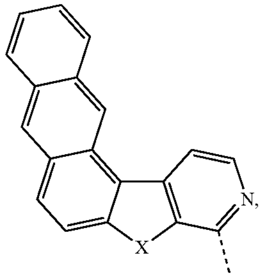
A43
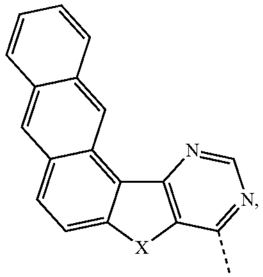
A44
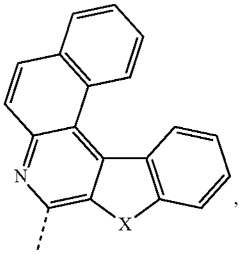
,
A45
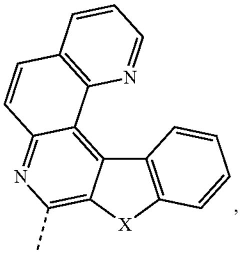
,
A46
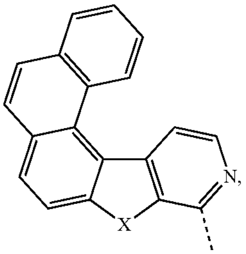
A47
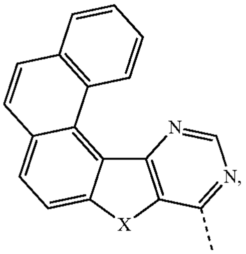
-continued
A48
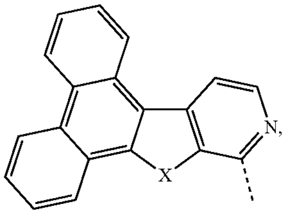
A49
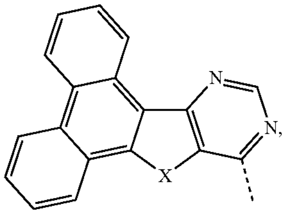
A50
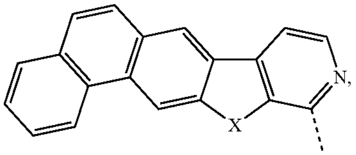
A51
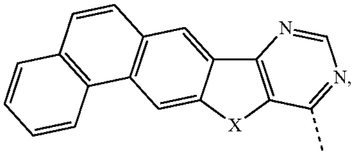
A57
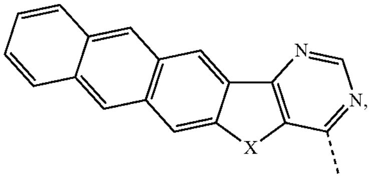
A58
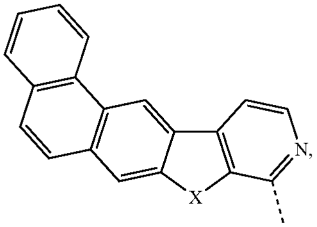
A59
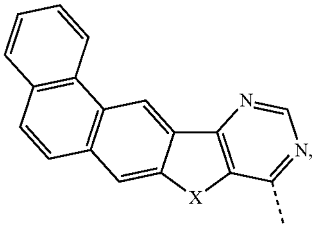

-continued
A[60]
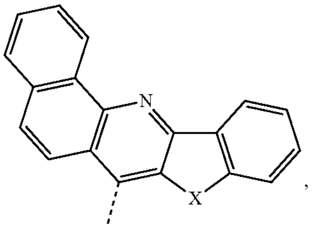
A[61]
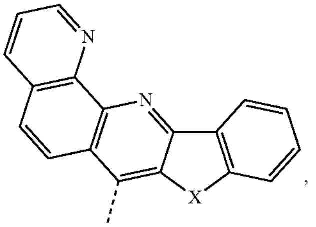
A[62]
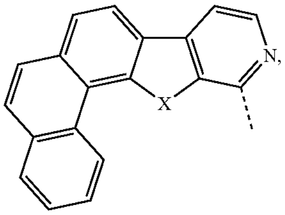
A[63]
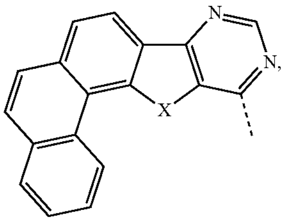
A[64]
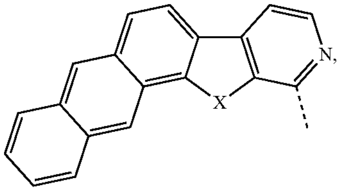
A[65]
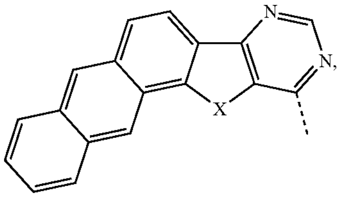
A[66]
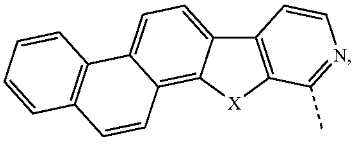
-continued
A[67]
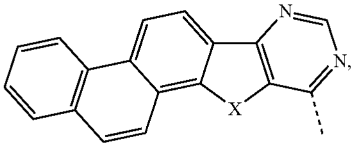
A[69]
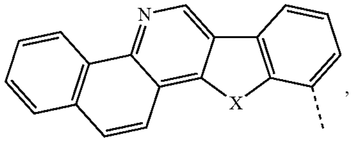
A[71]
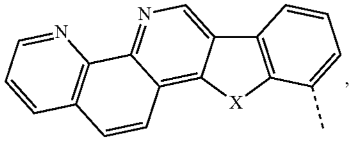
A[73]
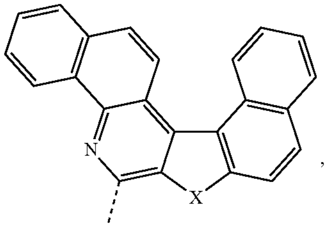
A[74]
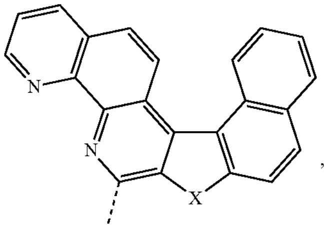
A[75]
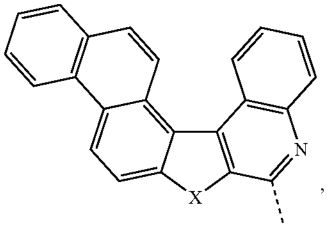
A[76]
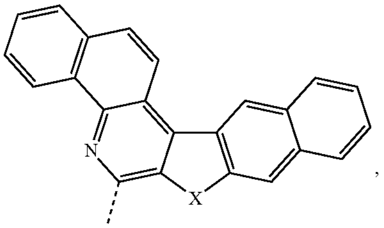

-continued
A[77]
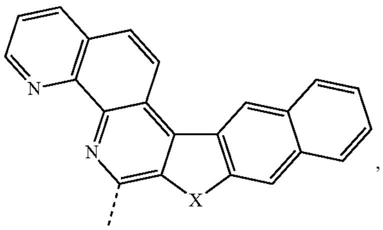
,
A[78]
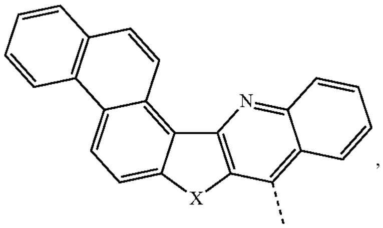
,
A[79]
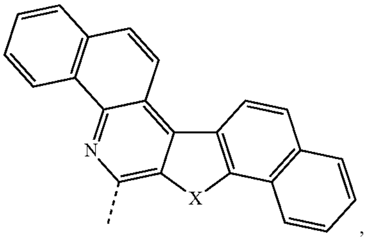
,
A[80]
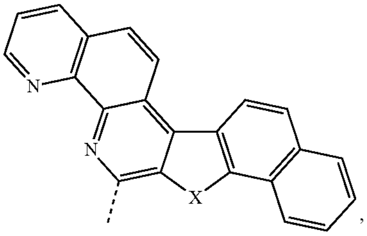
,
A[81]
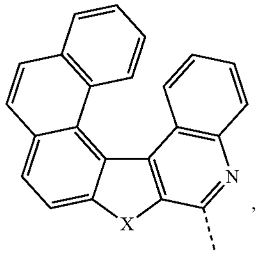
,
A[82]
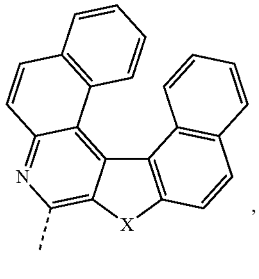
,
-continued
A[83]
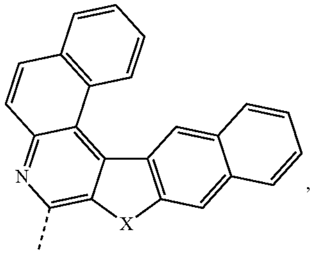
,
A[84]
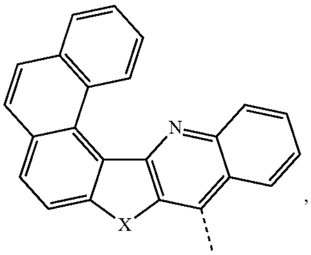
,
A[85]
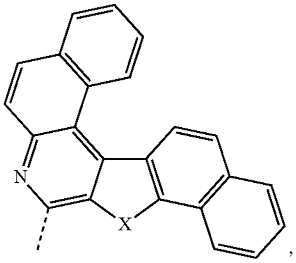
,
A[86]
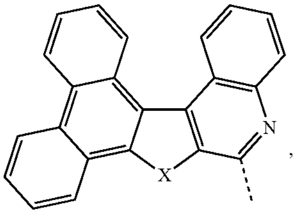
,
A[87]
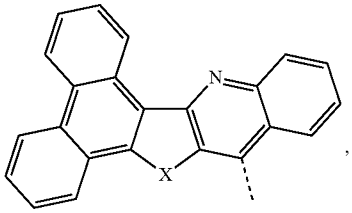
,
A[88]
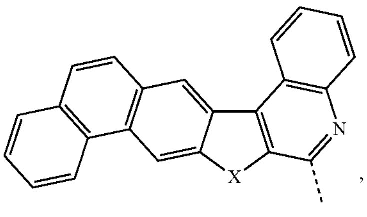
, -continued
A[89]
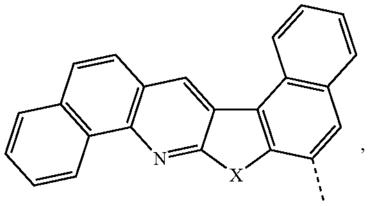
,
A[90]
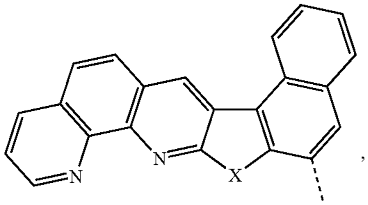
,
A[91]
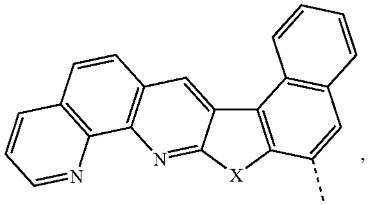
,
A[92]
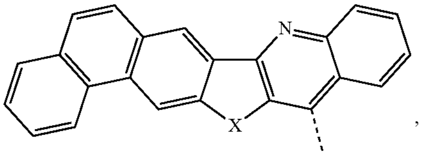
,
A[95]
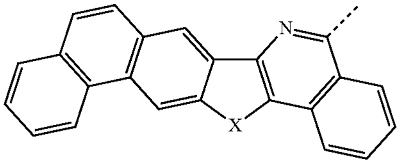
,
A[98]
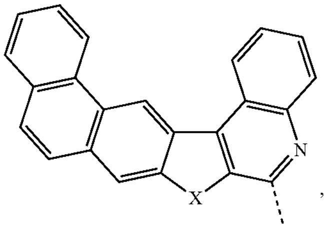
,
A[99]
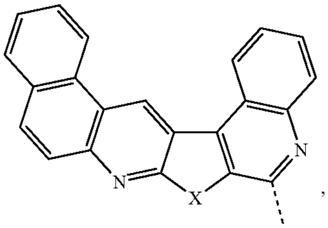
,
-continued
A[100]
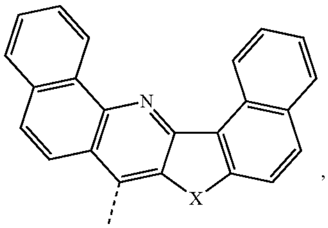
,
A[101]
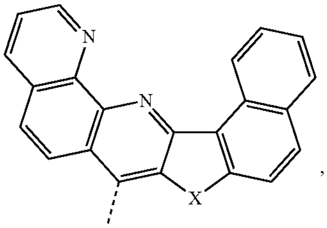
,
A[102]
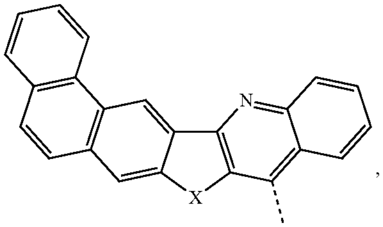
,
A[103]
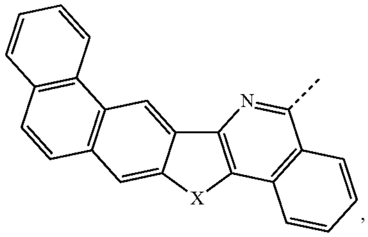
,
A[104]
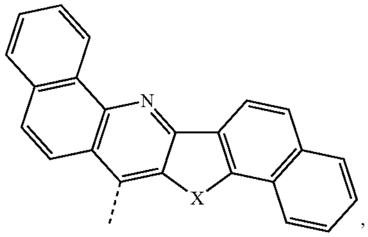
,
A[105]
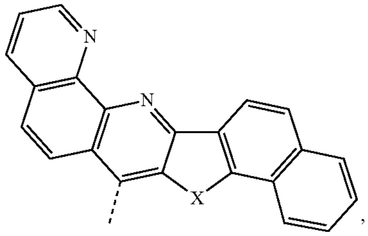
, -continued
A107
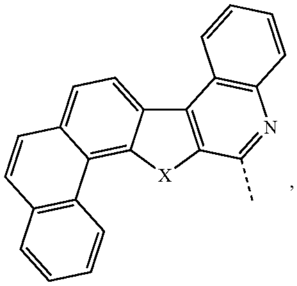
,
A108
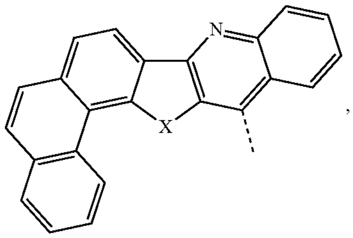
,
A109
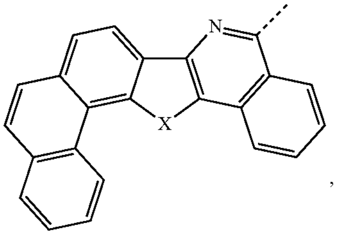
,
A110
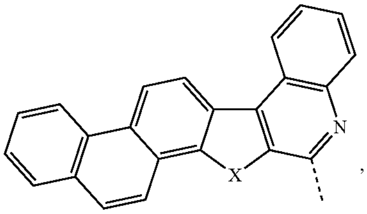
,
A113
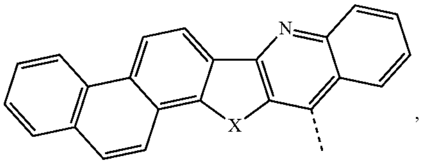
,
A116
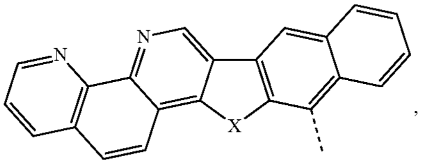
,
A117
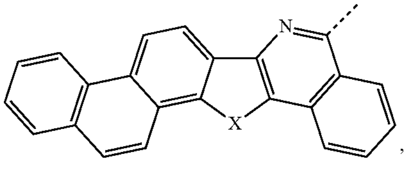
,
-continued
A120
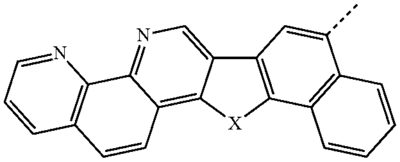
,
A117
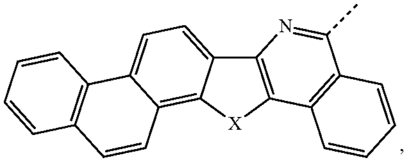
,
A121
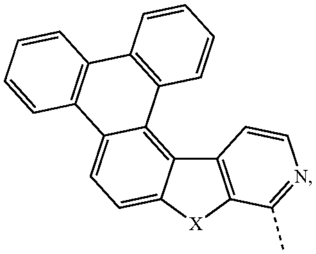
A122
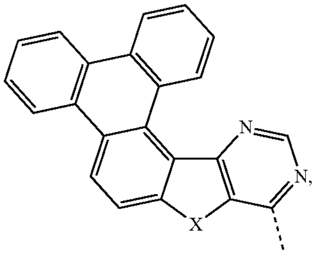
A123
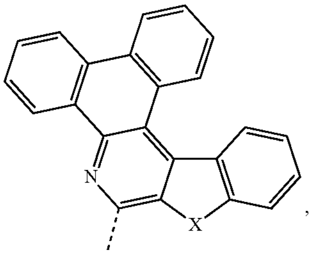
,
A124
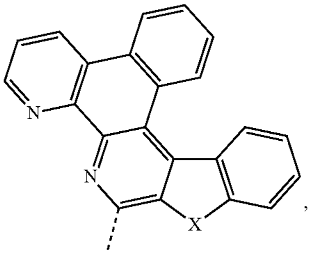
, A[126]
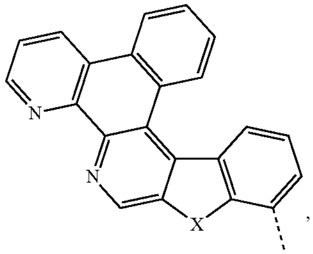
,
A[127]
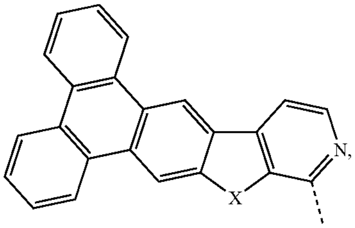
A[128]
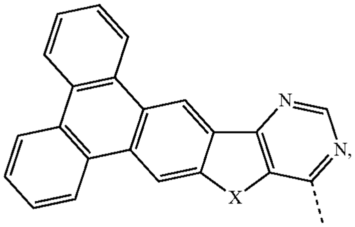
A[129]
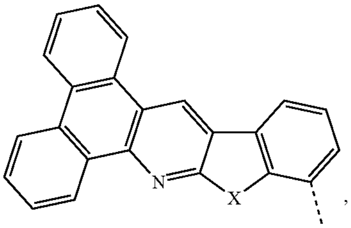
,
A[130]
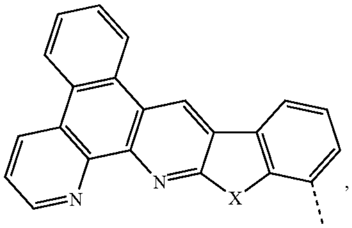
,
A[131]
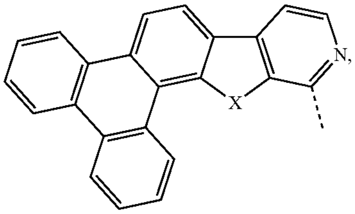
A[132]
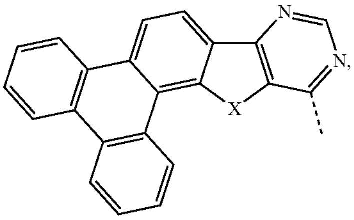
A[133]
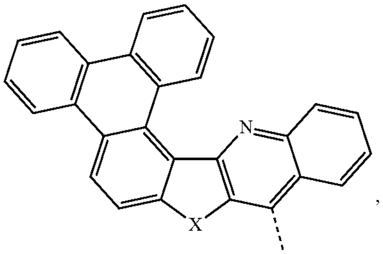
,
A[134]
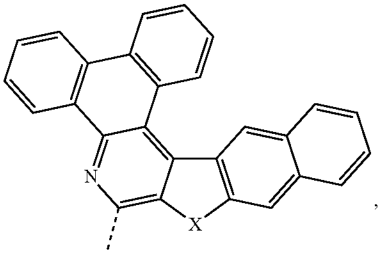
,
A[135]
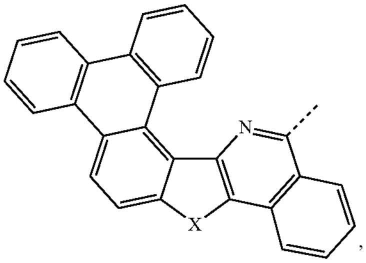
,
A[136]
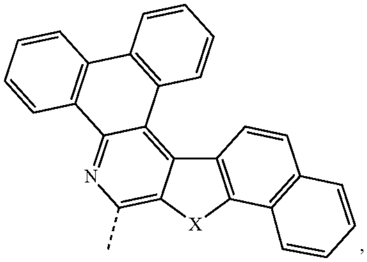
,
A[137]
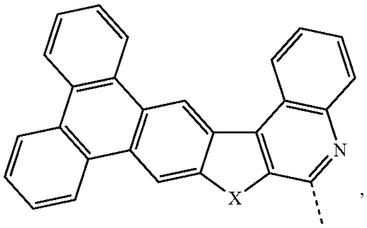
, -continued

A[139]

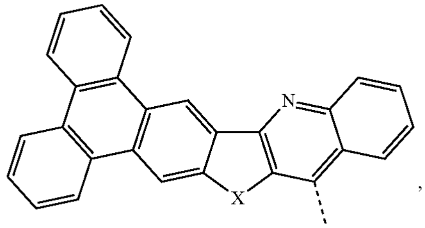

,

A[140]

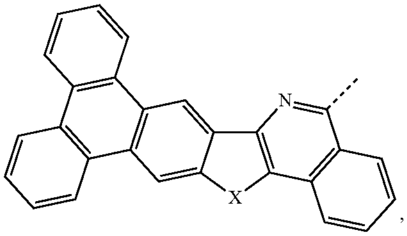

,

A[141]

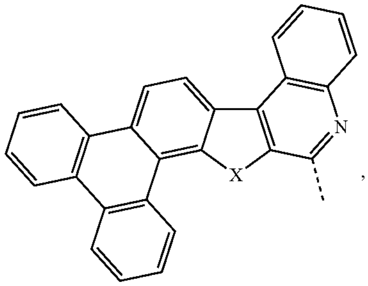

,

A[142]

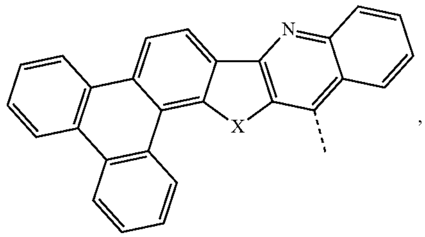

,

A[143]

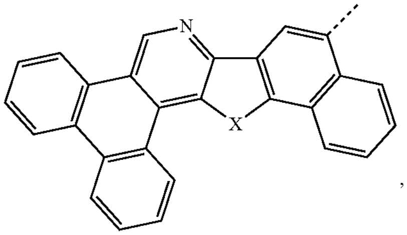

, and

A[144]

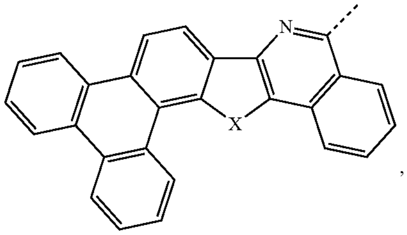

, wherein the dotted lines represent a possible substitution.

9. The compound of claim 8, wherein the compound is Compound x(Label) having the formula $A^iD^j$, wherein, x=144j+i−144, where i is an integer from 1, 3 to 8, 10, 12, 14, 16 to 37, 40, 42 to 51, 57 to 67, 69, 71, 73 to 92, 95, 98 to 105, 107 to 110, 113, 116, 117, 120 to 124, 126 to 137, 139 to 144, and j is an integer from 7 to 8, 10 to 29, 31 to 33, 36, 41 to 43, 45 to 49, 54 to 58, 61, 64 to 76, 79 to 244, Label is the X in the corresponding $A^i$, wherein the dotted line in each $D^j$ represents a bond to the corresponding $A^i$.

10. The compound of claim 1, wherein at least one of $X^1$ to $X^4$ is N.

11. The compound of claim 1, wherein at least one of $X^7$ to $X^{10}$ is N.

12. The compound of claim 1, wherein at least one pair of adjacent substituents of $X^1$ to $X^{10}$ are joined or fused together to form a ring.

13. The compound of claim 1, wherein the compound has a structure of formula 1-2.

14. A first organic light emitting device comprising:

an anode;

a cathode; and an organic layer, disposed between the anode and the cathode, comprising a compound having a formula selected from the group consisting of:

Formula 1-1

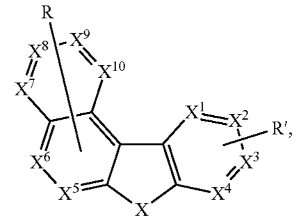

,

Formula 1-2

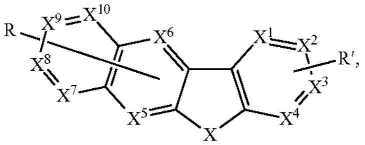

, and

Formula 1-3

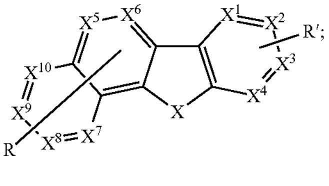

;

wherein X is selected from the group consisting of O, S, and Se;

wherein $X^1$ to $X^{10}$ are each independently selected from the group consisting of carbon and nitrogen;

wherein at least one of $X^1$ to $X^6$ is nitrogen;

wherein R and R' each independently represent from mono to the possible maximum number of substitutions, or no substitution;

wherein R and R' are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein at least one of $X^4$ and $X^5$ is carbon, which is substituted by a $D^j$ selected from the group consisting of:
$D^7$
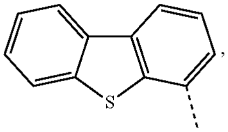
$D^8$
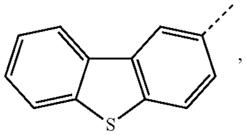
$D^{10}$
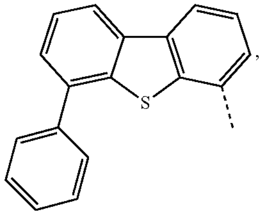
$D^{11}$
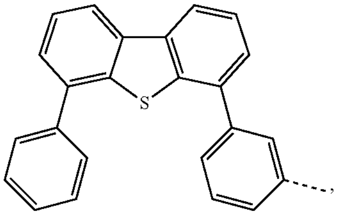
$D^{12}$
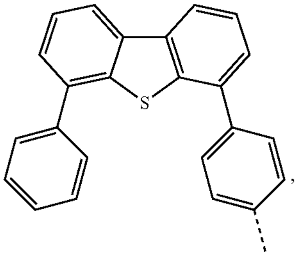
$D^{13}$
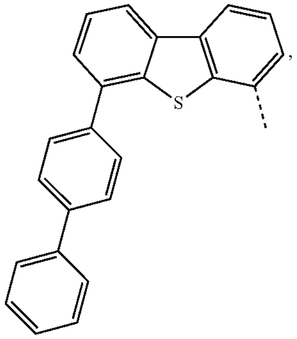
-continued
$D^{14}$
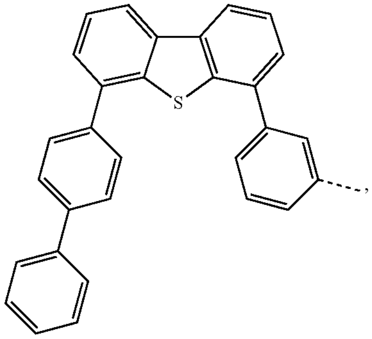
$D^{15}$
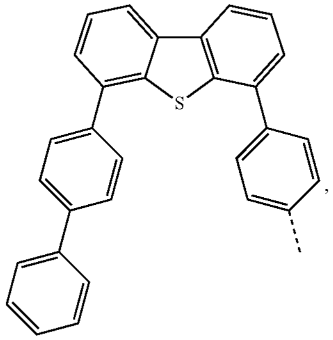
$D^{16}$
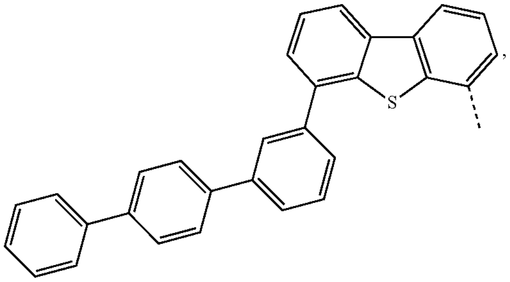
$D^{17}$
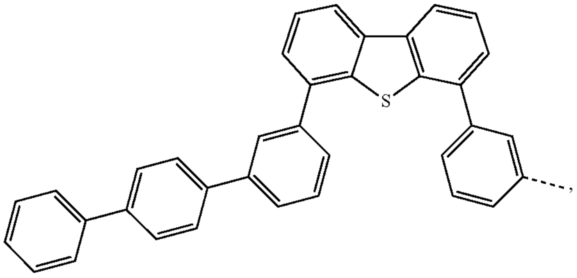
$D^{18}$
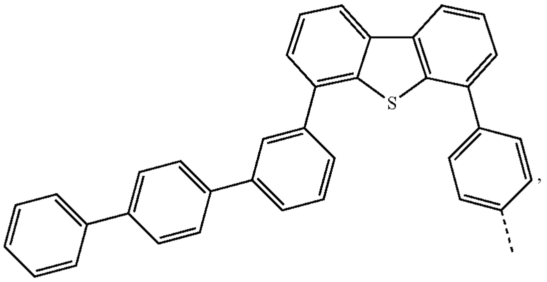

-continued
D[19]
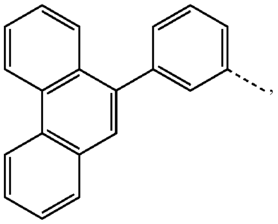
D[20]
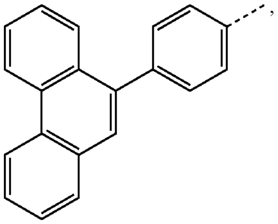
D[21]
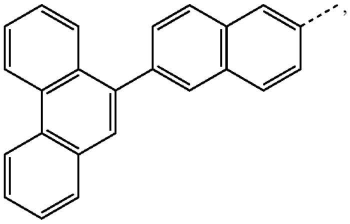
D[22]
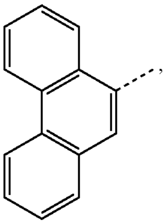
D[23]
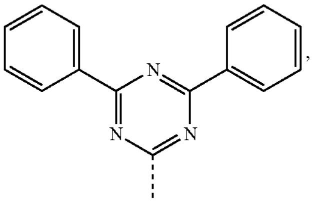
D[24]
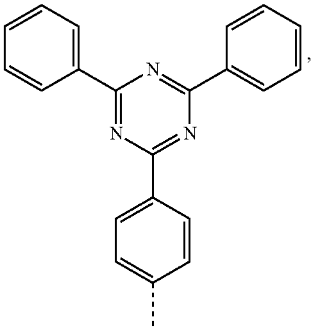
-continued
D[25]
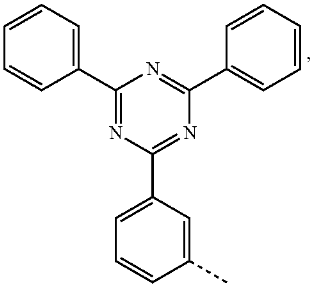
D[26]
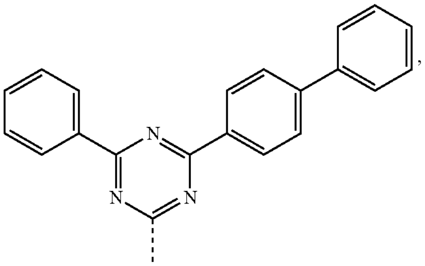
D[27]
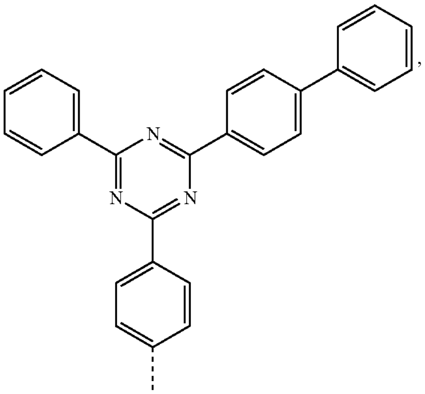
D[28]
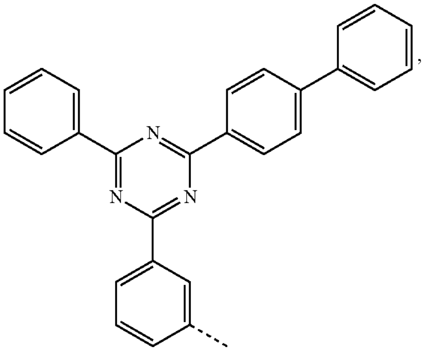
D[29]
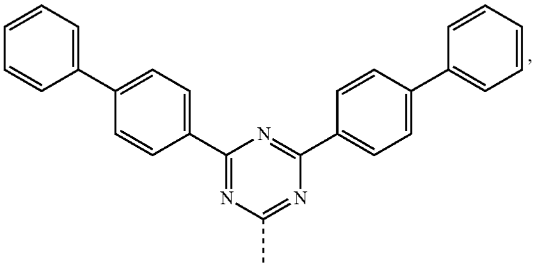

-continued
D[31]
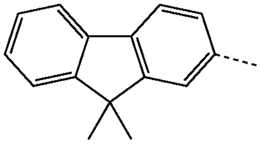,
D[32]
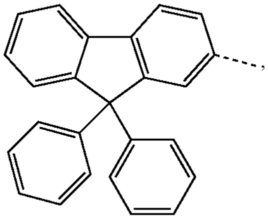
D[33]
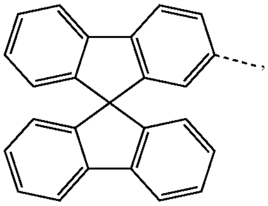
D[36]
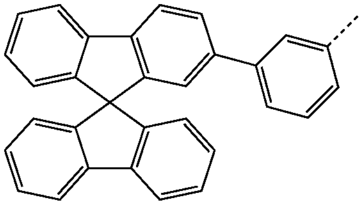,
D[41]
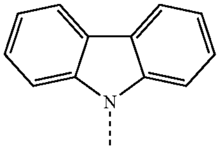,
D[42]
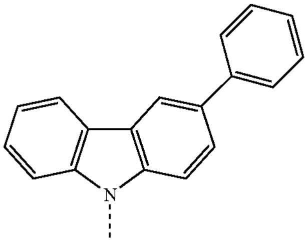,
D[43]
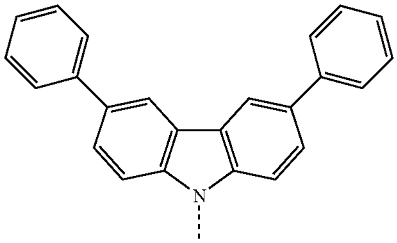,
-continued
D[45]
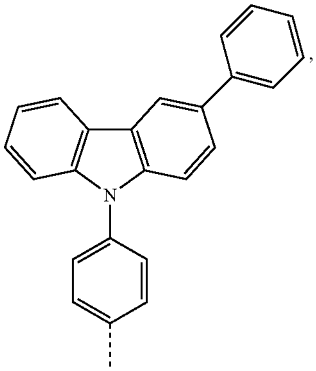,
D[46]
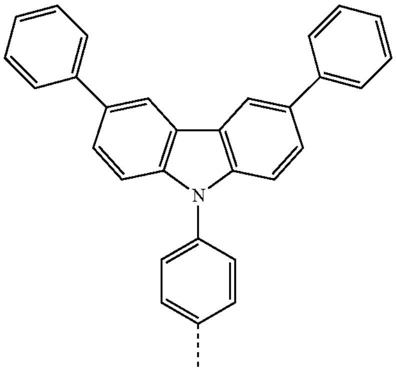,
D[47]
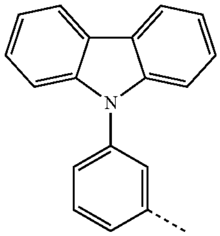,
D[48]
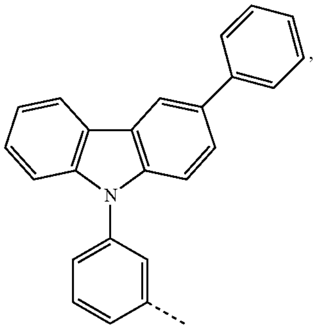, -continued
$D^{49}$
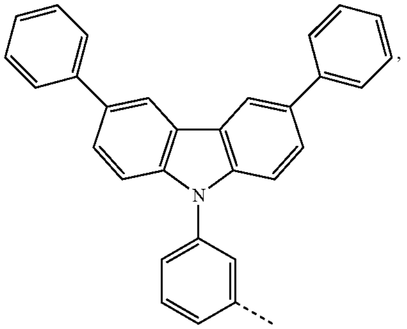
$D^{54}$
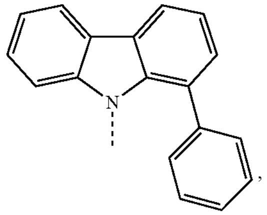
$D^{55}$
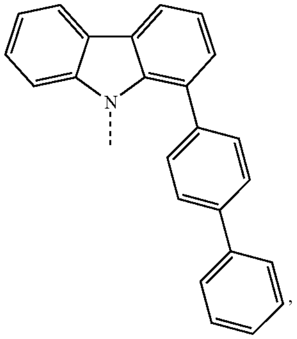
$D^{56}$
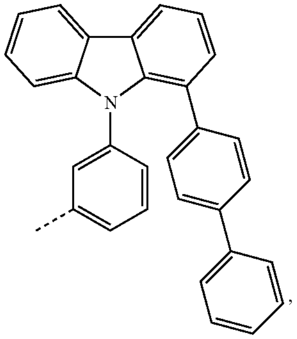
$D^{57}$
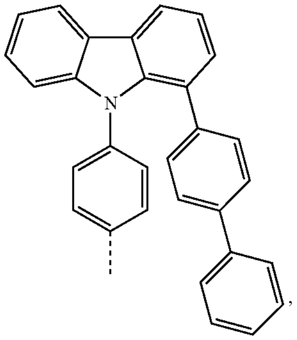
-continued
$D^{58}$
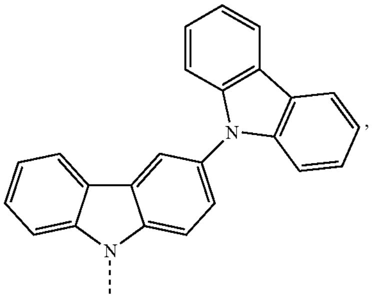
$D^{61}$
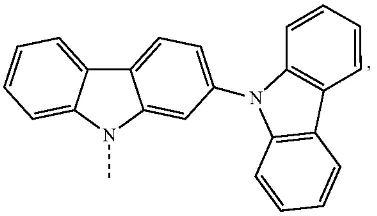
$D^{64}$
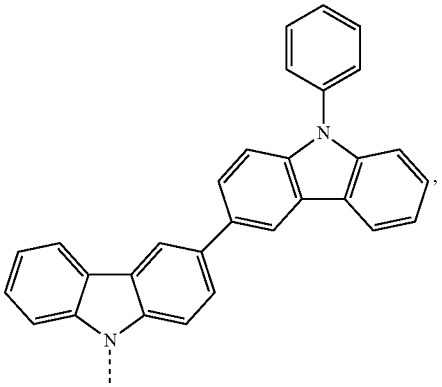
$D^{65}$
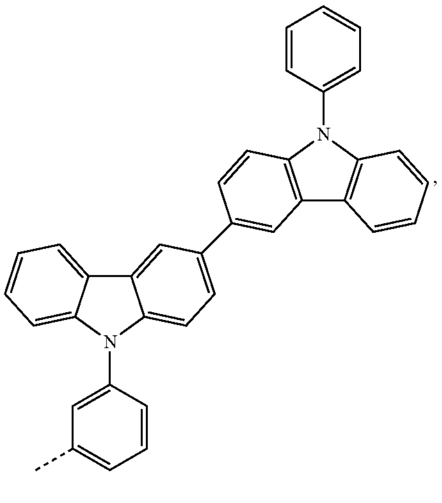

D66
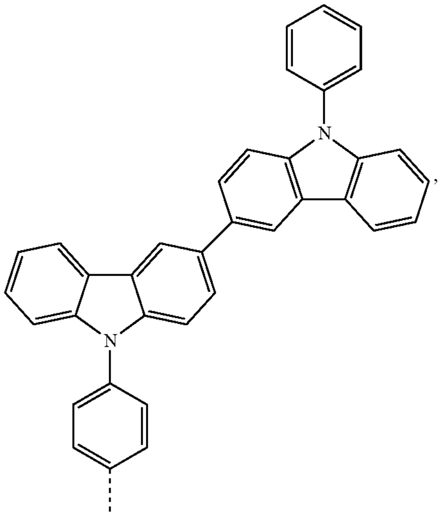
,
D67
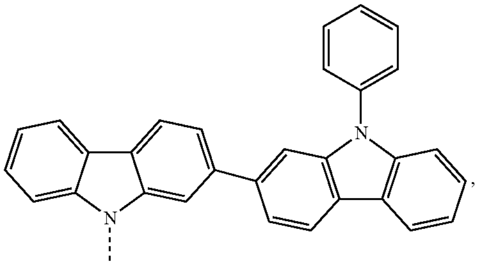
,
D68
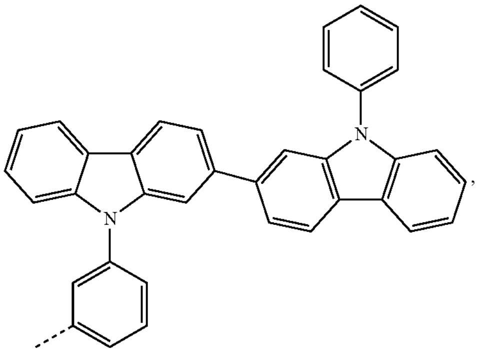
,
D69
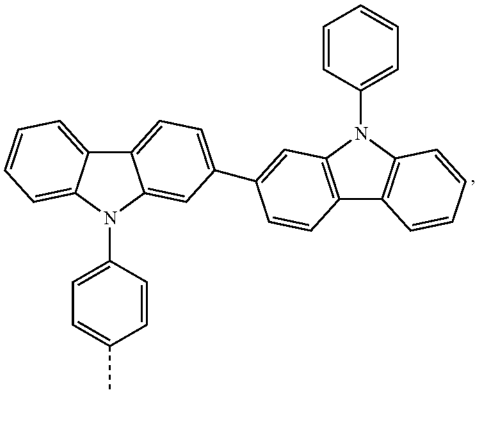
,
D70
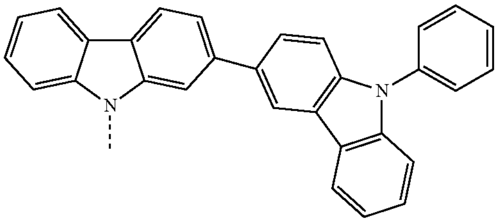
,
D71
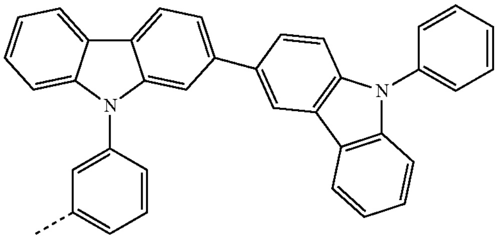
,
D72
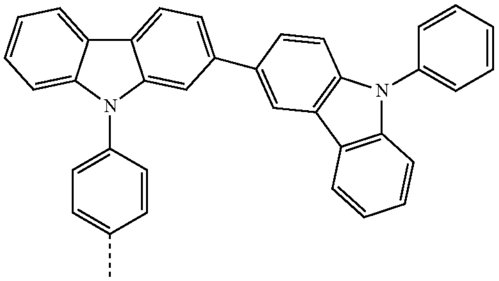
,
D73
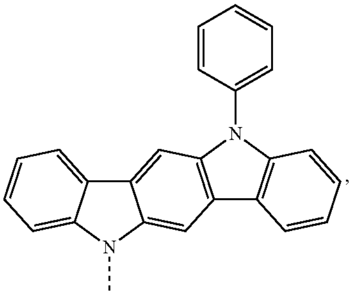
,
D74
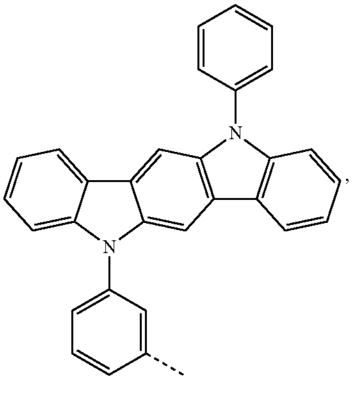
, -continued
D[75]
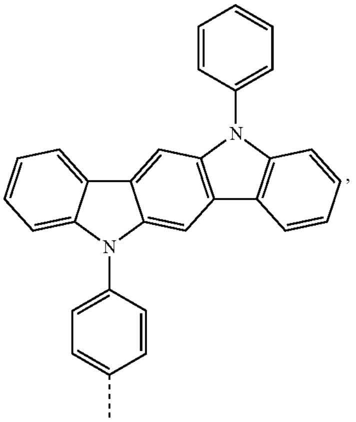
D[76]
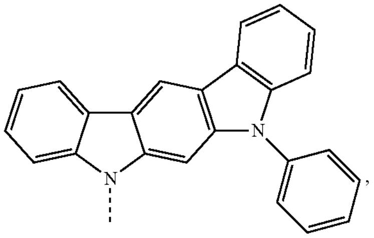
D[79]
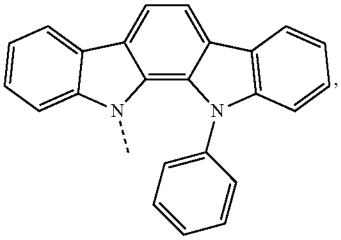
D[80]
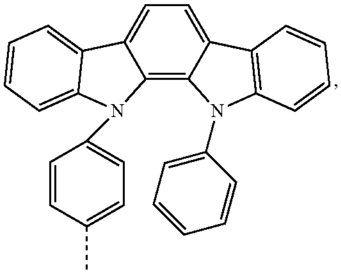
D[81]
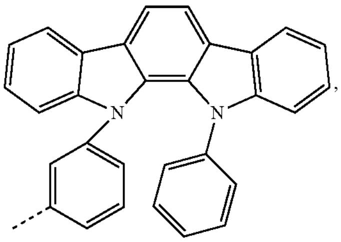
-continued
D[82]
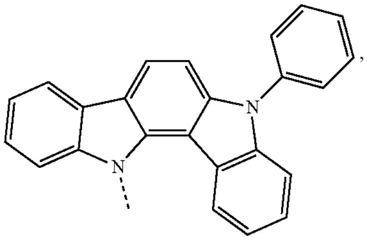
D[83]
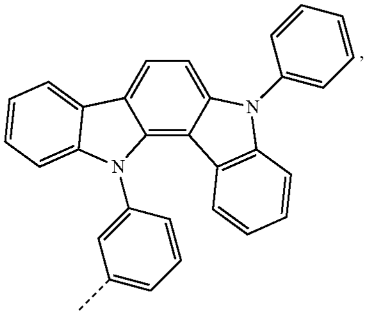
D[84]
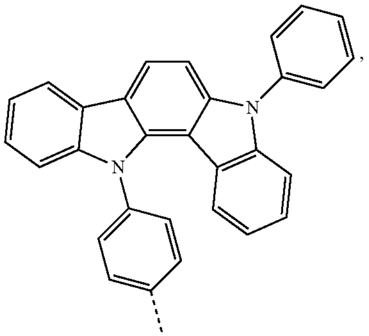
D[85]
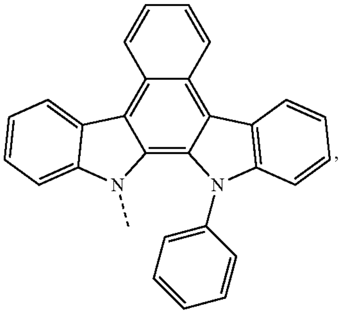
D[86]
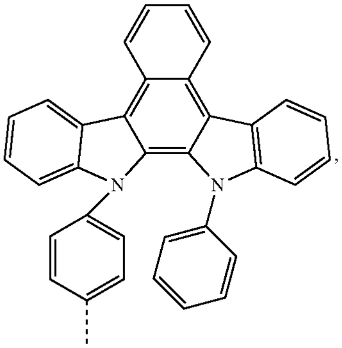

-continued
D[87]
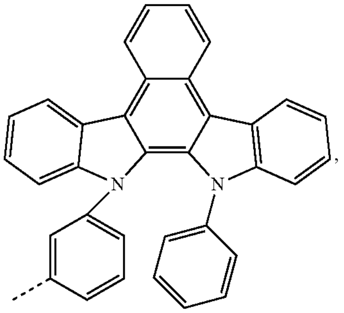
D[88]
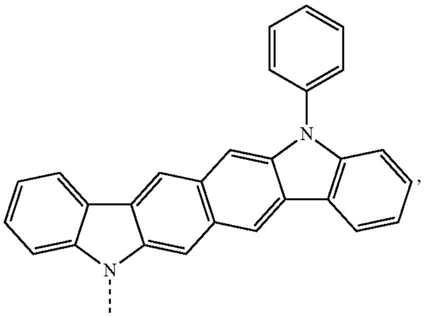
D[89]
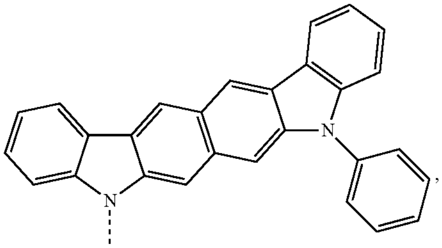
D[90]
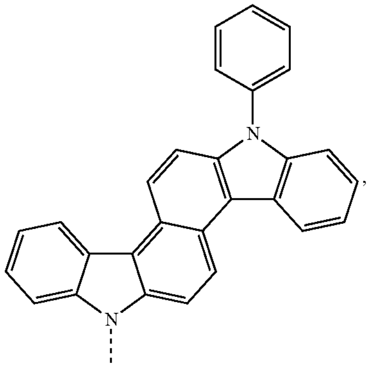
D[91]
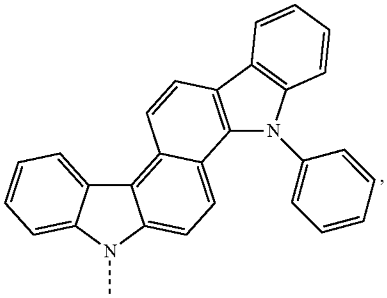
-continued
D[92]
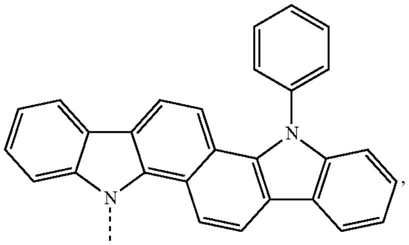
D[93]
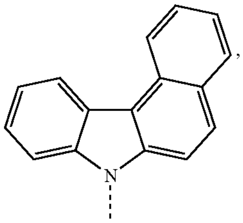
D[94]
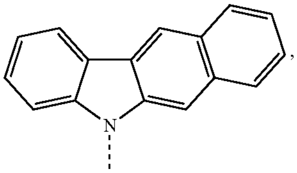
D[95]
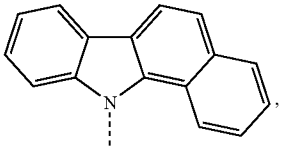
D[96]
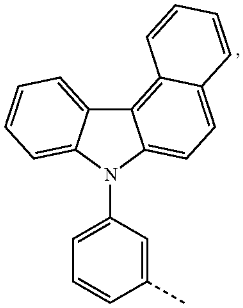
D[97]
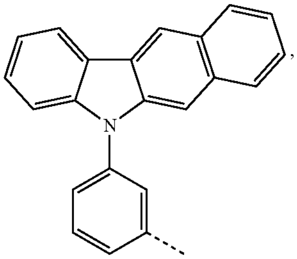

-continued
D[98]
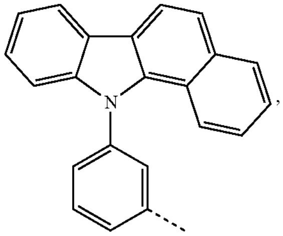
,
D[99]
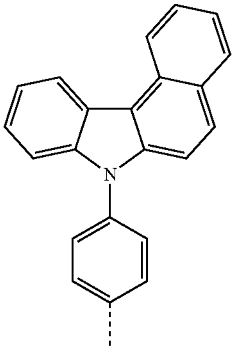
,
D[100]
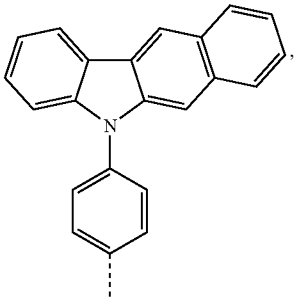
,
D[101]
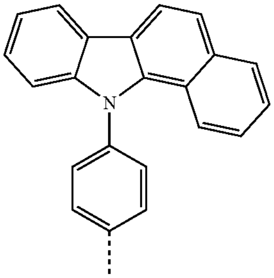
,
D[102]
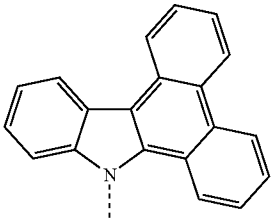
,
-continued
D[103]
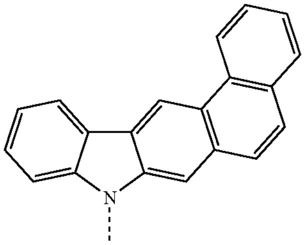
,
D[104]
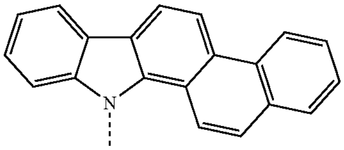
,
D[105]
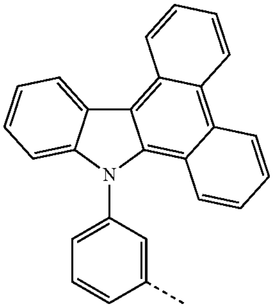
,
D[106]
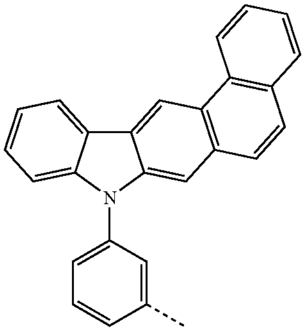
,
D[107]
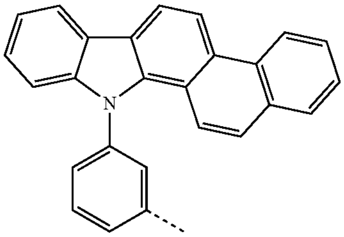
, -continued
D[108]
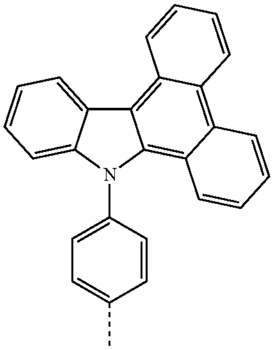
,
D[109]
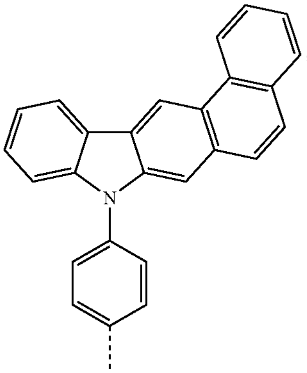
,
D[110]
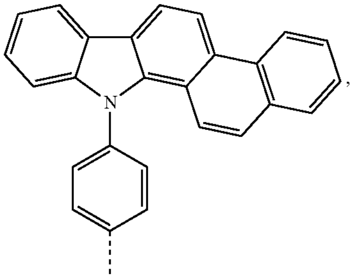
,
D[111]
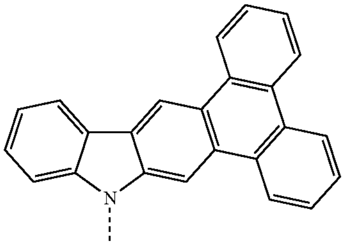
,
D[112]
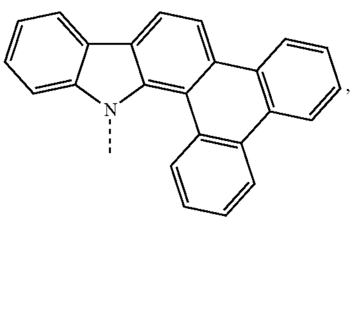
,
-continued
D[113]
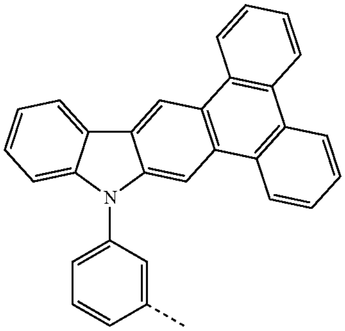
,
D[114]
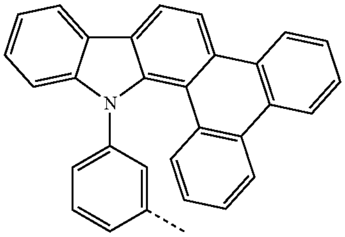
,
D[115]
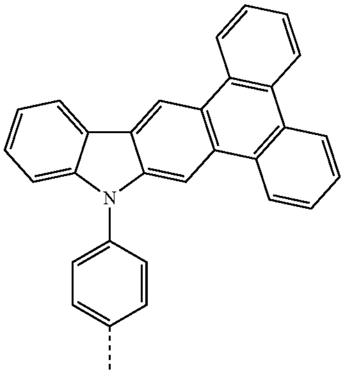
,
D[116]
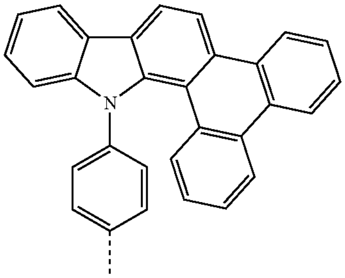
,
D[117]
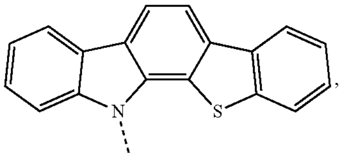
,
D[118]
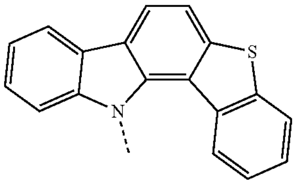
, -continued
D[119]
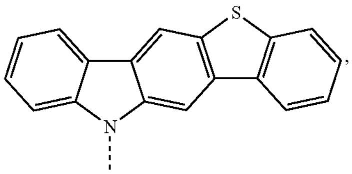
D[120]
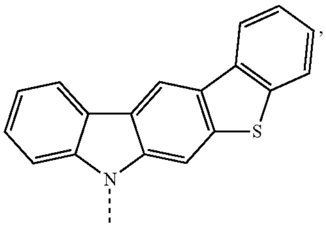
D[121]
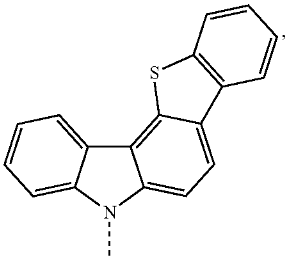
D[122]
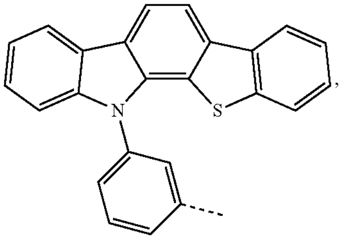
D[123]
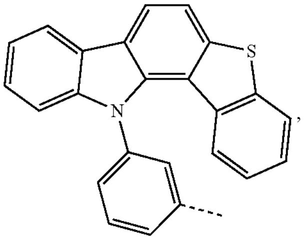
D[124]
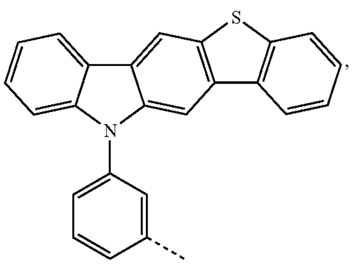
-continued
D[125]
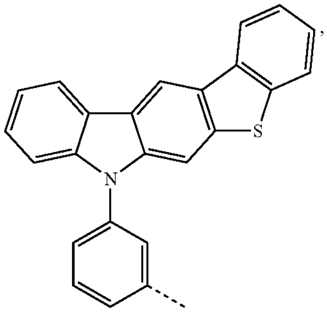
D[126]
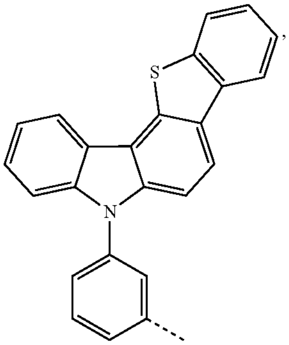
D[127]
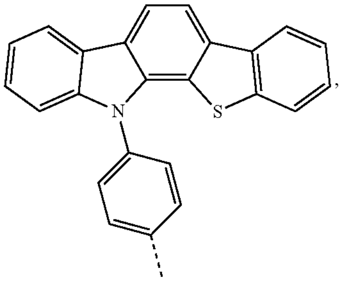
D[128]
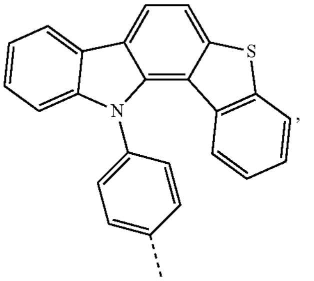
D[129]
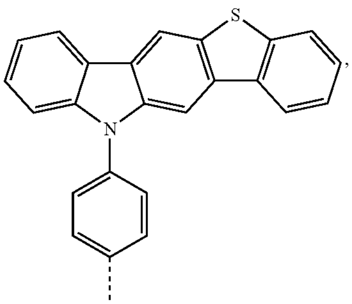

-continued
D[130]
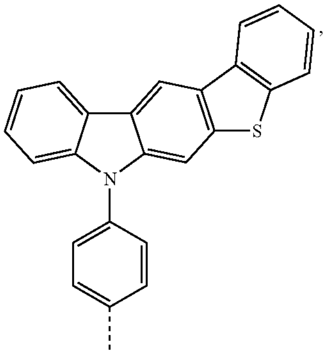
D[131]
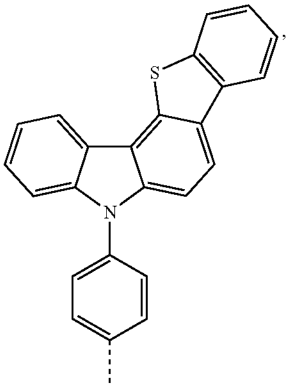
D[132]
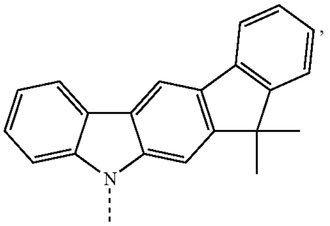
D[133]
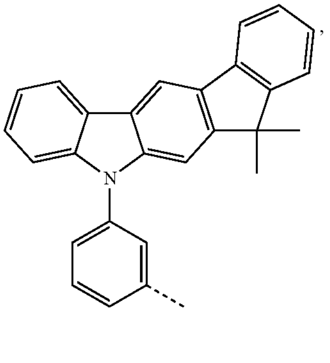
-continued
D[134]
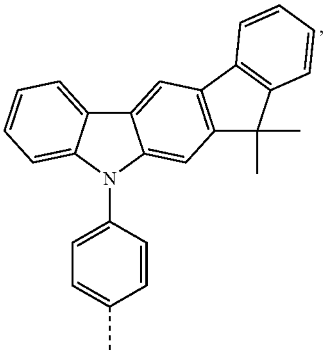
D[135]
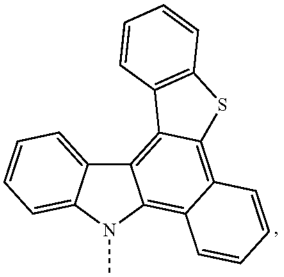
D[136]
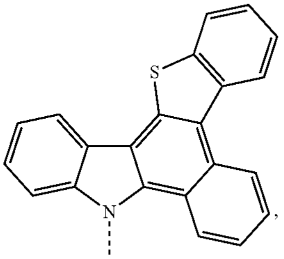
D[137]
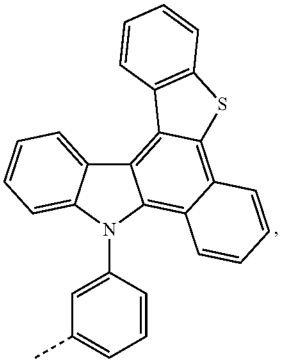
D[138]
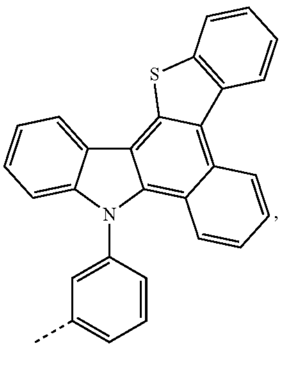

-continued
D[139]
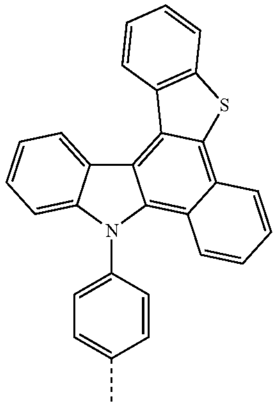
,
D[140]
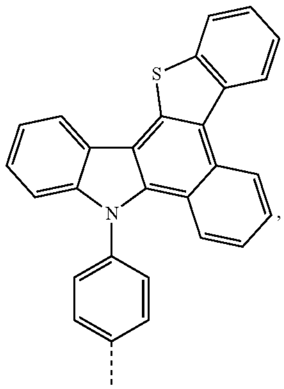
,
D[141]
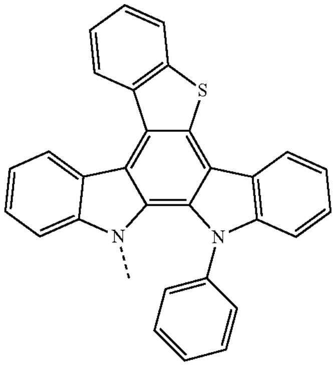
,
D[142]
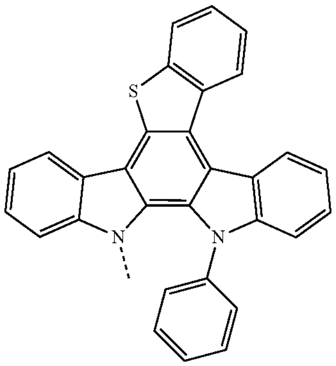
,
-continued
D[143]
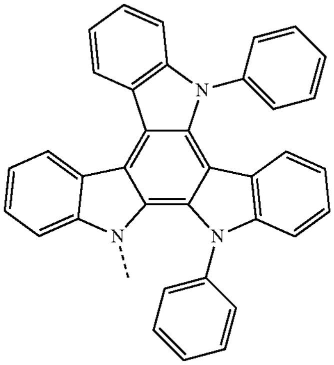
,
D[144]
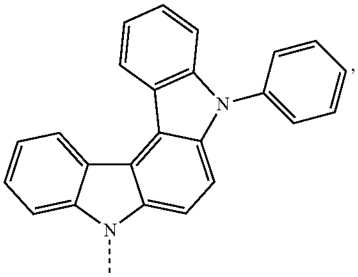
,
D[145]
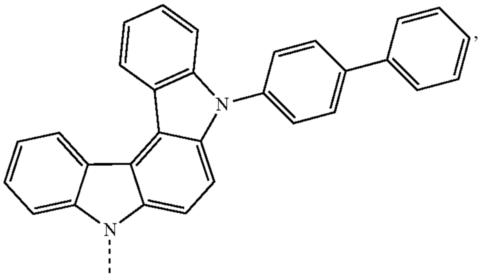
,
D[146]
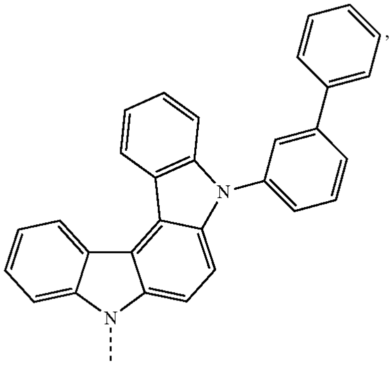
, -continued
D[147]
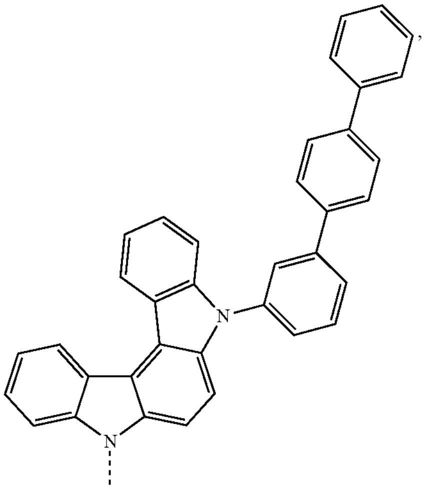
D[148]
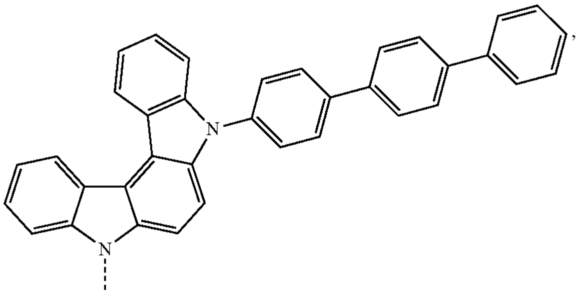
D[149]
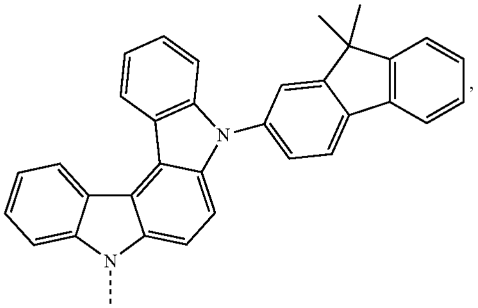
D[150]
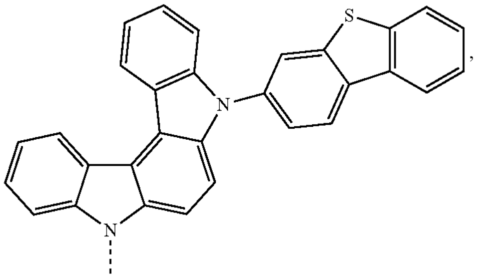
-continued
D[151]
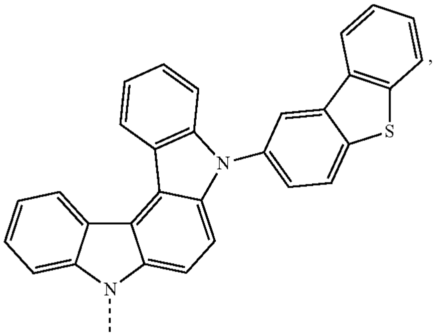
D[152]
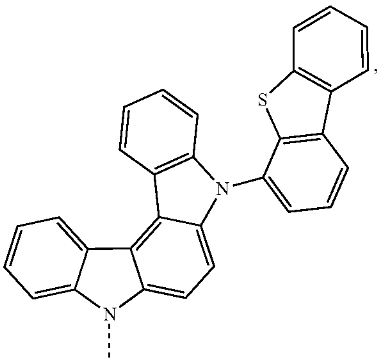
D[153]
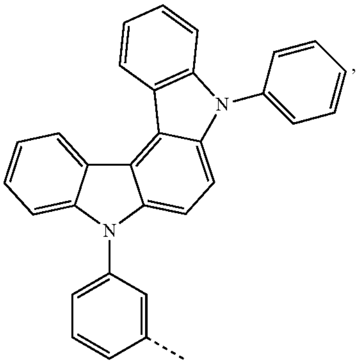
D[154]
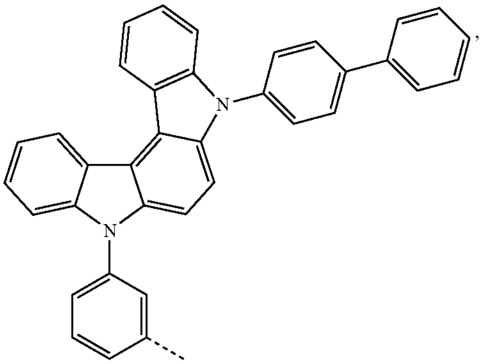

-continued
D[155]
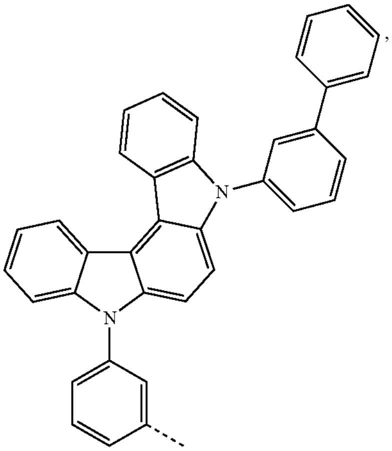
D[156]
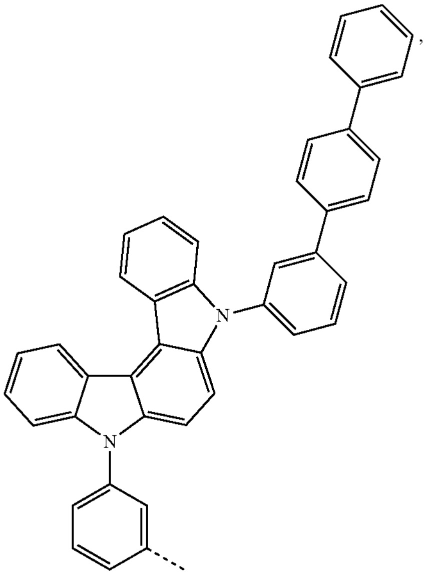
D[157]
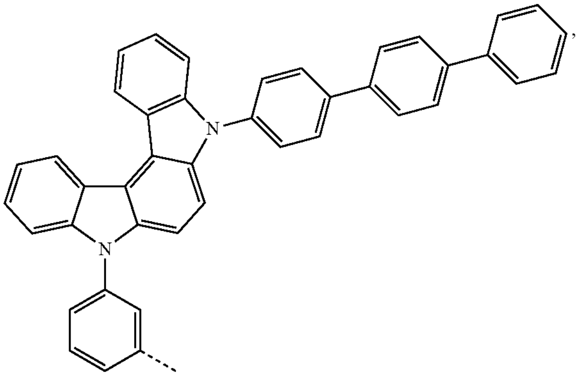
-continued
D[158]
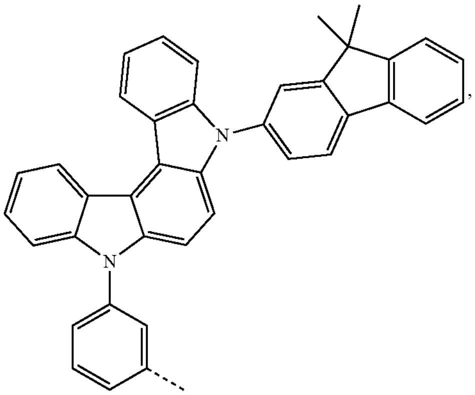
D[159]
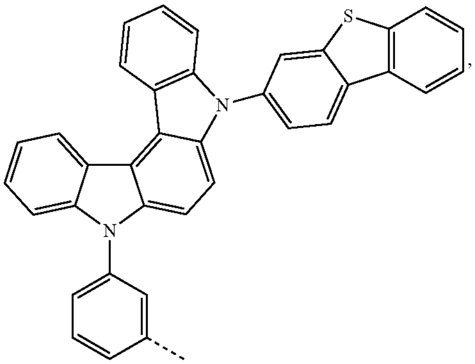
D[160]
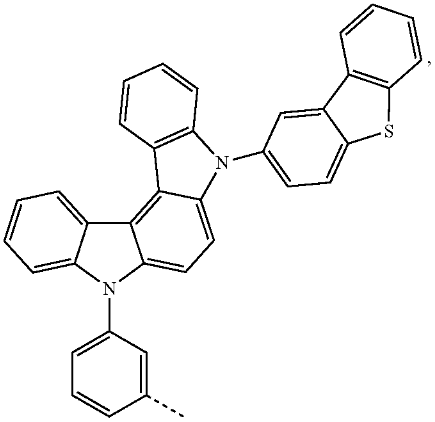
D[161]
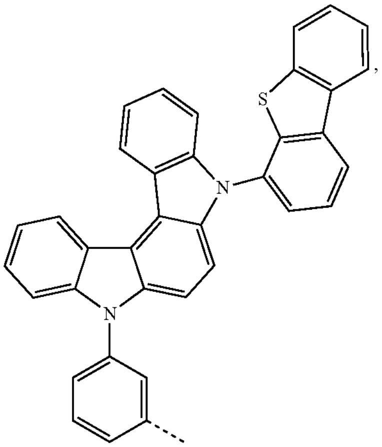

-continued
D[162]
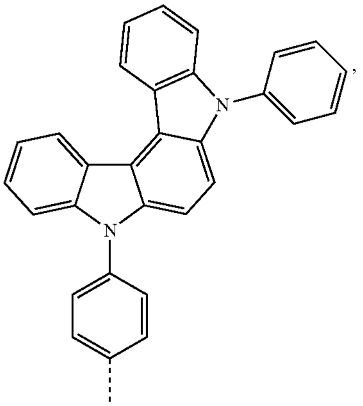
D[163]
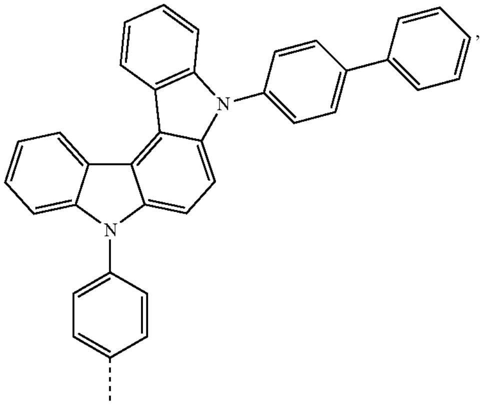
D[164]
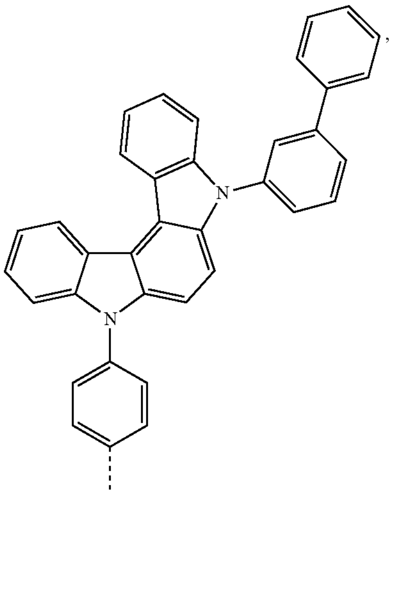
-continued
D[165]
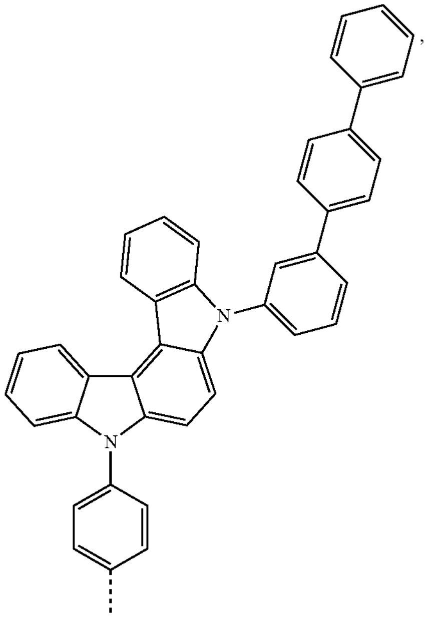
D[166]
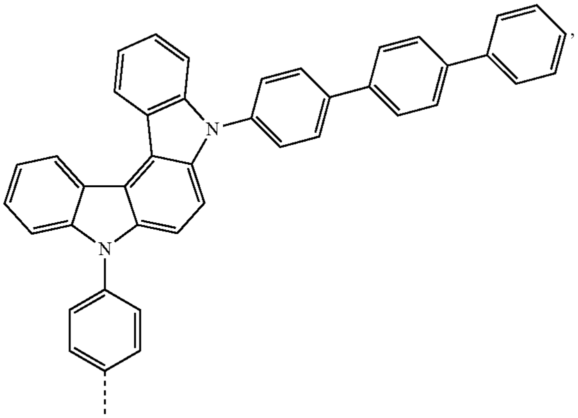
D[167]
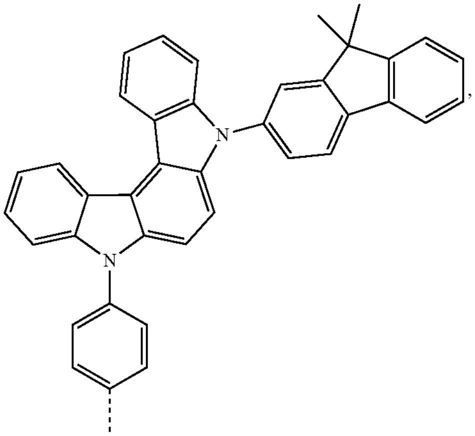

-continued
D[168]
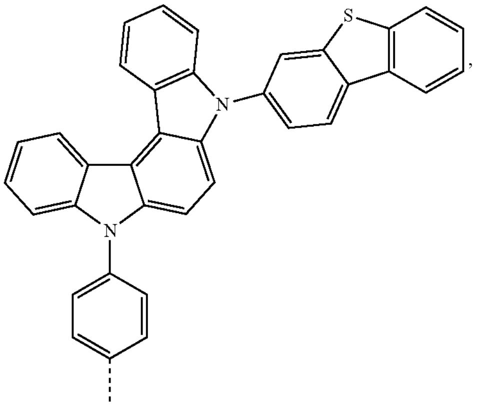
D[169]
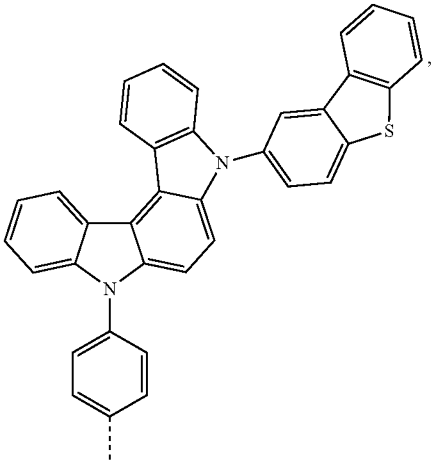
D[170]
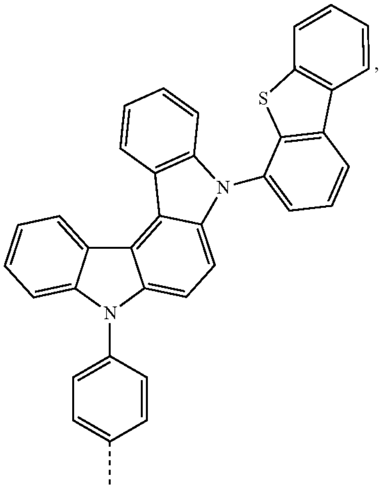
-continued
D[171]
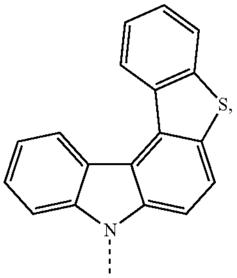
D[172]
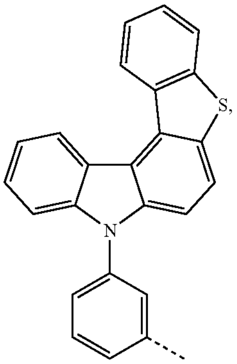
D[173]
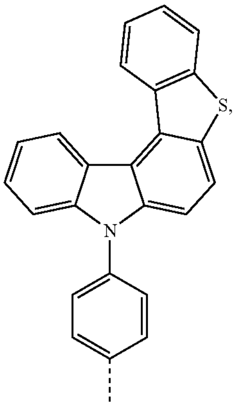
D[174]
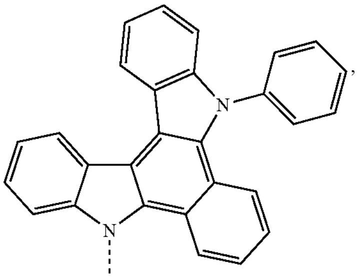
D[175]
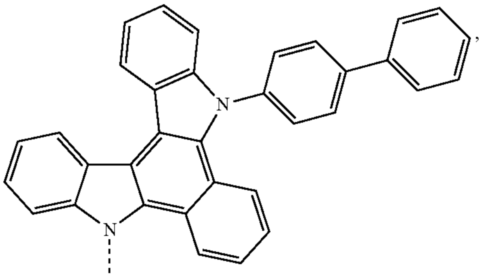

-continued
D[176]
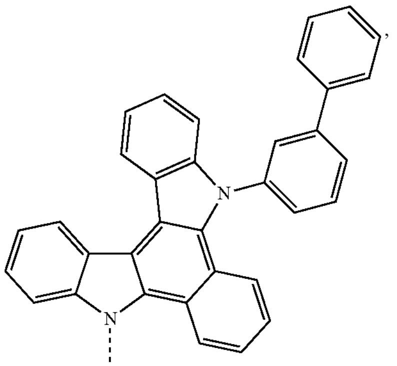
D[177]
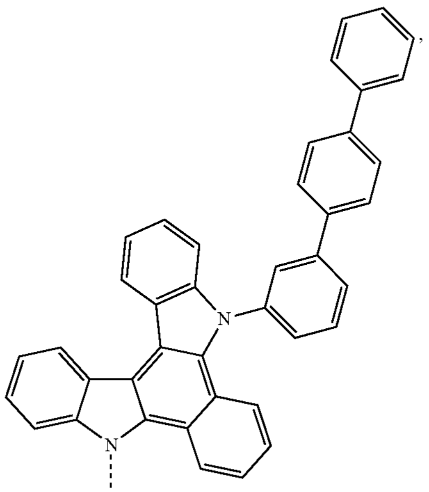
D[178]
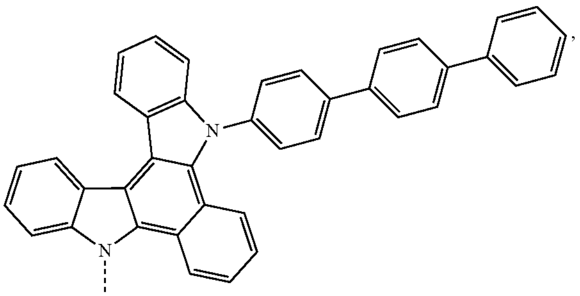
D[179]
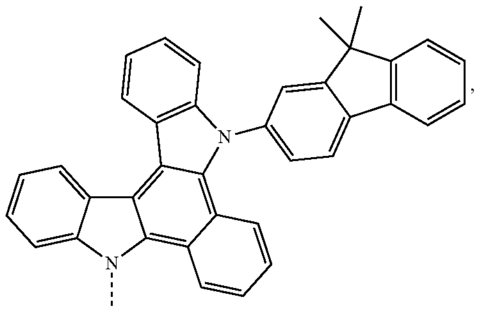
-continued
D[180]
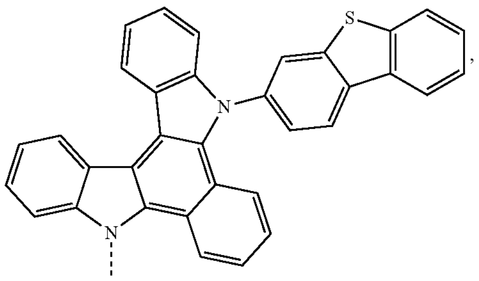
D[181]
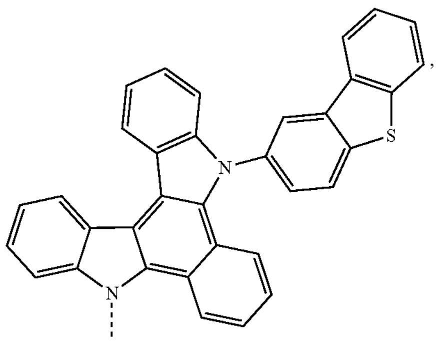
D[182]
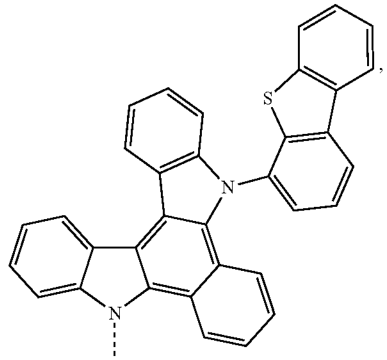
D[183]
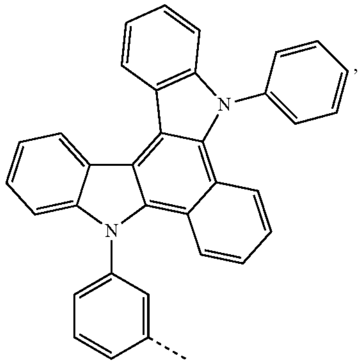

-continued
D184
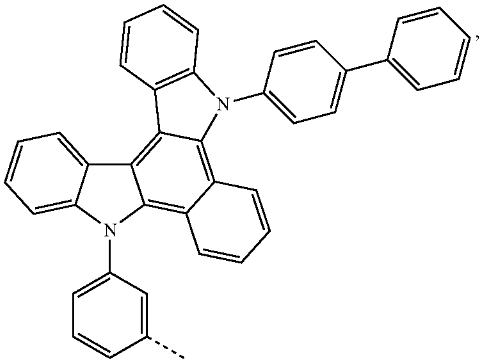
D185
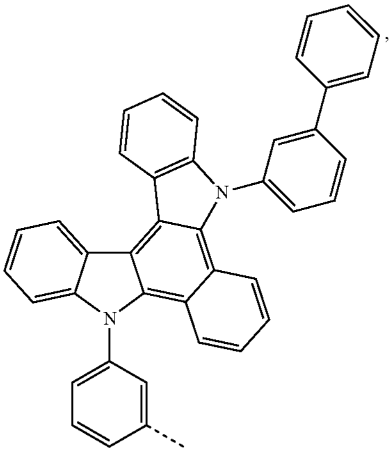
D186
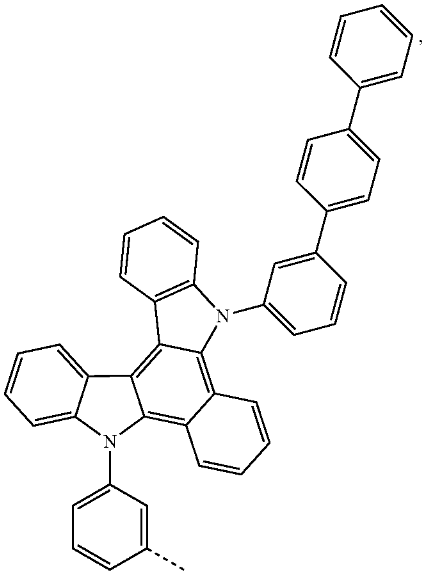
-continued
D187
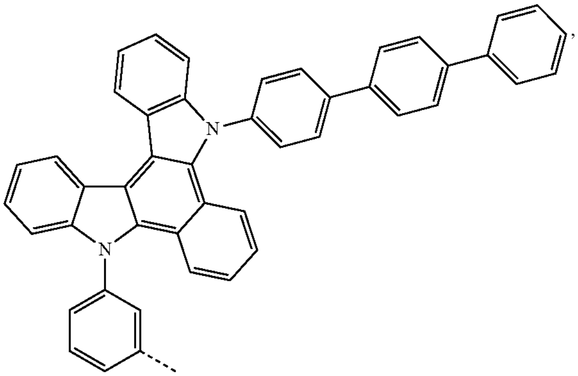
D188
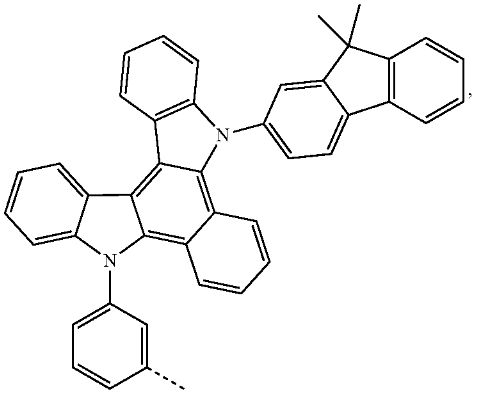
D189
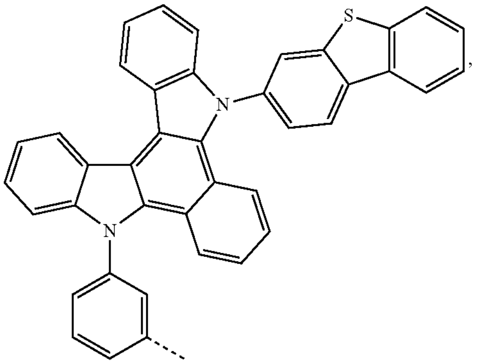
D190
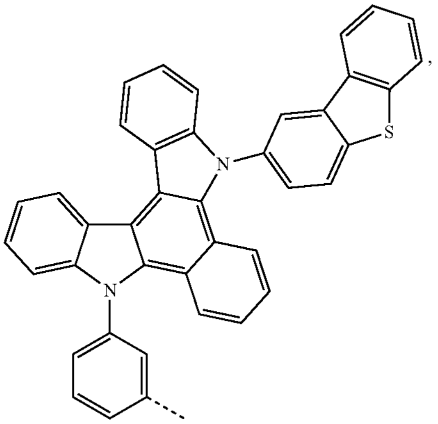

-continued
D[191]
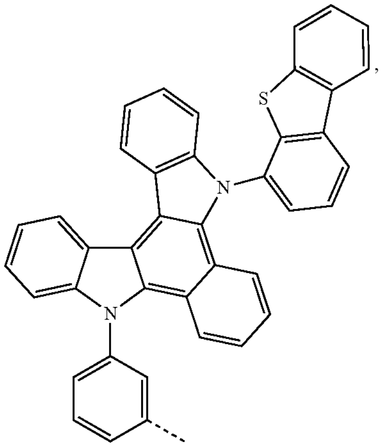
D[192]
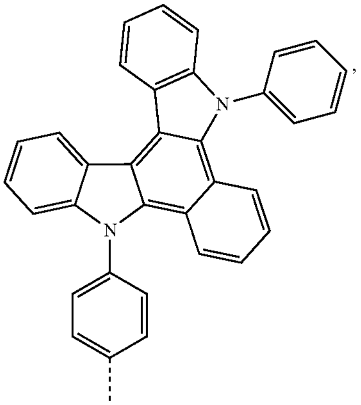
D[193]
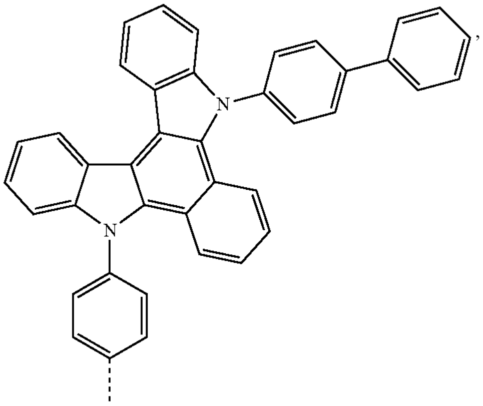
-continued
D[194]
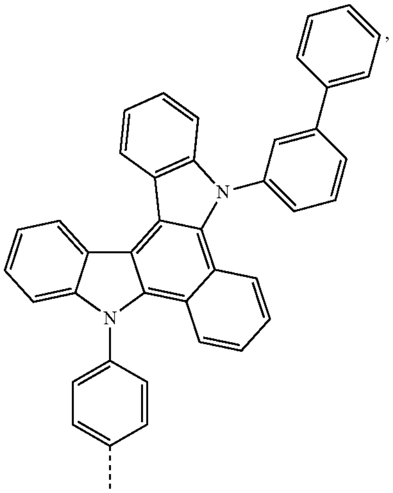
D[195]
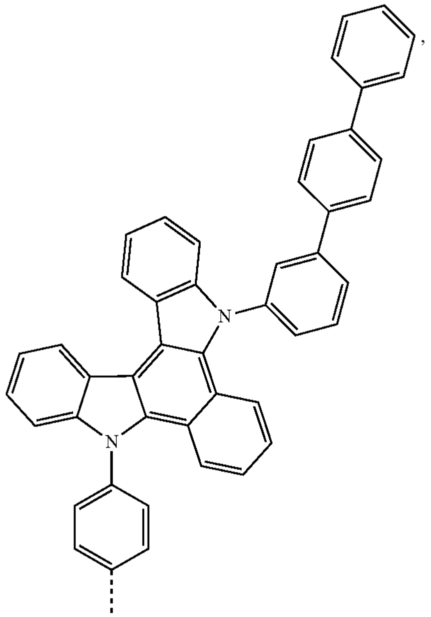
D[196]
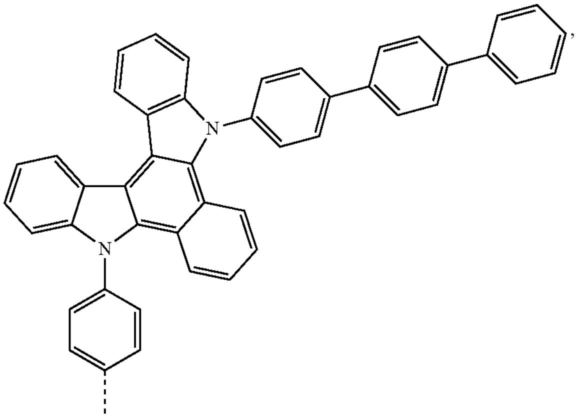

-continued
D[197]
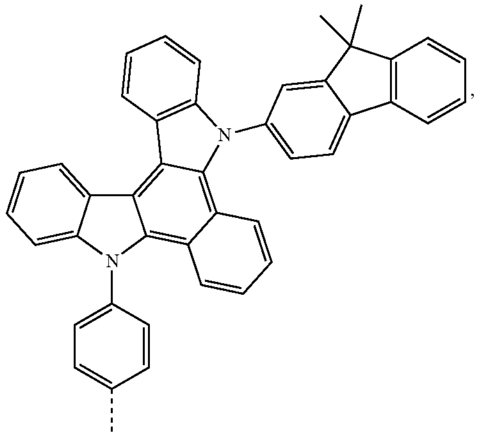
D[198]
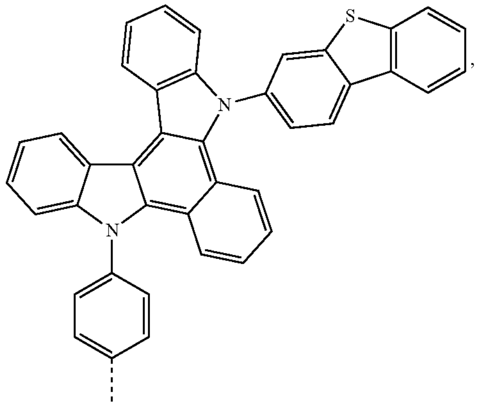
D[199]
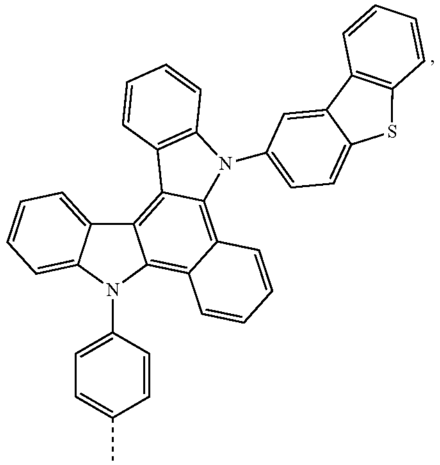
-continued
D[200]
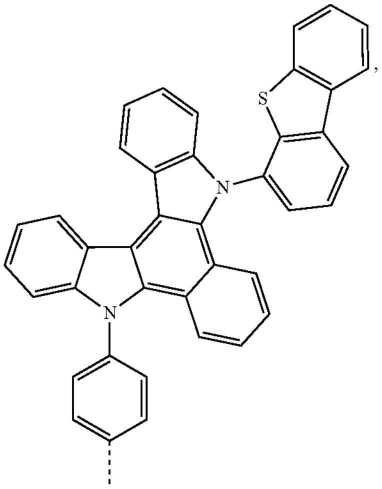
D[201]
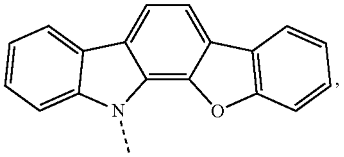
D[202]
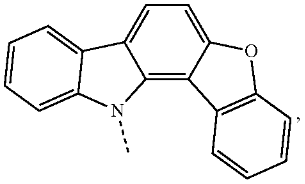
D[203]
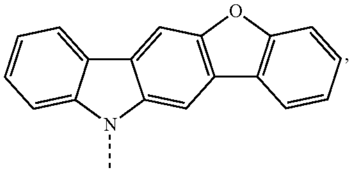
D[204]
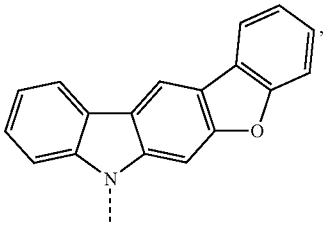
D[205]
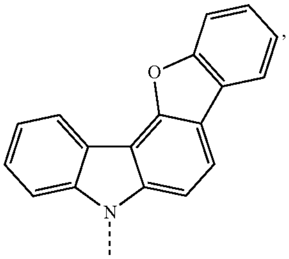

-continued
D[206]
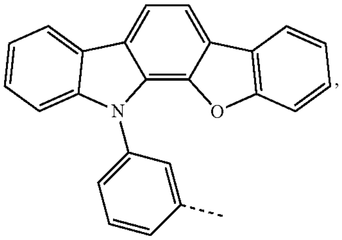
D[207]
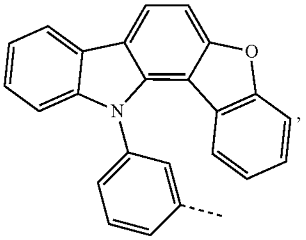
D[208]
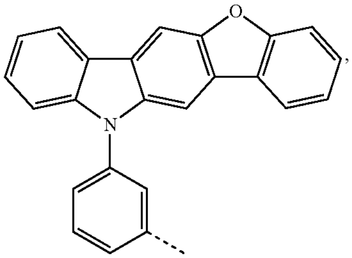
D[209]
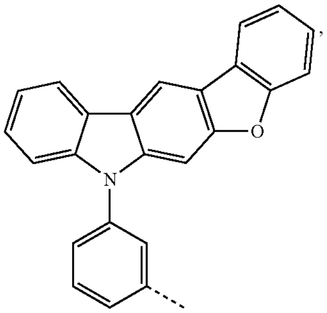
D[210]
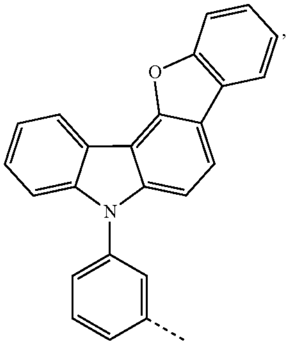
-continued
D[211]
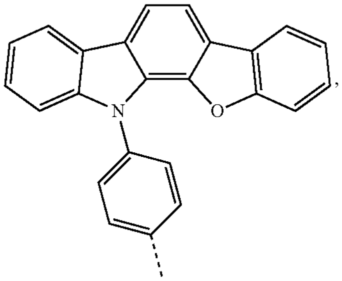
D[212]
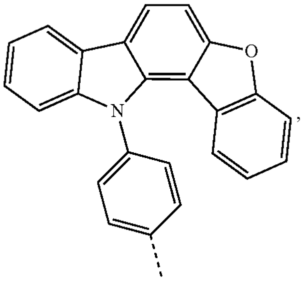
D[213]
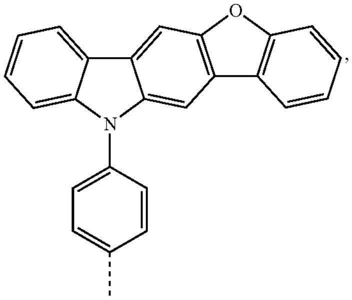
D[214]
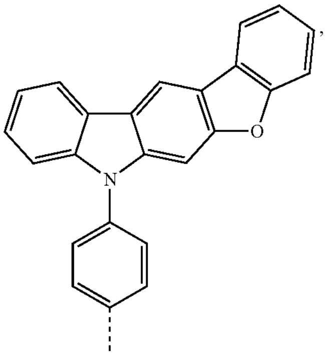
D[215]
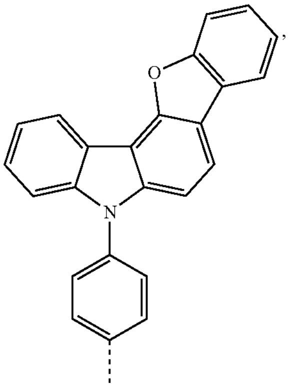

-continued
D[216]
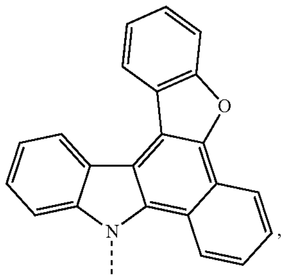
D[217]
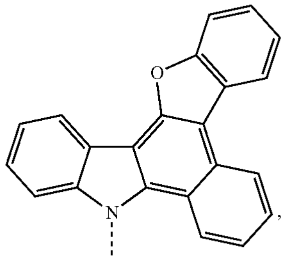
D[218]
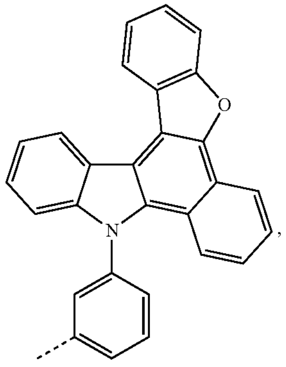
D[219]
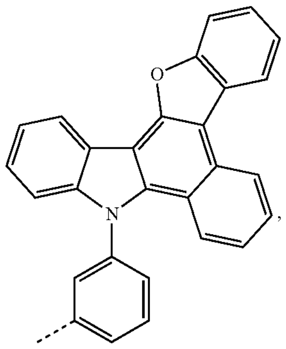
-continued
D[220]
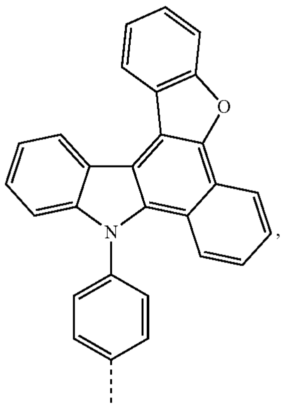
D[221]
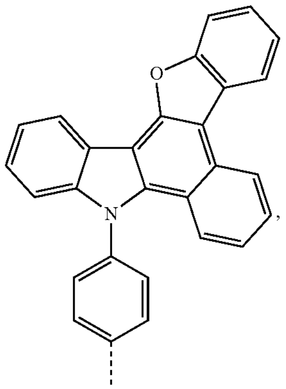
D[222]
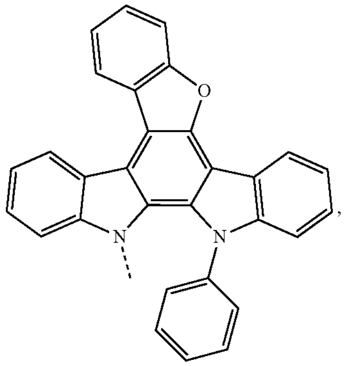
D[223]
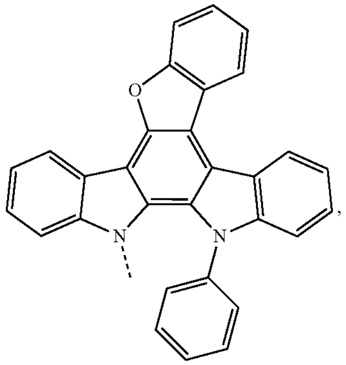

-continued
D[224]
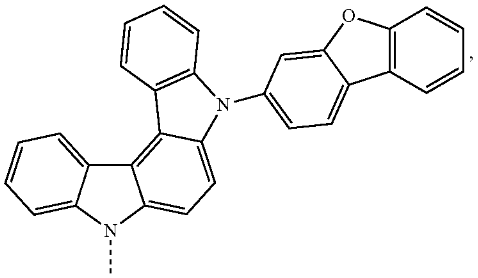
D[225]
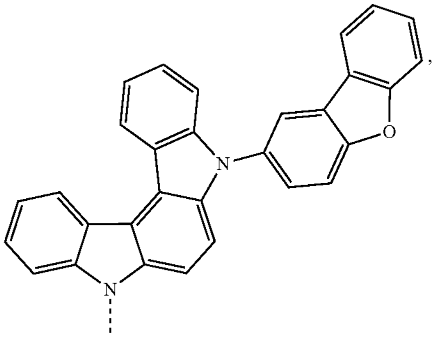
D[226]
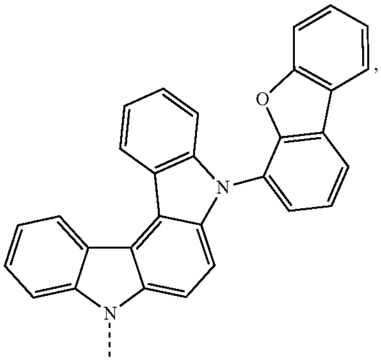
D[227]
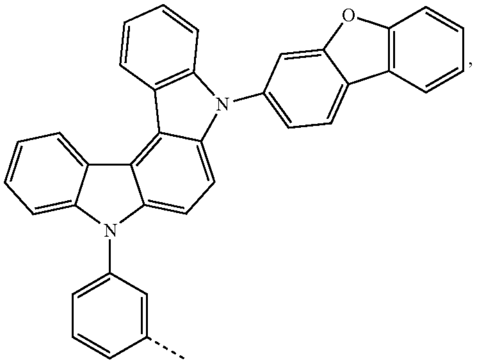
-continued
D[228]
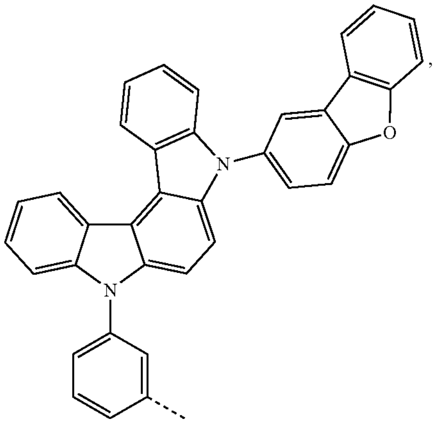
D[229]
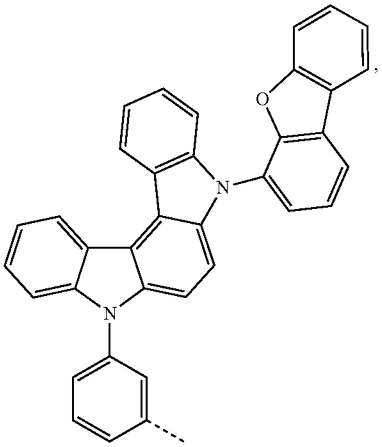
D[230]
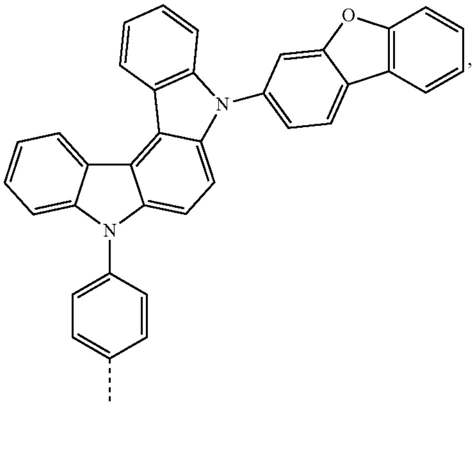

-continued
D231
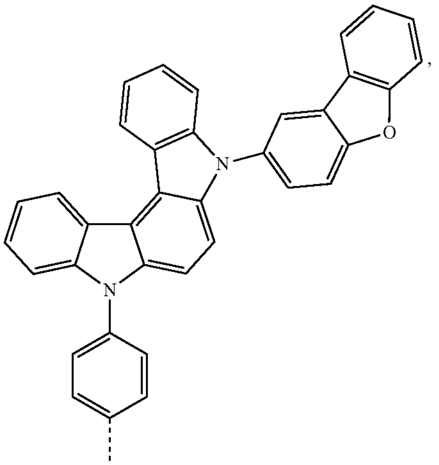
D232
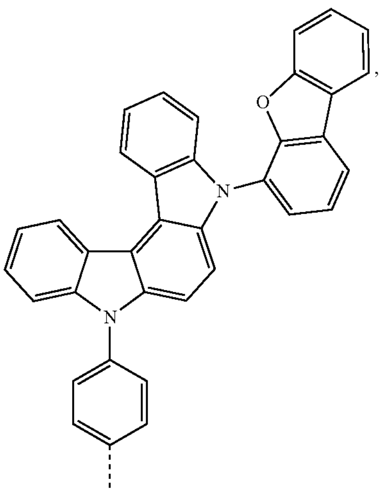
D233
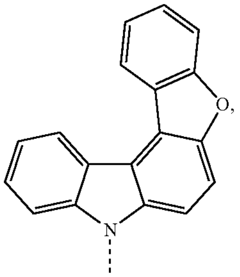
D234
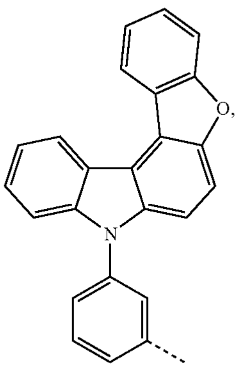
-continued
D235
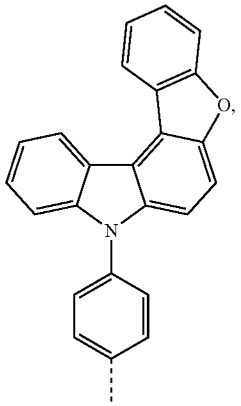
D236
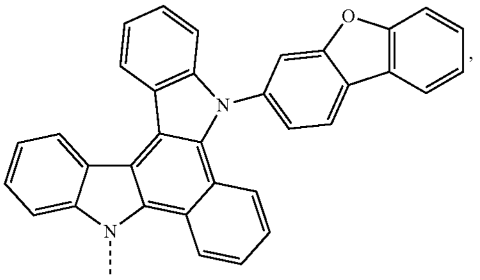
D237
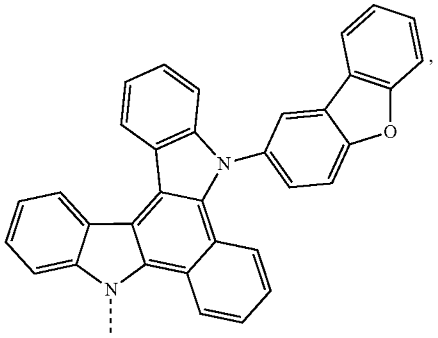
D238
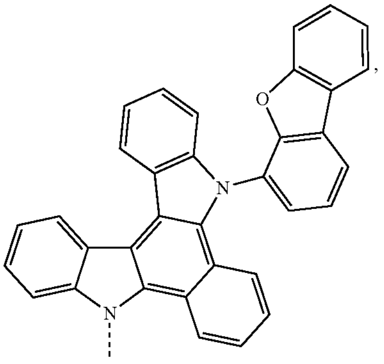

-continued

D239

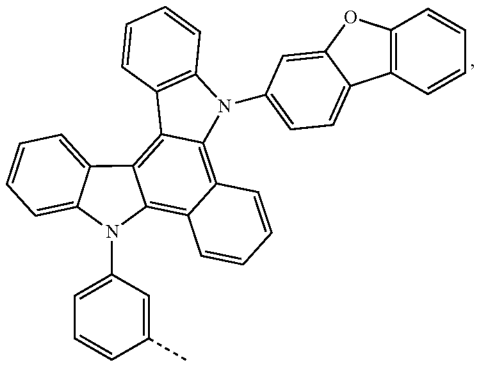

,

D240

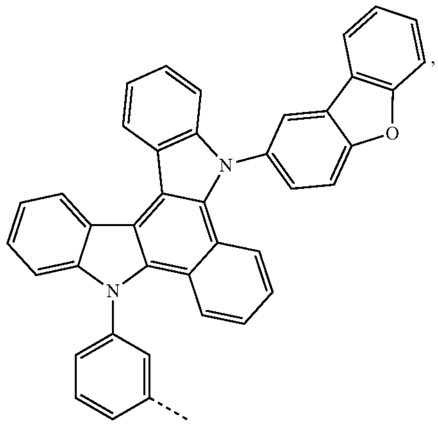

,

D241

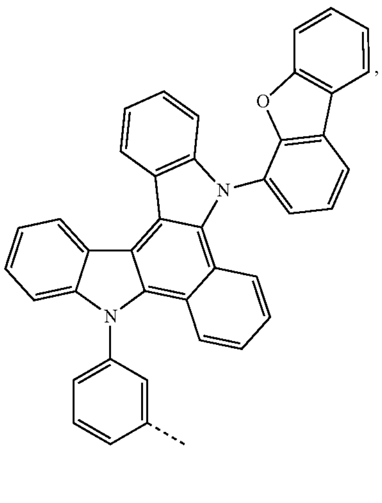

,

-continued

D242

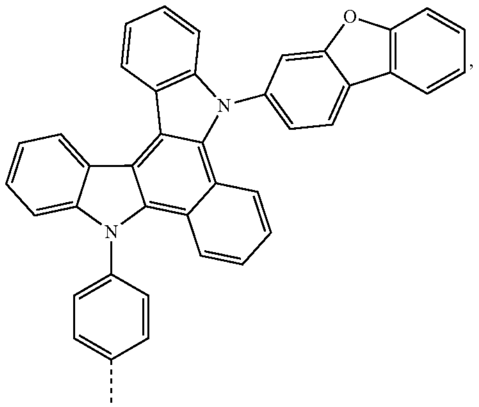

,

D243

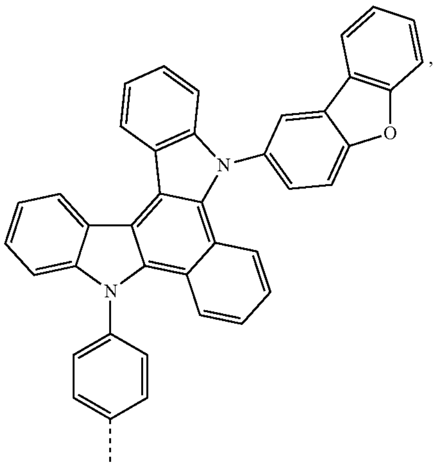

, and

D244

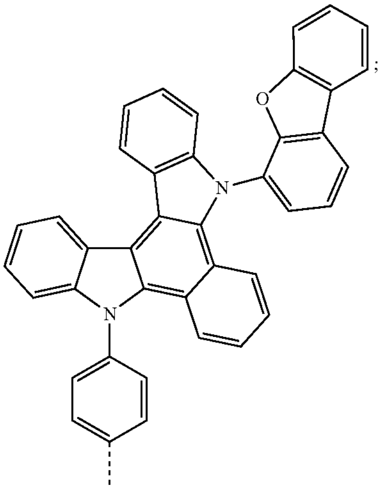

;

wherein any adjacent substitutions on the same ring are optionally joined or fused into a ring; and wherein at least one of the following is true: (i) at least one of $X^5$ and $X^6$ is N, (ii) at least one of $X^7$ to $X^{10}$ is N, (iii) each of X' to $X^4$ is carbon;

provided that when adjacent substitutions on $X^5$ and $X^6$ in Formula I-1 and I-3 fuse into a six-member ring, this ring and the ring having $X^7$ to $X^{10}$ cannot be pyridine at the same time.

15. The first organic light emitting device of claim 14, wherein the organic layer is an emissive layer and the compound is a host.

16. The first organic light emitting device of claim 14, wherein the organic layer further comprises a phosphorescent emissive dopant; wherein the emissive dopant is a transition metal complex having at least one ligand or part of the ligand if the ligand is more than bidentate, selected from the group consisting of:

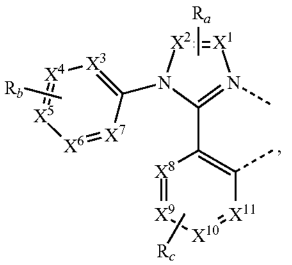

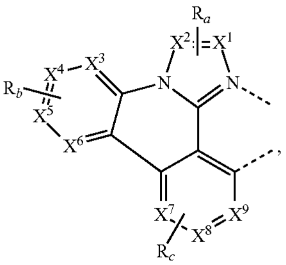

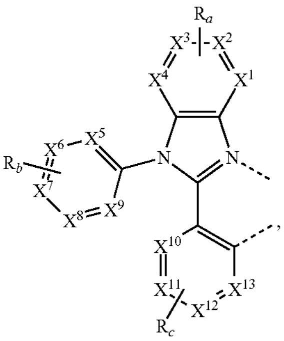

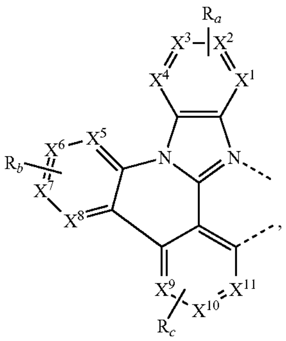

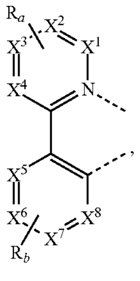

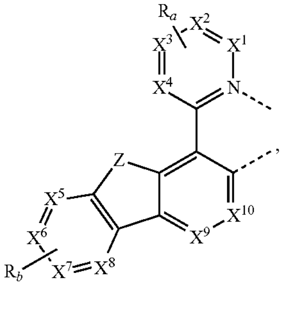

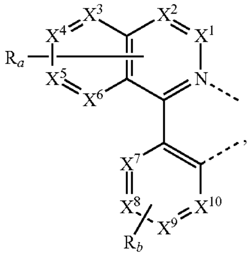

-continued

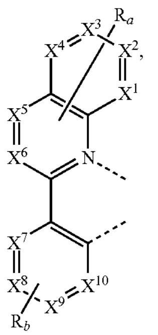

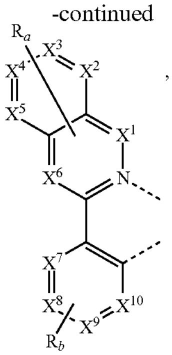

,

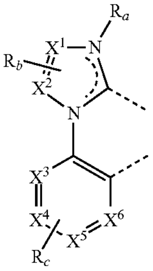

,

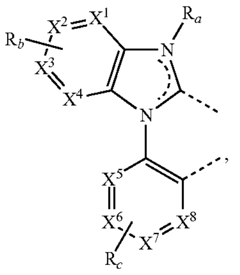

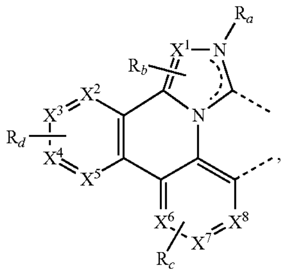

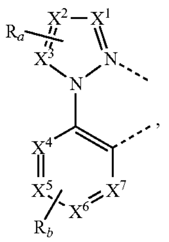

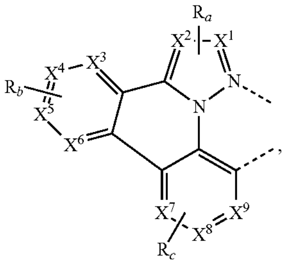

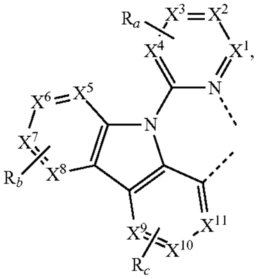

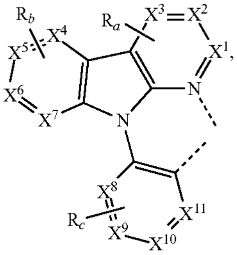

and

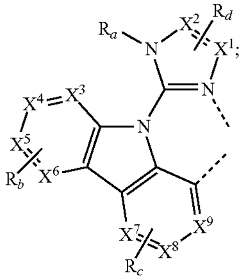

wherein each $X^1$ to $X^{13}$ are independently selected from the group consisting of carbon and nitrogen;

wherein Z is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R'', $R_a$, $R_b$, $R_c$, and $R_d$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutions of $R_a$, $R_b$, $R_c$, and $R_d$ are optionally fused or joined to form a ring or form a multidentate ligand.

17. The first organic light emitting device of claim 14, wherein the organic layer is a charge carrier blocking layer and the compound is a charge carrier blocking material in the organic layer, or the organic layer is a charge carrier transporting layer and the compound is a charge carrier transporting material in the organic layer.

18. The first organic light emitting device of claim 14, wherein the device is selected from the group consisting of a consumer product, an electronic component module, an organic light-emitting device, and a lighting panel.

19. The first organic light emitting device of claim 14, wherein the organic layer is an emissive layer and the compound is an emitter.

20. The first organic light emitting device of claim 19, wherein the first organic light emitting device emits a luminescent radiation at room temperature when a voltage is applied across the first organic light emitting device, and wherein the luminescent radiation comprises a delayed fluorescence process.

21. The first organic light emitting device of claim 19, wherein the emissive layer further comprises a first phosphorescent emitting material.

22. A formulation comprising a compound having a formula selected from the group consisting of:

Formula 1-1

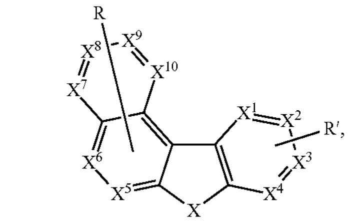

Formula 1-2

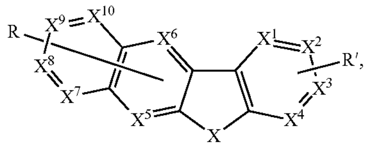

and

Formula 1-3

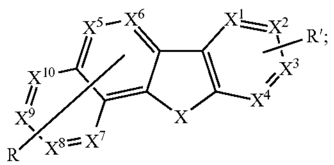

wherein X is selected from the group consisting of O, S, and Se;

wherein $X^1$ to $X^{10}$ are each independently selected from the group consisting of carbon and nitrogen;

wherein at least one of $X^1$ to $X^6$ is nitrogen;

wherein R and R' each independently represent from mono to the possible maximum number of substitutions, or no substitution;

wherein R and R' are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof;

wherein at least one of $X^4$ and $X^5$ is carbon, which is substituted by a $D^j$ selected from the group consisting of:

$D^7$

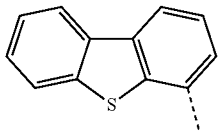

, $D^8$

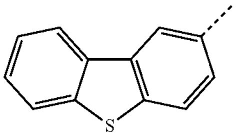

, $D^{10}$

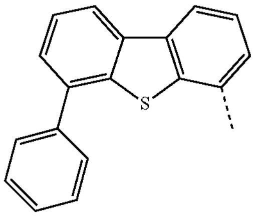

, $D^{11}$

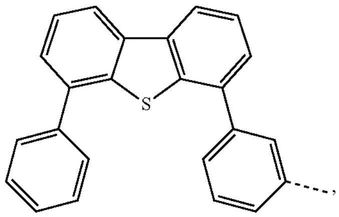

, $D^{12}$

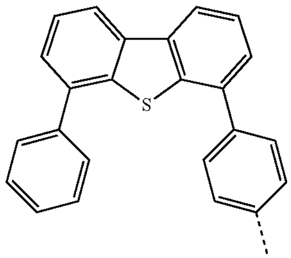

,

-continued
$D^{13}$
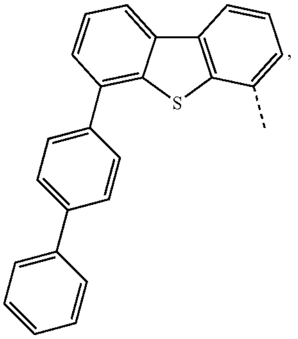
$D^{14}$
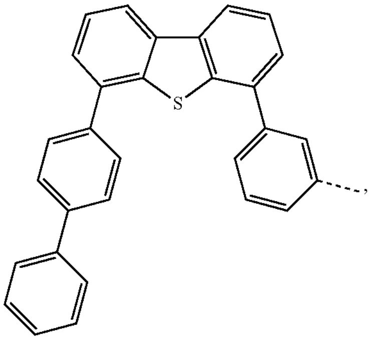
$D^{15}$
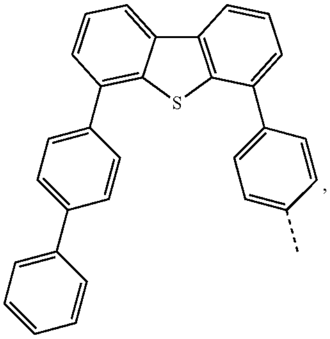
$D^{16}$
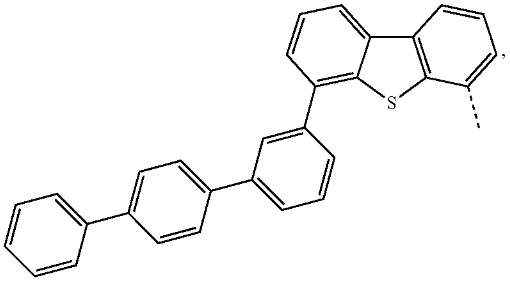
$D^{17}$
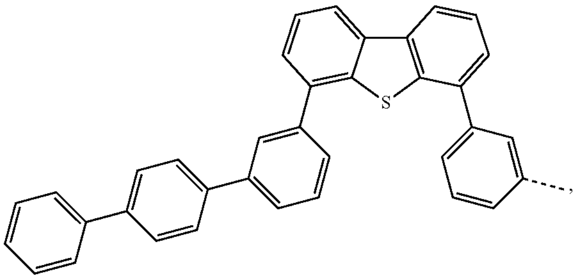
-continued
$D^{18}$
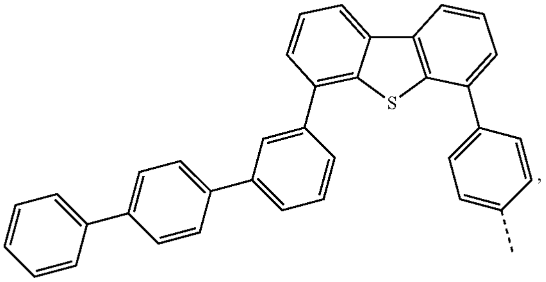
$D^{19}$
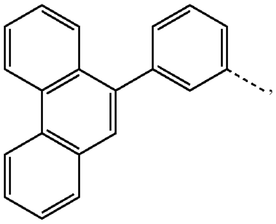
$D^{20}$
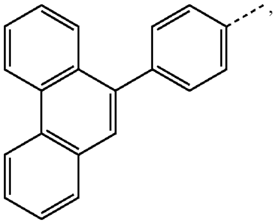
$D^{21}$
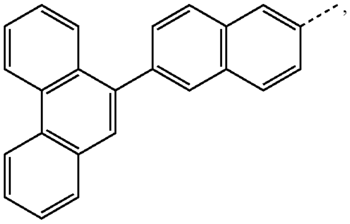
$D^{22}$
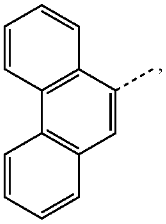
$D^{23}$
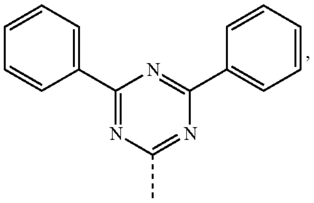

-continued
D[24]
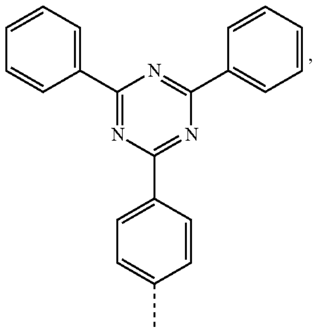
D[25]
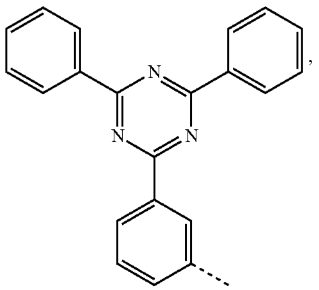
D[26]
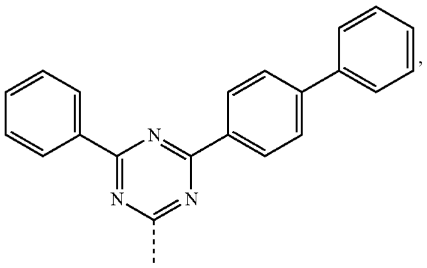
D[27]
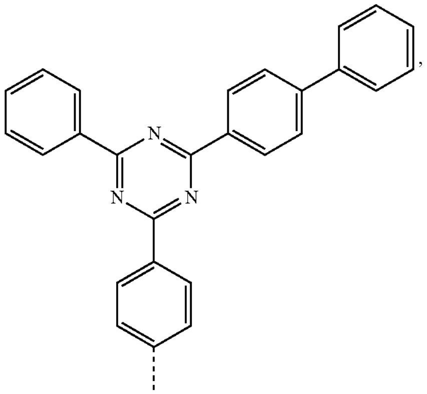
-continued
D[28]
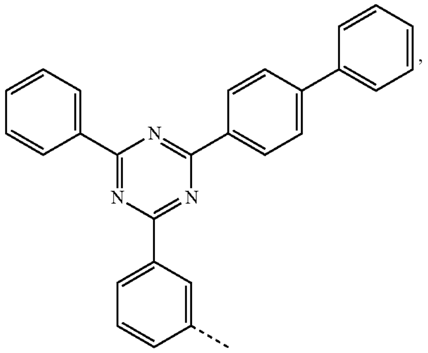
D[29]
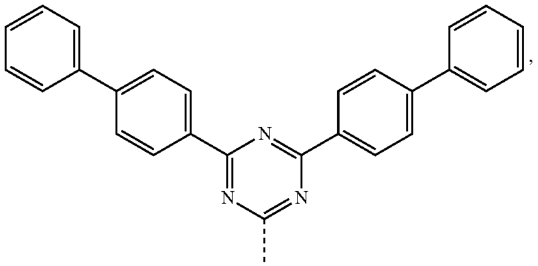
D[31]
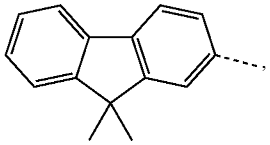
D[32]
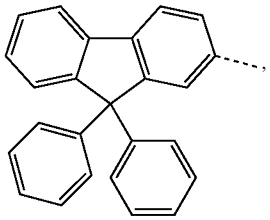
D[33]
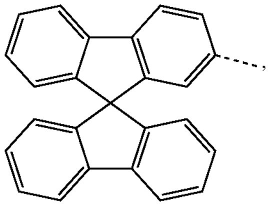
D[36]
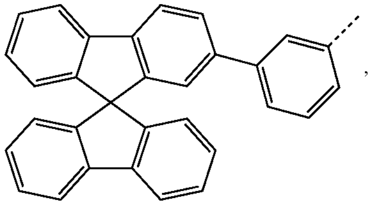

-continued
D[41]
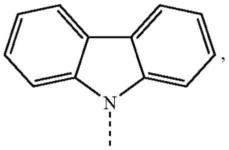
D[42]
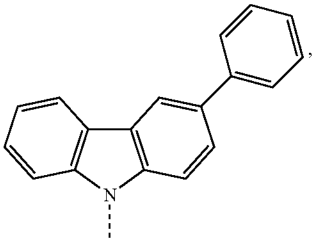
D[43]
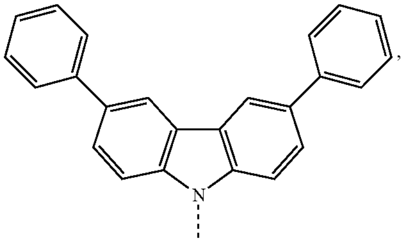
D[45]
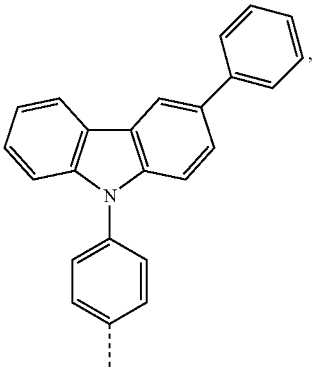
D[46]
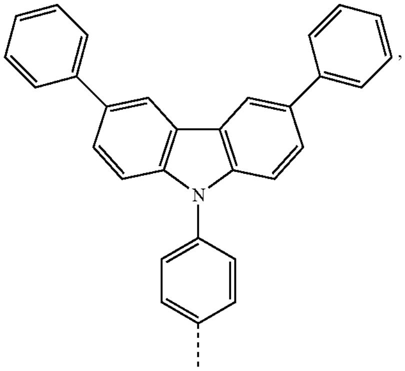
-continued
D[47]
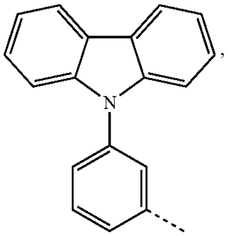
D[48]
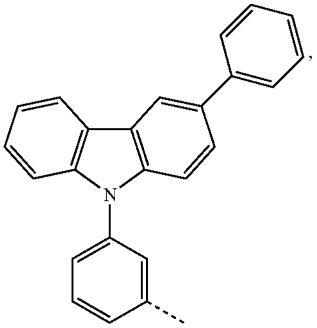
D[49]
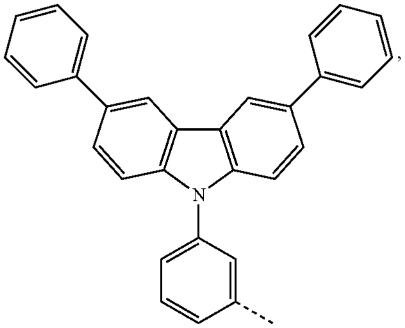
D[54]
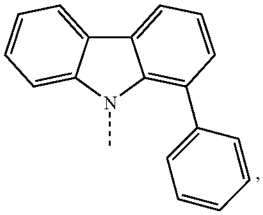
D[55]
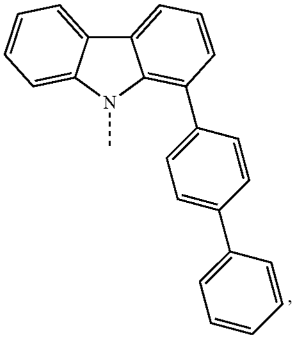

-continued
D[56]
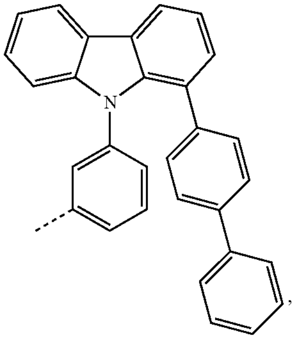
,
D[57]
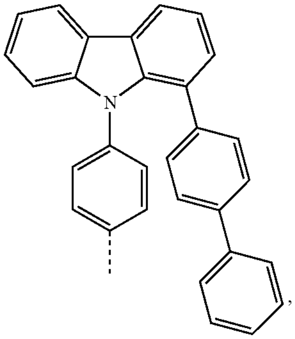
,
D[58]
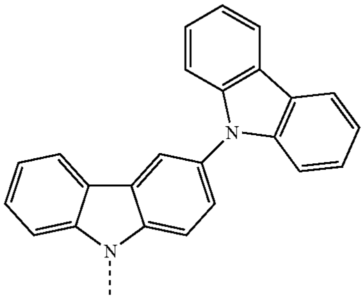
,
D[61]
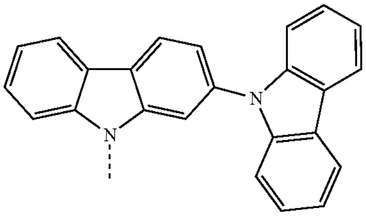
,
D[64]
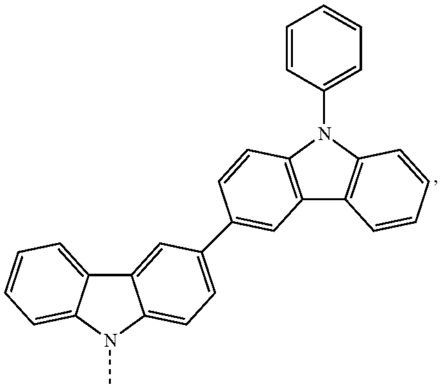
,
-continued
D[65]
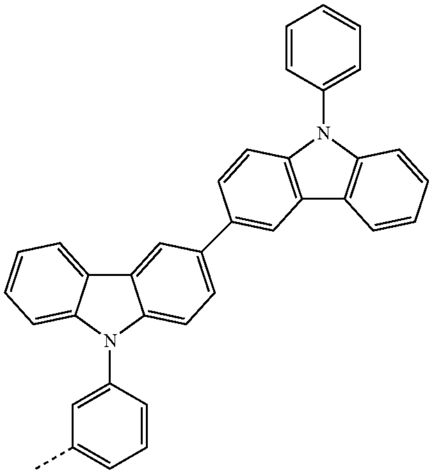
,
D[66]
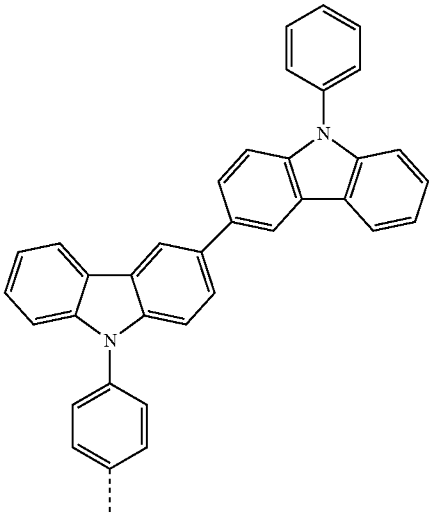
,
D[67]
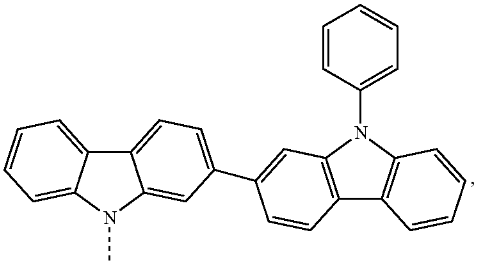
,
D[68]
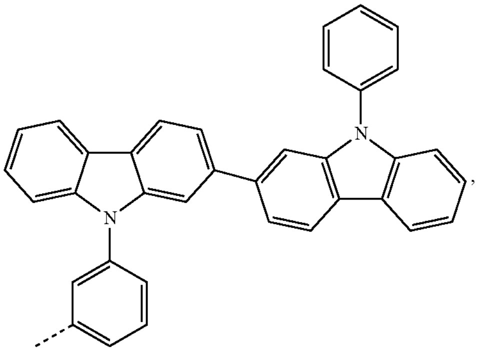
, -continued
D69
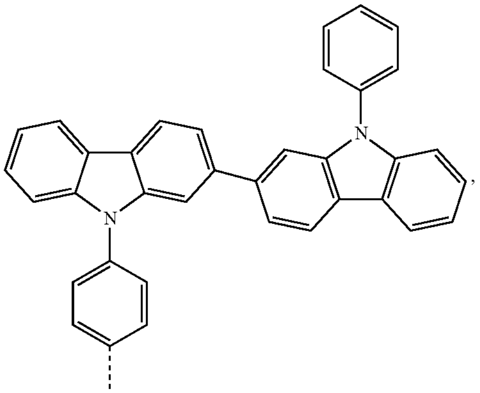
D70
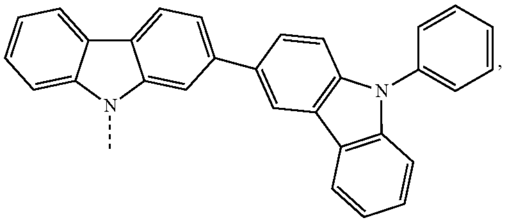
D71
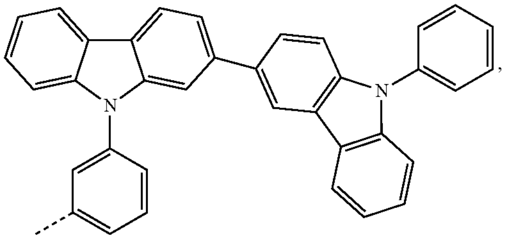
D72
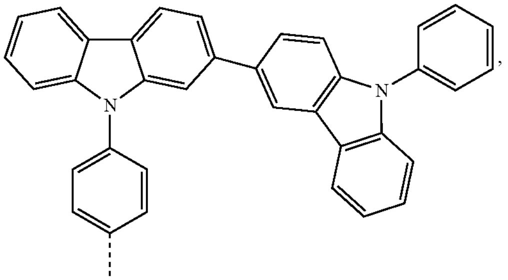
D73
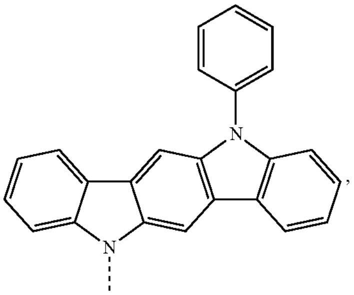
-continued
D74
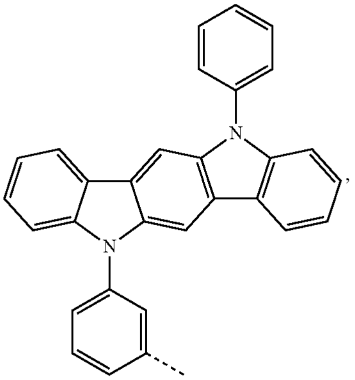
D75
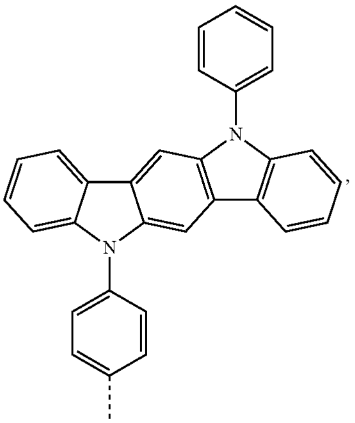
D76
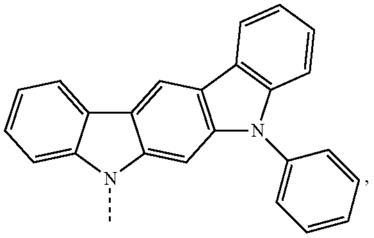
D79
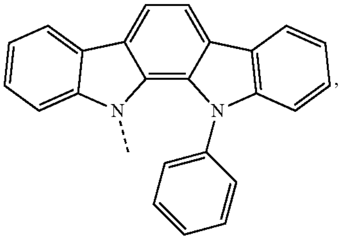
D80
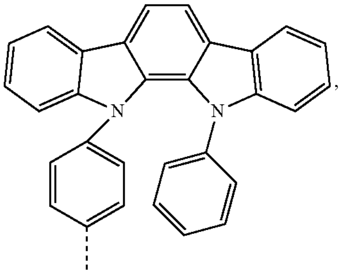

-continued
D[81]
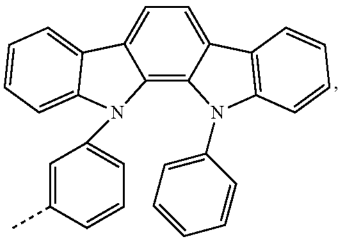
,
D[82]
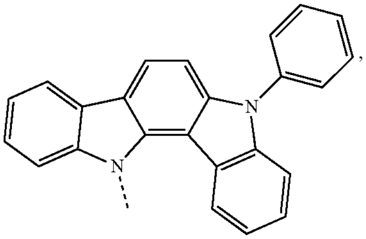
,
D[83]
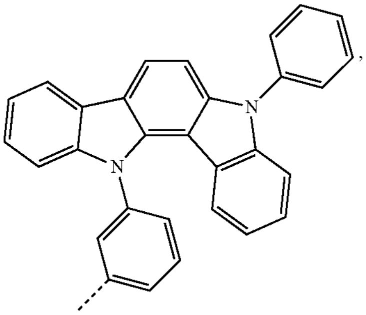
,
D[84]
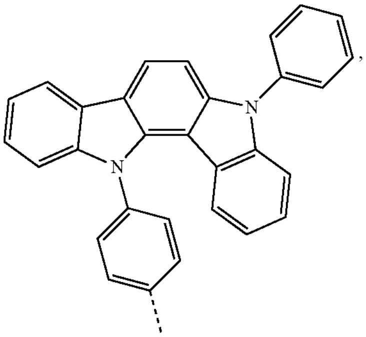
,
D[85]
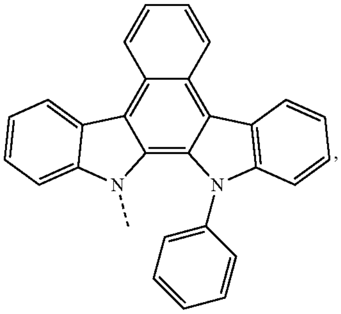
,
-continued
D[86]
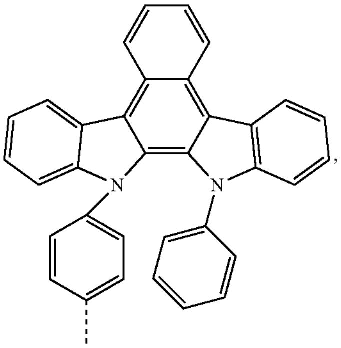
,
D[87]
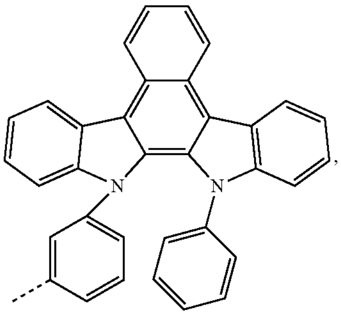
,
D[88]
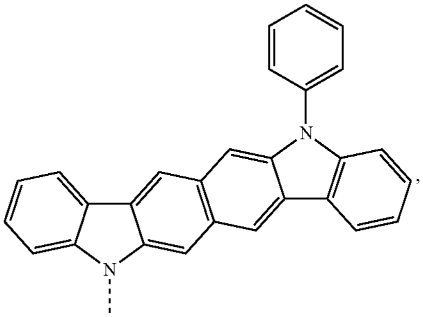
,
D[89]
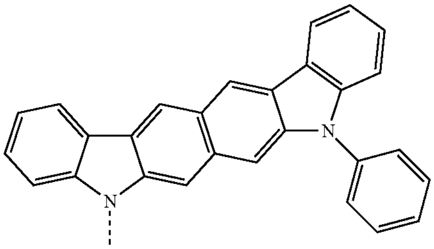
,
D[90]
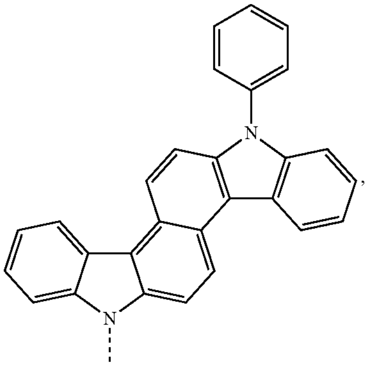
, -continued
D$^{91}$
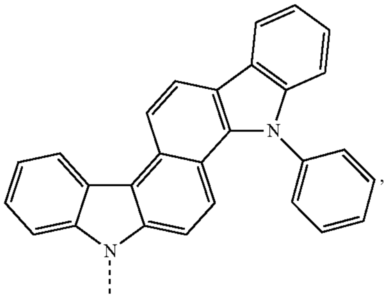
D$^{92}$
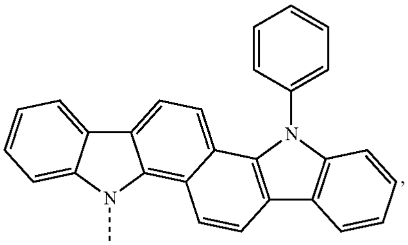
D$^{93}$
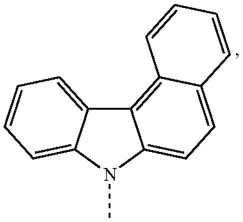
D$^{94}$
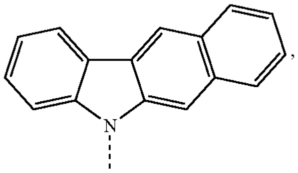
D$^{95}$
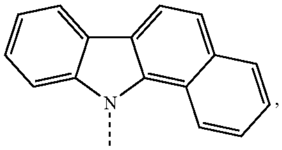
D$^{96}$
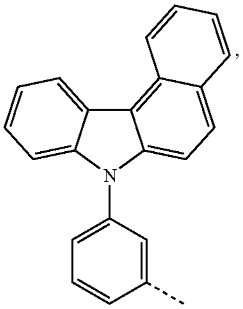
-continued
D$^{97}$
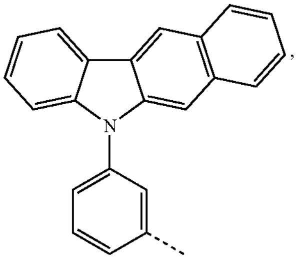
D$^{98}$
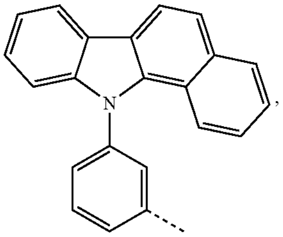
D$^{99}$
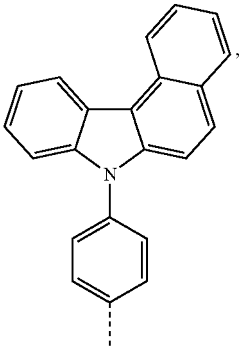
D$^{100}$
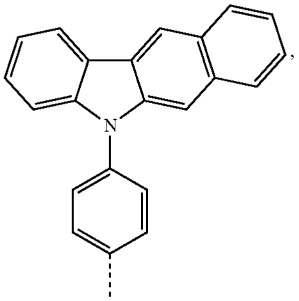
D$^{101}$
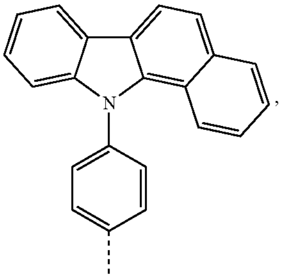

-continued
D[102]
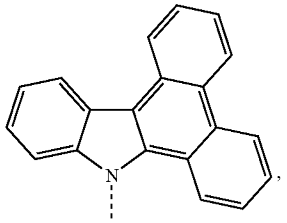
D[103]
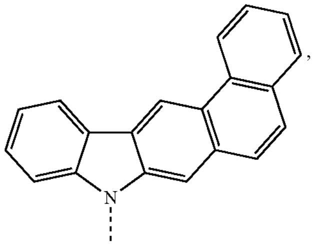
D[104]
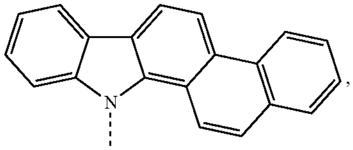
D[105]
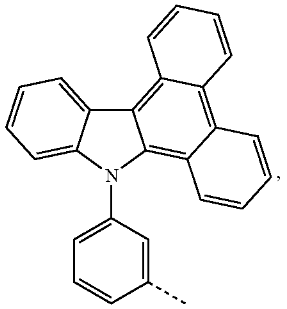
D[106]
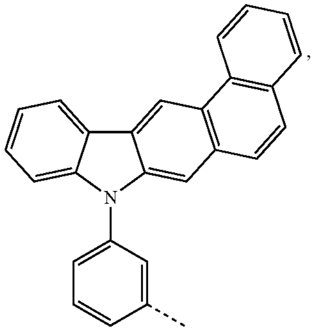
D[107]
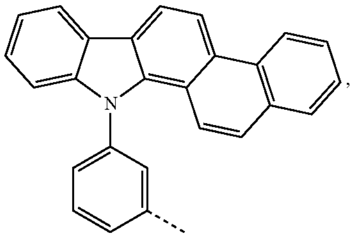
-continued
D[108]
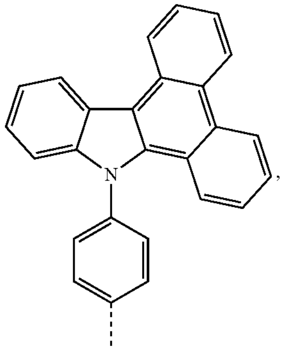
D[109]
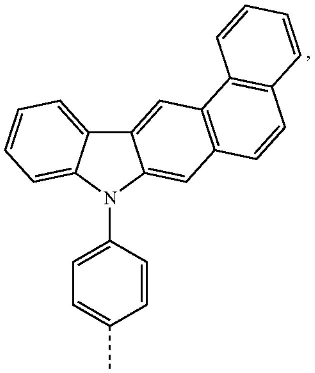
D[110]
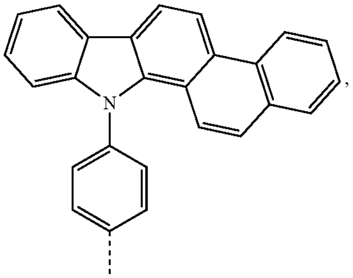
D[111]
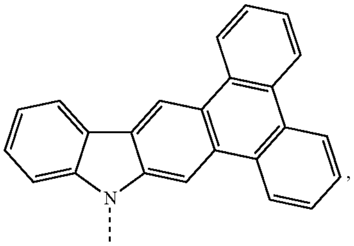
D[112]
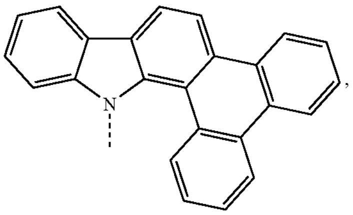

-continued
D113
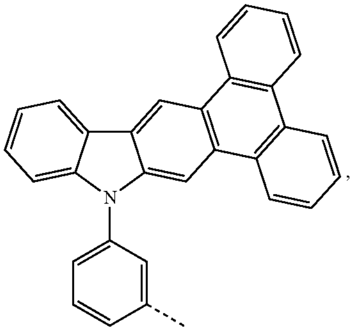
D114
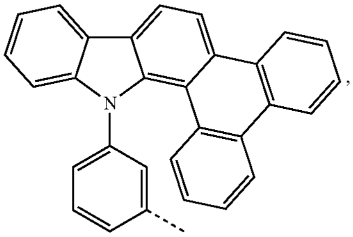
D115
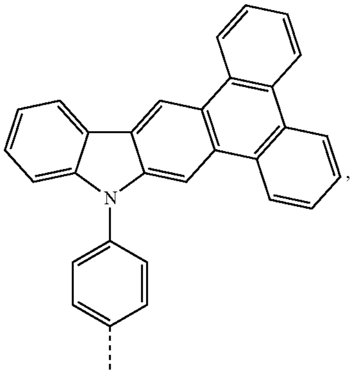
D116
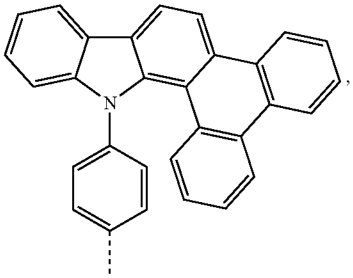
D117
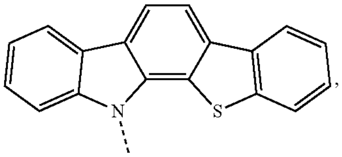
D118
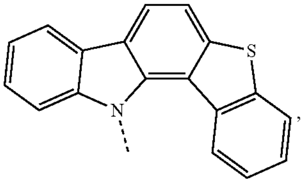
-continued
D119
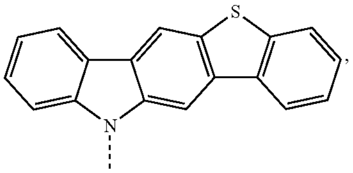
D120
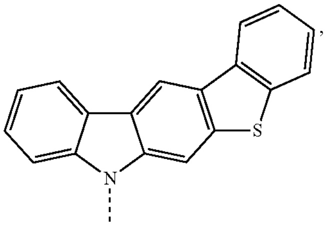
D121
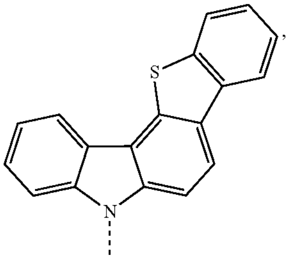
D122
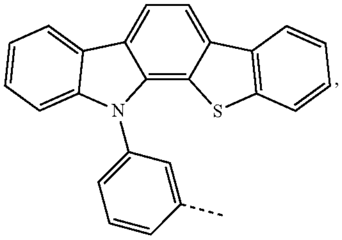
D123
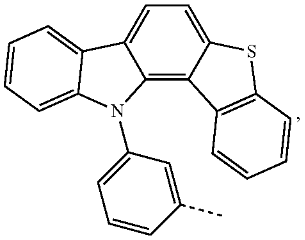
D124
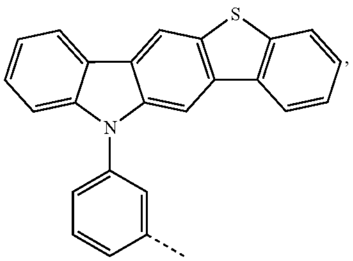

-continued
D[125]
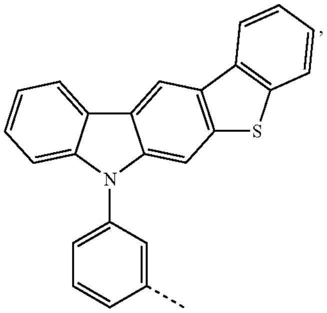
D[126]
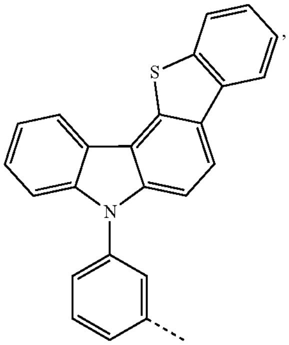
D[127]
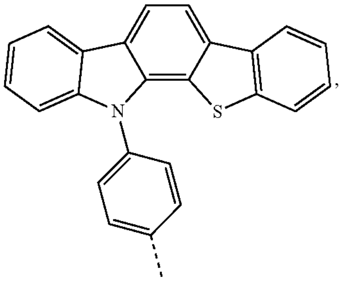
D[128]
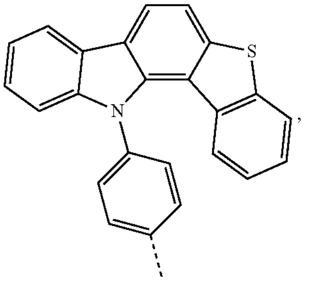
D[129]
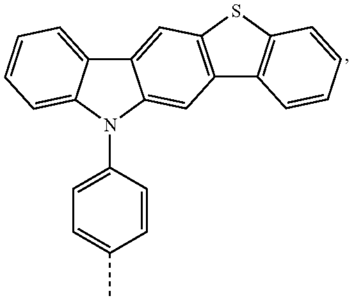
-continued
D[130]
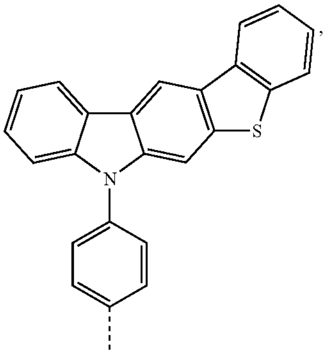
D[131]
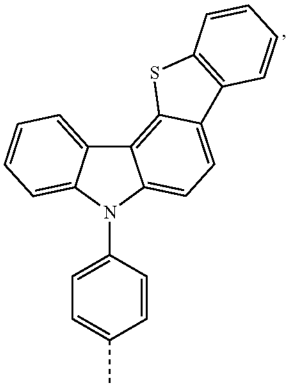
D[132]
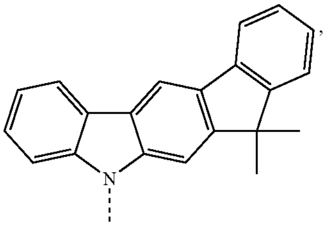
D[133]
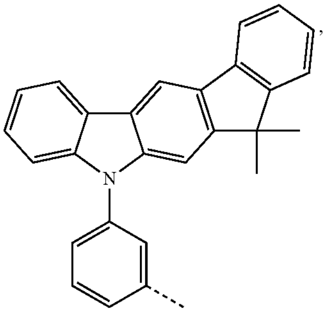

-continued
D[134]
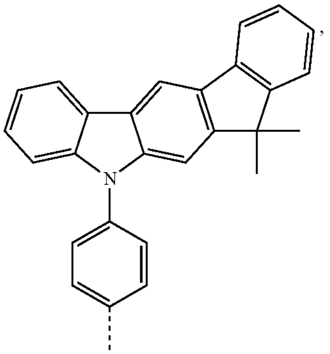
D[135]
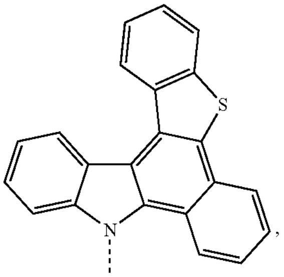
D[136]
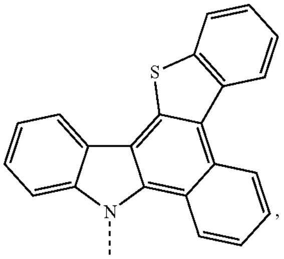
D[137]
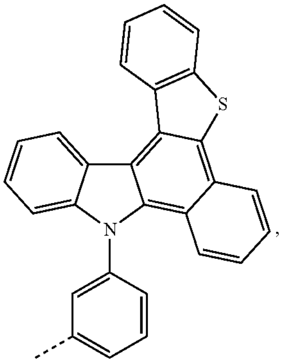
D[138]
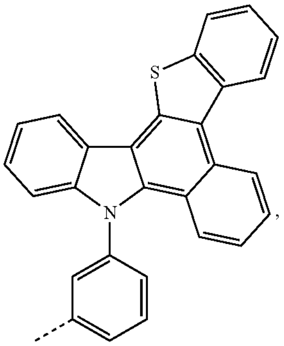
-continued
D[139]
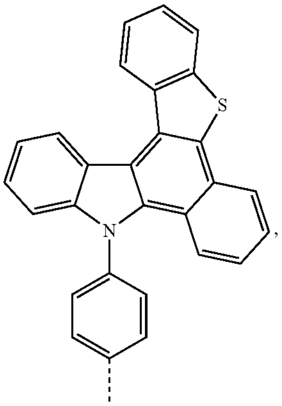
D[140]
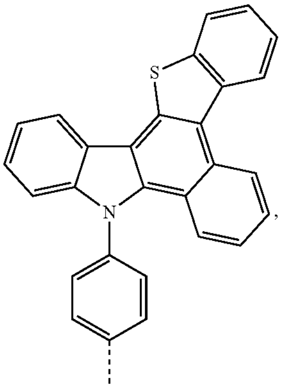
D[141]
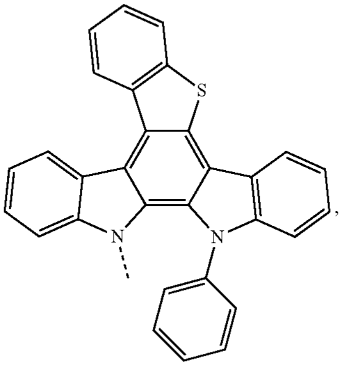
D[142]
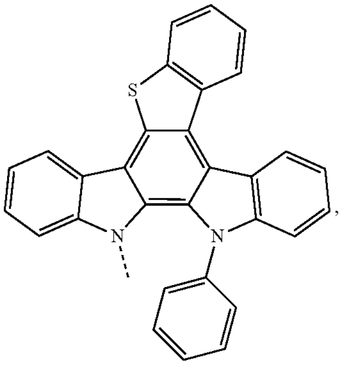

-continued
D[143]
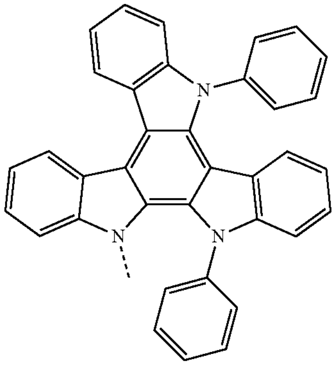
,
D[144]
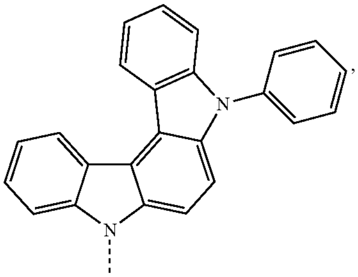
,
D[145]
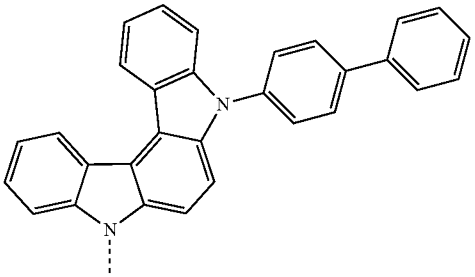
,
D[146]
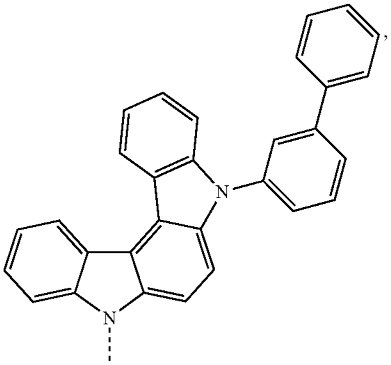
,
-continued
D[147]
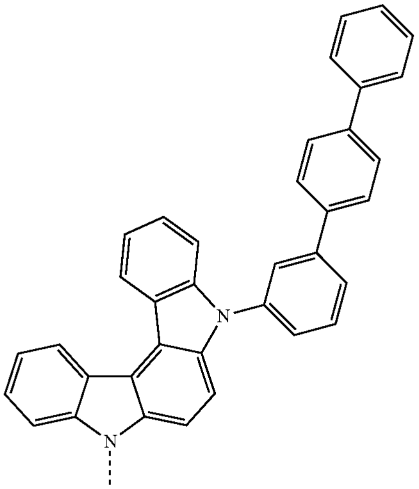
,
D[148]
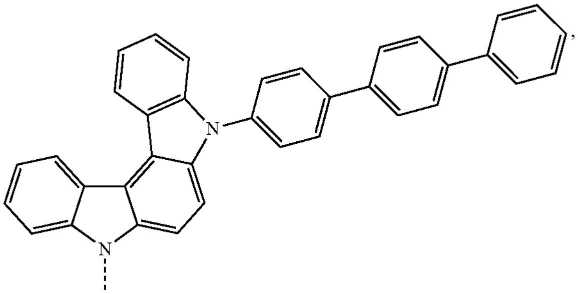
,
D[149]
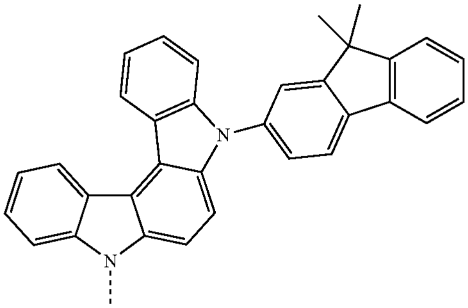
,
D[150]
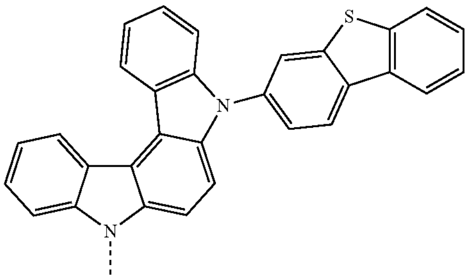
, D[151]
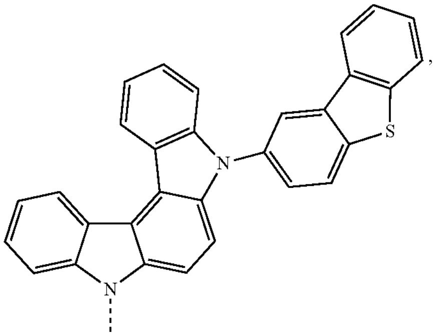
D[152]
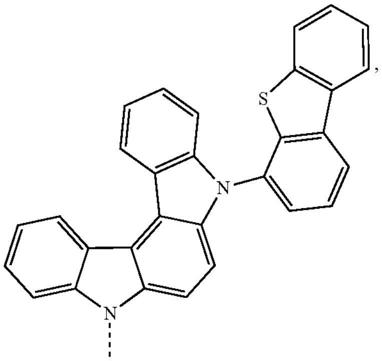
D[153]
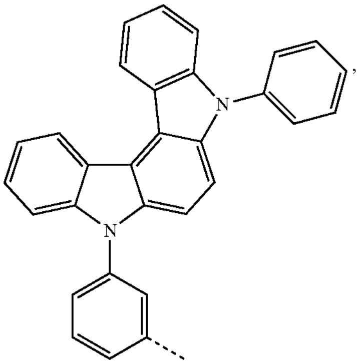
D[154]
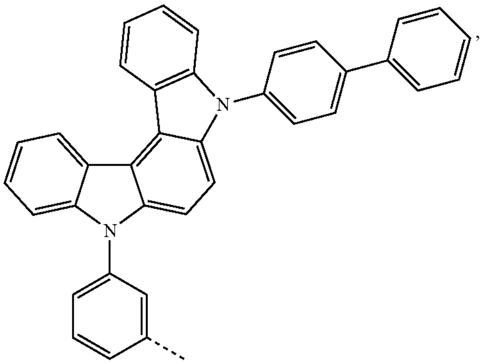
D[155]
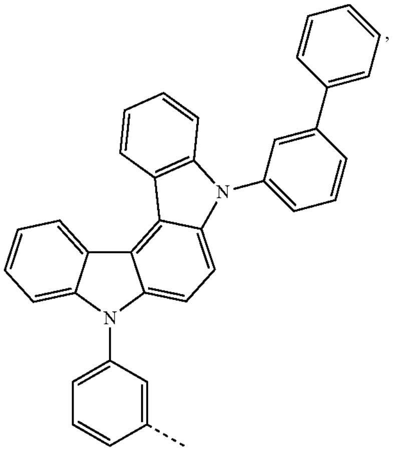
D[156]
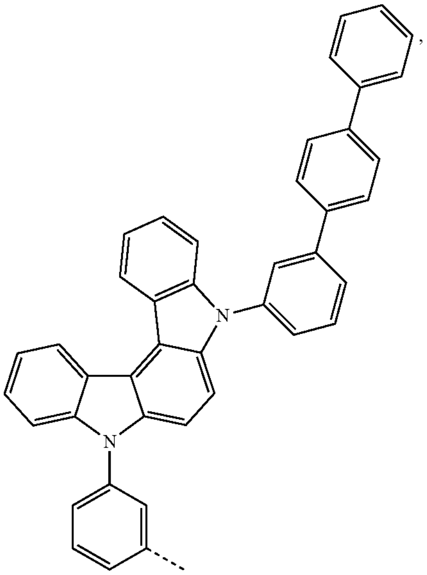
D[157]
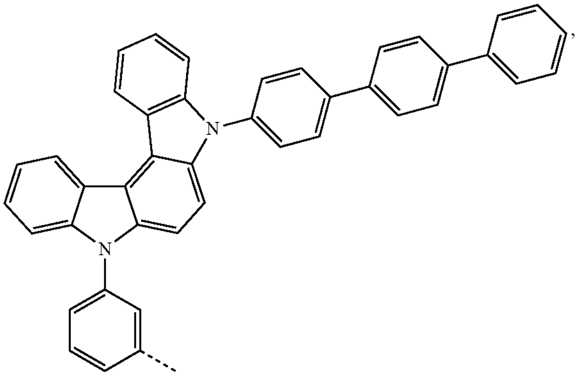

-continued
D[158]
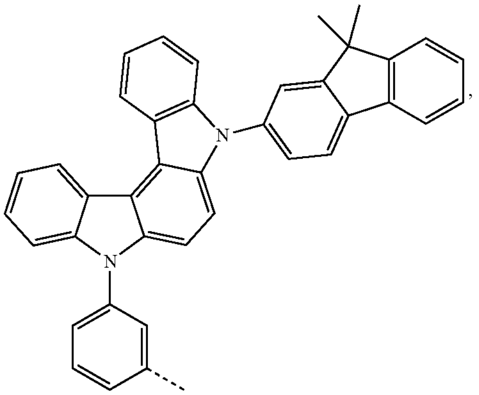
D[159]
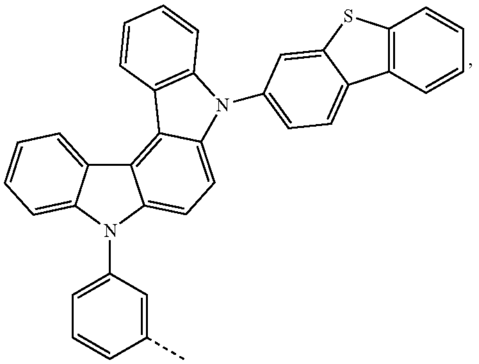
D[160]
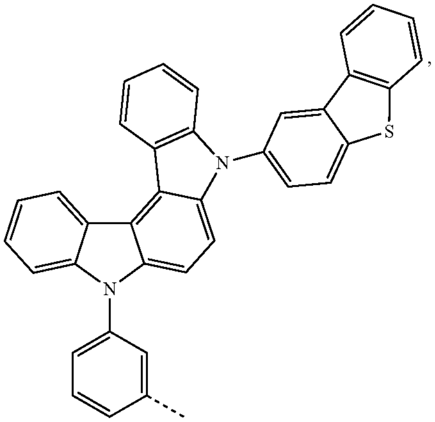
D[161]
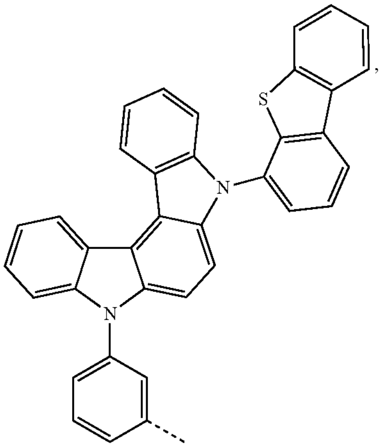
-continued
D[162]
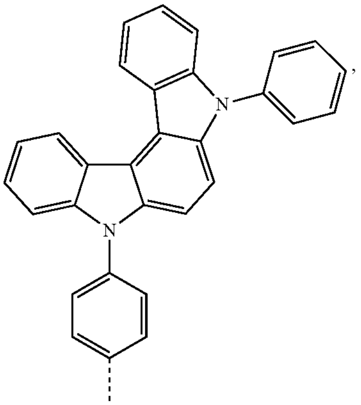
D[163]
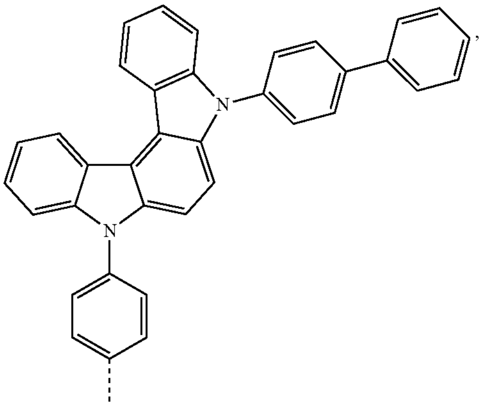
D[164]
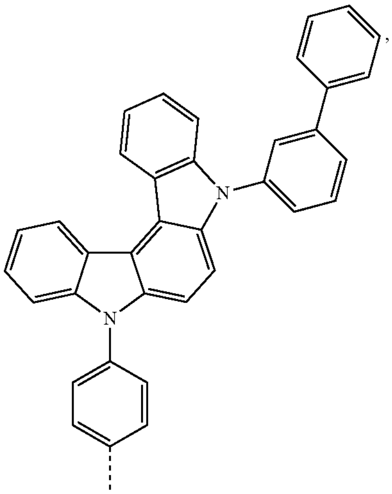

-continued
D165
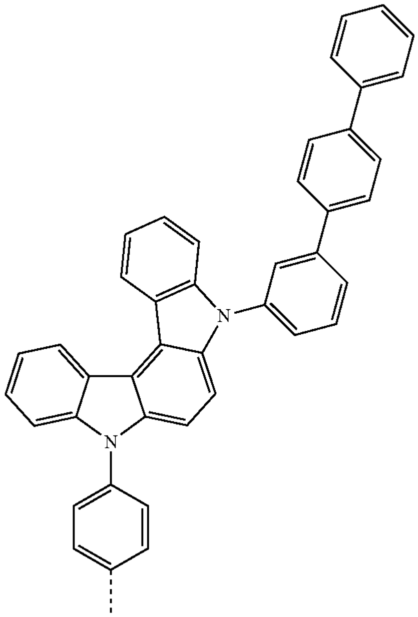,
D166
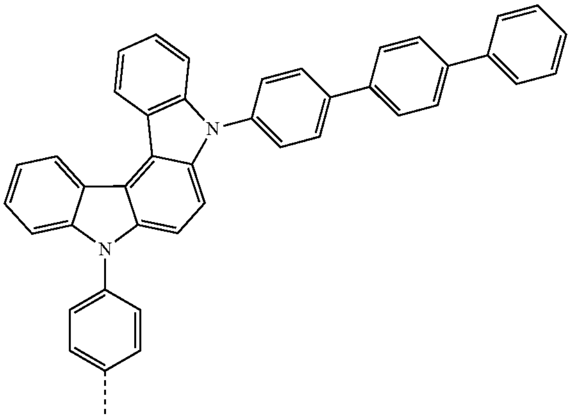,
D167
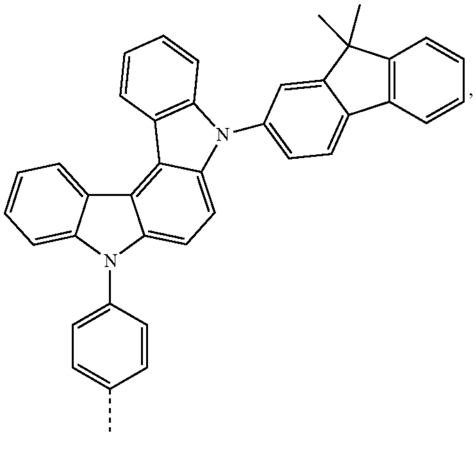,
-continued
D168
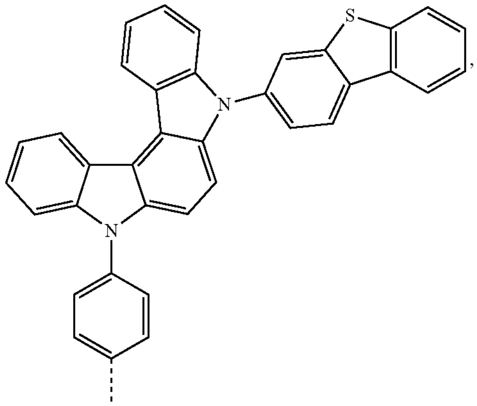,
D169
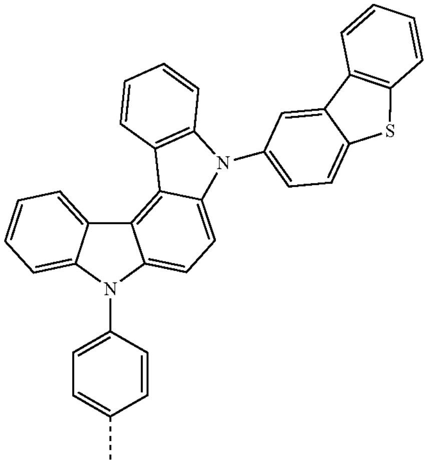,
D170
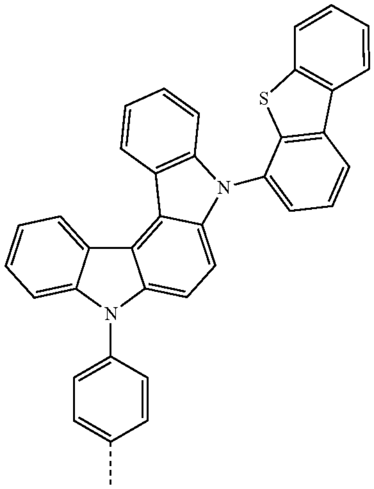, -continued
D[171]
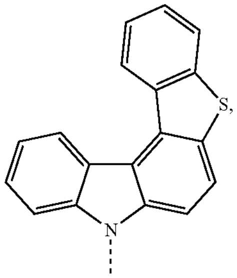
D[172]
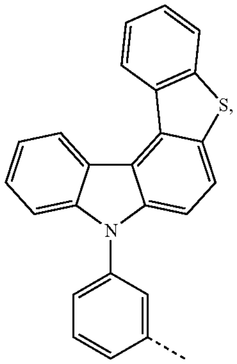
D[173]
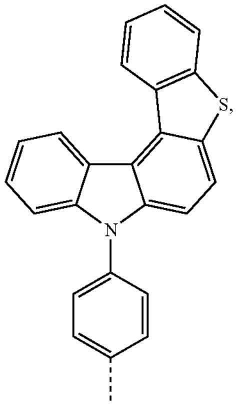
D[174]
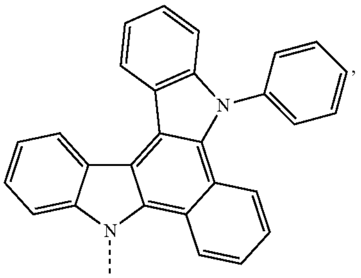
D[175]
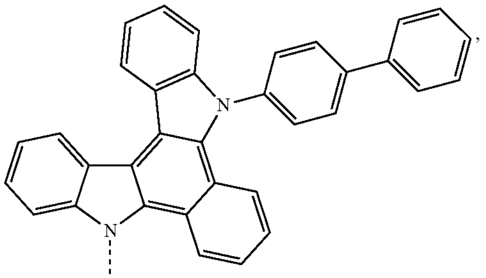
-continued
D[176]
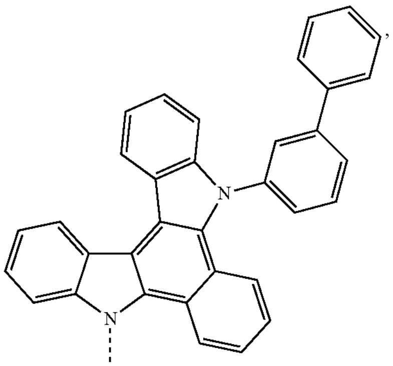
D[177]
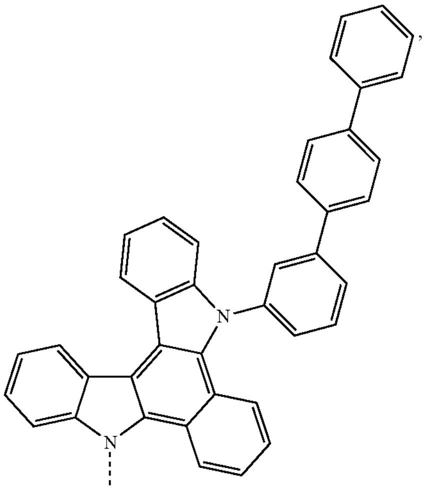
D[178]
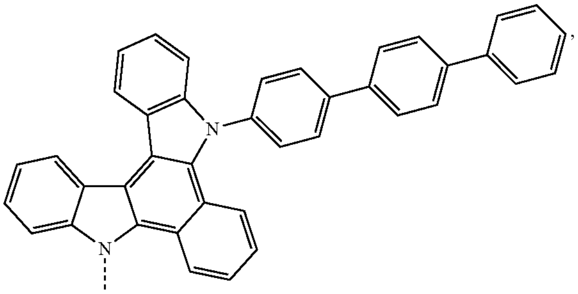
D[179]
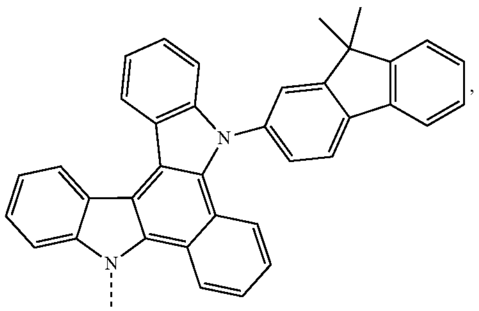

-continued
D[180]
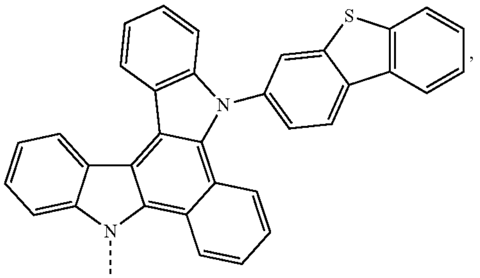
D[181]
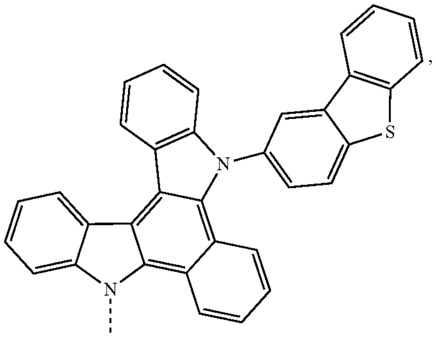
D[182]
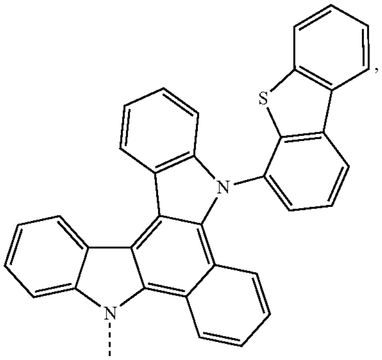
D[183]
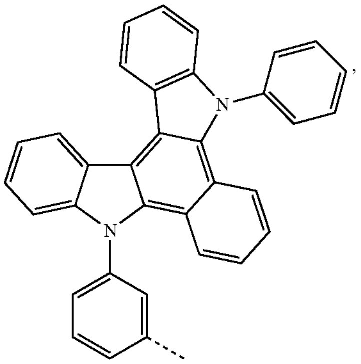
-continued
D[184]
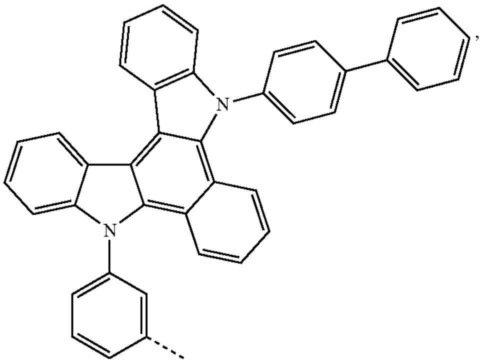
D[185]
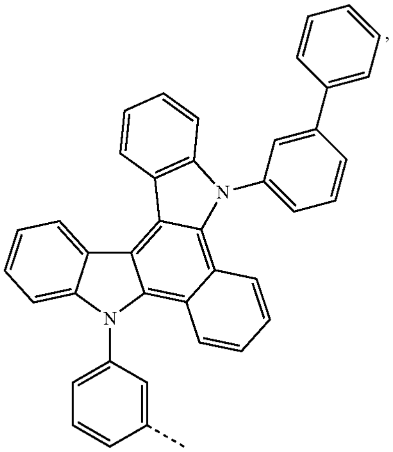
D[186]
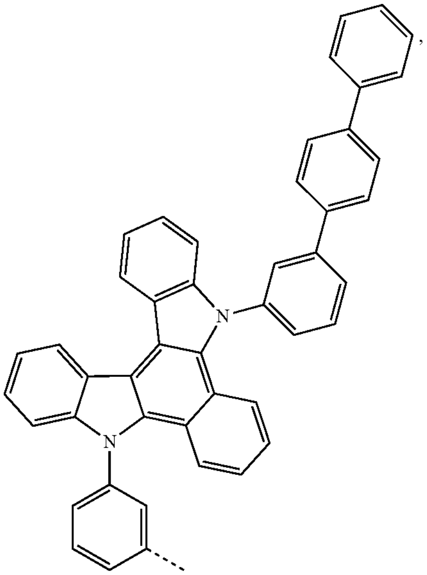

-continued
D[187]
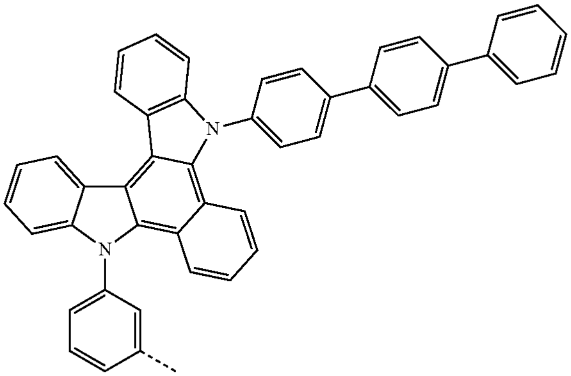
,
D[188]
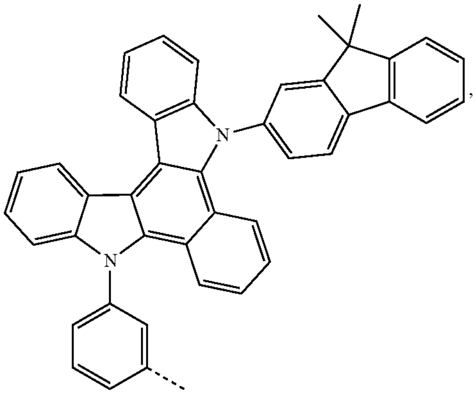
,
D[189]
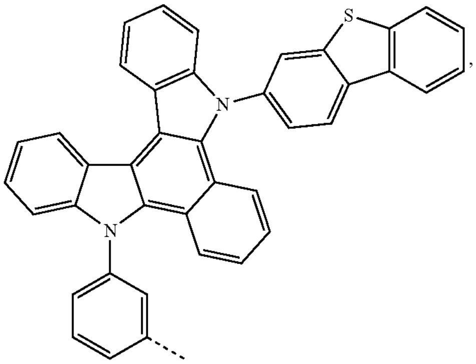
,
D[190]
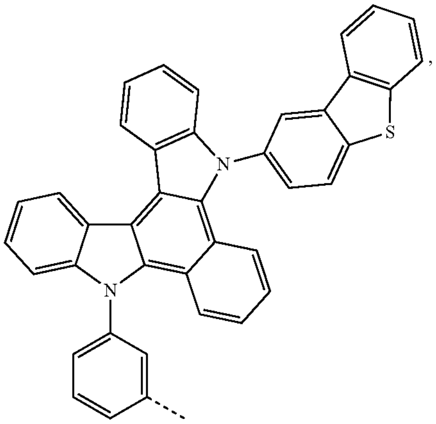
,
-continued
D[191]
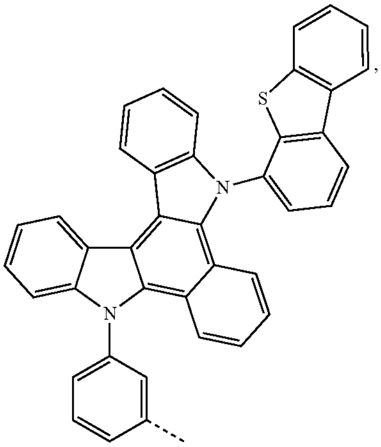
,
D[192]
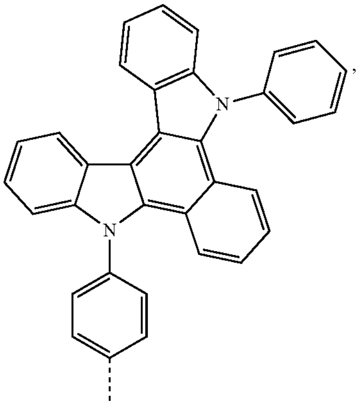
,
D[193]
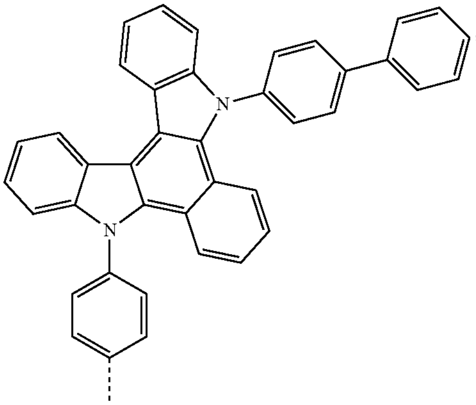
, -continued
D[194]
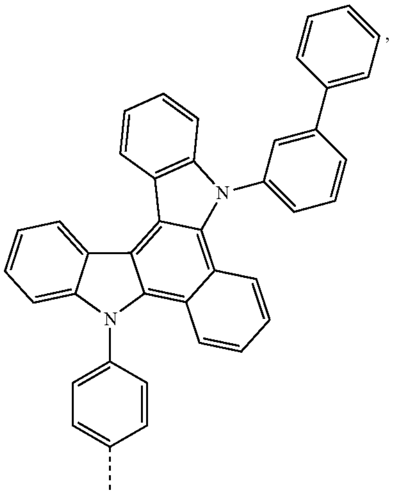
D[195]
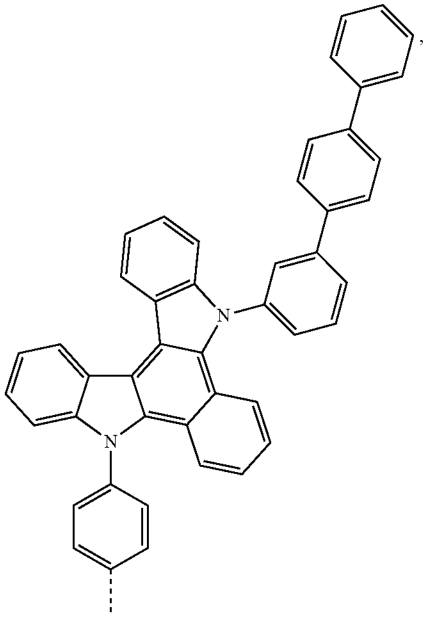
D[196]
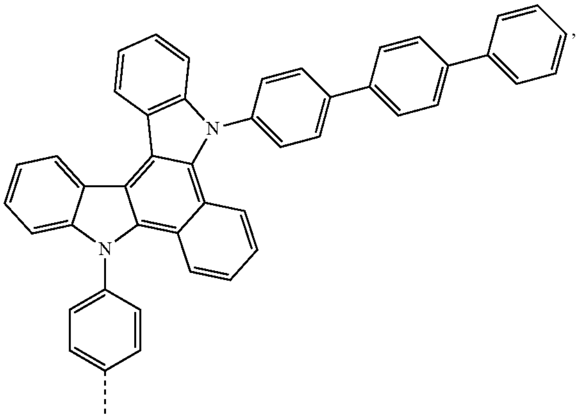
-continued
D[197]
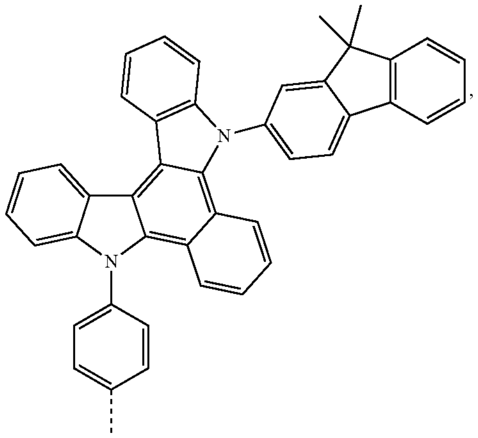
D[198]
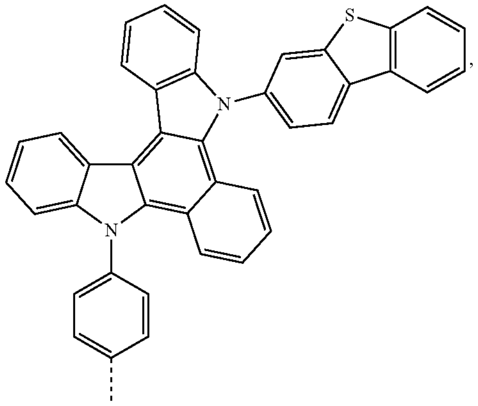
D[199]
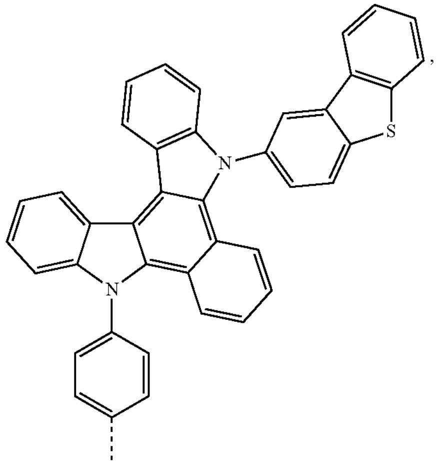

-continued
D[200]
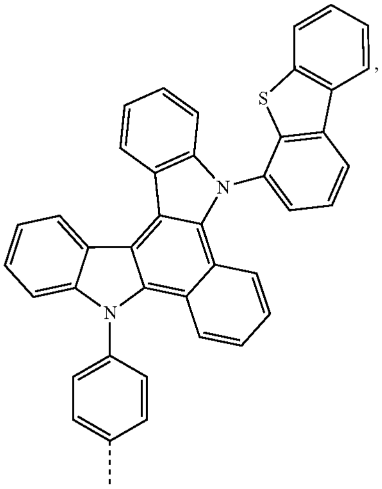
D[201]
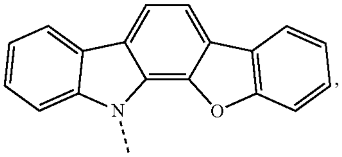
D[202]
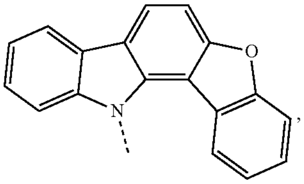
D[203]
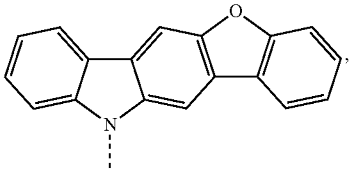
D[204]
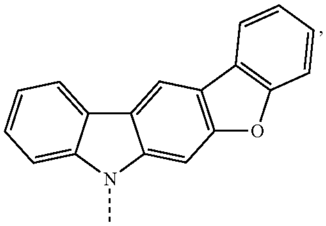
D[205]
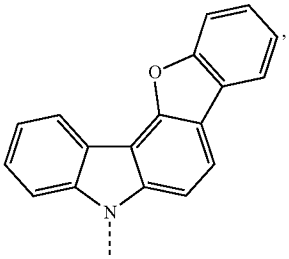
-continued
D[206]
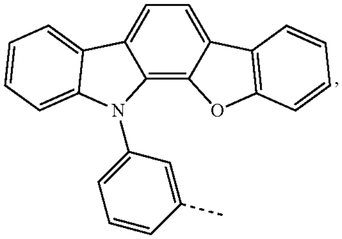
D[207]
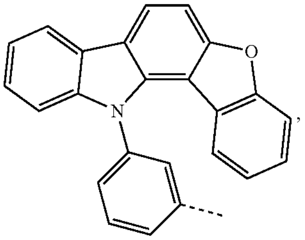
D[208]
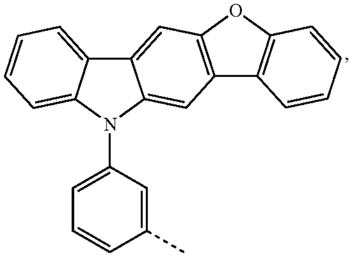
D[209]
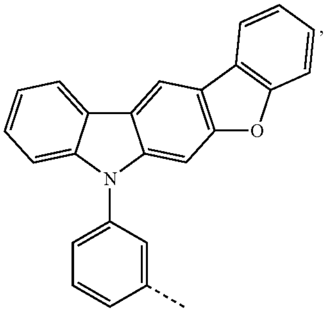
D[210]
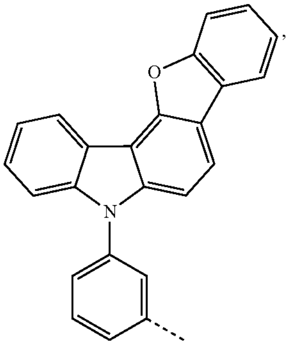

-continued
D211
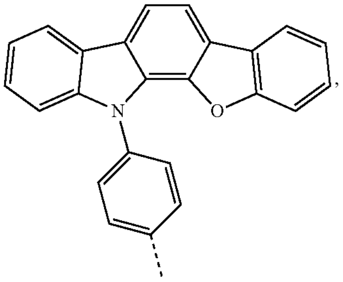
D212
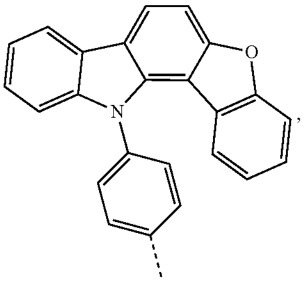
D213
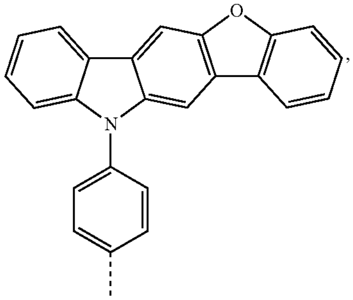
D214
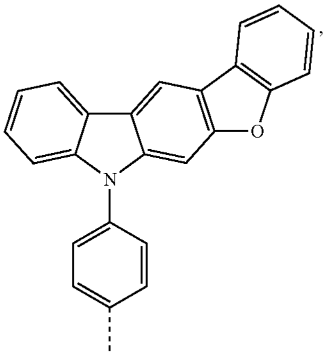
D215
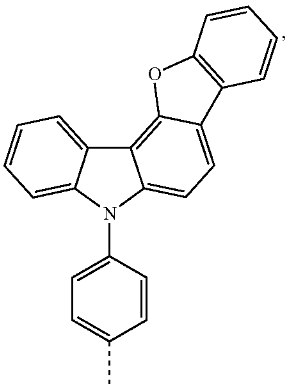
-continued
D216
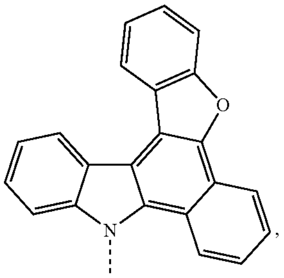
D217
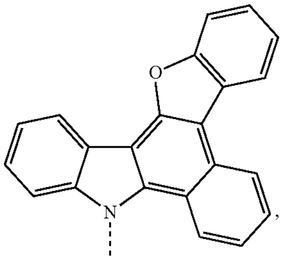
D218
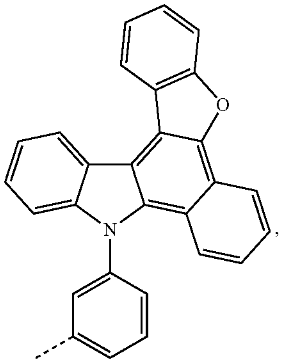
D219
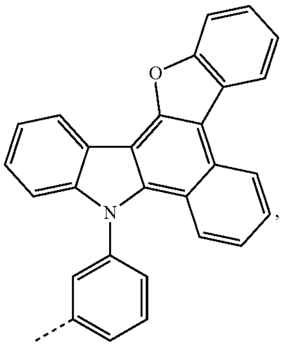

-continued
D[220]
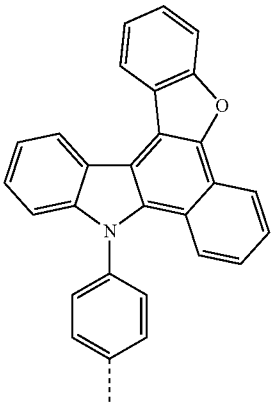
,
D[221]
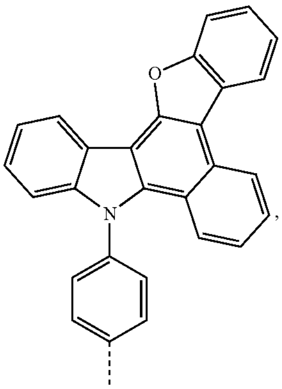
,
D[222]
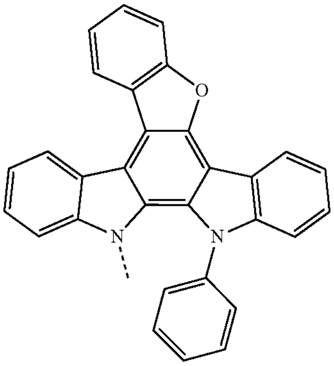
,
D[223]
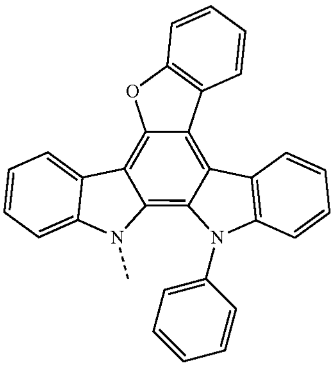
,
-continued
D[224]
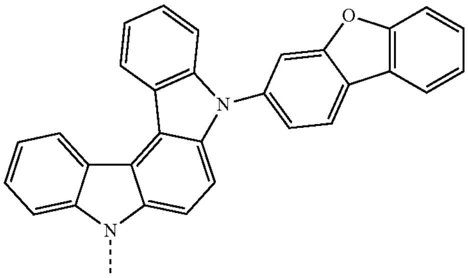
,
D[225]
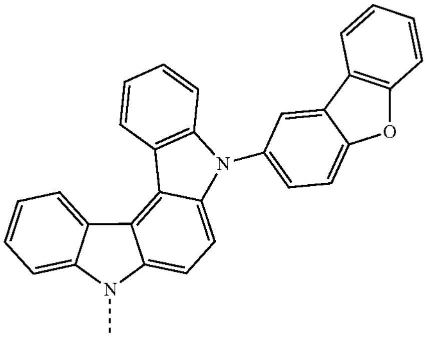
,
D[226]
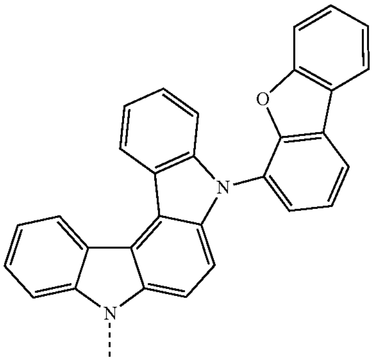
,
D[227]
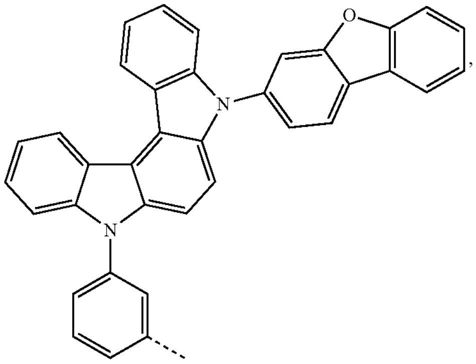
, -continued
D[228]
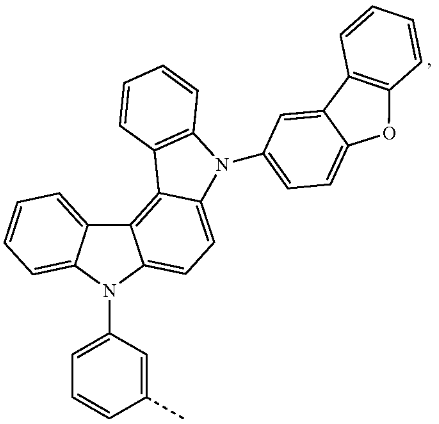
D[229]
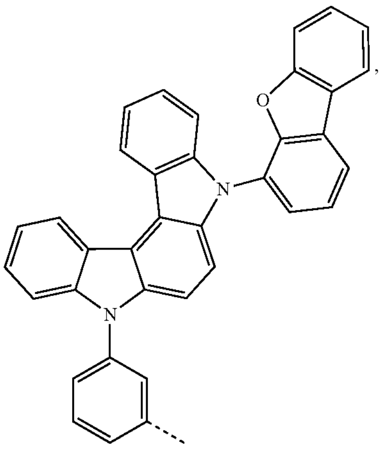
D[230]
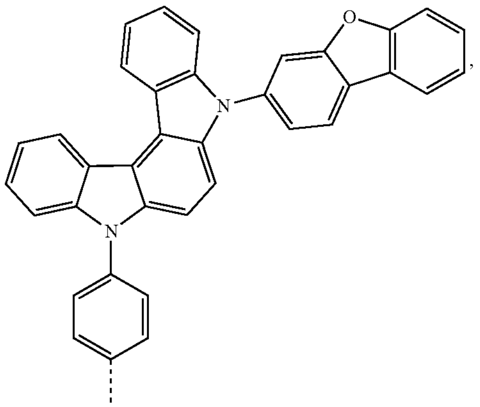
-continued
D[231]
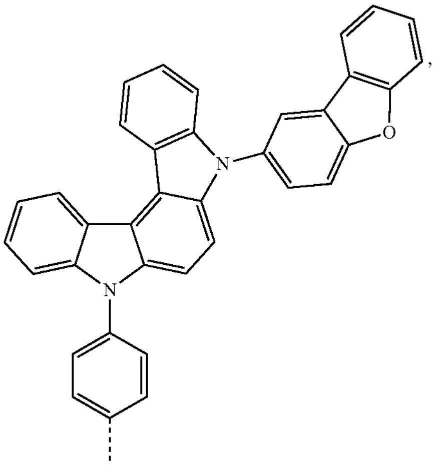
D[232]
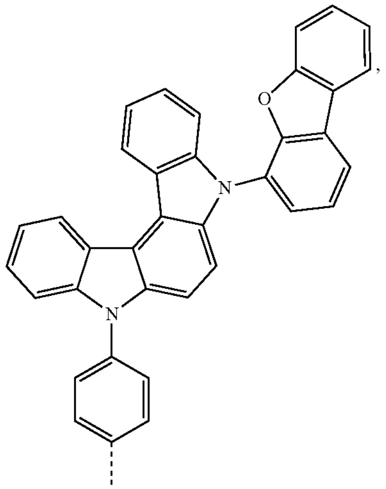
D[233]
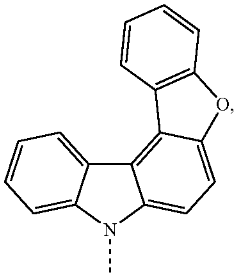
D[234]
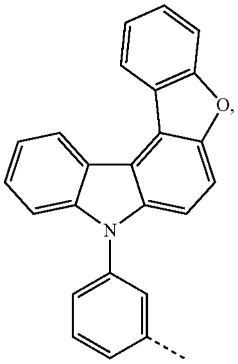

-continued
D[235]
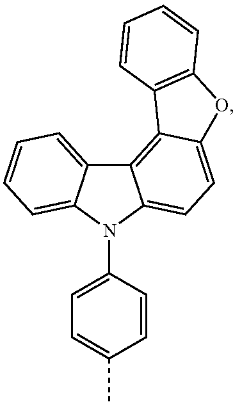
,
D[236]
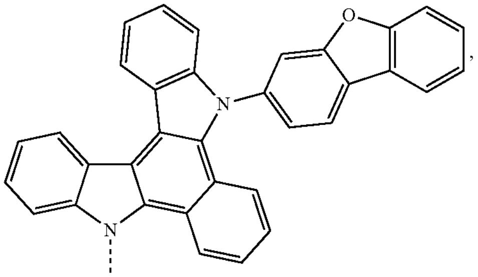
,
D[237]
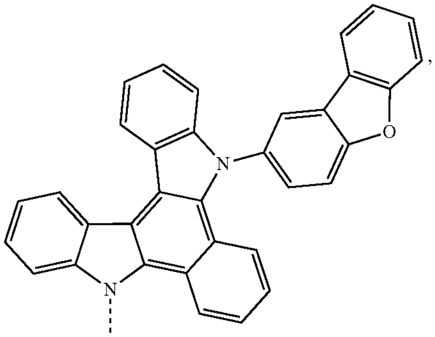
,
D[238]
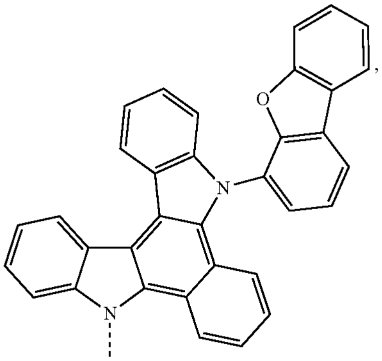
,
-continued
D[239]
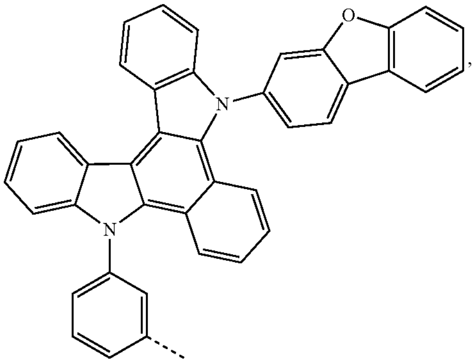
,
D[240]
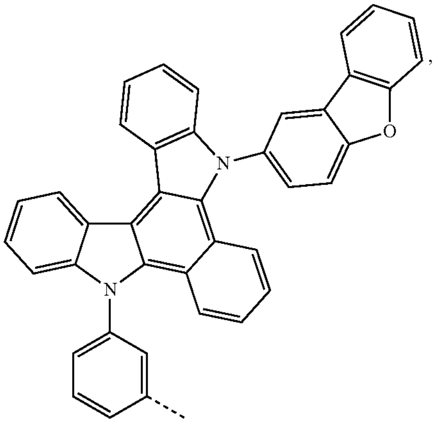
,
D[241]
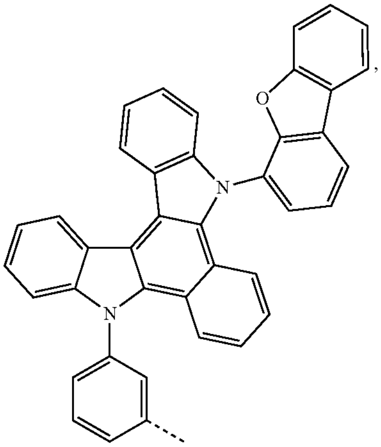
, -continued

D[242]

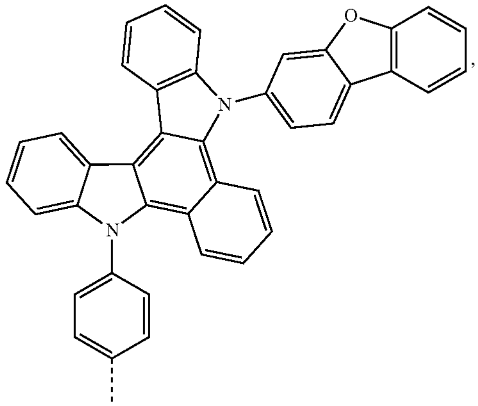

,

D[243]

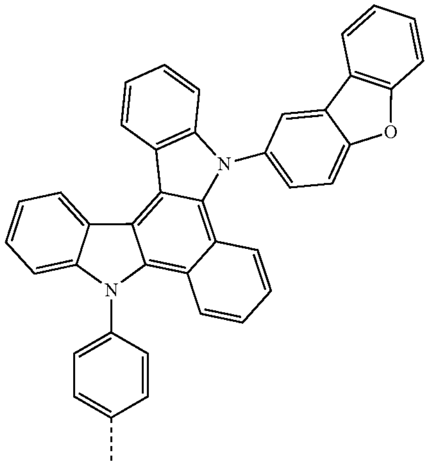

, and

-continued

D[244]

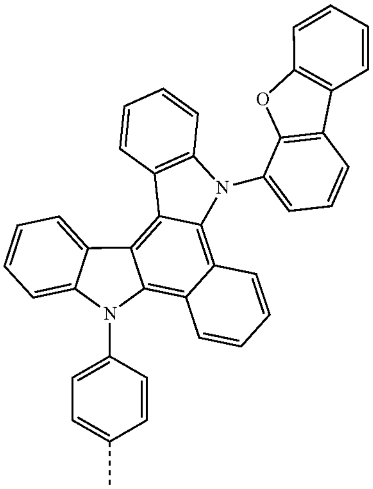

;

wherein any adjacent substitutions on the same ring are optionally joined or fused into a ring; and wherein at least one of the following is true: (i) at least one of $X^5$ and $X^6$ is N, (ii) at least one of $X^7$ to $X^{10}$ is N, (iii) each of $X^1$ to $X^4$ is carbon;

provided that when adjacent substitutions on $X^5$ and $X^6$ in Formula I-1 and I-3 fuse into a six-member ring, this ring and the ring having $X^7$ to $X^{10}$ cannot be pyridine at the same time.

* * * * *